US009808516B2

(12) United States Patent
Brockstedt et al.

(10) Patent No.: US 9,808,516 B2
(45) Date of Patent: Nov. 7, 2017

(54) IMMUNOGENIC FUSION PROTEINS FOR THE TREATMENT OF CANCER

(71) Applicants: Aduro Biotech, Inc., Berkeley, CA (US); The Johns Hopkins University, Baltimore, MD (US)

(72) Inventors: Dirk G. Brockstedt, Richmond, CA (US); Charles G. Drake, Baltimore, MD (US); Marcella Fasso, Richmond, CA (US); Peter M. Lauer, Albany, CA (US); William G. Hanson, Walnut Creek, CA (US); Meredith Lai Ling Leong, Oakland, CA (US); Christopher Steven Rae, Richmond, CA (US)

(73) Assignees: Aduro Biotech, Inc., Berkeley, CA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/097,271

(22) Filed: Apr. 12, 2016

(65) Prior Publication Data

US 2016/0324945 A1    Nov. 10, 2016

Related U.S. Application Data

(60) Provisional application No. 62/146,626, filed on Apr. 13, 2015, provisional application No. 62/146,654, filed on Apr. 13, 2015, provisional application No. 62/263,174, filed on Dec. 4, 2015.

(51) Int. Cl.
| | |
|---|---|
| A61K 39/00 | (2006.01) |
| C12N 9/12 | (2006.01) |
| C07K 14/47 | (2006.01) |
| C12N 9/16 | (2006.01) |
| C12N 9/48 | (2006.01) |

(52) U.S. Cl.
CPC ...... *A61K 39/0011* (2013.01); *C07K 14/4703* (2013.01); *C12N 9/12* (2013.01); *C12N 9/16* (2013.01); *C12N 9/485* (2013.01); *C12Y 207/10001* (2013.01); *C12Y 301/03005* (2013.01); *C12Y 304/17021* (2013.01); *A61K 2039/523* (2013.01); *C07K 2319/40* (2013.01)

(58) Field of Classification Search
None
See application file for complete search history.

(56) References Cited

U.S. PATENT DOCUMENTS

| | | | |
|---|---|---|---|
| 5,830,702 A | 11/1998 | Portnoy et al. | |
| 6,051,237 A | 4/2000 | Paterson | |
| 6,224,868 B1 | 5/2001 | Wong et al. | |
| 6,565,852 B1 | 5/2003 | Paterson | |
| 7,588,930 B2 | 9/2009 | Paterson et al. | |
| 9,200,057 B2 * | 12/2015 | Lauer ................. | A61K 39/0011 |
| 2004/0197343 A1 | 10/2004 | Dubensky et al. | |
| 2004/0228877 A1 | 11/2004 | Dubensky et al. | |
| 2005/0037010 A1 | 2/2005 | Monahan et al. | |
| 2007/0207170 A1 | 9/2007 | Dubensky et al. | |
| 2008/0286781 A1 | 11/2008 | Monahan et al. | |
| 2011/0245480 A1 | 10/2011 | Dubensky, Jr. et al. | |
| 2012/0264625 A1 | 10/2012 | Monahan et al. | |
| 2014/0037662 A1 * | 2/2014 | Lauer ................. | A61K 39/0011 |
| | | | 424/185.1 |
| 2014/0186387 A1 * | 7/2014 | Lauer ................. | C07K 14/195 |
| | | | 424/190.1 |
| 2014/0315314 A1 | 10/2014 | Dubensky, Jr. et al. | |
| 2014/0356366 A1 | 12/2014 | Cheong et al. | |
| 2016/0074491 A1 | 3/2016 | Lauer | |
| 2016/0346369 A1 | 12/2016 | Lauer | |

FOREIGN PATENT DOCUMENTS

| | | |
|---|---|---|
| EP | 2808035 A1 | 12/2014 |
| WO | WO 2004/006837 | 1/2004 |
| WO | WO 2004/018999 A2 | 3/2004 |
| WO | WO 2004/112825 | 12/2004 |
| WO | WO 2007/103225 A2 | 9/2007 |
| WO | WO 2007/117371 | 10/2007 |
| WO | WO 2012/068360 A1 | 5/2012 |
| WO | WO 2014/106123 A1 | 7/2014 |
| WO | WO 2016/168198 A1 | 10/2016 |
| WO | WO 2016/168214 A2 | 10/2016 |

OTHER PUBLICATIONS

Ayyoub, M., et al., "SSX Antigens as Tumor Vaccine Targets in Human Sarcoma", *Cancer Immunity*, vol. 3: 13 (2003).
Brockstedt, D. G., et al., "*Listeria*-based Cancer Vaccines That Segregate Immunogenicity From Toxicity", *PNAS*, vol. 101, No. 38: 13832-13837 and slides (2004).
Camilli, A., et al., "Dual Roles of plcA in *Listeria Monocytogenes* Pathogenesis", *Molecular Microbiology*, vol. 8, No. 1: 143-157 (1993).
Cecco, S., et al., "Cancer Vaccines in Phase II/III Clinical Trials: State of the Art and Future Perspectives", *Current Cancer Drug Targets*, vol. 11: 85-102 (2011).
Eisenhauer, E. A., et al., "New Response Evaluation Criteria in Solid Tumours: Revised RECIST Guideline (version 1.1)", *European Journal of Cancer*, vol. 45: 228-247 (2009).
Fujio, K., et al., "A Vaccine Strategy with Multiple Prostatic Acid Phosphatase-fused Cytokines for Prostate Cancer Treatment", *Oncology Reports*, vol. 33: 1585-1592 (2015).
Gurel, B., et al., "NKX3.1 as a Marker of Prostatic Origin in Metastatic Tumors," *Am J Surg Pathol*, 34(8):1097-1105 (2010).
Invitation to Pay Additional Fees for International Application No. PCT/US2016/027167, entitled: "Immunogenic Fusion Proteins for the Treatment of Cancer," dated Aug. 10, 2016.
Lauer, P., et al., "Construction, Characterization, and Use of Two *Listeria monocytogenes* Site-Specific Phage Integration Vectors", *Journal of Bacteriology*, vol. 184, No. 15: 4177-4186 (2002).

(Continued)

*Primary Examiner* — Laura B Goddard
(74) *Attorney, Agent, or Firm* — Hamilton, Brook, Smith & Reynolds, P.C.

(57) ABSTRACT

Provided herein are compositions and methods for eliciting an immune response in a subject. In particular, the present disclosure is directed to immunogenic fusion proteins and methods of eliciting an immune response using host cells comprising nucleic acid molecules encoding said fusion proteins.

9 Claims, 12 Drawing Sheets

(56) References Cited

OTHER PUBLICATIONS

Lauer, P., et al., "Constitutive Activation of the PrfA Regulon Enhances the Potency of Vaccines Based on Live-Attenuated and Killed but Metabolically Active *Listeria monocytogenes*Strains", *Infection and Immunity*, vol. 76, No. 8: 3742-3753 (2008).
Notification of Transmittal of the International Search Report and the Written Opinion of the International Searching Authority, or the Declaration for International Application No. PCT/US2016/027167, entitled: "Immunogenic Fusion Proteins for the Treatment of Cancer", dated Oct. 20, 2016.
Notification of Transmittal of the International Search Report and the Written Opinion of the International Searching Authority, or the Declaration for International Application No. PCT/US2016/027136, entitled: "Epidermal Growth Factor Receptor Variant III-Mesothelin Fusions and Methods of Using the Same", dated Jun. 28, 2016.
Sinnathamby, G., et al., "Priming and Activation of Human Ovarian and Breast Cancer-specific CD8+ T Cells by Polyvalent Listeria monocytogenes-based Vaccines", *Journal of Immunotherapy*, vol. 32, No. 8: 856-869 Abstract only (2009).
Smith, H.A. and McNeel, D. G., "The SSX Family of Cancer-Testis Antigens as Target Proteins for Tumor Therapy", *Clinical and Developmental Immunology*, vol. 2010: 18 pages (2010).
Toes, R.E.M., et al., "Discrete Cleavage Motifs of Constitutive and Immunoproteasomes Revealed by Quantitative Analysis of Cleavage Products", *J. Exp. Med.*, vol. 194, No. 1: 1-12 (2001).
Wolchok, J.D., et al., "Guidelines for the Evaluation of Immune Therapy Activity in Solid Tumors: Immune-Related Response Criteria", *Clin. Cancer Res.*, vol. 15, No. 23 :74127420 (2009).
Arlen et al.; "Strategies for the development of PSA-based vaccines for the treatment of advanced prostate cancer," *Expert Rev Vaccines*, 2(4):483-493 (2003).
Le et al.; "Next-Generation Cancer Vaccine Approaches: Integrating Lessons Learned From Current Successes with Promising Biotechnologic Advances," Journal of the National Comprehensive Cancer Network : *JNCCN*. 11(7):766-772 (2013).
Shahabi et al.; "Development of a *Listeria monocytogenes*based vaccine against prostate cancer," *Cancer Immunol Immunother.*, 57(9):1301-1313 (2008).
Weiskirch et al.; "*Listeria monocytogenes*: a potent vaccine vector for neoplastic and infectious disease," *Immunol Rev.*,158:159-169 (1997).

* cited by examiner

| Lane | strain | construct | relative expression |
|---|---|---|---|
| 1 | Lm11 | neg control | - |
| 2 | BH2868 | ActAN100-hPAP$_{33\text{-}386}$ | 1x |
| 3 | PL1631 | ActAN100*-EGFRvIIIx1-PAP$_{33\text{-}386}$ | 2.4x |
| 4 | PL1629 | ActAN100*-EGFRvIIIx2-PAP$_{33\text{-}386}$ | 19.6x |
| 5 | PL1627 | ActAN100*-EGFRvIIIx3-PAP$_{33\text{-}386}$ | 127x |
| 6 | PL1625 | ActAN100*-EGFRvIIIx4-PAP$_{33\text{-}386}$ | 157x |
| 7 | PL1623 | ActAN100*-EGFRvIIIx5-PAP$_{33\text{-}386}$ | 213x |

IMMUNOGENIC FUSION PROTEINS FOR THE TREATMENT OF CANCER

RELATED APPLICATIONS

This application claims the benefit of U.S. Provisional Application No. 62/146,626, filed on Apr. 13, 2015, and U.S. Provisional Application No. 62/146,654, filed on Apr. 13, 2015 and U.S. Provisional Application No. 62/263,174, filed on Dec. 4, 2015. The entire teachings of the above applications are incorporated herein by reference.

GOVERNMENT SUPPORT

This invention was made with government support under contract W81WH-12-1-0439 from the U.S. Army Medical Research Acquisition Activity (USAMRAA). The government has certain rights in the invention.

INCORPORATION BY REFERENCE OF MATERIAL IN ASCII TEXT FILE

This application incorporates by reference the Sequence Listing contained in the following ASCII text file:

a) File name: 53161001003_SEQUENCELISTING.txt; created Jul. 29, 2016, 147 KB in size.

BACKGROUND

Other than skin cancer, prostate cancer is the most common cancer in American men. According to the American Cancer Society, an estimated 220,800 new cases of prostate cancer and 27,540 deaths from prostate cancer will occur in 2015 in the United States alone. About 1 man in 7 will be diagnosed with prostate cancer during his lifetime. Advances in cancer diagnosis and treatment during the last decade have increased treatment options but have not provided curative treatments for patients with metastatic prostate cancer. Additional therapies are needed for these patients.

SUMMARY OF THE INVENTION

Disclosed herein are fusion proteins comprising an epidermal growth factor receptor variant III (EGFRvIII) polypeptide and a synovial sarcoma, X breakpoint 2 (SSX2) polypeptide. In some embodiments, the fusion proteins can comprise one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10. In other embodiments the fusion proteins can comprise an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4.

Also provided are nucleic acid molecules encoding the EGFRvIII-SSX2 fusion proteins. In some embodiments, the nucleic acid molecule can comprise one or more EGFRvIII polynucleotides that are at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the SSX2 polynucleotide as set forth in SEQ ID NO:9. In some aspects, the nucleic acid molecule is operably linked to a promoter.

Disclosed herein are fusion proteins comprising an EGFRvIII polypeptide and a prostatic acid phosphatase (PAP) polypeptide. In some embodiments, the fusion proteins can comprise an amino acid sequence at least i) 90% identical, ii) 95% identical, or iii) 99% identical iii) 99% identical, or iv) 100% identical to EGFRvIIIx5-PAP$_{33-386}$ as set forth in amino acid residues 89 to 606 SEQ ID NO:12. In other embodiments, the fusion protein can comprise one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14.

Also provided are nucleic acid molecules encoding the EGFRvIII-PAP fusion proteins. In some embodiments, the nucleic acid molecule can comprise one or more EGFRvIII polynucleotides that are at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the PAP$_{33-386}$ polynucleotide as set forth in SEQ ID NO:13. In some aspects, the nucleic acid molecule is operably linked to a promoter.

Disclosed herein are fusion proteins comprising an EGFRvIII polypeptide, an NK3 homeobox 1 (NKX3.1) polypeptide, and a prostate-specific membrane antigen (PSMA) polypeptide. In some embodiments, the fusion proteins can comprise one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20. In other embodiments, the fusion proteins can comprise an amino acid sequence at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in amino acid residues 89 to 1177 of SEQ ID NO:23. In other embodiments, the fusion proteins can comprise one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20. In other embodiments, the fusion proteins can comprise an amino acid sequence at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in amino acid residues 89 to 1177 of SEQ ID NO:16.

Also provided are nucleic acid molecules encoding the EGFRvIII-NKX3.1-PSMA fusion proteins. In some embodiments, the nucleic acid molecule can comprise one or more EGFRvIII polynucleotides that are at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1$_{11-234}$ polynucleotide as set forth in SEQ ID NO:24, and a polynucleotide that is at least i) 90% identical, ii) 95% identical, iii) 99% identical, or iv) 100% identical to the PSMA$_{1-20, 44-138, 169-750}$ as set forth in SEQ ID NO:19. In some aspects, the nucleic acid molecule is operably linked to a promoter. In other embodiments, the nucleic acid molecules can comprise one or more EGFRvIII polynucleotides that are at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1 (R41G)$_{11-234}$ polynucleotide as set forth in SEQ ID NO:17, and a polynucleotide that is at least i) 90% identical, ii) 95% identical, iii) 99% identical, or iv) 100% identical to the PSMA$_{1-20, 44-138, 169-750}$ as set forth in SEQ ID NO:19. In some aspects, the nucleic acid molecule is operably linked to a promoter.

Disclosed herein are fusion proteins comprising an NKX3.1 polypeptide and a PAP polypeptide. In some embodiments, the fusion proteins can comprise an amino acid sequence at least i) 90% identical, ii) 95% identical, iii) 99% identical, or iv) 100% identical to NKX3.1-PAP$_{33-386}$ as set forth in amino acid residues 89 to 678 of SEQ ID NO:27. In some embodiments, the fusion proteins can comprise a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14.

Also provided are nucleic acid molecules encoding the NKX3.1-PAP fusion proteins. In some embodiments, the nucleic acid molecules can comprise a polynucleotide that is at least i) 90% identical, ii) 95% identical, iii) 99% identical, or iv) 100% identical to the NKX3.1 polynucleotide as set forth in SEQ ID NO:28 and a polynucleotide that is at least i) 90% identical, ii) 95% identical, iii) 99% identical, or iv) 100% identical to the PAP$_{33-386}$ polynucleotide as set forth in SEQ ID NO:13. In some aspects, the nucleic acid molecule is operably linked to a promoter.

Disclosed herein are host cells comprising one or more of the disclosed nucleic acid molecules. In some embodiments, the host cells can comprise one or more nucleic acid molecules comprising a nucleic acid sequence encoding:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;

c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;

f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; or g) an ActAN100-PAP$_{30-386}$ fusion protein, wherein the fusion protein comprises an ActAN100 polypeptide comprising an amino acid sequence at least i) 90% identical, ii) 95% identical, iii) 99% identical, or iv) 100% identical to amino acid residues 1 to 100 of SEQ ID NO:33 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or h) any combination thereof.

In some aspects, the one or more nucleic acid molecules listed in a)-h) are operably linked to a promoter.

Methods of eliciting an immune response in a subject are also provided. In some embodiments, the methods can comprise administering to the subject a composition comprising a host cell, said host cell comprising one or more nucleic acid molecules, said nucleic acid molecules comprising a nucleic acid sequence encoding:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv)

100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;
b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;
c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;
d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;
e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;
f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10;
g) an ActAN100*-PAP$_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or
h) any combination thereof.

In some aspects, the one or more nucleic acid molecules listed in a)-h) are operably linked to a promoter.

Provided are methods of eliciting an immune response in a subject comprising, administering to the subject a composition comprising a host cell, wherein the host cell expresses one or more fusion proteins comprising:
a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;
b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;
c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;
d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;
e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;
f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10;

g) an ActAN100*-PAP$_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or h) any combination thereof.

Further provided are methods of increasing expression of an antigenic polypeptide. In some embodiments, the methods can comprise expressing in a host cell a nucleic acid molecule, said nucleic acid molecule comprising a nucleic acid sequence encoding:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;

c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;

f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10;

g) an ActAN100*-PAP$_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or h) any combination thereof.

In some aspects, the one or more nucleic acid molecules listed in a)-h) are operably linked to a promoter.

Disclosed herein are methods of treating cancer in a subject in need thereof, said methods comprising administering to the subject a therapeutically effective amount of a composition comprising a host cell, wherein the host cell comprises one or more of the disclosed nucleic acid molecules. In some embodiments, the methods can comprise administering to the subject a therapeutically effective amount of a composition comprising a host cell, wherein the host cell comprises one or more nucleic acid molecules comprising a nucleic acid sequence encoding:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP33-386 as set forth in SEQ ID NO:14;

c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;

f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10;

g) an ActAN100-PAP$_{30-386}$ fusion protein, wherein the fusion protein comprises an ActAN100 polypeptide comprising an amino acid sequence at least i) 90% identical, ii) 95% identical, iii) 99% identical, or iv) 100% identical to ActAN100 as set forth in to amino acid residues 1 to 100 of SEQ ID NO:33 and a PAP polypeptide comprising an amino acid sequence at least i) 90% identical, ii) 95% identical, iii) 99% identical, or iv) 100% identical to PAP30-386 as set forth in amino acid residues 103-459 of SEQ ID NO:33; or h) any combination thereof.

In some aspects, the one or more nucleic acid molecules listed in a)-h) are operably linked to a promoter.

Provided are methods of treating cancer in a subject in need thereof, said method comprising administering to the subject a therapeutically effective amount of a composition comprising a host cell, wherein the host cell expresses one or more fusion proteins comprising:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;

c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;

f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; or g) an ActAN100-PAP$_{30-386}$ fusion protein, wherein the fusion protein comprises an ActAN100 polypeptide comprising an amino acid sequence at least i) 90% identical, ii) 95% identical, iii) 99% identical, or iv) 100% identical to ActAN100 as set forth in to amino acid residues 1 to 100 of SEQ ID NO:33 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or h) any combination thereof.

BRIEF DESCRIPTION OF THE DRAWINGS

The summary, as well as the following detailed description, is further understood when read in conjunction with the appended drawings. For the purpose of illustrating the disclosed compositions and methods, there are shown in the drawings exemplary embodiments of the compositions and methods; however, the compositions and methods are not limited to the specific embodiments disclosed. In the drawings:

(FIG. 3A) SSX2-specific immunity; (FIG. 3B) PAP-specific immunity; (FIG. 3C) NKX3.1-specific immunity; (FIG. 3D) PSMA-specific immunity; and (FIG. 3E) EGFRvIII-specific immunity.

(FIG. 5B) Intracellular western blot results. Lane 1: Lm11 (negative control), lane 2: BH4598 (ActAN100*-SSX2), lane 3: BH4602 (ActAN100*-EGFRvIIIx5-SSX2).

DETAILED DESCRIPTION OF THE INVENTION

Figure 1:
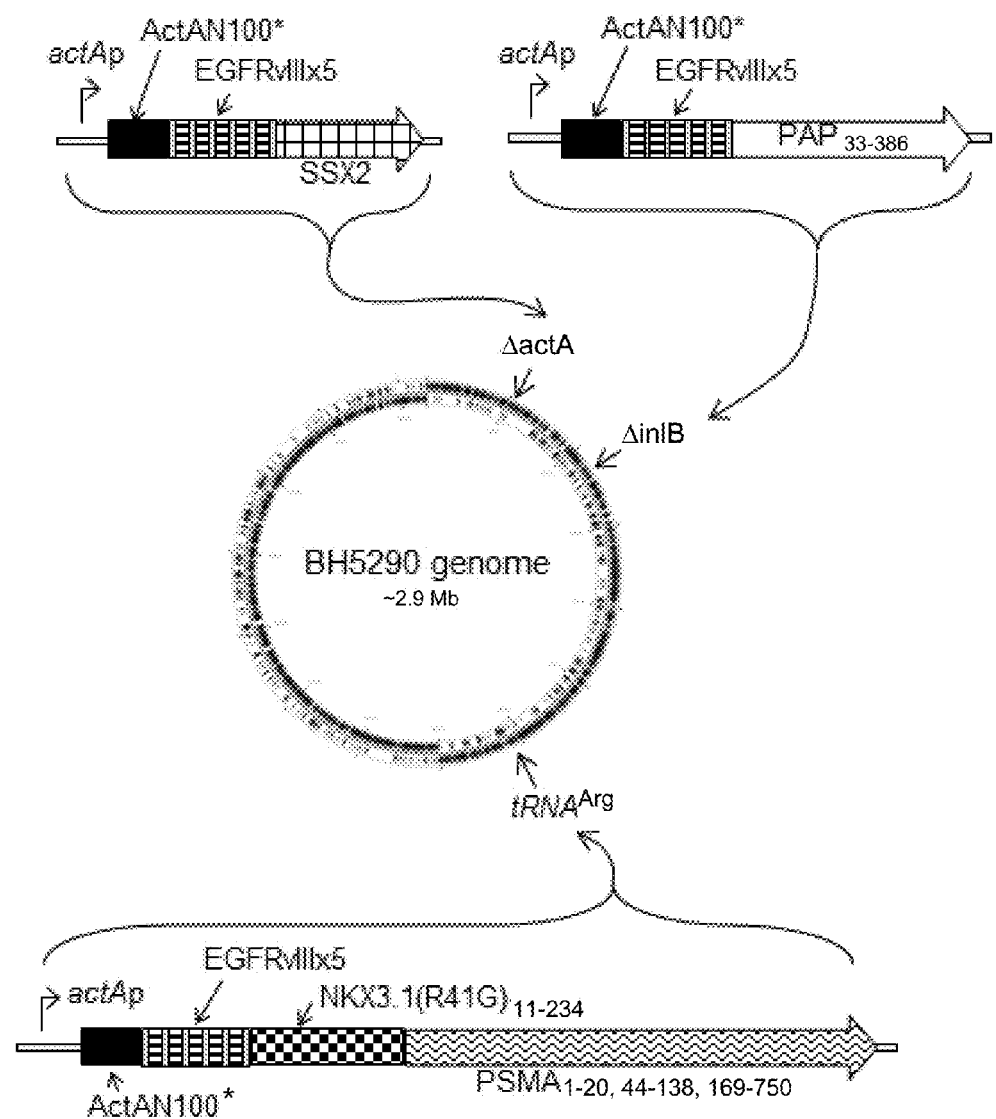
FIG. 1 illustrates an exemplary schematic diagram of the BH5290 strain, with five cancer antigenic polypeptides expressed as three separate immunogenic fusion proteins.
Figure 2:
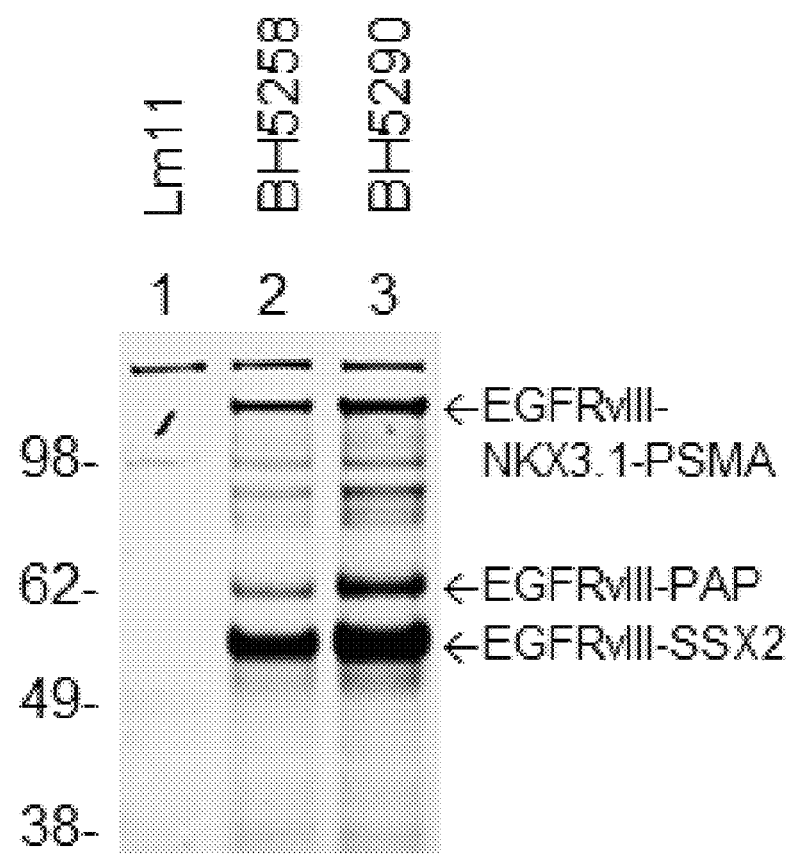
FIG. 2 illustrates the expression of immunogenic fusions comprising the NKX3.1(R41G) variation.
Figure 3A:
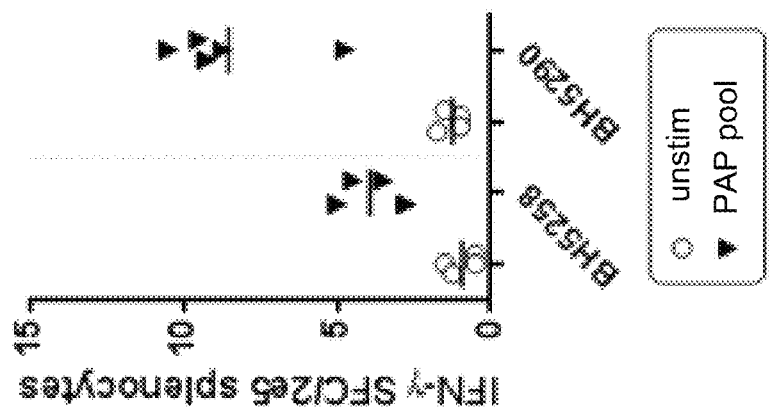
FIG. 3A-FIG. 3E illustrate immunogenicity of exemplary immunogenic fusion proteins comprising the NKX3.1 (R41G) variation.
Figure 3B:
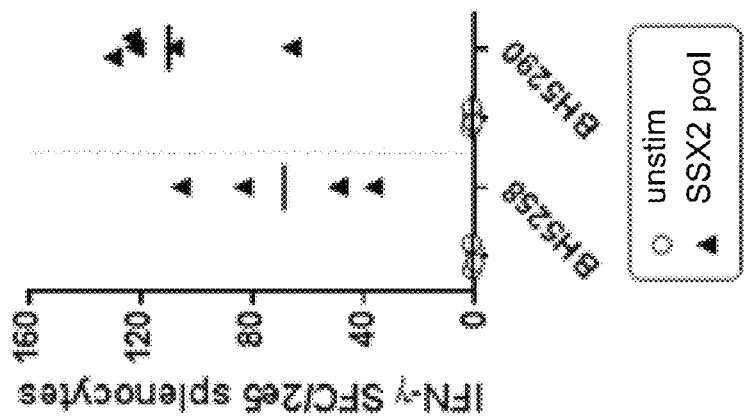
Figure 3C:
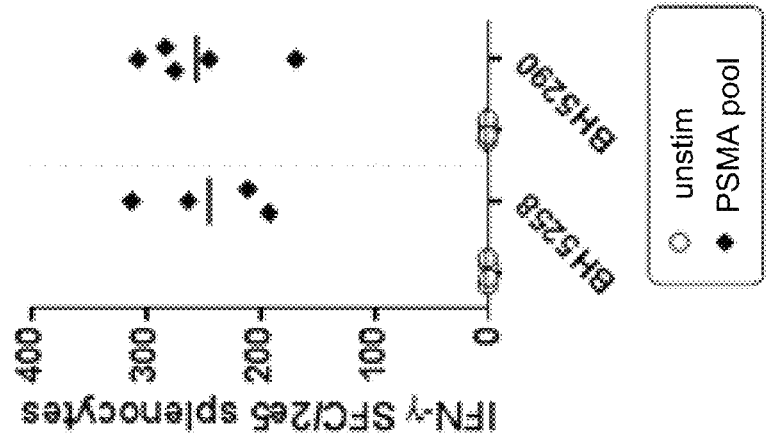
Figure 3D:
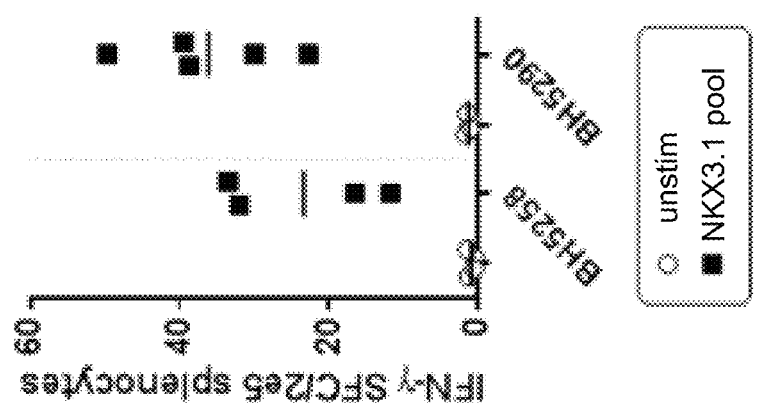
Figure 3E:
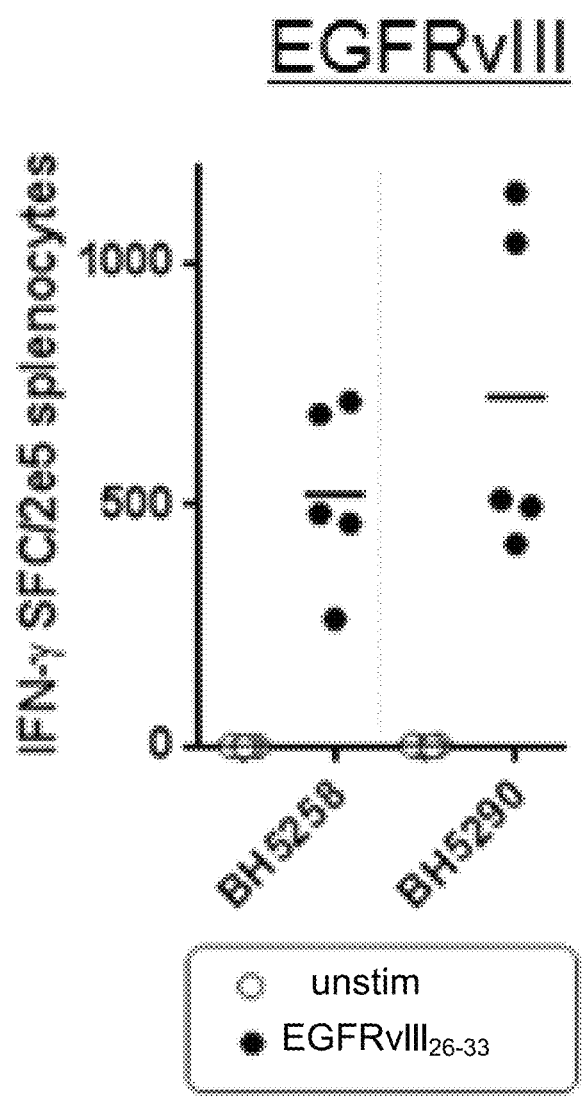

A description of example embodiments of the invention follows.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Unless specifically stated otherwise, any description as to a possible mechanism or mode of action or reason for improvement is meant to be illustrative only, and the disclosed compositions and methods are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

As used herein, the singular forms "a," "an," and "the" include the plural.

The following abbreviations are used throughout the disclosure: EGFRvIII (Epidermal Growth Factor Receptor variant III neoantigen junction region); EGFRvIIIx5 (5 copies of EGFRvIII); SSX2 (synovial sarcoma, X breakpoint 2) (accession no. Q16385); NKX3.1 (NK3 homeobox 1 polypeptide) (accession no. Q99801); PSMA (prostate-specific membrane antigen) (accession no. Q04609); PAP (prostatic acid phosphatase) (accession no. P15309); Lm (Listeria monocytogenes); LADD (double-deleted Listeria monocytogenes).

The delta symbol (Δ or ".DELTA.") refers to a deletion. For example, "ΔactA" (or ".DELTA.actA") means that all, or part, of the actA gene is deleted.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have malignancy expressing one or more, and preferably each of, EGFRvIII, SSX2, NKX3.1, PMSA, and PAP. In certain embodiments, the subject is suffering from prostate cancer, and preferably metastatic prostate cancer.

The terms "percent identical," "sequence identity," and "percent identity" as used herein refers to the percent of amino acids that are the same (i.e. identical) between two or more polypeptides. Sequence identity between two or more polypeptides can be determined by aligning the amino acid sequences of the polypeptides and scoring the number of positions in the aligned polypeptides that contain the same amino acid residue and comparing that to the number of positions in the aligned polypeptides that differ. Polypeptides can differ at a position, for example, by containing a different amino acid (i.e. substitution or mutation) or by lacking an amino acid (i.e. amino acid insertion or amino acid deletion in one or both of the polypeptides). Sequence identity can be calculated by dividing the number of positions that contain the same amino acid residue by the total number of amino acid residues in the polypeptide. Percent identity, for example, can be calculated by dividing the number of positions that contain the same amino acid residue by the total number of amino acid residues in the polypeptide and multiplying by 100.

"Immunogenic fragment thereof" includes portions of fusion proteins that are able to elicit an immunogenic response in a subject. In some aspects, the immunogenic fragment comprises, consists of, or consists essentially of the fusion protein. In other aspects, the immunogenic fragment comprises, consists of, or consists essentially of signal sequence(s)-fusion protein.

As used herein, "fusion protein" refers to a protein made from the joining of two or more polypeptides. Fusion proteins can be generated by chemically conjugating the polypeptides. Preferably, fusion proteins are generated by genetic fusion, in which nucleic acid molecules encoding the individual polypeptides are joined in-frame, such that transcription and translation of the nucleic acid molecules generates a single protein comprising the individual polypeptides. The disclosed fusion proteins may have one or more linker residues between the polypeptides.

As used herein, "signal sequence" refers to polypeptide sequences, and nucleotide sequences encoding the same, that function to drive secretion of the fusion protein. The signal sequence is operably linked to the polypeptide(s) comprising the fusion protein and is translational reading frame with the polypeptide(s) comprising the fusion protein. "Signal sequences" can also be referred to as "secretory signal sequences."

As used herein, "operably linked" refers to the juxtaposition of control sequences, such as a promoter ribosome binding site in a manner that the normal function of the components is maintained. "Control sequences" typically refer to DNA sequences necessary for the expression of an operably linked coding sequence in the host organism. The control sequences can include a promoter, a ribosome binding site and, optionally, a Shine/Dalgarno sequence. Thus, a coding sequence "operably linked" to an encoded signal sequence refers to a configuration wherein the coding sequence is joined to the signal sequence in such a manner that the signal peptide is processed by the host cell and the processed protein is secreted. A signal sequence operably linked to a promoter is joined to the promoter in such a manner that the transcription and translation of the secretion signal sequence is controlled by the promoter, ribosome binding site, and Shine/Dalgarno sequence if required.

As used herein "i) 90% identical, ii) 95% identical, iii) 99% identical, or iv) 100% identical" encompasses at least 90% identical, 91% identical, 92% identical, 93% identical, 94% identical, 95% identical, 96% identical, 97% identical, 98% identical, 99% identical, or 100% identical to the reference item (e.g., a biological sequence).

For EGFRvIII polypeptides and immunogenic fusion proteins containing the same, any sequence variability described herein must occur outside of amino acid residues 7 to 14 of SEQ ID NO:6 (EEKKGNYV). In other words, sequence variability can occur in amino acid residues 1 to 6 of SEQ ID NO:6 (PASRAL) or immunogenic fusion proteins containing the same and/or amino acid residues 15 to 21 of SEQ ID NO:6 (VTDHGSC) or immunogenic fusion proteins containing the same. For example, an EGFRvIII polypeptide comprising an amino acid sequence at least 90% identical to SEQ ID NO:6, encompasses amino acid sequences that are 90% identical, 91% identical, 92% identical, 93% identical, 94% identical, 95% identical, 96% identical, 97% identical, 98% identical, 99% identical, or 100% identical to SEQ ID NO:6, wherein the variability occurs in amino acid residues 1 to 6 or 15 to 21 of SEQ ID NO:6. Accordingly, each EGFRvIII polypeptide and immunogenic fusion protein containing the same will contain amino acid residues 7 to 14 of SEQ ID NO:6 (EEKKGNYV).

EGFRvIII polypeptides can be adjusted in length to include shorter portions of SEQ ID NO:6. For example, in some embodiments, the EGFRvIII polypeptide can comprise, consist of, or consist essentially of an amino acid sequence at least 90% identical to amino acid residues 6 to 18 of SEQ ID NO:6. In some embodiments, the one or more copies of EGFRvIII polypeptide can comprise, consist of, or consist essentially of an amino acid sequence at least 90% identical to amino acid residues 6 to 14 of SEQ ID NO:6. As described above, the variability in these shorter polypeptides will occur in amino acid residues 1 to 6 or 15 to 21 of SEQ ID NO:6. Accordingly, for an amino acid sequence at least 90% identical to amino acid residues 6 to 18 of SEQ ID NO:6, the variability can occur at amino acid residue 6 or 15 to 18 of SEQ ID NO:6. For an amino acid sequence at least 90% identical to amino acid residues 6 to 14 of SEQ ID NO:6, the variability can occur at amino acid residue 6.

Throughout the disclosure, immunogenic fusion proteins comprising, and nucleic acids encoding immunogenic fusion proteins that comprise, one or more EGFRvIII polypeptide are described. The EGFRvIII polypeptide can be encoded by any one of the EGFRvIII nucleotide sequences provided in Table 1. Accordingly, throughout the disclosure, when the EGFRvIII polynucleotide is referred as being "at least i) 90% identical, ii) 95% identical, iii) 99% identical, or iv) 100% identical to SEQ ID NO:5" (the consensus sequence in Table 1), it is intended to include: at least i) 90% identical, ii) 95% identical, iii) 99% identical, or iv) 100% identical to SEQ ID NO:42; at least i) 90% identical, ii) 95% identical, iii) 99% identical, or iv) 100% identical to SEQ ID NO:43; at least i) 90% identical, ii) 95% identical, iii) 99% identical, or iv) 100% identical to SEQ ID NO:44; at least i) 90% identical, ii) 95% identical, iii) 99% identical, or iv) 100% identical to SEQ ID NO:45; and/or at least i) 90% identical, ii) 95% identical, iii) 99% identical, or iv) 100% identical to SEQ ID NO:46. Similarly, the nucleotide sequences encoding the various immunogenic fusion proteins can comprise any one of SEQ ID NOs:42-46. Therefore, each EGFRvIII-containing immunogenic fusion protein provided herein can be encoded by a nucleic acid molecule, wherein the nucleic acid molecule comprises one or more polynucleotide that is at least i) 90% identical, ii) 95% identical, iii) 99% identical, or iv) 100% identical to SEQ ID NO:42, at least i) 90% identical, ii) 95% identical, iii) 99% identical, or iv) 100% identical to SEQ ID NO:43, at least i) 90% identical, ii) 95% identical, iii) 99% identical, or iv) 100% identical to SEQ ID NO:44, at least i) 90% identical, ii) 95% identical, iii) 99% identical, or iv) 100% identical to SEQ ID NO:45, and/or at least i) 90% identical, ii) 95% identical, iii) 99% identical, or iv) 100% identical to SEQ ID NO:46. In some aspects, the nucleic acid molecule is operably linked to a promoter.

TABLE 1

EGFRvIII Nucleotide Sequence(s)

| | | |
|---|---|---|
| repeat 1 (SEQ ID NO: 42) | 1 | 63 |
| | (1) CCAGCTAGTCGTGCATTAGAGGAGAAAAAGGGGAATTACGTGGTGACGGATCATGGATCGTGT | |
| repeat 2 (SEQ ID NO: 43) | (1) CCTGCATCACGAGCACTTGAAGAGAAAAAAGGAAACTATGTTGTGACCGATCATGGTAGCTGC | |
| repeat 3 (SEQ ID NO: 44) | (1) CCAGCATCTAGAGCTTTAGAGGAAAAGAAGGGTAACTATGTCGTAACAGATCATGGAAGTTGT | |
| repeat 4 (SEQ ID NO: 45) | (1) CCAGCTTCTCGCGCATTAGAAGAAAAGAAAGGCAATTATGTTGTAACAGACCATGGTAGTTGT | |
| repeat 5 (SEQ ID NO: 46) | (1) CCGGCTTCTCGTGCGCTAGAAGAGAAGAAAGGAAATTACGTAGTTACAGACCACGGCTCTTGC | |
| Consensus (SEQ ID NO: 5) | (1) CCdGCwwswmGhGCdyTwGArGArAArAArGGnAAyTAyGTnGTdACvGAyCAyGGhwsbTGy | |

Immunogenic Fusion Proteins

Disclosed herein are immunogenic fusion proteins and nucleic acid molecules encoding said fusion proteins. Exemplary immunogenic fusion proteins are provided in Tables 2 and 3. Table 1 provides exemplary combinations of antigens expressed by the fusion proteins. Table 3 provides exemplary expression cassettes, bacterial strains, and amino acid ranges of the various fusions proteins.

TABLE 2

Exemplary Antigen Combinations

| | | |
|---|---|---|
| EGFRvIII | SSX2$_{1-234}$ | |
| EGFRvIII | SSX2$_{2-234}$ | |
| EGFRvIII | PAP$_{33-386}$ | |
| EGFRvIII | NKX3.1$_{11-234}$ | PSMA$_{1-20, 44-138, 169-750}$ |
| EGFRvIII | NKX3.1(R41G)$_{11-234}$ | PSMA$_{1-20, 44-138, 169-750}$ |
| NKX3.1 | PAP$_{33-386}$ | |

The immunogenic fusion proteins can comprise any of the above combinations of antigens (i.e. EGFRvIII, SSX2, NKX3.1, PAP, PSMA). The antigens described herein may include a sequence that is a MHC class I epitope or a MHC class II epitope from the full-length protein sequence.

EGFR is a receptor tyrosine kinase critical for cell growth and survival. The EGFR gene is frequently overexpressed or mutated in human cancers, including head and neck, colon, pancreas, breast, ovary, kidney, and malignant gliomas. EGFR receptor variant III (EGFRvIII) results from a 267 amino acid deletion of exons 2 to 7 and the fusion of exon 1 with exon 8, yielding a tumor-specific peptide with a novel glycine at the junction. EGFRvIII exhibits constitutive, ligand-independent signaling. In one embodiment, a described EGFRvIII polynucleotide comprises a sequence encoding at least one MHC class I epitope or at least one MHC class II epitope. Similarly, the EGFRvIII polypeptides described herein include at least one MHC class I epitope or at least one MHC class II epitope. The sequence of the N-terminal 10 residues of the EGFRvIII mutation is LEEKKGNYVV, as set forth in SEQ ID NO:61.

SSX2 belongs to the family of highly homologous synovial sarcoma X (SSX) breakpoint proteins. These proteins may function as transcriptional repressors. The SSX2 gene, and also the SSX1 and SSX4 family members, have been involved in t(X; 18)(p11.2; q11.2) translocations that are characteristically found in all synovial sarcomas. This translocation results in the fusion of the synovial sarcoma translocation gene on chromosome 18 to one of the SSX genes on chromosome X. The encoded hybrid proteins are likely responsible for transforming activity. Alternative splicing of this gene results in multiple transcript variants. In one embodiment, a described SSX2 polynucleotide comprises a sequence encoding at least one MHC class I epitope or at least one MHC class II epitope. Similarly, the SSX2 polypeptides described herein include at least one MHC class I epitope or at least one MHC class II epitope. A SSX2 sequence (Swiss Prot entry Q16385) is set forth as SEQ ID NO:62:

```
            10         20         30         40
     MNGDDAFARR PTVGAQIPEK IQKAFDDIAK YFSKEEWEKM 50         60         70         80
     KASEKIFYVY MKRKYEAMTK LGFKATLPPF MCNKRAEDFQ 90        100        110        120
     GNDLDNDPNR GNQVERPQMT FGRLQGISPK IMPKKPAEEG 130        140        150        160
     NDSEEVPEAS GPQNDGKELC PPGKPTTSEK IHERSGPKRG 170        180
     EHAWTHRLRE RKQLVIYEEI SDPEEDDE
```

NKX3.1 (NK3 homeobox 1 polypeptide) (accession no. Q99801) is a transcription factor, which binds preferentially the consensus sequence 5'-TAAGT[AG]-3' and can behave as a transcriptional repressor. NKX3.1 plays an important role in normal prostate development, regulating proliferation of glandular epithelium and in the formation of ducts in prostate. In one embodiment, a described NKX3.1 polynucleotide comprises a sequence encoding at least one MHC class I epitope or at least one MHC class II epitope. Similarly, the NKX3.1 polypeptides described herein include at least one MHC class I epitope or at least one MHC class II epitope. The human canonical sequence of NKX3.1 (Swiss Prot entry Q99801) is set forth as SEQ ID NO:29:

```
            10         20         30         40
     MLRVPEPRPG EAKAEGAAPP TPSKPLTSFL IQDILRDGAQ 50         60         70         80
     RQGGRTSSQR QRDPEPEPEP EPEGGRSRAG AQNDQLSTGP 90        100        110        120
     RAAPEEAETL AETEPERHLG SYLLDSENTS GALPRLPQTP
```

```
                130         140         150         160
           KQPQKRSRAA  FSHTQVIELE  RKFSHQKYLS  APERAHLAKN 170         180         190         200
           LKLTETQVKI  WFQNRRYKTK  RKQLSSELGD  LEKHSSLPAL 210         220         230
           KEEAFSRASL  VSVYNSYPYY  PYLYCVGSWS  PAFW
```

PSMA (prostate-specific membrane antigen) (accession no. Q04609) has both folate hydrolase and N-acetylated-alpha-linked-acidic dipeptidase (NAALADase) activity. PSMA as a preference for tri-alpha-glutamate peptides. In the intestine, PSMA is required for the uptake of folate; in the brain, PSMA modulates excitatory neurotransmission through the hydrolysis of the neuropeptide, N-aceylaspartylglutamate (NAAG), thereby releasing glutamate. PSMA is also involved in prostate tumor progression. In one embodiment, a described PSMA polynucleotide comprises a sequence encoding at least one MHC class I epitope or at least one MHC class II epitope. Similarly, the PSMA polypeptides described herein include at least one MHC class I epitope or at least one MHC class II epitope. The human canonical sequence of PSMA (Swiss Prot entry Q04609) is set forth as SEQ ID NO:63:

```
                 10          20          30          40
            MWNLLHETDS  AVATARRPRW  LCAGALVLAG  GFFLLGFLFG 50          60          70          80
            WFIKSSNEAT  NITPKHNMKA  FLDELKAENI  KKFLYNFTQI 90         100         110         120
            PHLAGTEQNF  QLAKQIQSQW  KEFGLDSVEL  AHYDVLLSYP 130         140         150         160
            NKTHPNYISI  INEDGNEIFN  TSLFEPPPPG  YENVSDIVPP 170         180         190         200
            FSAFSPQGMP  EGDLVYVNYA  RTEDFFKLER  DMKINCSGKI 210         220         230         240
            VIARYGKVFR  GNKVKNAQLA  GAKGVILYSD  PADYFAPGVK 250         260         270         280
            SYPDGWNLPG  GGVQRGNILN  LNGAGDPLTP  GYPANEYAYR 290         300         310         320
            RGIAEAVGLP  SIPVHPIGYY  DAQKLLEKMG  GSAPPDSSWR 330         340         350         360
            GSLKVPYNVG  PGFTGNFSTQ  KVKMHIHSTN  EVTRIYNVIG 370         380         390         400
            TLRGAVEPDR  YVILGGHRDS  WVFGGIDPQS  GAAVVHEIVR 410         420         430         440
            SFGTLKKEGW  RPRRTILFAS  WDAEEFGLLG  STEWAEENSR 450         460         470         480
            LLQERGVAYI  NADSSIEGNY  TLRVDCTPLM  YSLVHNLTKE 490         500         510         520
            LKSPDEGFEG  KSLYESWTKK  SPSPEFSGMP  RISKLGSGND 530         540         550         560
            FEVFFQRLGI  ASGRARYTKN  WETNKFSGYP  LYHSVYETYE 570         580         590         600
            LVEKFYDPMF  KYHLTVAQVR  GGMVFELANS  IVLPFDCRDY 610         620         630         640
            AVVLRKYADK  IYSISMKHPQ  EMKTYSVSFD  SLFSAVKNFT 650         660         670         680
```
```
            EIASKFSERL  QDFDKSNPIV  LRMMNDQLMF  LERAFIDPLG 690         700         710         720
            LPDRPFYRHV  IYAPSSHNKY  AGESFPGIYD  ALFDIESKVD 730         740         750
            PSKAWGEVKR  QIYVAAFTVQ  AAAETLSEVA
```

PAP (prostatic acid phosphatase) (accession no. P15309) is a non-specific tyrosine phosphatase that dephosphorylates a diverse number of substrates under acidic conditions (pH 4-6) including alkyl, aryl, and acyl orthophosphate monoesters and phosphorylated proteins. PAP has lipid phosphatase activity and inactivates lysophosphatidic acid in seminal plasma. In one embodiment, a described PAP polynucleotide comprises a sequence encoding at least one MHC class I epitope or at least one MHC class II epitope. Similarly, the PAP polypeptides described herein include at least one MHC class I epitope or at least one MHC class II epitope. The human canonical sequence of PAP (Swiss Prot entry P15309) is set forth as SEQ ID NO:64:

```
                 10          20          30          40
            MRAAPLLLAR  AASLSLGFLF  LLFFWLDRSV  LAKELKFVTL 50          60          70          80
            VFRHGDRSPI  DTFPTDPIKE  SSWPQGFGQL  TQLGMEQHYE 90         100         110         120
            LGEYIRKRYR  KFLNESYKHE  QVYIRSTDVD  RTLMSAMTNL 130         140         150         160
            AALFPPEGVS  IWNPILLWQP  IPVHTVPLSE  DQLLYLPFRN 170         180         190         200
            CPRFQELESE  TLKSEEFQKR  LHPYKDFIAT  LGKLSGLHGQ 210         220         230         240
            DLFGIWSKVY  DPLYCESVHN  FTLPSWATED  TMTKLRELSE 250         260         270         280
            LSLLSLYGIH  KQKEKSRLQG  GVLVNEILNH  MKRATQIPSY 290         300         310         320
            KKLIMYSAHD  TTVSGLQMAL  DVYNGLLPPY  ASCHLTELYF 330         340         350         360
            EKGEYFVEMY  YRNETQHEPY  PLMLPGCSPS  CPLERFAELV 370         380
            GPVIPQDWST  ECMTTNSHQG  TEDSTD
```

The predictive algorithm "BIMAS" ranks potential HLA binding epitopes according to the predictive half-time dis-association of peptide/HLA complexes. The "SYFPEITHI" algorithm ranks peptides according to a score that accounts for the presence of primary and secondary HLA-binding anchor residues. Both computerized algorithms score candidate epitopes based on amino acid sequences within a given protein that have similar binding motifs to previously published HLA binding epitopes. Other algorithms can also be used to identify candidates for further biological testing.

TABLE 3

| Expression cassette | Strain(s) | total # of amino acids in fusion protein | antigenic region of fusion protein | Amino acids |
|---|---|---|---|---|
| ActAN100*-EGFRvIII-SSX2 | BH5290, BH5258 | 475 | EGFRvIIIx5-SSX2 | 89-475 |
| ActAN100*-EGFRvIII-PAP$_{33-386}$ | BH5290, BH5258 | 606 | EGFRvIIIx5-PAP$_{33-386}$ | 89-606 |
| ActAN100*-EGFRvIII-NKX3.1(R41G)$_{11-234}$-PSMA$_{1-20, 44-138, 169-750}$ | BH5290 | 1177 | EGFRvIII-NKX3.1(R41G)$_{11-234}$-PSMA$_{1-20, 44-138, 169-750}$ | 89-1177 |
| ActAN100*-EGFRvIII-NKX3.1$_{11-234}$-PSMA$_{1-20, 44-138, 169-750}$ | BH5258 | 1177 | EGFRvIII-NKX3.1$_{11-234}$-PSMA$_{1-20, 44-138, 169-750}$ | 89-1177 |
| ActAN100*-SSX2$_{2-234}$ | BH4598 | 310 | SSX2$_{2-234}$ | 89-310 |
| ActAN100*-EGFRvIII-SSX2$_{2-234}$ | BH4602 | 474 | EGFRvIII-SSX2$_{2-234}$ | 89-474 |
| ActAN100*-NKX3.1-PAP$_{33-386}$ | BH4598, BH4602 | 678 | NKX3.1-PAP$_{33-386}$ | 89-678 |
| ActAN100-PAP$_{30-386}$ | BH2868 | 491 | PAP$_{30-386}$ | 103-459 |
| ActAN100*-EGFRvIIIx1-PAP$_{33-386}$ | PL1631 | 476 | EGFRvIIIx1-PAP$_{33-386}$ | 89-476 |
| ActAN100*-EGFRvIIIx2-PAP$_{33-386}$ | PL1629 | 509 | EGFRvIIIx2-PAP$_{33-386}$ | 89-509 |
| ActAN100*-EGFRvIIIx3-PAP$_{33-386}$ | PL1627 | 541 | EGFRvIIIx3-PAP$_{33-386}$ | 89-541 |
| ActAN100*-EGFRvIIIx4-PAP$_{33-386}$ | PL1625 | 573 | EGFRvIIIx4-PAP$_{33-386}$ | 89-573 |
| ActAN100*-EGFRvIIIx5-PAP$_{33-386}$ | PL1623 | 606 | EGFRvIIIx5-PAP$_{33-386}$ | 89-606 |

EGFRvIII-SSX2 Fusion Proteins

Disclosed herein are fusion proteins comprising an epidermal growth factor receptor variant III (EGFRvIII) polypeptide and a synovial sarcoma, X breakpoint 2 (SSX2) polypeptide.

The fusion protein can comprise one or more copies of an EGFRvIII polypeptide. In some embodiments, the fusion protein can comprise one EGFRvIII polypeptide. In other embodiments, the fusion protein can comprise a plurality of EGFRvIII polypeptides. Suitable numbers of copies of the EGFRvIII polypeptide include, but are not limited to, 2, 3, 4, 5, or more copies. In some embodiments, for example, the fusion protein can comprise one EGFRvIII polypeptide (referred to as EGFRvIIIx1). Thus, in some aspects, the fusion protein can comprise an EGFRvIIIx1-SSX2 fusion protein. In some embodiments, for example, the fusion protein can comprise two copies of the EGFRvIII polypeptide (referred to as EGFRvIIIx2). Thus, in some aspects, the fusion protein can comprise an EGFRvIIIx2-SSX2 fusion protein. In some embodiments, for example, the fusion protein can comprise three copies of the EGFRvIII polypeptide (referred to as EGFRvIIIx3). Thus, in some aspects, the fusion protein can comprise an EGFRvIIIx3-SSX2 fusion protein. In some embodiments, for example, the fusion protein can comprise four copies of the EGFRvIII polypeptide (referred to as EGFRvIIIx4). Thus, in some aspects, the fusion protein can comprise an EGFRvIIIx4-SSX2 fusion protein. In some embodiments, for example, the fusion protein can comprise five copies of the EGFRvIII polypeptide (referred to as EGFRvIIIx5). Thus, in some aspects, the fusion protein can comprise an EGFRvIIIx5-SSX2 fusion protein.

Each of the one or more copies of the EGFRvIII polypeptide can comprise an amino acid sequence that is at least 90% identical, 91% identical, 92% identical, 93% identical, 94% identical, 95% identical, 96% identical, 97% identical, 98% identical, 99% identical, or 100% identical to SEQ ID NO:6. In some embodiments, for example, the EGFRvIII polypeptide can comprise an amino acid sequence at least i) 90% identical, ii) 95% identical, iii) 99% identical, or iv) 100% identical to SEQ ID NO:6. In other embodiments, the EGFRvIII polypeptide can comprise 2, 3, 4, 5, or more copies of an EGFRvIII polypeptide, each copy having an amino acid sequence at least i) 90% identical, ii) 95% identical, iii) 99% identical, or iv) 100% identical to SEQ ID NO:6. In some embodiments, the EGFRvIII polypeptide is SEQ ID NO:6. An exemplary amino acid sequence of EGFRvIIIx5 is set forth in SEQ ID NO:8.

In some aspects, each of the one or more copies of the EGFRvIII polypeptide can consist of an amino acid sequence that is at least 90% identical, 91% identical, 92% identical, 93% identical, 94% identical, 95% identical, 96% identical, 97% identical, 98% identical, 99% identical, or 100% identical to SEQ ID NO:6. In some aspects, each of the one or more copies of the EGFRvIII polypeptide can consist essentially of an amino acid sequence that is at least 90% identical, 91% identical, 92% identical, 93% identical, 94% identical, 95% identical, 96% identical, 97% identical, 98% identical, 99% identical, or 100% identical to SEQ ID NO:6.

The one or more copies of EGFRvIII polypeptide can comprise, consist of, or consist essentially of an amino acid sequence at least 90% identical to amino acid residues 6 to 18 of SEQ ID NO:6. In some embodiments, the one or more copies of EGFRvIII polypeptide can comprise, consist of, or consist essentially of an amino acid sequence at least 90% identical to amino acid residues 6 to 14 of SEQ ID NO:6.

The EGFRvIII polypeptides can be flanked by one or more cleaver sequences at the N-terminus, C-terminus, or both the N-and C-terminus of the EGFRvIII polypeptide. Cleaver sequences are configured to be processed by proteases present in the subject. Where the EGFRvIII polypeptide comprises 2 or more copies of the EGFRvIII polypeptide, cleaver sequences can be present between the individual copies of the EGFRvIII polypeptides. For example, and without intending to be limiting, SEQ ID NO:8 contains 5 copies of the EGFRvIII polypeptide (each copy of the EGFRvIII polypeptide set forth in SEQ ID NO:6) and cleaver sequences (ASKVL/ADGSVKTS (SEQ ID NO:54), ASKVA/GDGSIK (SEQ ID NO:55), LSKVL/ADGSVK (SEQ ID NO:56), ASKVA/GDGSIK (SEQ ID NO:57), and LSKVL/ADGSVK (SEQ ID NO:58); wherein "/" represents an EGFRvIII polypeptide). These cleaver sequences are exemplary in nature only. Suitable cleaver sequences are described in U.S. patent application Ser. No. 13/988,076 (U.S. Patent Publ. No. 2014/037662); Toes, et al., J. Exp. Med. (2001) 194: 1-12; Lauer et al., Infect. Immun. (2008) 76: 3742-53; and Sinnathamby et al., J. Immunother. (2009) 32: 856-69, each of which are incorporated by reference in its entirety.

The EGFRvIII polypeptide can be fused to the N-terminus or C-terminus of the SSX2 polypeptide. Preferably, the EGFRvIII polypeptide can be fused to the N-terminus of the SSX2 polypeptide.

Suitable SSX2 polypeptides include amino acids 1-234 of SSX2 ("SSX2" or "SSX2$_{1-234}$") and amino acids 2-234 of SSX2 ("SSX2$_{2-234}$"). In some embodiments, the SSX2 polypeptide can comprise, consist of, or consist essentially of an amino acid sequence at least i) 90% identical, ii) 95% identical, iii) 99% identical, or iv) 100% identical to SSX2 as set forth in SEQ ID NO:10. In some aspects, the SSX2 polypeptide is SEQ ID NO:10. In some embodiments, the SSX2 polypeptide can comprise, consist of, or consist essentially of an amino acid sequence at least i) 90% identical, ii) 95% identical, iii) 99% identical, or iv) 100% identical to SSX2$_{2-234}$ as set forth in amino acid residues 2-234 of SEQ ID NO:10.

The fusion protein can comprise one or more EGFRvIII polypeptides, wherein the EGFRvIII polypeptides comprise an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10. In some embodiments, the fusion protein can comprise one or more EGFRvIII polypeptides, wherein the EGFRvIII polypeptides comprise an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2$_{2-234}$ as set forth in amino acid residues 2-234 of SEQ ID NO:10.

The fusion protein can comprise an amino acid sequence that is at least i) 90% identical, ii) 95% identical, iii) 99% identical, or iv) 100% identical to EGFRvIIIx5-SSX2 as set forth as amino acid residues 89 to 475 of SEQ ID NO:4.

The disclosed fusion proteins can further comprise a signal sequence, wherein the signal sequence is in translational reading frame with the EGFRvIII polypeptide and the SSX2 polypeptide. Suitable signal sequences include, for example, ActAN100 (as set forth in SEQ ID NO:60), ActAN100* (as set forth in SEQ ID NO:2), LLO441 (as set forth in SEQ ID NO:49), LLO441ΔPEST (as set forth in SEQ ID NO:51), and LLO441 Δ26 (as set forth in SEQ ID NO:53). In some embodiments, the signal sequence can comprise an amino acid sequence at least i) 90% identical, ii) 95% identical, iii) 99% identical, or iv) 100% identical to ActAN100 as set forth in SEQ ID NO:60. In some embodiments, the signal sequence can comprise an amino acid sequence that is at least i) 90% identical, ii) 95% identical, iii) 99% identical, or iv) 100% identical to ActAN100* as set forth as SEQ ID NO:2. Accordingly, in some embodiments, the fusion protein can comprise an amino acid sequence at least i) 90% identical, ii) 95% identical, iii) 99% identical, or iv) 100% identical to ActAN100*-EGFRvIIIx5-SSX2 as set forth in SEQ ID NO:4.

The disclosed fusion proteins can be expressed in a number of suitable host cells as disclosed elsewhere herein. In some embodiments, for example, the fusion protein can be expressed in a bacterium, such as *Listeria monocytogenes* or a genetically modified form thereof.

Also disclosed are nucleic acid molecules encoding an EGFRvIII-SSX2 fusion protein. The disclosed nucleic acid molecules can encode any of the EGFRvIII-SSX2 fusion proteins disclosed herein.

The nucleic acid molecules can encode an EGFRvIII-SSX2 fusion protein with one or more EGFRvIII polypeptides. In some embodiments, the nucleic acid molecule can encode an EGFRvIII-SSX2 fusion protein with one EGFRvIII polypeptide. In other embodiments, the nucleic acid molecule can encode an EGFRvIII-SSX2 fusion protein with a plurality of EGFRvIII polypeptides. Suitable numbers of EGFRvIII polypeptides encoded by the disclosed nucleic acid molecules include, but are not limited to, 2, 3, 4, 5, or more copies. In some embodiments, the nucleic acid molecules can encode an EGFRvIII-SSX2 fusion protein with 5 copies of the EGFRvIII polypeptide (EGFRvIIIx5). Each EGFRvIII polypeptide can be encoded by an EGFRvIII polynucleotide having a nucleotide sequence at least i) 90% identical, ii) 95% identical, iii) 99% identical, or iv) 100% identical to SEQ ID NO:5. An exemplary nucleic acid sequence of an EGFRvIIIx5 polynucleotide is set forth in SEQ ID NO:7. Accordingly, the disclosed nucleic acid molecules can encode an EGFRvIII-SSX2 fusion protein comprising one or more EGFRvIII polypeptides, wherein the EGFRvIII polypeptides are encoded by a polynucleotide that is at least i) 90% identical, ii) 95% identical, iii) 99% identical, or iv) 100% identical to the EGFRvIII polynucleotide as set forth in SEQ ID NO:5. In some aspects, the nucleic acid molecule is operably linked to a promoter. For example, the nucleic acid molecules can encode an EGFRvIII-SSX2 fusion protein, wherein the EGFRvIII polypeptide is encoded by a polynucleotide that is at least i) 90% identical, ii) 95% identical, iii) 99% identical, or iv) 100% identical to the EGFRvIIIx5 polynucleotide as set forth in SEQ ID NO:7. In some aspects, the nucleic acid molecule is operably linked to a promoter.

The disclosed nucleic acid molecules can encode an EGFRvIII-SSX2 fusion protein, wherein the SSX2 polypeptide is encoded by a polynucleotide that is at least i) 90% identical, ii) 95% identical, iii) 99% identical, or iv) 100% identical to the SSX2 polynucleotide as set forth in SEQ ID NO:9. In some aspects, the nucleic acid molecule is operably linked to a promoter.

In some embodiments, the nucleic acid molecule can comprise one or more polynucleotides that are at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the SSX2 polynucleotide as set forth in SEQ ID NO:9. In some aspects, the nucleic acid molecule is operably linked to a promoter.

The nucleic acid molecule can encode an EGFRvIIIx5-SSX2 fusion protein. In some embodiments, the nucleic acid molecule can comprise a polynucleotide that is at least i) 90% identical, ii) 95% identical, iii) 99% identical, or iv) 100% identical to the EGFRvIIIx5 polynucleotide as set forth in SEQ ID NO:7 and a polynucleotide that is at least i) 90% identical, ii) 95% identical, iii) 99% identical, or iv) 100% identical to the SSX2 polynucleotide as set forth in SEQ ID NO:9. In some aspects, the nucleic acid molecule is operably linked to a promoter.

The nucleic acid molecule can further comprise a promoter, a signal sequence, or both, wherein the promoter, signal sequence, or both are operably linked with the nucleotide sequence encoding the EGFRvIII polypeptide and the nucleotide sequence encoding the SSX2 polypeptide. Suitable promoters include, for example, actA (as set forth in SEQ ID NO:21) or hly (as set forth in SEQ ID NO:47). The promoter can comprise, for example, a nucleotide sequence that is at least i) 90% identical, ii) 95% identical, iii) 99% identical, or iv) 100% identical to an actA promoter as set forth in SEQ ID NO:21. Suitable signal sequences include, for example, ActAN100 (as set forth in SEQ ID NO:59), ActAN100* (as set forth in SEQ ID NO:1), LLO441 (as set forth in SEQ ID NO:48), LLO441ΔPEST (as set forth in SEQ ID NO:50), and LLO441Δ26 (as set forth in SEQ ID NO:52). The signal sequence can comprise, for example, a nucleotide sequence that is at least i) 90% identical, ii) 95% identical, iii) 99% identical, or iv) 100% identical to ActAN100* as set forth in SEQ ID NO:1. Accordingly, in some embodiments, the nucleic acid molecule encoding the EGFRvIII-SSX2 fusion protein can comprise, consist of, or consist essentially of a polynucleotide that is at least i) 90% identical, ii) 95% identical, iii) 99% identical, or iv) 100% identical to actA-ActAN100*-EGFRvIIIx5-SSX2 as set forth in SEQ ID NO:3.

The nucleic acid molecules can further comprise additional nucleic acid sequences including, but not limited to, restriction endonuclease cleavage sites (cloning linkers). The nucleic acid molecules can be generated using a number of suitable restriction endonucleases, wherein the endonuclease cleavage site(s) may remain in the final nucleic acid molecule.

Additional nucleic acid sequences that can be included in the nucleic acid molecules include "cleaver sequences" (as defined elsewhere herein) which flank the individual EGFRvIII polynucleotides.

The nucleic acid molecule can be part of an expression cassette. The expression cassette can comprise a promoter, an open reading frame comprising the disclosed nucleic acid molecules, and a 3' untranslated region. The expression cassette can be used to direct a host cell's machinery to produce the disclosed fusion proteins.

Vectors comprising the disclosed nucleic acid molecules are also provided. Suitable vectors include, for example, bacterial vectors, viral vectors, naked DNA vectors, and naked RNA vectors.

EGFRvIII-PAP Fusion Proteins

Disclosed herein are fusion proteins comprising an EGFRvIII polypeptide and a prostatic acid phosphatase (PAP) polypeptide.

The fusion protein can comprise one or more copies of an EGFRvIII polypeptide. In some embodiments, the fusion protein can comprise one EGFRvIII polypeptide. In other embodiments, the fusion protein can comprise a plurality of EGFRvIII polypeptides. Suitable numbers of copies of the EGFRvIII polypeptide include, but are not limited to, 2, 3, 4, 5, or more copies. In some embodiments, for example, the fusion protein can comprise one EGFRvIII polypeptide (referred to as EGFRvIIIx1). Thus, in some aspects, the fusion protein can comprise an EGFRvIIIx1-PAP fusion protein. In some embodiments, for example, the fusion protein can comprise two copies of the EGFRvIII polypeptide (referred to as EGFRvIIIx2). Thus, in some aspects, the fusion protein can comprise an EGFRvIIIx2-PAP fusion protein. In some embodiments, for example, the fusion protein can comprise three copies of the EGFRvIII polypeptide (referred to as EGFRvIIIx3). Thus, in some aspects, the fusion protein can comprise an EGFRvIIIx3-PAP fusion protein. In some embodiments, for example, the fusion protein can comprise four copies of the EGFRvIII polypep-tide (referred to as EGFRvIIIx4). Thus, in some aspects, the fusion protein can comprise an EGFRvIIIx4-PAP fusion protein. In some embodiments, for example, the fusion protein can comprise five copies of the EGFRvIII polypeptide (referred to as EGFRvIIIx5). Thus, in some aspects, the fusion protein can comprise an EGFRvIIIx5-PAP fusion protein.

Each of the one or more copies of the EGFRvIII polypeptide can comprise an amino acid sequence that is at least 90% identical, 91% identical, 92% identical, 93% identical, 94% identical, 95% identical, 96% identical, 97% identical, 98% identical, 99% identical, or 100% identical to SEQ ID NO:6. In some embodiments, for example, the EGFRvIII polypeptide can comprise an amino acid sequence at least i) 90% identical, ii) 95% identical, iii) 99% identical, or iv) 100% identical to SEQ ID NO:6. In other embodiments, the EGFRvIII polypeptide can comprise 2, 3, 4, 5, or more copies of an EGFRvIII polypeptide, each copy having an amino acid sequence at least 90% identical to SEQ ID NO:6. An exemplary amino acid sequence of EGFRvIIIx5 is set forth in SEQ ID NO:8.

In some aspects, each of the one or more copies of the EGFRvIII polypeptide can consist of an amino acid sequence that is at least 90% identical, 91% identical, 92% identical, 93% identical, 94% identical, 95% identical, 96% identical, 97% identical, 98% identical, 99% identical, or 100% identical to SEQ ID NO:6. In some aspects, each of the one or more copies of the EGFRvIII polypeptide can consist essentially of an amino acid sequence that is at least 90% identical, 91% identical, 92% identical, 93% identical, 94% identical, 95% identical, 96% identical, 97% identical, 98% identical, 99% identical, or 100% identical to SEQ ID NO:6.

In some embodiments, the one or more copies of EGFRvIII polypeptide can comprise, consist of, or consist essentially of an amino acid sequence at least i) 90% identical, ii) 95% identical, iii) 99% identical, or iv) 100% identical to amino acid residues 6 to 18 of SEQ ID NO:6. In some embodiments, the one or more copies of EGFRvIII polypeptide can comprise, consist of, or consist essentially of an amino acid sequence at least i) 90% identical, ii) 95% identical, iii) 99% identical, or iv) 100% identical to amino acid residues 6 to 14 of SEQ ID NO:6.

The EGFRvIII polypeptides can be flanked by one or more cleaver sequences at the N-terminus, C-terminus, or both the N-and C-terminus of the EGFRvIII polypeptide. Cleaver sequences are configured to be processed by proteases present in the subject. Where the EGFRvIII polypeptide comprises 2 or more copies of the EGFRvIII polypeptide, cleaver sequences can be present between the individual copies of the EGFRvIII polypeptides. For example, and without intending to be limiting, SEQ ID NO:8 contains 5 copies of the EGFRvIII polypeptide (each copy of the EGFRvIII polypeptide set forth in SEQ ID NO:6) and cleaver sequences (ASKVL/ADGSVKTS (SEQ ID NO:54), ASKVA/GDGSIK (SEQ ID NO:55), LSKVL/ADGSVK (SEQ ID NO:56), ASKVA/GDGSIK (SEQ ID NO:57), and LSKVL/ADGSVK (SEQ ID NO:58); wherein "/" represents an EGFRvIII polypeptide). These cleaver sequences are exemplary in nature only. Suitable cleaver sequences are described in U.S. patent application Ser. No. 13/988,076 (U.S. Patent Publ. No. 2014/037662); Toes, et al., J. Exp. Med. (2001) 194: 1-12; Lauer et al., Infect. Immun. (2008) 76: 3742-53; and Sinnathamby et al., J. Immunother. (2009) 32: 856-69, each of which are incorporated by reference in its entirety.

The EGFRvIII polypeptide can be fused to the N-terminus or C-terminus of the PAP polypeptide. Preferably, EGFRvIII polypeptide can be fused to the N-terminus of the PAP polypeptide Suitable PAP polypeptides include amino acids 33-386 of PAP ("PAP$_{33-386}$"). Thus, in some embodiments, the PAP polypeptide can comprise an amino acid sequence at least i) 90% identical, ii) 95% identical, iii) 99% identical, or iv) 100% identical to PAP$_{33-386}$ as set forth in SEQ ID NO:14. In some embodiments, the PAP polypeptide can consist of an amino acid sequence at least i) 90% identical, ii) 95% identical, iii) 99% identical, or iv) 100% identical to PAP$_{33-386}$ as set forth in SEQ ID NO:14. In some embodiments, the PAP polypeptide can consist essentially of an amino acid sequence at least i) 90% identical, ii) 95% identical, iii) 99% identical, or iv) 100% identical to PAP$_{33-386}$ as set forth in SEQ ID NO:14.

In some embodiments, the fusion protein can comprise a polypeptide that is at least i) 90% identical, ii) 95% identical, iii) 99% identical, or iv) 100% identical to the EGFRvIII polypeptide as set forth in SEQ ID NO:6 and a polypeptide that is at least i) 90% identical, ii) 95% identical, iii) 99% identical, or iv) 100% identical to the PAP$_{33-386}$ polypeptide as set forth in SEQ ID NO:14. For example, the fusion protein can comprise an amino acid sequence at least i) 90% identical, ii) 95% identical, iii) 99% identical, or iv) 100% identical to EGFRvIIIx1-PAP$_{33-386}$ as set forth in amino acid residues 89 to 476 of SEQ ID NO:35. In some embodiments, the fusion protein can comprise two polypeptides that are at least i) 90% identical, ii) 95% identical, iii) 99% identical, or iv) 100% identical to the EGFRvIII polypeptide as set forth in SEQ ID NO:6 and a polypeptide at least i) 90% identical, ii) 95% identical, iii) 99% identical, or iv) 100% identical to the PAP$_{33-386}$ polypeptide as set forth in SEQ ID NO:14. For example, the fusion protein can comprise an amino acid sequence at least i) 90% identical, ii) 95% identical, iii) 99% identical, or iv) 100% identical to EGFRvIIIx2-PAP$_{33-386}$ as set forth in amino acid residues 89 to 509 of SEQ ID NO:37. In some embodiments, the fusion protein can comprise three polypeptides that are at least i) 90% identical, ii) 95% identical, iii) 99% identical, or iv) 100% identical to the EGFRvIII polypeptide as set forth in SEQ ID NO:6 and a polypeptide that is at least i) 90% identical, ii) 95% identical, iii) 99% identical, or iv) 100% identical to the PAP$_{33-386}$ polypeptide as set forth in SEQ ID NO:14. For example, the fusion protein can comprise an amino acid sequence at least i) 90% identical, ii) 95% identical, iii) 99% identical, or iv) 100% identical to EGFRvIIIx3-PAP$_{33-386}$ as set forth in amino acid residues 89 to 541 of SEQ ID NO:39. In some embodiments, the fusion protein can comprise four polypeptides that are at least i) 90% identical, ii) 95% identical, iii) 99% identical, or iv) 100% identical to the EGFRvIII polypeptide as set forth in SEQ ID NO:6 and a polypeptide that is at least i) 90% identical, ii) 95% identical, iii) 99% identical, or iv) 100% identical to the PAP$_{33-386}$ polypeptide as set forth in SEQ ID NO:14. For example, the fusion protein can comprise an amino acid sequence at least i) 90% identical, ii) 95% identical, iii) 99% identical, or iv) 100% identical to EGFRvIIIx4-PAP$_{33-386}$ as set forth in amino acid residues 89 to 573 of SEQ ID NO:41. In some embodiments, the fusion protein can comprise five polypeptides that are at least i) 90% identical, ii) 95% identical, iii) 99% identical, or iv) 100% identical to the EGFRvIII polypeptide as set forth in SEQ ID NO:6 and a polypeptide at least i) 90% identical, ii) 95% identical, iii) 99% identical, or iv) 100% identical to the PAP$_{33-386}$ polypeptide as set forth in SEQ ID NO:14. For example, the fusion protein can comprise an amino acid sequence at least i) 90% identical, ii) 95% identical, iii) 99% identical, or iv) 100% identical to EGFRvIIIx5-PAP$_{33-386}$ as set forth in amino acid residues 89 to 606 of SEQ ID NO:12.

The disclosed fusion proteins further comprise a signal sequence, wherein the signal sequence is in translational reading frame with the EGFRvIII polypeptide and the PAP polypeptide. Suitable signal sequences include, for example, ActAN100 (as set forth in SEQ ID NO:60), ActAN100* (as set forth in SEQ ID NO:2), LLO441 (as set forth in SEQ ID NO:49), LLO441ΔPEST (as set forth in SEQ ID NO:51), and LLO441Δ26 (as set forth in SEQ ID NO:53). In some embodiments, the signal sequence can comprise an amino acid sequence that is at least i) 90% identical, ii) 95% identical, iii) 99% identical, or iv) 100% identical to ActAN100* as set forth as SEQ ID NO:2. In some embodiments, the signal sequence can comprise an amino acid sequence at least i) 90% identical, ii) 95% identical, iii) 99% identical, or iv) 100% identical to ActAN100 as set forth in SEQ ID NO:60. Accordingly, in some embodiments, the fusion protein can comprise an amino acid sequence at least i) 90% identical, ii) 95% identical, iii) 99% identical, or iv) 100% identical to ActAN100*-EGFRvIIIx1-PAP$_{33-386}$ as set forth in SEQ ID NO:35. In some embodiments, the fusion protein can comprise an amino acid sequence at least i) 90% identical, ii) 95% identical, iii) 99% identical, or iv) 100% identical to ActAN100*-EGFRvIIIx2-PAP$_{33-386}$ as set forth in SEQ ID NO:37. In some embodiments, the fusion protein can comprise an amino acid sequence at least i) 90% identical, ii) 95% identical, iii) 99% identical, or iv) 100% identical to ActAN100*-EGFRvIIIx3-PAP$_{33-386}$ as set forth in SEQ ID NO:39. In some embodiments, the fusion protein can comprise an amino acid sequence at least i) 90% identical, ii) 95% identical, iii) 99% identical, or iv) 100% identical to ActAN100*-EGFRvIIIx4-PAP$_{33-386}$ as set forth in SEQ ID NO:41. In some embodiments, the fusion protein can comprise an amino acid sequence at least i) 90% identical, ii) 95% identical, iii) 99% identical, or iv) 100% identical to ActAN100*-EGFRvIIIx5-PAP$_{33-386}$ as set forth in SEQ ID NO:12.

The disclosed fusion proteins can be expressed in a number of suitable host cells as disclosed elsewhere herein. In some embodiments, for example, the fusion protein can be expressed in a bacterium, such as *Listeria monocytogenes* or a genetically modified form thereof.

Also disclosed are nucleic acid molecules encoding an EGFRvIII-PAP fusion protein. The disclosed nucleic acid molecules can encode any of the EGFRvIII-PAP fusion proteins disclosed herein.

The nucleic acid molecules can encode an EGFRvIII-PAP fusion protein with one or more EGFRvIII polypeptides. In some embodiments, the nucleic acid molecule can encode an EGFRvIII-PAP fusion protein with one EGFRvIII polypeptide. In other embodiments, the nucleic acid molecule can encode an EGFRvIII-PAP fusion protein with a plurality of EGFRvIII polypeptides. Suitable numbers of EGFRvIII polypeptides encoded by the disclosed nucleic acid molecules include, but are not limited to, 2, 3, 4, 5, or more copies. In some embodiments, the nucleic acid molecules can encode an EGFRvIII-PAP fusion protein with 1 copy of the EGFRvIII polypeptide (EGFRvIIIx1), 2 copies of the EGFRvIII polypeptide (EGFRvIIIx2), 3 copies of the EGFRvIII polypeptide (EGFRvIIIx3), 4 copies of the EGFRvIII polypeptide (EGFRvIIIx4), or 5 copies of the EGFRvIII polypeptide (EGFRvIIIx5). An exemplary nucleic acid sequence of an EGFRvIII polynucleotide is set forth in SEQ ID NO:5 and an exemplary nucleic acid sequence of an EGFRvIIIx5 polynucleotide is set forth in SEQ ID NO:7. Accordingly, the disclosed nucleic acid molecules can encode an EGFRvIII-PAP fusion protein, wherein the fusion protein comprises 1, 2, 3, 4, or 5 copies of an EGFRvIII polypeptide encoded by a polynucleotide that is at least i) 90% identical, ii) 95% identical, iii) 99% identical, or iv) 100% identical to the EGFRvIII polynucleotide as set forth in SEQ ID NO:5. In some aspects, the nucleic acid molecule is operably linked to a promoter. In some aspects, the disclosed nucleic acid molecules can encode an EGFRvIII-PAP fusion protein, wherein the EGFRvIII polypeptide is encoded by a polynucleotide that is at least i) 90% identical, ii) 95% identical, iii) 99% identical, or iv) 100% identical to the EGFRvIIIx5 polynucleotide as set forth in SEQ ID NO:7. In some aspects, the nucleic acid molecule is operably linked to a promoter.

The disclosed nucleic acid molecules can encode an EGFRvIII-PAP fusion protein, wherein the PAP polypeptide is encoded by a polynucleotide that is at least i) 90% identical, ii) 95% identical, iii) 99% identical, or iv) 100% identical to the $PAP_{33-386}$ polynucleotide as set forth in SEQ ID NO:13. In some aspects, the nucleic acid molecule is operably linked to a promoter.

In some embodiments, the nucleic acid molecule can comprise one or more EGFRvIII polynucleotides, wherein each EGFRvIII polynucleotide is at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the $PAP_{33-386}$ polynucleotide as set forth in SEQ ID NO:13. In some aspects, the nucleic acid molecule is operably linked to a promoter. In some embodiments, the nucleic acid molecule can comprise a polynucleotide that is at least i) 90% identical, ii) 95% identical, iii) 99% identical, or iv) 100% identical to the EGFRvIIIx5 polynucleotide as set forth in SEQ ID NO:7 and a polynucleotide that is at least i) 90% identical, ii) 95% identical, iii) 99% identical, or iv) 100% identical to the $PAP_{33-386}$ polynucleotide as set forth in SEQ ID NO:13. In some aspects, the nucleic acid molecule is operably linked to a promoter.

The nucleic acid molecule can further comprise a promoter, a signal sequence, or both, wherein the promoter, signal sequence, or both are operably linked with the nucleotide sequence encoding the EGFRvIII polypeptide and the nucleotide sequence encoding the PAP polypeptide. Suitable promoters include, for example, actA (as set forth in SEQ ID NO:21) or hly (as set forth in SEQ ID NO:47). The promoter can comprise, for example, a nucleotide sequence that is at least i) 90% identical, ii) 95% identical, iii) 99% identical, or iv) 100% identical to an actA promoter as set forth in SEQ ID NO:21. Suitable signal sequences include, for example, ActAN100 (as set forth in SEQ ID NO:59), ActAN100* (as set forth in SEQ ID NO:1), LLO441 (as set forth in SEQ ID NO:48), LLO441ΔPEST (as set forth in SEQ ID NO:50), and LLO441Δ26 (as set forth in SEQ ID NO:52). The signal sequence can comprise, for example, a nucleotide sequence that is at least i) 90% identical, ii) 95% identical, iii) 99% identical, or iv) 100% identical to ActAN100* as set forth in SEQ ID NO:1. Accordingly, in some embodiments, the nucleic acid molecule encoding the EGFRvIII-PAP fusion protein can comprise, consist of, or consist essentially of a polynucleotide that is at least i) 90% identical, ii) 95% identical, iii) 99% identical, or iv) 100% identical to actA-ActAN100*-EGFRvIIIx1-$PAP_{33-386}$ as set forth in SEQ ID NO:34. In some embodiments, the nucleic acid molecule encoding the EGFRvIII-PAP fusion protein can comprise, consist of, or consist essentially of a polynucleotide that is at least i) 90% identical, ii) 95% identical, iii) 99% identical, or iv) 100% identical to actA-ActAN100*-EGFRvIIIx2-$PAP_{33-386}$ as set forth in SEQ ID NO:36. In some embodiments, the nucleic acid molecule encoding the EGFRvIII-PAP fusion protein can comprise, consist of, or consist essentially of a polynucleotide that is at least i) 90% identical, ii) 95% identical, iii) 99% identical, or iv) 100% identical to actA-ActAN100*-EGFRvIIIx3-$PAP_{33-386}$ as set forth in SEQ ID NO:38. In some embodiments, the nucleic acid molecule encoding the EGFRvIII-PAP fusion protein can comprise, consist of, or consist essentially of a polynucleotide that is at least i) 90% identical, ii) 95% identical, iii) 99% identical, or iv) 100% identical to actA-ActAN100*-EGFRvIIIx4-$PAP_{33-386}$ as set forth in SEQ ID NO:40. In some embodiments, the nucleic acid molecule encoding the EGFRvIII-PAP fusion protein can comprise, consist of, or consist essentially of a polynucleotide that is at least i) 90% identical, ii) 95% identical, iii) 99% identical, or iv) 100% identical to actA-ActAN100*-EGFRvIIIx5-$PAP_{33-386}$ as set forth in SEQ ID NO:11.

The nucleic acid molecules can further comprise additional nucleic acid sequences including, but not limited to, restriction endonuclease cleavage sites (cloning linkers) and "cleaver sequences" (as defined elsewhere herein).

The nucleic acid molecule can be part of an expression cassette. The expression cassette can comprise a promoter, an open reading frame comprising the disclosed nucleic acid molecules, and a 3' untranslated region. The expression cassette can be used to direct a host cell's machinery to produce the disclosed fusion proteins.

Vectors comprising the disclosed nucleic acid molecules are also provided. Suitable vectors include, for example, bacterial vectors, viral vectors, naked DNA vectors, and naked RNA vectors.

EGFRvIII-NKX3.1-PSMA Fusion Proteins

Disclosed herein are fusion proteins comprising an EGFRvIII polypeptide, an NK3 homeobox 1 (NKX3.1) polypeptide, and a prostate-specific membrane antigen (PSMA) polypeptide.

The fusion protein can comprise one or more copies of an EGFRvIII polypeptide. In some embodiments, the fusion protein can comprise one EGFRvIII polypeptide. In other embodiments, the fusion protein can comprise a plurality of EGFRvIII polypeptides. Suitable numbers of copies of the EGFRvIII polypeptide include, but are not limited to, 2, 3, 4, 5, or more copies. In some embodiments, for example, the fusion protein can comprise one EGFRvIII polypeptide (referred to as EGFRvIIIx1). In some embodiments, for example, the fusion protein can comprise two copies of the EGFRvIII polypeptide (referred to as EGFRvIIIx2). In some embodiments, for example, the fusion protein can comprise three copies of the EGFRvIII polypeptide (referred to as EGFRvIIIx3). In some embodiments, for example, the fusion protein can comprise four copies of the EGFRvIII polypeptide (referred to as EGFRvIIIx4). In some embodiments, for example, the fusion protein can comprise five copies of the EGFRvIII polypeptide (referred to as EGFRvIIIx5).

Each of the one or more copies of the EGFRvIII polypeptide can comprise an amino acid sequence that is at least 90% identical, 91% identical, 92% identical, 93% identical, 94% identical, 95% identical, 96% identical, 97% identical, 98% identical, 99% identical, or 100% identical to SEQ ID NO:6. In some embodiments, for example, the EGFRvIII polypeptide can comprise an amino acid sequence at least i) 90% identical, ii) 95% identical, iii) 99% identical, or iv)

100% identical to SEQ ID NO:6. In other embodiments, the EGFRvIII polypeptide can comprise 2, 3, 4, 5, or more copies of an EGFRvIII polypeptide, each copy having an amino acid sequence at least i) 90% identical, ii) 95% identical, iii) 99% identical, or iv) 100% identical to SEQ ID NO:6. An exemplary amino acid sequence of EGFRvIIIx5 is set forth in SEQ ID NO:8.

In some aspects, each of the one or more copies of the EGFRvIII polypeptide can consist of an amino acid sequence that is at least 90% identical, 91% identical, 92% identical, 93% identical, 94% identical, 95% identical, 96% identical, 97% identical, 98% identical, 99% identical, or 100% identical to SEQ ID NO:6. In some aspects, each of the one or more copies of the EGFRvIII polypeptide can consist essentially of an amino acid sequence that is at least 90% identical, 91% identical, 92% identical, 93% identical, 94% identical, 95% identical, 96% identical, 97% identical, 98% identical, 99% identical, or 100% identical to SEQ ID NO:6.

In some embodiments, the one or more copies of EGFRvIII polypeptide can comprise, consist, of, or consist essentially of an amino acid sequence at least i) 90% identical, ii) 95% identical, iii) 99% identical, or iv) 100% identical to amino acid residues 6 to 18 of SEQ ID NO:6. In some embodiments, the one or more copies of EGFRvIII polypeptide can comprise, consist, of, or consist essentially of an amino acid sequence at least i) 90% identical, ii) 95% identical, iii) 99% identical, or iv) 100% identical to amino acid residues 6 to 14 of SEQ ID NO:6.

The EGFRvIII polypeptides can be flanked by one or more cleaver sequences at the N-terminus, C-terminus, or both the N-and C-terminus of the EGFRvIII polypeptide. Cleaver sequences are configured to be processed by proteases present in the subject. Where the EGFRvIII polypeptide comprises 2 or more copies of the EGFRvIII polypeptide, cleaver sequences can be present between the individual copies of the EGFRvIII polypeptides. For example, and without intending to be limiting, SEQ ID NO:8 contains 5 copies of the EGFRvIII polypeptide (each copy of the EGFRvIII polypeptide set forth in SEQ ID NO:6) and cleaver sequences (ASKVL/ADGSVKTS (SEQ ID NO:54), ASKVA/GDGSIK (SEQ ID NO:55), LSKVL/ADGSVK (SEQ ID NO:56), ASKVA/GDGSIK (SEQ ID NO:57), and LSKVL/ADGSVK (SEQ ID NO:58); wherein "/" represents an EGFRvIII polypeptide). These cleaver sequences are exemplary in nature only. Suitable cleaver sequences are described in U.S. patent application Ser. No. 13/988,076 (U.S. Patent Publ. No. 2014/037662); Toes, et al., J. Exp. Med. (2001) 194: 1-12; Lauer et al., Infect. Immun. (2008) 76: 3742-53; and Sinnathamby et al., J. Immunother. (2009) 32: 856-69, each of which are incorporated by reference in its entirety.

Preferably, the fusion protein can comprise an EGFRvIII polypeptide fused to the N-terminus of the NKX3.1 polypeptide, and an NKX3.1 polypeptide fused to the N-terminus of the PSMA polypeptide. Other orders of the EGFRvIII polypeptide, NKX3.1 polypeptide, and PSMA polypeptide are also suitable. For example: EGFRvIII-PSMA-NKX1; PSMA-NKX-EGFRvIII; PSMA-EGFRvIII-NKX1; NKX1-EGFRvIII-PSMA; and NKX1-PSMA-EGFRvIII fusion proteins are suitable.

Suitable NKX3.1 polypeptides include amino acids 11-234 of NKX3.1 ("NKX3.1$_{11\text{-}234}$"). In some embodiments, the NKX3.1 polypeptide can comprise an amino acid sequence at least i) 90% identical, ii) 95% identical, iii) 99% identical, or iv) 100% identical to NKX3.1$_{11\text{-}234}$ as set forth in SEQ ID NO:25. In some embodiments, the NKX3.1 polypeptide can consist of an amino acid sequence at least i) 90% identical, ii) 95% identical, iii) 99% identical, or iv) 100% identical to NKX3.1$_{11\text{-}234}$ as set forth in SEQ ID NO:25. In some embodiments, the NKX3.1 polypeptide can consist essentially of an amino acid sequence at least i) 90% identical, ii) 95% identical, iii) 99% identical, or iv) 100% identical to NKX3.1$_{11\text{-}234}$ as set forth in SEQ ID NO:25.

The NKX3.1$_{11\text{-}234}$ polypeptide can have an arginine (R) to glycine (G) mutation at amino acid 41 ("NKX3.1 (R41G)"). In some embodiments, the NKX3.1 polypeptide can comprise an amino acid sequence at least i) 90% identical, ii) 95% identical, iii) 99% identical, or iv) 100% identical to NKX3.1(R41G)$_{11\text{-}234}$ as set forth in SEQ ID NO:18. In some embodiments, the NKX3.1 polypeptide can consist of an amino acid sequence at least i) 90% identical, ii) 95% identical, iii) 99% identical, or iv) 100% identical to NKX3.1(R41G)$_{11\text{-}234}$ as set forth in SEQ ID NO:18. In some embodiment, the NKX3.1 polypeptide can consist essentially of an amino acid sequence at least i) 90% identical, ii) 95% identical, iii) 99% identical, or iv) 100% identical to NKX3.1(R41G)$_{11\text{-}234}$ as set forth in SEQ ID NO:18.

Suitable PSMA polypeptides include amino acids 1-20 and 44-750 of PSMA (PSMA$_{1\text{-}20,\ 44\text{-}750}$) or amino acids 1-20, 44-138, and 169-750 of PSMA ("PSMA$_{1\text{-}20,\ 44\text{-}138,\ 169\text{-}750}$"). Preferably, the PSMA polypeptide can comprise an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20. In some embodiments, the PSMA polypeptide can consist of an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20. In some embodiments, the PSMA polypeptide can consist essentially of an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20.

EGFRvIII-NKX3.1$_{11\text{-}234}$-PSMA$_{1\text{-}20,\ 44\text{-}138,\ 169\text{-}750}$ fusion proteins can comprise:
a) one or more EGFRvIII polypeptides having an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11\text{-}234}$ as set forth in SEQ ID NO:25, and a PSMA polypeptide comprising an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20;
b) an EGFRvIIIx5 polypeptide having an amino acid sequence at least i) 90% identical, ii) 95% identical, iii) 99% identical, or iv) 100% identical to SEQ ID NO:8, a NKX3.1 polypeptide comprising an amino acid sequence at least i) 90% identical, ii) 95% identical, iii) 99% identical, or iv) 100% identical to NKX3.1$_{11\text{-}234}$ as set forth in SEQ ID NO:25, and a PSMA polypeptide comprising an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20; or
c) an amino acid sequence at least i) 90% identical, ii) 95% identical, iii) 99% identical, or iv) 100% identical to EGFRvIIIx5-NKX3.1$_{11\text{-}234}$-PSMA$_{1\text{-}20,\ 44\text{-}138,\ 169\text{-}750}$ as set forth in amino acid residues 89 to 1177 of SEQ ID NO:23.

EGFRvIIIx5-NKX3.1(R41G)$_{11\text{-}234}$-

PSMA$_{1-20, 44-138, 169-750}$ fusion proteins can comprise:
  a) one or more EGFRvIII polypeptides having an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;
  b) an EGFRvIIIx5 polypeptide having an amino acid sequence at least i) 90% identical, ii) 95% identical, iii) 99% identical, or iv) 100% identical to SEQ ID NO:8, a NKX3.1 polypeptide comprising an amino acid sequence at least i) 90% identical, ii) 95% identical, iii) 99% identical, or iv) 100% identical to NKX3.1 (R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20; or
  c) an amino acid sequence at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in amino acid residues 89 to 1177 of SEQ ID NO:16.

The disclosed fusion proteins can further comprise a signal sequence. In some embodiments, the fusion protein can further comprise a signal sequence, wherein the signal sequence is in translational reading frame with the EGFRvIII polypeptide, NKX3.1 polypeptide, and the PSMA polypeptide. Suitable signal sequences include, for example, ActAN100 (as set forth in SEQ ID NO:60), ActAN100* (as set forth in SEQ ID NO:2), LLO441 (as set forth in SEQ ID NO:49), LLO441ΔPEST (as set forth in SEQ ID NO:51), and LLO441Δ26 (as set forth in SEQ ID NO:53). In some embodiments, the signal sequence can comprise an amino acid sequence at least i) 90% identical, ii) 95% identical, iii) 99% identical, or iv) 100% identical to ActAN100 as set forth in SEQ ID NO:60. In some embodiments, the signal sequence can comprise an amino acid sequence that is at least i) 90% identical, ii) 95% identical, iii) 99% identical, or iv) 100% identical to ActAN100* as set forth as SEQ ID NO:2. Accordingly, in some embodiments, the EGFRvIII-NKX3.1$_{11-234}$-PSMA$_{1-20, 44-138, 169-750}$ fusion proteins can comprise, consist of, or consist essentially of an amino acid sequence at least i) 90% identical, ii) 95% identical, iii) 99% identical, or iv) 100% identical to ActAN100*-EGFRvIIIx5-NKX3.1$_{11-234}$-PSMA$_{1-20, 44-138, 169-750}$ as set forth in SEQ ID NO:23. In some embodiments, the EGFRvIII-NKX3.1 (R41G)$_{11-234}$-PSMA$_{1-20, 44-138, 169-750}$ fusion proteins can comprise, consist of, or consist essentially of an amino acid sequence at least i) 90% identical, ii) 95% identical, iii) 99% identical, or iv) 100% identical to ActAN100*-EGFRvIIIx5-NKX3.1(R41G)$_{11-234}$-PSMA$_{1-20, 44-138, 169-750}$ as set forth in SEQ ID NO:16.

The disclosed fusion proteins can be expressed in a number of suitable host cells as disclosed elsewhere herein. In some embodiments, for example, the fusion protein can be expressed in a bacterium, such as *Listeria monocytogenes* or a genetically modified form thereof.

Also disclosed are nucleic acid molecules encoding a EGFRvIII-NKX3.1-PSMA fusion proteins. The disclosed nucleic acid molecules can encode any of the EGFRvIII-NKX3.1-PSMA fusion proteins disclosed herein.

The nucleic acid molecules can encode a EGFRvIII-NKX3.1-PSMA fusion protein with one or more EGFRvIII polypeptides. In some embodiments, the nucleic acid molecule can encode a EGFRvIII-NKX3.1-PSMA fusion protein with one EGFRvIII polypeptide. In other embodiments, the nucleic acid molecule can encode a EGFRvIII-NKX3.1-PSMA fusion protein with a plurality of EGFRvIII polypeptides. Suitable numbers of EGFRvIII polypeptides encoded by the disclosed nucleic acid molecules include, but are not limited to, 2, 3, 4, 5, or more copies. In some embodiments, the nucleic acid molecules can encode a EGFRvIII-NKX3.1-PSMA fusion protein with 5 copies of the EGFRvIII polypeptide (EGFRvIIIx5). An exemplary nucleic acid sequence of an EGFRvIII polynucleotide is set forth in SEQ ID NO:5 and an exemplary nucleic acid sequence of an EGFRvIIIx5 polynucleotide is set forth in SEQ ID NO:7. Accordingly, the disclosed nucleic acid molecules can encode a EGFRvIII-NKX3.1-PSMA fusion protein, wherein fusion protein comprises a plurality of EGFRvIII polypeptides each encoded by a polynucleotide that is at least i) 90% identical, ii) 95% identical, iii) 99% identical, or iv) 100% identical to the EGFRvIIIx5 polynucleotide as set forth in SEQ ID NO:5. In some aspects, the nucleic acid molecule is operably linked to a promoter. The disclosed nucleic acid molecules can encode a EGFRvIII-NKX3.1-PSMA fusion protein, wherein the EGFRvIII polypeptide is encoded by a polynucleotide that is at least i) 90% identical, ii) 95% identical, iii) 99% identical, or iv) 100% identical to the EGFRvIIIx5 polynucleotide as set forth in SEQ ID NO:7. In some aspects, the nucleic acid molecule is operably linked to a promoter.

The disclosed nucleic acid molecules can encode a EGFRvIII-NKX3.1-PSMA fusion protein, wherein the NKX3.1 polypeptide is encoded by a polynucleotide that is at least i) 90% identical, ii) 95% identical, iii) 99% identical, or iv) 100% identical to the NKX3.1$_{11-234}$ polynucleotide as set forth in SEQ ID NO:24. In some aspects, the nucleic acid molecule is operably linked to a promoter. Alternatively, the disclosed nucleic acid molecules can encode a EGFRvIII-NKX3.1-PSMA fusion protein, wherein the NKX3.1 polypeptide is encoded by a polynucleotide that is at least i) 90% identical, ii) 95% identical, iii) 99% identical, or iv) 100% identical to the NKX3.1(R41G)$_{11-234}$ polynucleotide as set forth in SEQ ID NO:17. In some aspects, the nucleic acid molecule is operably linked to a promoter.

The disclosed nucleic acid molecules can encode a EGFRvIII-NKX3.1-PSMA fusion protein, wherein the PSMA polypeptide is encoded by a polynucleotide that is at least i) 90% identical, ii) 95% identical, iii) 99% identical, or iv) 100% identical to the PSMA$_{1-20, 44-138, 169-750}$ as set forth in SEQ ID NO:19. In some aspects, the nucleic acid molecule is operably linked to a promoter.

The nucleic acid molecule encoding the EGFRvIII-NKX3.1$_{11-234}$-PSMA$_{1-20, 44-138, 169-750}$ fusion proteins can comprise, consist of, or consist essentially of:
  a) one or more EGFRvIII polynucleotides that are at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1$_{11-234}$ polynucleotide as set forth in SEQ ID NO:24, and a polynucleotide that is at least i) 90% identical, ii) 95% identical, iii) 99% identical, or iv) 100% identical to the PSMA$_{1-20, 44-138, 169-750}$ as set forth in SEQ ID NO: 19; or b) a polynucleotide that is at least i) 90% identical, ii) 95% identical, iii) 99% identical, or iv) 100% identical to the EGFRvIIIx5 polynucleotide as set forth in SEQ ID NO:7, a polynucleotide that is at least i) 90% identical, ii) 95% identical, iii) 99% identical, or iv) 100% identical to the NKX3.1$_{11-234}$ polynucleotide as set forth in SEQ ID NO:24, and a polynucleotide that is at least i) 90% identical, ii) 95% identical, iii) 99% identical, or iv) 100% identical to the PSMA$_{1-20, 44-138, 169-750}$ as set forth in SEQ ID NO:19.

In some aspects, the nucleic acid molecules listed above are operably linked to a promoter.

The nucleic acid molecule encoding the EGFRvIII-NKX3.1(R41G)$_{11-234}$-PSMA$_{1-20, 44-138, 169-750}$ fusion proteins can comprise, consist of, or consist essentially of:

a) one or more EGFRvIII polynucleotides that are at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1 (R41G)$_{11-234}$ polynucleotide as set forth in SEQ ID NO:17, and a polynucleotide that is at least i) 90% identical, ii) 95% identical, iii) 99% identical, or iv) 100% identical to the PSMA$_{1-20, 44-138, 169-750}$ as set forth in SEQ ID NO:19; or b) a polynucleotide that is at least i) 90% identical, ii) 95% identical, iii) 99% identical, or iv) 100% identical to the EGFRvIIIx5 polynucleotide as set forth in SEQ ID NO:7, a polynucleotide that is at least i) 90% identical, ii) 95% identical, iii) 99% identical, or iv) 100% identical to the NKX3.1(R41G)$_{11-234}$ polynucleotide as set forth in SEQ ID NO:17, and a polynucleotide that is at least i) 90% identical, ii) 95% identical, iii) 99% identical, or iv) 100% identical to the PSMA$_{1-20, 44-138, 169-750}$ as set forth in SEQ ID NO:19.

In some aspects, the nucleic acid molecules listed above are operably linked to a promoter.

The nucleic acid molecule can further comprise a promoter, a signal sequence, or both, wherein the promoter, signal sequence, or both are operably linked with the nucleotide sequence encoding the EGFRvIII polypeptide, the NKX3.1 polypeptide, and the PSMA polypeptide. Suitable promoters include, for example, actA (as set forth in SEQ ID NO:21) or hly (as set forth in SEQ ID NO:47). The promoter can comprise, for example, a nucleotide sequence that is at least i) 90% identical, ii) 95% identical, iii) 99% identical, or iv) 100% identical to an actA promoter as set forth in SEQ ID NO:21. Suitable signal sequences include, for example, ActAN100 (as set forth in SEQ ID NO:59), ActAN100* (as set forth in SEQ ID NO:1), LLO441 (as set forth in SEQ ID NO:48), LLO441ΔPEST (as set forth in SEQ ID NO:50), and LLO441Δ26 (as set forth in SEQ ID NO:52). The signal sequence can comprise, for example, a nucleotide sequence that is at least i) 90% identical, ii) 95% identical, iii) 99% identical, or iv) 100% identical to ActAN100* as set forth in SEQ ID NO:1. Accordingly, in some embodiments, the nucleic acid molecule encoding the EGFRvIII-NKX3.1-PSMA fusion protein can comprise, consist of, or consist essentially of a polynucleotide that is at least i) 90% identical, ii) 95% identical, iii) 99% identical, or iv) 100% identical to actA-ActAN100*-EGFRvIIIx5-NKX3.1$_{11-234}$-PSMA$_{1-20, 44-138, 169-750}$ as set forth as SEQ ID NO:22. In other embodiments, the nucleic acid molecule encoding the EGFRvIII-NKX3.1-PSMA fusion protein can comprise, consist of, or consist essentially of a polynucleotide that is at least i) 90% identical, ii) 95% identical, iii) 99% identical, or iv) 100% identical to actA-ActAN100*-EGFRvIIIx5-NKX3.1(R41G)$_{11-234}$-PSMA$_{1-20, 44-138, 169-750}$ as set forth as SEQ ID NO:15.

The nucleic acid molecules can further comprise additional nucleic acid sequences including, but not limited to, restriction endonuclease cleavage sites (cloning linkers) and "cleaver sequences" (as described elsewhere herein).

The nucleic acid molecule can be part of an expression cassette. The expression cassette can comprise a promoter, an open reading frame comprising the disclosed nucleic acid molecules, and a 3' untranslated region. The expression cassette can be used to direct a host cell's machinery to produce the disclosed fusion proteins.

Vectors comprising the disclosed nucleic acid molecules are also provided. Suitable vectors include, for example, bacterial vectors, viral vectors, naked DNA vectors, and naked RNA vectors.

NKX3.1-PAP Fusion Proteins

Disclosed herein are fusion proteins comprising an NK3 homeobox 1 (NKX3.1) polypeptide and a PAP polypeptide.

Suitable NKX3.1 polypeptides include full length NKX3.1 (amino acids 1-234 of NKX3.1; "NKX3.1"). In some embodiments, the NKX3.1 polypeptide can comprise an amino acid sequence at least i) 90% identical, ii) 95% identical, iii) 99% identical, or iv) 100% identical to NKX3.1 as set forth in SEQ ID NO:29. In some embodiments, the NKX3.1 polypeptide can consist of an amino acid sequence at least i) 90% identical, ii) 95% identical, iii) 99% identical, or iv) 100% identical to NKX3.1 as set forth in SEQ ID NO:29. In some embodiments, the NKX3.1 polypeptide can consist essentially of an amino acid sequence at least i) 90% identical, ii) 95% identical, iii) 99% identical, or iv) 100% identical to NKX3.1 as set forth in SEQ ID NO:29.

Suitable PAP polypeptides include amino acids 33-386 of PAP ("PAP$_{33-386}$"). Thus, in some embodiments, the PAP polypeptide can comprise an amino acid sequence at least i) 90% identical, ii) 95% identical, iii) 99% identical, or iv) 100% identical to PAP$_{33-386}$ as set forth in SEQ ID NO:14. In some embodiments, the PAP polypeptide can consist of an amino acid sequence at least i) 90% identical, ii) 95% identical, iii) 99% identical, or iv) 100% identical to PAP$_{33-386}$ as set forth in SEQ ID NO:14. In some embodiments, the PAP polypeptide can consist essentially of an amino acid sequence at least i) 90% identical, ii) 95% identical, iii) 99% identical, or iv) 100% identical to PAP$_{33-386}$ as set forth in SEQ ID NO:14.

The NKX3.1 polypeptide can be fused to the N-terminus or C-terminus of the PAP polypeptide. Preferably, the NKX3.1 polypeptide can be fused to the N-terminus of the PAP polypeptide.

The fusion protein can comprise, consist of, or consist essentially of a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14.

The fusion protein can comprise, consist of, or consist essentially of an amino acid sequence at least i) 90% identical, ii) 95% identical, iii) 99% identical, or iv) 100% identical to NKX3.1-PAP$_{33-386}$ as set forth in amino acid residues 89 to 678 of SEQ ID NO:27.

The disclosed fusion proteins can further comprise a signal sequence. In some embodiments, the fusion protein can further comprise a signal sequence, wherein the signal sequence is in translational reading frame with the NKX3.1 polypeptide and the PAP polypeptide. Suitable signal sequences include, for example, ActAN100 (as set forth in SEQ ID NO:60), ActAN100* (as set forth in SEQ ID NO:2), LLO441 (as set forth in SEQ ID NO:49), LLO441ΔPEST (as set forth in SEQ ID NO:51), and LLO441Δ26 (as set forth in SEQ ID NO:53). In some embodiments, the signal sequence can comprise an amino acid sequence at least i) 90% identical, ii) 95% identical, iii) 99% identical, or iv) 100% identical to ActAN100 as set forth in SEQ ID NO:60. In some embodiments, the signal sequence can comprise an amino acid sequence that is at least i) 90% identical, ii) 95% identical, iii) 99% identical, or iv) 100% identical to ActAN100* as set forth as SEQ ID NO:2. Accordingly, in some embodiments, the fusion protein can comprise an amino acid sequence at least i) 90% identical, ii) 95% identical, iii) 99% identical, or iv) 100% identical to ActAN100*-NKX3.1-PAP$_{33-386}$ as set forth in SEQ ID NO:27.

The disclosed fusion proteins can be expressed in a number of suitable host cells as disclosed elsewhere herein. In some embodiments, for example, the fusion protein can be expressed in a bacterium, such as Listeria monocytogenes or a genetically modified form thereof.

Also disclosed are nucleic acid molecules encoding an NKX3.1-PAP fusion protein. The disclosed nucleic acid molecules can encode any of the NKX3.1-PAP fusion proteins disclosed herein.

The disclosed nucleic acid molecules can encode an NKX3.1-PAP fusion protein, wherein the NKX3.1 polypeptide is encoded by a polynucleotide that is at least i) 90% identical, ii) 95% identical, iii) 99% identical, or iv) 100% identical to the NKX3.1 polynucleotide as set forth in SEQ ID NO:28. In some aspects, the nucleic acid molecule is operably linked to a promoter.

The disclosed nucleic acid molecules can encode an NKX3.1-PAP fusion protein, wherein the PAP polypeptide is encoded by a polynucleotide that is at least i) 90% identical, ii) 95% identical, iii) 99% identical, or iv) 100% identical to the PAP$_{33-386}$ polynucleotide as set forth in SEQ ID NO:13. In some aspects, the nucleic acid molecule is operably linked to a promoter.

The nucleic acid molecule can encode an NKX3.1-PAP$_{33-386}$ fusion protein. In some embodiments, for example, the nucleic acid molecule can comprise a polynucleotide that is at least i) 90% identical, ii) 95% identical, iii) 99% identical, or iv) 100% identical to the NKX3.1 polynucleotide as set forth in SEQ ID NO:28 and a polynucleotide that is at least i) 90% identical, ii) 95% identical, iii) 99% identical, or iv) 100% identical to the PAP$_{33-386}$ polynucleotide as set forth in SEQ ID NO:13. In some aspects, the nucleic acid molecule is operably linked to a promoter.

The nucleic acid molecule can further comprise a promoter, a signal sequence, or both, wherein the promoter, signal sequence, or both are operably linked with the nucleotide sequence encoding the NKX3.1 polypeptide and the nucleotide sequence encoding the PAP polypeptide. Suitable promoters include, for example, actA (as set forth in SEQ ID NO:21) or hly (as set forth in SEQ ID NO:47). The promoter can comprise, for example, a nucleotide sequence that is at least i) 90% identical, ii) 95% identical, iii) 99% identical, or iv) 100% identical to an actA promoter as set forth in SEQ ID NO:21. Suitable signal sequences include, for example, ActAN100 (as set forth in SEQ ID NO:59), ActAN100* (as set forth in SEQ ID NO:1), LLO441 (as set forth in SEQ ID NO:48), LLO441ΔPEST (as set forth in SEQ ID NO:50), and LLO441Δ26 (as set forth in SEQ ID NO:52). The signal sequence can comprise, for example, a nucleotide sequence that is at least i) 90% identical, ii) 95% identical, iii) 99% identical, or iv) 100% identical to ActAN100* as set forth in SEQ ID NO:1. Accordingly, in some embodiments, the nucleic acid molecule encoding the NKX3.1-PAP fusion protein can comprise, consist of, or consist essentially of a polynucleotide that is at least i) 90% identical, ii) 95% identical, iii) 99% identical, or iv) 100% identical to actA-ActAN100*-NKX3.1-PAP$_{33-386}$ as set forth in SEQ ID NO:26.

The nucleic acid molecules can further comprise additional nucleic acid sequences including, but not limited to, restriction endonuclease cleavage sites (cloning linkers).

The nucleic acid molecule can be part of an expression cassette. The expression cassette can comprise a promoter, an open reading frame comprising the disclosed nucleic acid molecules, and a 3' untranslated region. The expression cassette can be used to direct a host cell's machinery to produce the disclosed fusion proteins.

Vectors comprising the disclosed nucleic acid molecules are also provided. Suitable vectors include, for example, bacterial vectors, viral vectors, naked DNA vectors, and naked RNA vectors.

ActAN100*-SSX2 Fusion Proteins

Disclosed herein are fusion proteins comprising an ActAN100* polypeptide and an SSX2 polypeptide.

Suitable SSX2 polypeptides include amino acids 1-234 of SSX2 ("SSX2" or "SSX2$_{1-234}$") and amino acids 2-234 of SSX2 ("SSX2$_{2-234}$"). In some embodiments, the SSX2 polypeptide can comprise an amino acid sequence at least i) 90% identical, ii) 95% identical, iii) 99% identical, or iv) 100% identical to SSX2 as set forth in SEQ ID NO:10. In some embodiments, the SSX2 polypeptide can consist of an amino acid sequence at least i) 90% identical, ii) 95% identical, iii) 99% identical, or iv) 100% identical to SSX2 as set forth in SEQ ID NO:10. In some embodiments, the SSX2 polypeptide can consist essentially of an amino acid sequence at least i) 90% identical, ii) 95% identical, iii) 99% identical, or iv) 100% identical to SSX2 as set forth in SEQ ID NO:10.

The ActAN100* polypeptide can comprise an amino acid sequence at least i) 90% identical, ii) 95% identical, iii) 99% identical, or iv) 100% identical to ActAN100* as set forth as SEQ ID NO:2.

In some embodiments, the fusion protein can comprise an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10. In some embodiments, the fusion protein can comprise an amino acid sequence at least i) 90% identical, ii) 95% identical, iii) 99% identical, or iv) 100% identical to ActAN100*-SSX2 as set forth in SEQ ID NO:31.

Other suitable signal sequences include, for example, ActAN100 (as set forth in SEQ ID NO:60), LLO441 (as set forth in SEQ ID NO:49), LLO441ΔPEST (as set forth in SEQ ID NO:51), and LLO441Δ26 (as set forth in SEQ ID NO:53).

The disclosed fusion proteins can be expressed in a number of suitable host cells as disclosed elsewhere herein. In some embodiments, for example, the fusion protein can be expressed in a bacterium, such as *Listeria monocytogenes* or a genetically modified form thereof.

Also disclosed are nucleic acid molecules encoding an ActAN100*-SSX2 fusion protein. In some embodiments, the nucleic acid molecule encoding the ActAN100*-SSX2 fusion protein can comprise, consist of, or consist essentially of an ActAN100* polynucleotide at least i) 90% identical, ii) 95% identical, iii) 99% identical, or iv) 100% identical to ActAN100* as set forth in SEQ ID NO:1 and a SSX2 polynucleotide at least i) 90% identical, ii) 95% identical, iii) 99% identical, or iv) 100% identical to the SSX2 as set forth in SEQ ID NO:9. In some aspects, the nucleic acid molecule is operably linked to a promoter. In some embodiments, the nucleic acid molecule encoding the ActAN100*-SSX2 fusion protein can comprise, consist of, or consist essentially of a polynucleotide that is at least i) 90% identical, ii) 95% identical, iii) 99% identical, or iv) 100% identical to actA-ActAN100*-SSX2 as set SEQ ID NO:30. In some aspects, the nucleic acid molecule is operably linked to a promoter.

Other suitable signal sequences include, for example, ActAN100 (as set forth in SEQ ID NO:59), LLO441 (as set forth in SEQ ID NO:48), LLO441ΔPEST (as set forth in SEQ ID NO:50), and LLO441Δ26 (as set forth in SEQ ID NO:52).

The nucleic acid molecules can further comprise additional nucleic acid sequences including, but not limited to, restriction endonuclease cleavage sites (cloning linkers). The nucleic acid molecules can be generated using a number of suitable restriction endonucleases, wherein the endonuclease cleavage site(s) may remain in the final nucleic acid molecule.

The nucleic acid molecule can be part of an expression cassette. The expression cassette can comprise a promoter, an open reading frame comprising the disclosed nucleic acid molecules, and a 3' untranslated region. The expression cassette can be used to direct a host cell's machinery to produce the disclosed fusion proteins.

Vectors comprising the disclosed nucleic acid molecules are also provided. Suitable vectors include, for example, bacterial vectors, viral vectors, naked DNA vectors, and naked RNA vectors.

ActAN100-PAP Fusion Proteins

Disclosed herein are fusion proteins comprising an ActAN100 polypeptide and an PAP polypeptide.

Suitable PAP polypeptides include amino acids 30-386 of PAP ("PAP$_{30-386}$"). In some embodiments, the PAP polypeptide can comprise an amino acid sequence at least i) 90% identical, ii) 95% identical, iii) 99% identical, or iv) 100% identical to PAP$_{30-386}$ as set forth in amino acid residues 103-459 of SEQ ID NO:33. In some embodiments, the PAP polypeptide can consist of an amino acid sequence at least i) 90% identical, ii) 95% identical, iii) 99% identical, or iv) 100% identical to PAP$_{30-386}$ as set forth in amino acid residues 103-459 of SEQ ID NO:33. In some embodiments, the PAP polypeptide can consist essentially of an amino acid sequence at least i) 90% identical, ii) 95% identical, iii) 99% identical, or iv) 100% identical to PAP$_{30-386}$ as set forth in amino acid residues 103-459 of SEQ ID NO:33.

Suitable signal sequences, for example, ActAN100 (as set forth in SEQ ID NO:60), ActAN100* (as set forth in SEQ ID NO: 2), LLO441 (as set forth in SEQ ID NO:49), LLO441ΔPEST (as set forth in SEQ ID NO:51), and LLO441Δ26 (as set forth in SEQ ID NO:53). In some embodiments, the ActAN100 polypeptide can comprise an amino acid sequence at least i) 90% identical, ii) 95% identical, iii) 99% identical, or iv) 100% identical to amino acid residues 1 to 100 of SEQ ID NO:33. In other embodiments, the ActAN100* polypeptide can comprise an amino acid sequence at least i) 90% identical, ii) 95% identical, iii) 99% identical, or iv) 100% identical to ActAN100* as set forth as SEQ ID NO:2.

The ActAN100-PAP fusion proteins can further comprise an SL8 polypeptide. The SL8 polypeptide is a T-cell epitope tag ("SIINFEKL" from chicken ovalbumin (OVA257-264)), which can be used to assist in the detection of an attached antigen by for example, Western blot. SL8 is a class I (Kb)-restricted peptide epitope that is presented by the class I MHC molecule, H-2Kb, relevant to the C57/BL6 mouse.

In some embodiments, the ActAN100-PAP fusion protein can comprise, consist of, or consist essentially of, an ActAN100 polypeptide comprising an amino acid sequence at least i) 90% identical, ii) 95% identical, iii) 99% identical, or iv) 100% identical to amino acid residues 1 to 100 of SEQ ID NO:33 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33. In some embodiments, the ActAN100-PAP fusion protein can comprise, consist of, or consist essentially of, an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33. In some embodiments, the fusion protein can comprise, consist of, or consist essentially of, an amino acid sequence at least i) 90% identical, ii) 95% identical, iii) 99% identical, or iv) 100% identical to ActAN100-PAP$_{30-386}$ as set forth in amino acid residues 1-459 of SEQ ID NO:33. In some embodiments, the fusion protein can comprise, consist of, or consist essentially of an amino acid sequence at least i) 90% identical, ii) 95% identical, iii) 99% identical, or iv) 100% identical to ActAN100-PAP$_{30-386}$-SL8 as set forth in SEQ ID NO:33.

The disclosed fusion proteins can be expressed in a number of suitable host cells as disclosed elsewhere herein. In some embodiments, for example, the fusion protein can be expressed in a bacterium, such as *Listeria monocytogenes* or a genetically modified form thereof.

Also disclosed are nucleic acid molecules encoding an ActAN100-PAP fusion proteins. In some embodiments, the nucleic acid molecule encoding the ActAN100-PAP fusion proteins can comprise, consist of, or consist essentially of a polynucleotide that is at least i) 90% identical, ii) 95% identical, iii) 99% identical, or iv) 100% identical to actA-ActAN100-PAP$_{30}$-386-SL8 as set SEQ ID NO:32. In some aspects, the nucleic acid molecule is operably linked to a promoter.

Suitable signal sequences include, for example, ActAN100 (as set forth in SEQ ID NO:59), LLO441 (as set forth in SEQ ID NO:48), LLO441ΔPEST (as set forth in SEQ ID NO:50), and LLO441Δ26 (as set forth in SEQ ID NO:52).

The nucleic acid molecules can further comprise additional nucleic acid sequences including, but not limited to, restriction endonuclease cleavage sites (cloning linkers). The nucleic acid molecules can be generated using a number of suitable restriction endonucleases, wherein the endonuclease cleavage site(s) may remain in the final nucleic acid molecule.

The nucleic acid molecule can be part of an expression cassette. The expression cassette can comprise a promoter, an open reading frame comprising the disclosed nucleic acid molecules, and a 3' untranslated region. The expression cassette can be used to direct a host cell's machinery to produce the disclosed fusion proteins.

Vectors comprising the disclosed nucleic acid molecules are also provided. Suitable vectors include, for example, bacterial vectors, viral vectors, naked DNA vectors, and naked RNA vectors.

Host Cells Comprising Nucleic Acid Molecules Encoding the Immunogenic Polypeptides Host cells comprising any of the disclosed nucleic acid molecules are also provided. Also disclosed are host cells expressing fusion proteins encoded by any of the disclosed nucleic acid molecules.

Suitable host cells include, for example, bacterium. Host cells can be attenuated, commensal, and/or killed but metabolically active. In an exemplary embodiment, the host cell can be an attenuated, commensal, and/or killed but metabolically active bacterium. Suitable bacterium include, but insertion mutant, or a combination thereof. For example, the *Listeria monocytogenes* can be a ΔactA/ΔinlB mutant.

The host cells can comprise one or more of the disclosed nucleic acid molecules. The one or more nucleic acid molecules can be integrated into the host cell genome. Such host cells can contain nucleic acids that are under the control of host cell expression sequences and thereby do not require eukaryotic transcriptional or translational elements. The nucleic acid molecules can be integrated into the actA locus, inlB locus or tRNA$^{Arg}$ locus. In some embodiments, the nucleic acid molecule can be integrated into the actA locus. In some embodiments, the nucleic acid molecule can be integrated into the inlB locus. In some embodiments, the nucleic acid molecule can be integrated into the tRNA$^{Arg}$ locus. Table 4 provides an exemplary list of host cells comprising nucleic acid molecules encoding immunogenic fusion proteins, in which the nucleic acid molecules are integrated into the host cell genome. The following list is intended to be exemplary only.

TABLE 4

| Strain | Background | locus | Antigen expression cassette |
|---|---|---|---|
| Lm11 | Lm ΔactA ΔinlB | — | — |
| DP-L4027 | Lm Δhly | — | — |
| BH5258 | Lm ΔactA ΔinlB | actA | ActAN100*-EGFRvIIIx5-SSX2 |
|  |  | inlB | ActAN100*-EGFRvIIIx5-PAP$_{33-386}$ |
|  |  | tRNA$^{Arg}$ | ActAN100*-EGFRvIIIx5-NKX3.1$_{11-234}$-PSMA$_{1-20, 44-138, 169-750}$ |
| BH5290 | Lm ΔactA ΔinlB | actA | ActAN100*-EGFRvIIIx5-SSX2 |
|  |  | inlB | ActAN100*-EGFRvIIIx5-PAP$_{33-386}$ |
|  |  | tRNA$^{Arg}$ | ActAN100*-EGFRvIIIx5-NKX3.1(R41G)$_{11-234}$-PSMA$_{1-20, 44-138, 169-750}$ |
| BH4598 | Lm ΔactA ΔinlB | inlB | ActAN100*-NKX3.1-PAP$_{33-386}$ |
|  |  | tRNA$^{Arg}$ | ActAN100*-SSX2 |
| BH4602 | Lm ΔactA ΔinlB | inlB | ActAN100*-NKX3.1-PAP$_{33-386}$ |
|  |  | tRNA$^{Arg}$ | ActAN100*-EGFRvIIIx5-SSX2 |
| BH2868 | Lm ΔactA ΔinlB | tRNA$^{Arg}$ | ActAN100*-PAP$_{33-386}$ |
| PL1631 | Lm ΔactA ΔinlB | tRNA$^{Arg}$ | ActAN100*-EGFRvIIIx1-PAP$_{33-386}$ |
| PL1629 | Lm ΔactA ΔinlB | tRNA$^{Arg}$ | ActAN100*-EGFRvIIIx2-PAP$_{33-386}$ |
| PL1627 | Lm ΔactA ΔinlB | tRNA$^{Arg}$ | ActAN100*-EGFRvIIIx3-PAP$_{33-386}$ |
| PL1625 | Lm ΔactA ΔinlB | tRNA$^{Arg}$ | ActAN100*-EGFRvIIIx4-PAP$_{33-386}$ |
| PL1623 | Lm ΔactA ΔinlB | tRNA$^{Arg}$ | ActAN100*-EGFRvIIIx5-PAP$_{33-386}$ | are not limited to, *Listeria monocytogenes, Shigella flexneri, Escherichia coli, Yersinia enterocolitica, Salmonella typhimurium, Salmonella typhi* or *mycobacterium* species, or modified forms thereof. In some embodiments, for example, the host cell can be *Listeria monocytogenes* or a modified form thereof. Modifications include mutations, alterations, and other genetic changes/variations, as well as heat-treatment or chemical modification, which reduce the toxicity of the host cell to a subject. The bacterium can be modified, for example, to reduce binding to cells within a subject, reduce spread from one cell to another within a subject, reduce extracellular growth in a subject, or reduce intracellular growth in a subject.

Bacterial strains suitable as host cells include those described in U.S. patent application Ser. No. 13/988,076 (U.S. Patent Publ. No. 2014/037662), herein incorporated by reference in its entirety. For example, the host cell can be a live-attenuated strain of *L. monocytogenes* which is genetically modified to comprise an attenuating mutation in actA and/or inlB, and preferably a deletion of all or a portion of actA and inlB (referred to herein as "Lm ΔactA/ΔinlB"), and contains a nucleic acid molecule encoding the immunogenic fusion protein. In some embodiments, the *Listeria monocytogenes* can be an actA deletion (ΔactA) mutant, an actA insertion mutant, an inlB deletion (ΔinlB) mutant, an inlB Conversely, the host cells can comprise a nucleic acid molecule encoding an immunogenic fusion protein wherein the nucleic acid molecule is within the host cell extrachromosomally. For example, one or more of the disclosed nucleic acid molecules encoding an immunogenic fusion protein can be inserted into an expression cassette on an episomal plasmid within the host cell.

In some embodiments, the host cells can comprise one or more of the disclosed nucleic acid molecules, wherein the nucleic acid molecule comprises:

a) one or more copies of a polynucleotide that is at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the SSX2 polynucleotide as set forth in SEQ ID NO:9;

b) one or more copies of a polynucleotide that is at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the PAP$_{33-386}$ polynucleotide as set forth in SEQ ID NO:13;

c) one or more copies of a polynucleotide that is at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1$_{11-234}$ polynucleotide as set forth in SEQ ID NO:24, and a polynucleotide that is at least i) 90% identical, ii) 95% identical, iii) 99% identical, or iv) 100% identical to the PSMA$_{1-20, 44-138, 169-750}$ as set forth in SEQ ID NO: 19;

d) one or more copies of a polynucleotide that is at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1 (R41G)$_{11-234}$ polynucleotide as set forth in SEQ ID NO:17, and a polynucleotide that is at least i) 90% identical, ii) 95% identical, iii) 99% identical, or iv) 100% identical to the PSMA$_{1-20, 44-138, 169-750}$ as set forth in SEQ ID NO:19;

e) a polynucleotide that is at least i) 90% identical, ii) 95% identical, iii) 99% identical, or iv) 100% identical to the NKX3.1 polynucleotide as set forth in SEQ ID NO:28 and a polynucleotide that is at least i) 90% identical, ii) 95% identical, iii) 99% identical, or iv) 100% identical to the PAP$_{33-386}$ polynucleotide as set forth in SEQ ID NO:13;

f) an ActAN100* polynucleotide at least i) 90% identical, ii) 95% identical, iii) 99% identical, or iv) 100% identical to ActAN100* as set forth in SEQ ID NO:1 and a SSX2 polynucleotide at least i) 90% identical, ii) 95% identical, iii) 99% identical, or iv) 100% identical to the SSX2 as set forth in SEQ ID NO:9;

g) a polynucleotide that is at least i) 90% identical, ii) 95% identical, iii) 99% identical, or iv) 100% identical to ActAN100-PAP$_{30-386}$-SL8 as set forth in SEQ ID NO:32; or h) any combination thereof, i) wherein the nucleic acid molecule is integrated into the actA locus, inlB locus or tRNA$^{Arg}$ locus, or wherein the nucleic acid molecule is inserted into an expression cassette on an episomal plasmid within the host cell.

In some aspects, the one or more nucleic acid molecules listed in a)-h) are operably linked to a promoter.

As disclosed elsewhere herein, the disclosed immunogenic fusion proteins and the nucleic acid molecules encoding the same can comprise one or more EGFRvIII polypeptides. Thus, "one or more copies of a polynucleotide that is at least i) 90% identical, ii) 95% identical, iii) 99% identical, or iv) 100% identical to the EGFRvIII polynucleotide as set forth in SEQ ID NO:5" includes, but is not limited to, immunogenic fusion proteins and the nucleic acid molecules encoding the same comprising 2, 3, 4, 5, or more copies of the EGFRvIII polypeptide.

In some embodiments, the host cells can comprise one or more of nucleic acid molecules, said nucleic acid molecules comprising:

a) a nucleotide sequence that is at least i) 90% identical, ii) 95% identical, iii) 99% identical, or iv) 100% identical to EGFRvIIIx5-SSX2 as set forth in SEQ ID NO:3;

b) a nucleotide sequence that is at least i) 90% identical, ii) 95% identical, iii) 99% identical, or iv) 100% identical to EGFRvIIIx5-PAP$_{33-386}$ as set forth in SEQ ID NO:11;

c) a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22;

d) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15;

e) a nucleotide sequence that is at least i) 90% identical, ii) 95% identical, iii) 99% identical, or iv) 100% identical to NKX3.1-PAP$_{33-386}$ as set forth in SEQ ID NO:26;

f) a nucleotide sequence that is at least i) 90% identical, ii) 95% identical, iii) 99% identical, or iv) 100% identical to ActAN100*-SSX2 as set forth in SEQ ID NO:30;

g) a nucleic acid sequence that is at least i) 90% identical, ii) 95% identical, iii) 99% identical, or iv) 100% identical to ActAN100-PAP$_{30-386}$-SL8 as set forth in SEQ ID NO:32;

h) a nucleotide sequence that is at least i) 90% identical, ii) 95% identical, iii) 99% identical, or iv) 100% identical to EGFRvIIIx1-PAP$_{33-386}$ as set forth in SEQ ID NO:34;

i) a nucleotide sequence that is at least i) 90% identical, ii) 95% identical, iii) 99% identical, or iv) 100% identical to EGFRvIIIx2-PAP$_{33-386}$ as set forth in SEQ ID NO:36;

j) a nucleotide sequence that is at least i) 90% identical, ii) 95% identical, iii) 99% identical, or iv) 100% identical to EGFRvIIIx3-PAP$_{33-386}$ as set forth in SEQ ID NO:38;

k) a nucleotide sequence that is at least i) 90% identical, ii) 95% identical, iii) 99% identical, or iv) 100% identical to EGFRvIIIx4-PAP$_{33-386}$ as set forth in SEQ ID NO:40;

l) any combination thereof, m) wherein the nucleic acid molecules are integrated into the actA locus, inlB locus or tRNA$^{Arg}$ locus, or wherein the nucleic acid molecules are inserted into an expression cassette on an episomal plasmid within the host cell.

In some aspects, the one or more nucleic acid molecules listed in a)-l) are operably linked to a promoter.

The host cell can comprise a nucleic acid molecule comprising: (a) a nucleotide sequence that is at least i) 90% identical, ii) 95% identical, iii) 99% identical, or iv) 100% identical to EGFRvIIIx5-SSX2 as set forth in SEQ ID NO:3; (b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and (c) a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22. In some aspects, the nucleic acid molecule is operably linked to a promoter. In some aspects, the nucleotide sequence that is at least i) 90% identical, ii) 95% identical, iii) 99% identical, or iv) 100% identical to EGFRvIIIx5-SSX2 as set forth in SEQ ID NO:3 can be integrated into the actA locus; the nucleotide sequence that is at least i) 90% identical, ii) 95% identical, iii) 99% identical, or iv) 100% identical to EGFRvIIIx5-PAP$_{33-386}$ as set forth in SEQ ID NO:11 can be integrated into the inlB locus; and the nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22 can be integrated into the tRNA$^{Arg}$ locus. In some aspects, the nucleic acid molecule is operably linked to a promoter.

The host cell can comprise a nucleic acid molecule comprising: (a) a nucleotide sequence that is at least i) 90% identical, ii) 95% identical, iii) 99% identical, or iv) 100% identical to EGFRvIIIx5-SSX2 as set forth in SEQ ID NO:3; (b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and (c) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15. In some aspects, the nucleic acid molecule is operably linked to a promoter. In some aspects, the nucleotide sequence that is at least i) 90% identical, ii) 95% identical, iii) 99% identical, or iv) 100% identical to EGFRvIIIx5-SSX2 as set forth in SEQ ID NO:3 can be integrated into the actA locus; the nucleotide sequence that is at least i) 90% identical, ii) 95% identical, iii) 99% identical, or iv) 100% identical to EGFRvIIIx5-PAP$_{33-386}$ as set forth in SEQ ID NO:11 can be integrated into the inlB locus; and the nucleotide sequence that is at least i) 90% identical, ii) 95% identical, iii) 99% identical, or iv) 100% identical to EGFRvIIIx5-NKX3.1(R41G)$_{11-234}$-PSMA$_{11-20, 44-138, 169-750}$ as set forth in SEQ ID NO:15 can be integrated into the tRNA$^{Arg}$ locus. In some aspects, the nucleic acid molecule is operably linked to a promoter.

The host cells can comprise a nucleic acid molecule comprising: (a) a nucleotide sequence that is at least i) 90% identical, ii) 95% identical, iii) 99% identical, or iv) 100% identical to NKX3.1-PAP$_{33-386}$ as set forth in SEQ ID NO:26; and (b) a nucleotide sequence that is at least i) 90% identical, ii) 95% identical, iii) 99% identical, or iv) 100% identical to EGFRvIIIx5-SSX2 as set forth in SEQ ID NO:3. In some aspects, the nucleic acid molecule is operably linked to a promoter. In some aspects, the nucleotide sequence that is at least i) 90% identical, ii) 95% identical, iii) 99% identical, or iv) 100% identical to NKX3.1-PAP$_{33-386}$ as set forth in SEQ ID NO:26 can be integrated into the inlB locus and the nucleotide sequence that is at least i) 90% identical, ii) 95% identical, iii) 99% identical, or iv) 100% identical to EGFRvIIIx5-SSX2 as set forth in SEQ ID NO:3 can be integrated into the tRNA$^{Arg}$ locus. In some aspects, the nucleic acid molecule is operably linked to a promoter.

The host cells can comprise a nucleic acid molecule comprising: (a) a nucleotide sequence that is at least i) 90% identical, ii) 95% identical, iii) 99% identical, or iv) 100% identical to NKX3.1-PAP$_{33-386}$ as set forth in SEQ ID NO:26; and (b) a nucleotide sequence that is at least i) 90% identical, ii) 95% identical, iii) 99% identical, or iv) 100% identical to ActAN100*-SSX2 as set forth in SEQ ID NO:30. In some aspects, the nucleic acid molecule is operably linked to a promoter. In some aspects, the nucleotide sequence that is at least i) 90% identical, ii) 95% identical, iii) 99% identical, or iv) 100% identical to NKX3.1-PAP$_{33-386}$ as set forth in SEQ ID NO:26 can be integrated into the inlB locus and the nucleotide sequence that is at least i) 90% identical, ii) 95% identical, iii) 99% identical, or iv) 100% identical to ActAN100*-SSX2 as set forth in SEQ ID NO:30 can be integrated into the tRNA$^{Arg}$ locus. In some aspects, the nucleic acid molecule is operably linked to a promoter.

The host cell can comprise one or more nucleic acid molecules comprising a nucleic acid sequence encoding:
a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;
b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;
c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;
d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;
e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;
f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; or
g) an ActAN100-PAP$_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33;
wherein the nucleic acid molecules are integrated into the actA locus, inlB locus or tRNA$^{Arg}$ locus, or wherein the nucleic acid molecules are inserted into an expression cassette on an episomal plasmid within the host cell.

In some aspects, the one or more nucleic acid molecules listed in a)-g) are operably linked to a promoter.

The host cell can express one or more fusion proteins comprising:

an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;

an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;

an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; or an ActAN100-PAP$_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33;

The host cell can comprise one or more nucleic acid molecules comprising a nucleic acid sequence encoding:
a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4 or an immunogenic fragment thereof;
b) an amino acid sequence at least i) 90% identical, ii) 95% identical, iii) 99% identical, or iv) 100% identical to EGFRvIIIx5-PAP$_{33-386}$ as set forth in amino acid residues 89 to 606 of SEQ ID NO:12 or an immunogenic fragment thereof;
c) an amino acid sequence at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in amino acid residues 89 to 1177 of SEQ ID NO:23 or an immunogenic fragment thereof;
d) an amino acid sequence at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in amino acid residues 89 to 1177 of SEQ ID NO:16 or an immunogenic fragment thereof;
e) an amino acid sequence at least i) 90% identical, ii) 95% identical, iii) 99% identical, or iv) 100% identical to NKX3.1-PAP$_{33-386}$ as set forth in amino acid residues 89 to 678 of SEQ ID NO:27 or an immunogenic fragment thereof;
f) an amino acid sequence at least i) 90% identical, ii) 95% identical, iii) 99% identical, or iv) 100% identical to ActAN100*-SSX2 as set forth in SEQ ID NO:31 or an immunogenic fragment thereof;
g) an amino acid sequence at least i) 90% identical, ii) 95% identical, iii) 99% identical, or iv) 100% identical to ActAN100-PAP$_{30-386}$ as set forth in amino acid residues 1-459 of SEQ ID NO:33 or an immunogenic fragment thereof;
h) an amino acid sequence at least i) 90% identical, ii) 95% identical, iii) 99% identical, or iv) 100% identical to EGFRvIIIx1-PAP$_{33-386}$ as set forth in amino acid residues 89 to 476 of SEQ ID NO:35 or an immunogenic fragment thereof;
i) an amino acid sequence at least i) 90% identical, ii) 95% identical, iii) 99% identical, or iv) 100% identical to EGFRvIIIx2-PAP$_{33-386}$ as set forth in amino acid residues 89 to 509 of SEQ ID NO:37 or an immunogenic fragment thereof;
j) an amino acid sequence at least i) 90% identical, ii) 95% identical, iii) 99% identical, or iv) 100% identical to EGFRvIIIx3-PAP$_{33-386}$ as set forth in amino acid residues 89 to 541 of SEQ ID NO:39 or an immunogenic fragment thereof;
k) an amino acid sequence at least i) 90% identical, ii) 95% identical, iii) 99% identical, or iv) 100% identical to EGFRvIIIx4-PAP$_{33-386}$ as set forth in amino acid residues 89 to 573 of SEQ ID NO:41 or an immunogenic fragment thereof; or
l) any combination thereof;
m) wherein the nucleic acid molecules are integrated into the actA locus, inlB locus or tRNA$^{Arg}$ locus, or wherein the nucleic acid molecules are inserted into an expression cassette on an episomal plasmid within the host cell.

In some aspects, the one or more nucleic acid molecules listed in a)-l) are operably linked to a promoter.

The host cell can express one or more fusion proteins comprising:
  a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4 or an immunogenic fragment thereof;
  b) an amino acid sequence at least i) 90% identical, ii) 95% identical, iii) 99% identical, or iv) 100% identical to EGFRvIIIx5-PAP$_{33\text{-}386}$ as set forth in amino acid residues 89 to 606 of SEQ ID NO:12 or an immunogenic fragment thereof;
  c) an amino acid sequence at least i) 90% identical, ii) 95% identical, iii) 99% identical, or iv) 100% identical to EGFRvIIIx5-NKX3.1$_{11\text{-}234}$-PSMA$_{1\text{-}20,\,44\text{-}138,\,169\text{-}750}$ as set forth in amino acid residues 89 to 1177 of SEQ ID NO:23 or an immunogenic fragment thereof;
  d) an amino acid sequence at least i) 90% identical, ii) 95% identical, iii) 99% identical, or iv) 100% identical to EGFRvIIIx5-NKX3.1(R41G)$_{11\text{-}234}$-PSMA$_{1\text{-}20,\,44\text{-}138,\,169\text{-}750}$ as set forth in amino acid residues 89 to 1177 of SEQ ID NO:16 or an immunogenic fragment thereof;
  e) an amino acid sequence at least i) 90% identical, ii) 95% identical, iii) 99% identical, or iv) 100% identical to NKX3.1-PAP$_{33\text{-}386}$ as set forth in amino acid residues 89 to 678 of SEQ ID NO:27 or an immunogenic fragment thereof;
  f) an amino acid sequence at least i) 90% identical, ii) 95% identical, iii) 99% identical, or iv) 100% identical to ActAN100*-SSX2 as set forth in SEQ ID NO:31 or an immunogenic fragment thereof;
  g) an amino acid sequence at least i) 90% identical, ii) 95% identical, iii) 99% identical, or iv) 100% identical to ActAN100-PAP$_{30\text{-}386}$ as set forth in amino acid residues 1-459 of SEQ ID NO:33 or an immunogenic fragment thereof;
  h) an amino acid sequence at least i) 90% identical, ii) 95% identical, iii) 99% identical, or iv) 100% identical to EGFRvIIIx1-PAP$_{33\text{-}386}$ as set forth in amino acid residues 89 to 476 of SEQ ID NO:35 or an immunogenic fragment thereof;
  i) an amino acid sequence at least i) 90% identical, ii) 95% identical, iii) 99% identical, or iv) 100% identical to EGFRvIIIx2-PAP$_{33\text{-}386}$ as set forth in amino acid residues 89 to 509 of SEQ ID NO:37 or an immunogenic fragment thereof;
  j) an amino acid sequence at least i) 90% identical, ii) 95% identical, iii) 99% identical, or iv) 100% identical to EGFRvIIIx3-PAP$_{33\text{-}386}$ as set forth in amino acid residues 89 to 541 of SEQ ID NO:39 or an immunogenic fragment thereof;
  k) an amino acid sequence at least i) 90% identical, ii) 95% identical, iii) 99% identical, or iv) 100% identical to EGFRvIIIx4-PAP$_{33\text{-}386}$ as set forth in amino acid residues 89 to 573 of SEQ ID NO:41 or an immunogenic fragment thereof; or
  l) any combination thereof;

Provided herein are recombinant *Listeria* bacterium that are modified to comprise any of the disclosed nucleic acid molecules. The nucleic acid molecule can be present in the *Listeria* extrachromosomally, or may be integrated into the bacterial genome. In some embodiments, for example, the host cell can be a *Listeria monocytogenes* ΔactA/ΔinlB mutant having a nucleic acid molecule encoding an immunogenic fusion protein integrated into the actA locus, inlB locus, or tRNA$^{Arg}$ locus. In some aspects, the nucleic acid molecule is operably linked to a promoter. The *Listeria* can be utilized as an expression platform for expressing the disclosed fusion proteins which are heterologous to the host cell. Such expression can lead to, for example, an immune response to the heterologous fusion protein in a subject containing the host cell.

Expression of the immunogenic fusion proteins are driven from the Lm actA promoter, which is highly induced when Lm has infected host cells. The actA gene resides in the PrfA regulon, a series of Lm virulence genes whose expression is controlled and induced by PrfA, a transcriptional activator protein that is induced in the context of the infected host cell. The expression cassette in the disclosed nucleic acid molecules exclusively utilizes Lm transcription, translation and secretion machinery and it does not contain any mammalian expression elements (such as promoter or terminator regions characteristic of mammalian expression systems). Therefore, unlike plasmid DNA-or viral-based vectors that must utilize the mammalian host cell machinery to express a designated gene of interest, and by definition, where gene transfer is a prerequisite for gene expression, Lm is a "self-contained" free-living organism. Within infected cells of the vaccinated host, the prokaryotic expression machinery of the disclosed host cells is utilized exclusively to synthesize the fusion protein within the host cell, which is subsequently secreted into the cytoplasm of an infect cell with the subject for antigen processing and presentation.

In some embodiments the host cell can comprise one or more nucleic acid molecules, wherein the one or more nucleic acid molecules comprises EGFRvIIIx5-SSX2 as set forth in SEQ ID NO:3, EGFRvIIIx5-PAP$_{33\text{-}386}$ as set forth in SEQ ID NO:11, and EGFRvIIIx5-NKX3.1(R41G)$_{11\text{-}234}$-PSMA$_{1\text{-}20,\,44\text{-}138,\,169\text{-}750}$ as set forth in SEQ ID NO:15. In some aspects, the nucleic acid molecule is operably linked to a promoter.

In some embodiments the host cell can comprise one or more nucleic acid molecules, wherein the one or more nucleic acid molecules consist of EGFRvIIIx5-SSX2 as set forth in SEQ ID NO:3, EGFRvIIIx5-PAP$_{33\text{-}386}$ as set forth in SEQ ID NO:11, and EGFRvIIIx5-NKX3.1(R41G)$_{11\text{-}234}$-PSMA$_{1\text{-}20,\,44\text{-}138,\,169\text{-}750}$ as set forth in SEQ ID NO:15. In some aspects, the nucleic acid molecule is operably linked to a promoter.

The host cells can be combined with a pharmaceutically acceptable excipient.

Also provided herein are vaccines comprising the disclosed host cells and a pharmaceutically acceptable excipient. The vaccines can be administered to a subject in an amount sufficient to elicit an appropriate immune response as disclosed herein.

Methods of Eliciting an Immune Response

Also disclosed herein are methods of eliciting an immune response in a subject comprising administering to the subject a composition comprising a host cell, wherein the host cell comprises a nucleic acid molecule encoding an immunogenic fusion protein. In some embodiments, the method comprising administering to the subject a composition comprising a host cell, wherein the host cell expresses one or more of the fusion proteins disclosed herein.

As used herein, "a host cell" includes one or more host cells, wherein each host cell can comprise one or more nucleic acid molecules encoding an immunogenic fusion protein. In some embodiments, the host cells can comprise the same nucleic acid molecule(s) encoding an immunogenic fusion protein. For example, and without intending to be limiting, the method can comprise administering to the subject a composition comprising a host cell, wherein the host cell comprises a nucleic acid molecule encoding EGFRvIII-SSX2. In some embodiments, the host cell can comprise different nucleic acid molecules encoding different immunogenic fusion proteins.

The methods can be carried out using any of the host cells disclosed herein, wherein the host cells comprise a nucleic acid molecule encoding an immunogenic fusion protein.

The methods of eliciting an immune response in a subject can comprise administering to the subject a composition comprising a host cell, said host cell comprising a one or more nucleic acid molecules, said nucleic acid molecules comprising a nucleic acid sequence encoding:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;

c) an EGFRvIII-NKX3.1$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20,\ 44-138,\ 169-750}$ as set forth in SEQ ID NO:20;

d) an EGFRvIII-NKX3.1(R41G)$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20,\ 44-138,\ 169-750}$ as set forth in SEQ ID NO:20;

e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;

f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10;

g) an ActAN100*-PAP$_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or h) any combination thereof.

In some aspects, the one or more nucleic acid molecules listed in a)-h) are operably linked to a promoter.

Disclosed herein are methods of eliciting an immune response in a subject comprising, administering to the subject a composition comprising a host cell, wherein the host cell expresses one or more fusion proteins comprising:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;

c) an EGFRvIII-NKX3.1$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20,\ 44-138,\ 169-750}$ as set forth in SEQ ID NO:20;

d) an EGFRvIII-NKX3.1(R41G)$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii)

95% identical, iii) 99% identical, or iv) 100% identical to PSMA$_{1-20,\ 44-138,\ 169-750}$ as set forth in SEQ ID NO:20;
e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;
f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10;
g) an ActAN100*-PAP$_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or
h) any combination thereof.

In some embodiments, the methods can comprise administering to the subject a composition comprising a host cell, wherein the host cell comprises a nucleic acid molecule encoding an immunogenic fusion protein, wherein the nucleic acid molecule comprises one or more copies of a polynucleotide that is at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the SSX2 polynucleotide as set forth in SEQ ID NO:9. In some aspects, the nucleic acid molecule is operably linked to a promoter. In some embodiments, the host cell expresses an immunogenic fusion protein encoded by the nucleic acid molecules.

In some embodiments, the methods can comprise administering to the subject a composition comprising a host cell, wherein the host cell comprises a nucleic acid molecule encoding an immunogenic fusion protein, wherein the nucleic acid molecule comprises one or more copies of a polynucleotide that is at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the PAP$_{33-386}$ polynucleotide as set forth in SEQ ID NO:13. In some aspects, the nucleic acid molecule is operably linked to a promoter. In some embodiments, the host cell expresses an immunogenic fusion protein encoded by the nucleic acid molecules.

In some embodiments, the methods can comprise administering to the subject a composition comprising a host cell, wherein the host cell comprises a nucleic acid molecule encoding an immunogenic fusion protein, wherein the nucleic acid molecule comprises one or more copies of a polynucleotide that is at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1$_{11-234}$ polynucleotide as set forth in SEQ ID NO:24, and a polynucleotide that is at least i) 90% identical, ii) 95% identical, iii) 99% identical, or iv) 100% identical to the PSMA$_{1-20,\ 44-138,\ 169-750}$ as set forth in SEQ ID NO:19. In some aspects, the nucleic acid molecule is operably linked to a promoter. In some embodiments, the host cell expresses an immunogenic fusion protein encoded by the nucleic acid molecules.

In some embodiments, the methods can comprise administering to the subject a composition comprising a host cell, wherein the host cell comprises a nucleic acid molecule encoding an immunogenic fusion protein, wherein the nucleic acid molecule comprises one or more copies of a polynucleotide that is at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1(R41G)$_{11-234}$ polynucleotide as set forth in SEQ ID NO:17, and a polynucleotide that is at least i) 90% identical, ii) 95% identical, iii) 99% identical, or iv) 100% identical to the PSMA$_{1-20,\ 44-138,\ 169-750}$ as set forth in SEQ ID NO:19. In some aspects, the nucleic acid molecule is operably linked to a promoter. In some embodiments, the host cell expresses an immunogenic fusion protein encoded by the nucleic acid molecules.

In some embodiments, the methods can comprise administering to the subject a composition comprising a host cell, wherein the host cell comprises a nucleic acid molecule encoding an immunogenic fusion protein, wherein the nucleic acid molecule comprises a polynucleotide that is at least i) 90% identical, ii) 95% identical, iii) 99% identical, or iv) 100% identical to the NKX3.1 polynucleotide as set forth in SEQ ID NO:28 and a polynucleotide that is at least i) 90% identical, ii) 95% identical, iii) 99% identical, or iv) 100% identical to the PAP$_{33-386}$ polynucleotide as set forth in SEQ ID NO:13. In some aspects, the nucleic acid molecule is operably linked to a promoter. In some embodiments, the host cell expresses an immunogenic fusion protein encoded by the nucleic acid molecules.

In some embodiments, the methods can comprise administering to the subject a composition comprising a host cell, wherein the host cell comprises a nucleic acid molecule encoding an immunogenic fusion protein, wherein the nucleic acid molecule comprises an ActAN100* polynucleotide at least i) 90% identical, ii) 95% identical, iii) 99% identical, or iv) 100% identical to ActAN100* as set forth in SEQ ID NO:1 and a SSX2 polynucleotide at least i) 90% identical, ii) 95% identical, iii) 99% identical, or iv) 100% identical to the SSX2 as set forth in SEQ ID NO:9. In some aspects, the nucleic acid molecule is operably linked to a promoter. In some embodiments, the host cell expresses an immunogenic fusion protein encoded by the nucleic acid molecules.

In some embodiments, the methods can comprise administering to the subject a composition comprising a host cell, wherein the host cell comprises a nucleic acid molecule encoding an immunogenic fusion protein, wherein the nucleic acid molecule comprises a polynucleotide that is at least i) 90% identical, ii) 95% identical, iii) 99% identical, or iv) 100% identical to ActAN100-PAP$_{30-386}$-SL8 as set forth in SEQ ID NO:32. In some aspects, the nucleic acid molecule is operably linked to a promoter. In some embodiments, the host cell expresses an immunogenic fusion protein encoded by the nucleic acid molecules.

In some embodiments, the methods can comprise administering to the subject a composition comprising a host cell, wherein the host cell comprises a nucleic acid molecule encoding an immunogenic fusion protein, wherein the nucleic acid molecule comprises any combination of the above nucleic acid molecules. In some aspects, the nucleic acid molecule is operably linked to a promoter. In some embodiments, the host cell expresses the immunogenic fusion protein encoded by the nucleic acid molecules.

The host cells can comprise one or more of the disclosed nucleic acid molecules, wherein the nucleic acid molecules comprise:

a) a nucleotide sequence that is at least i) 90% identical, ii) 95% identical, iii) 99% identical, or iv) 100% identical to EGFRvIIIx5-SSX2 as set forth in SEQ ID NO:3;

b) a nucleotide sequence that is at least i) 90% identical, ii) 95% identical, iii) 99% identical, or iv) 100% identical to EGFRvIIIx5-PAP$_{33-386}$ as set forth in SEQ ID NO:11;

c) a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22;

d) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15;

e) a nucleotide sequence that is at least i) 90% identical, ii) 95% identical, iii) 99% identical, or iv) 100% identical to NKX3.1-PAP$_{33-386}$ as set forth in SEQ ID NO:26;

f) a nucleotide sequence that is at least i) 90% identical, ii) 95% identical, iii) 99% identical, or iv) 100% identical to ActAN100*-SSX2 as set forth in SEQ ID NO:30;

g) a nucleic acid sequence that is at least i) 90% identical, ii) 95% identical, iii) 99% identical, or iv) 100% identical to ActAN100-PAP$_{30-386}$-SL8 as set forth in SEQ ID NO:32;

h) a nucleotide sequence that is at least i) 90% identical, ii) 95% identical, iii) 99% identical, or iv) 100% identical to EGFRvIIIx1-PAP$_{33-386}$ as set forth in SEQ ID NO:34;

i) a nucleotide sequence that is at least i) 90% identical, ii) 95% identical, iii) 99% identical, or iv) 100% identical to EGFRvIIIx2-PAP$_{33-386}$ as set forth in SEQ ID NO:36;

j) a nucleotide sequence that is at least i) 90% identical, ii) 95% identical, iii) 99% identical, or iv) 100% identical to EGFRvIIIx3-PAP$_{33-386}$ as set forth in SEQ ID NO:38;

k) a nucleotide sequence that is at least i) 90% identical, ii) 95% identical, iii) 99% identical, or iv) 100% identical to EGFRvIIIx4-PAP$_{33-386}$ as set forth in SEQ ID NO:40; or l) a combination thereof.

In some aspects, the one or more nucleic acid molecules listed in a)-l) are operably linked to a promoter.

In some embodiments, the host cell expresses one or more fusion proteins, the one or more fusion proteins being expressed from a nucleic acid molecule comprising:

a) a nucleotide sequence that is at least i) 90% identical, ii) 95% identical, iii) 99% identical, or iv) 100% identical to EGFRvIIIx5-SSX2 as set forth in SEQ ID NO:3;

b) a nucleotide sequence that is at least i) 90% identical, ii) 95% identical, iii) 99% identical, or iv) 100% identical to EGFRvIIIx5-PAP$_{33-386}$ as set forth in SEQ ID NO:11;

c) a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22;

d) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15;

e) a nucleotide sequence that is at least i) 90% identical, ii) 95% identical, iii) 99% identical, or iv) 100% identical to NKX3.1-PAP$_{33-386}$ as set forth in SEQ ID NO:26;

f) a nucleotide sequence that is at least i) 90% identical, ii) 95% identical, iii) 99% identical, or iv) 100% identical to ActAN100*-SSX2 as set forth in SEQ ID NO:30;

g) a nucleic acid sequence that is at least i) 90% identical, ii) 95% identical, iii) 99% identical, or iv) 100% identical to ActAN100-PAP$_{30-386}$-SL8 as set forth in SEQ ID NO:32;

h) a nucleotide sequence that is at least i) 90% identical, ii) 95% identical, iii) 99% identical, or iv) 100% identical to EGFRvIIIx1-PAP$_{33-386}$ as set forth in SEQ ID NO:34;

i) a nucleotide sequence that is at least i) 90% identical, ii) 95% identical, iii) 99% identical, or iv) 100% identical to EGFRvIIIx2-PAP$_{33-386}$ as set forth in SEQ ID NO:36;

j) a nucleotide sequence that is at least i) 90% identical, ii) 95% identical, iii) 99% identical, or iv) 100% identical to EGFRvIIIx3-PAP$_{33-386}$ as set forth in SEQ ID NO:38;

k) a nucleotide sequence that is at least i) 90% identical, ii) 95% identical, iii) 99% identical, or iv) 100% identical to EGFRvIIIx4-PAP$_{33-386}$ as set forth in SEQ ID NO:40; or l) a combination thereof.

In some aspects, the one or more nucleic acid molecules listed in a)-l) are operably linked to a promoter.

The methods can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx5-SSX2 as set forth in SEQ ID NO:3. In some aspects, the nucleic acid molecule is operably linked to a promoter. In some embodiments, the host cell expresses the fusion protein encoded by the nucleic acid molecules.

The methods can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx5-PAP$_{33-386}$ as set forth in SEQ ID NO:11. In some aspects, the nucleic acid molecule is operably linked to a promoter. In some embodiments, the host cell expresses the fusion protein encoded by the nucleic acid molecules.

The methods can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx5-NKX3.1$_{11-234}$-PSMA$_{1-20,\ 44-138,\ 169-750}$ as set forth in SEQ ID NO:22. In some aspects, the nucleic acid molecule is operably linked to a promoter. In some embodiments, the host cell expresses the fusion protein encoded by the nucleic acid molecules.

The methods can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20,\ 44-138,\ 169-750}$ as set forth in SEQ ID NO:15. In some aspects, the nucleic acid molecule is operably linked to a promoter. In some embodiments, the host cell expresses the fusion protein encoded by the nucleic acid molecules.

The methods can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to NKX3.1-PAP$_{33-386}$ as set forth in SEQ ID NO:26. In some aspects, the nucleic acid molecule is operably linked to a promoter. In some embodiments, the host cell expresses the fusion protein encoded by the nucleic acid molecules.

The methods can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to ActAN100*-SSX2 as set SEQ ID NO:30. In some aspects, the nucleic acid molecule is operably linked to a promoter. In some embodiments, the host cell expresses the fusion protein encoded by the nucleic acid molecules.

The methods can comprise administering to the subject a composition comprising a host cell, wherein the host cell comprises a nucleic acid molecule encoding an immunogenic fusion protein, wherein the nucleic acid molecule comprises a nucleic acid sequence that is at least i) 90% identical, ii) 95% identical, iii) 99% identical, or iv) 100% identical to ActAN100-PAP$_{30-386}$-SL8 as set SEQ ID NO:32. In some aspects, the nucleic acid molecule is operably linked to a promoter. In some embodiments, the host cell expresses the fusion protein encoded by the nucleic acid molecules.

The method can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx1-PAP$_{33-386}$ as set forth in SEQ ID NO:34. In some aspects, the nucleic acid molecule is operably linked to a promoter. In some embodiments, the host cell expresses the fusion protein encoded by the nucleic acid molecules.

The method can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx2-PAP$_{33-386}$ as set forth in SEQ ID NO:36. In some aspects, the nucleic acid molecule is operably linked to a promoter. In some embodiments, the host cell expresses the fusion protein encoded by the nucleic acid molecules.

The method can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx3-PAP$_{33-386}$ as set forth in SEQ ID NO:38. In some aspects, the nucleic acid molecule is operably linked to a promoter. In some embodiments, the host cell expresses the fusion protein encoded by the nucleic acid molecules.

The method can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx4-PAP$_{33-386}$ as set forth in SEQ ID NO:40. In some aspects, the nucleic acid molecule is operably linked to a promoter. In some embodiments, the host cell expresses the fusion protein encoded by the nucleic acid molecules.

The method can comprise administering to the subject a composition comprising a host cell, wherein the host cell comprises a nucleic acid molecule encoding an immunogenic fusion protein, wherein the nucleic acid molecule comprises a nucleotide sequence that is at least i) 90% identical, ii) 95% identical, iii) 99% identical, or iv) 100% identical to EGFRvIIIx5-PAP$_{33-386}$ as set forth in SEQ ID NO:11. In some aspects, the nucleic acid molecule is operably linked to a promoter. In some embodiments, the host cell expresses the fusion protein encoded by the nucleic acid molecules.

As described previously herein, the nucleic acid molecules can be integrated into the actA locus, inlB locus, or tRNA$^{Arg}$ locus or can be inserted into an expression cassette on an episomal plasmid within the host cell.

In some embodiments, the methods can comprise administering to the subject a composition comprising a host cell, wherein the host cell comprises one or more nucleic acid molecules encoding immunogenic fusion proteins. Any of the herein described host cells comprising one or more nucleic acid molecules can be used in the methods.

The methods can comprise administering to the subject a composition comprising a host cell, wherein the host cell comprises a nucleic acid molecule encoding an immunogenic fusion protein, wherein the nucleic acid molecule comprises: (a) a nucleotide sequence that is at least i) 90% identical, ii) 95% identical, iii) 99% identical, or iv) 100% identical to EGFRvIIIx5-SSX2 as set forth in SEQ ID NO:3; (b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and (c) a nucleotide sequence that is at least i) 90% identical, ii) 95% identical, iii) 99% identical, or iv) 100% identical to EGFRvIIIx5-NKX3.1$_{11-234}$-PSMA$_{1-20,\ 44-438,\ 160-750}$ as set forth in SEQ ID NO:22. In some aspects, the nucleic acid molecule is operably linked to a promoter. In some aspects, the nucleotide sequence that is at least i) 90% identical, ii) 95% identical, iii) 99% identical, or iv) 100% identical to EGFRvIIIx5-SSX2 as set forth in SEQ ID NO:3 can be integrated into the actA locus; the nucleotide sequence that is at least i) 90% identical, ii) 95% identical, iii) 99% identical, or iv) 100% identical to EGFRvIIIx5-PAP$_{33-386}$ as set forth in SEQ ID NO:11 can be integrated into the inlB locus; and the nucleotide sequence that is at least i) 90% identical, ii) 95% identical, iii) 99% identical, or iv) 100% identical to EGFRvIIIx5-NKX3.1$_{11-234}$-PSMA$_{1-20,\ 44-138,\ 169-750}$ as set forth in SEQ ID NO:22 can be integrated into the tRNA$^{Arg}$ locus. In some aspects, the nucleic acid molecule is operably linked to a promoter. In some embodiments, the host cell expresses the fusion protein encoded by the nucleic acid molecules.

The methods can comprise administering to the subject a composition comprising a host cell, wherein the host cell comprises a nucleic acid molecule encoding an immunogenic fusion protein, wherein the nucleic acid molecule comprises: (a) a nucleotide sequence that is at least i) 90% identical, ii) 95% identical, iii) 99% identical, or iv) 100% identical to EGFRvIIIx5-SSX2 as set forth in SEQ ID NO:3; (b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and (c) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20,\ 44-138,\ 169-750}$ as set forth in SEQ ID NO:15. In some aspects, the nucleic acid molecule is operably linked to a promoter. In some aspects, the nucleotide sequence that is at least i) 90% identical, ii) 95% identical, iii) 99% identical, or iv) 100% identical to EGFRvIIIx5-SSX2 as set forth in SEQ ID NO:3 can be integrated into the actA locus; the nucleotide sequence that is at least i) 90% identical, ii) 95% identical, iii) 99% identical, or iv) 100% identical to EGFRvIIIx5-PAP$_{33-386}$ as set forth in SEQ ID NO:11 can be integrated into the inlB locus; and the nucleotide sequence that is at least i) 90% identical, ii) 95% identical, iii) 99% identical, or iv) 100% identical to EGFRvIIIx5-NKX3.1(R41G)$_{11-234}$-PSMA$_{1-20,\ 44-138,\ 169-750}$ as set forth in SEQ ID NO:15 can be integrated into the tRNA$^{Arg}$ locus. In some aspects, the nucleic acid molecule is operably linked to a promoter. In some embodiments, the host cell expresses the fusion protein encoded by the nucleic acid molecules.

The methods can comprise administering to the subject a composing comprising a host cell, wherein the host cell expresses one or more fusion proteins, the fusion proteins being expressed from a nucleic acid molecule comprising:
a) a nucleotide sequence that is at least i) 90% identical, ii) 95% identical, iii) 99% identical, or iv) 100% identical to EGFRvIIIx5-SSX2 as set forth in SEQ ID NO:3;
b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and
c) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20,\ 44-138,\ 169-750}$ as set forth in SEQ ID NO:15.

In some aspects, the one or more nucleic acid molecules listed in a)-c) are operably linked to a promoter.

In some embodiments, the one or more nucleic acid molecules consist of EGFRvIIIx5-SSX2 as set forth in SEQ ID NO:3, EGFRvIIIx5-PAP$_{33-386}$ as set forth in SEQ ID NO:11, and EGFRvIIIx5-NKX3.1(R41G)$_{11-234}$-PSMA$_{1-20,\ 44-138,\ 169-750}$ as set forth in SEQ ID NO:15. In some aspects, the nucleic acid molecule is operably linked to a promoter.

The methods can comprise administering to the subject a composition comprising a host cell, wherein the host cell comprises a nucleic acid molecule encoding an immunogenic fusion protein, wherein the nucleic acid molecule comprises: (a) a nucleotide sequence that is at least i) 90% identical, ii) 95% identical, iii) 99% identical, or iv) 100% identical to NKX3.1-PAP$_{33-386}$ as set forth in SEQ ID NO:26; and (b) a nucleotide sequence that is at least i) 90% identical, ii) 95% identical, iii) 99% identical, or iv) 100% identical to EGFRvIIIx5-SSX2 as set forth in SEQ ID NO:3. In some aspects, the nucleic acid molecule is operably linked to a promoter. In some aspects, the nucleotide sequence that is at least i) 90% identical, ii) 95% identical, iii) 99% identical, or iv) 100% identical to NKX3.1-PAP$_{33-386}$ as set forth in SEQ ID NO:26 can be integrated into the inlB locus and the nucleotide sequence that is at least i) 90% identical, ii) 95% identical, iii) 99% identical, or iv) 100% identical to EGFRvIIIx5-SSX2 as set forth in SEQ ID NO:3 can be integrated into the tRNA$^{Arg}$ locus. In some aspects, the nucleic acid molecule is operably linked to a promoter. In some embodiments, the host cell expresses the fusion protein encoded by the nucleic acid molecules.

The methods can comprise administering to the subject a composition comprising a host cell, wherein the host cell comprises a nucleic acid molecule encoding an immunogenic fusion protein, wherein the nucleic acid molecule comprises: (a) a nucleotide sequence that is at least i) 90% identical, ii) 95% identical, iii) 99% identical, or iv) 100% identical to NKX3.1-PAP$_{33-386}$ as set forth in SEQ ID NO:26; and (b) a nucleotide sequence that is at least i) 90% identical, ii) 95% identical, iii) 99% identical, or iv) 100% identical to ActAN100*-SSX2 as set forth in SEQ ID NO:30. In some aspects, the nucleic acid molecule is operably linked to a promoter. In some aspects, the nucleotide sequence that is at least i) 90% identical, ii) 95% identical, iii) 99% identical, or iv) 100% identical to NKX3.1-PAP$_{33-386}$ as set forth in SEQ ID NO:26 can be integrated into the inlB locus and the nucleotide sequence that is at least i) 90% identical, ii) 95% identical, iii) 99% identical, or iv) 100% identical to ActAN100*-SSX2 as set forth in SEQ ID NO:30 can be integrated into the tRNA$^{Arg}$ locus. In some aspects, the nucleic acid molecule is operably linked to a promoter. In some embodiments, the host cell expresses the fusion protein encoded by the nucleic acid molecules.

Any of the host cells disclosed herein are suitable for use in the disclosed methods. For example, the host cell can be a live-attenuated strain of Listeria monocytogenes which is genetically modified to comprise an attenuating mutation in actA and/or inlB, and preferably a deletion of all or a portion of actA and inlB (referred to herein as "Lm ΔactA/ΔinlB"), and contains a nucleic acid molecule encoding for an immunogenic fusion protein. In some embodiments, the Listeria monocytogenes can be an actA deletion mutant, an actA insertion mutant, an inlB deletion mutant, an inlB insertion mutant, or a combination thereof. For example, the Listeria monocytogenes can be a ΔactA/ΔinlB mutant.

Suitable modes of administering the composition to the subject include, but are not limited to, intravenously, orally, subcutaneously, intradermally, intramuscularly, intraperitoneally, transmucosally, nasal administration, or any combination thereof. In some embodiments, the administering step can be performed intravenously.

The host cell can be utilized as an expression platform for expressing the disclosed immunogenic fusion proteins within the subject, thus eliciting an immune response to the heterologous fusion protein in a subject containing the host cell. For example, the fusion protein can be expressed and secreted from the host cell in the cytosol of an infected cell within the subject. Infected cells include any cell within the subject that can take up the host cell. In some embodiments, the infected cell can be an antigen presenting cell. Antigen presenting cells (APCs) are cells of the immune system used for presenting antigen to T cells. APCs include dendritic cells, monocytes, macrophages, marginal zone Kupffer cells, microglia, Langerhans cells, T cells, and B cells. In some embodiments, the fusion protein can be expressed in one or more cells of the subject.

In some embodiments, methods can comprise administering to the subject a composition comprising a host cell, wherein the host cell comprises a nucleic acid molecule encoding for fusion proteins comprising:
 a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4 or an immunogenic fragment thereof;
 b) an amino acid sequence at least i) 90% identical, ii) 95% identical, iii) 99% identical, or iv) 100% identical to EGFRvIIIx5-PAP$_{33-386}$ as set forth in amino acid residues 89 to 606 of SEQ ID NO:12 or an immunogenic fragment thereof;
 c) an amino acid sequence at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in amino acid residues 89 to 1177 of SEQ ID NO:23 or an immunogenic fragment thereof;
 d) an amino acid sequence at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in amino acid residues 89 to 1177 of SEQ ID NO:16 or an immunogenic fragment thereof;
 e) an amino acid sequence at least i) 90% identical, ii) 95% identical, iii) 99% identical, or iv) 100% identical to NKX3.1-PAP$_{33-386}$ as set forth in amino acid residues 89 to 678 of SEQ ID NO:27 or an immunogenic fragment thereof;
 f) an amino acid sequence at least i) 90% identical, ii) 95% identical, iii) 99% identical, or iv) 100% identical to EGFRvIIIx1-PAP$_{33-386}$ as set forth in amino acid residues 89 to 476 of SEQ ID NO:35 or an immunogenic fragment thereof;
 g) an amino acid sequence at least i) 90% identical, ii) 95% identical, iii) 99% identical, or iv) 100% identical to EGFRvIIIx2-PAP$_{33-386}$ as set forth in amino acid residues 89 to 509 of SEQ ID NO:37 or an immunogenic fragment thereof;
 h) an amino acid sequence at least i) 90% identical, ii) 95% identical, iii) 99% identical, or iv) 100% identical to EGFRvIIIx3-PAP$_{33-386}$ as set forth in amino acid residues 89 to 541 of SEQ ID NO:39 or an immunogenic fragment thereof;
 i) an amino acid sequence at least i) 90% identical, ii) 95% identical, iii) 99% identical, or iv) 100% identical to EGFRvIIIx4-PAP$_{33-386}$ as set forth in amino acid residues 89 to 573 of SEQ ID NO:41 or an immunogenic fragment thereof; or
 j) any combination thereof.

In some aspects, the one or more nucleic acid molecules listed in a)-j) are operably linked to a promoter.

The disclosed methods can be used to elicit an EGFRvIII immune response, an SSX2 immune response, a PAP immune response, a NKX3.1 immune response, a PSMA immune response, immunity against *Listeria*, or any combination thereof. Accordingly, provided are methods of eliciting an EGFRvIII immune response in a subject comprising administering to the subject a composition comprising a host cell, wherein the host cell comprises a nucleic acid molecule encoding an immunogenic fusion protein. Also provided are methods of eliciting an SSX2 immune response in a subject comprising administering to the subject a composition comprising a host cell, wherein the host cell comprises a nucleic acid molecule encoding an immunogenic fusion protein. Also provided are methods of eliciting a PAP immune response in a subject comprising administering to the subject a composition comprising a host cell, wherein the host cell comprises a nucleic acid molecule encoding an immunogenic fusion protein. Also provided are methods of eliciting an NKX3.1 immune response in a subject comprising administering to the subject a composition comprising a host cell, wherein the host cell comprises a nucleic acid molecule encoding an immunogenic fusion protein. Also provided are methods of eliciting a PSMA immune response in a subject comprising administering to the subject a composition comprising a host cell, wherein the host cell comprises a nucleic acid molecule encoding an immunogenic fusion protein. Further provided are methods of eliciting immunity against *Listeria* in a subject comprising administering to the subject a composition comprising *Listeria monocytogenes*, wherein the host cell comprises a nucleic acid molecule encoding an immunogenic fusion protein.

Methods of Increasing Expression of an Antigenic Peptide

Also disclosed herein are methods of increasing expression of an antigenic peptide comprising expressing in a host cell one or more of the disclosed nucleic acid molecules.

The methods of increasing expression of an antigenic polypeptide can comprise expressing in a host cell a nucleic acid molecule, said nucleic acid molecule comprising a nucleic acid sequence encoding:
 a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;
 b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;
 c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11\text{-}234}$ as set forth in SEQ ID NO:25, and a PSMA polypeptide comprising an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20;

d) an EGFRvIII-NKX3.1(R41G)$_{11\text{-}234}$-PSMA$_{1\text{-}20,\ 44\text{-}138,\ 169\text{-}750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11\text{-}234}$ as set forth in SEQ ID NO:18, and a PSMA polypeptide comprising an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20;

e) a NKX3.1-PAP$_{33\text{-}386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33\text{-}386}$ as set forth in SEQ ID NO:14;

f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10;

g) an ActAN100*-PAP$_{30\text{-}386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30\text{-}386}$ as set forth in amino acid residues 103-459 of SEQ ID NO:33; or h) any combination thereof.

In some aspects, the one or more nucleic acid molecules listed in a)-h) are operably linked to a promoter.

The methods can be carried out using any of the nucleic acid molecules disclosed herein. In some embodiments, the methods can comprise expressing in a host cell a nucleic acid molecule comprising one or more copies of a polynucleotide that is at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the SSX2 polynucleotide as set forth in SEQ ID NO:9. In some aspects, the nucleic acid molecule is operably linked to a promoter. In some embodiments, the methods can comprise expressing in a host cell a nucleic acid molecule comprising one or more copies of a polynucleotide that is at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the PAP$_{33\text{-}386}$ polynucleotide as set forth in SEQ ID NO:13. In some aspects, the nucleic acid molecule is operably linked to a promoter. In some embodiments, the methods can comprise expressing in a host cell a nucleic acid molecule comprising one or more copies of a polynucleotide that is at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1$_{11\text{-}234}$ polynucleotide as set forth in SEQ ID NO:24, and a polynucleotide that is at least i) 90% identical, ii) 95% identical, iii) 99% identical, or iv) 100% identical to the PSMA$_{1\text{-}20,\ 44\text{-}138,\ 169\text{-}750}$ as set forth in SEQ ID NO:19. In some aspects, the nucleic acid molecule is operably linked to a promoter. In some embodiments, the methods can comprise expressing in a host cell a nucleic acid molecule comprising one or more copies of a polynucleotide that is at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1(R41G)$_{11\text{-}234}$ polynucleotide as set forth in SEQ ID NO:17, and a polynucleotide that is at least i) 90% identical, ii) 95% identical, iii) 99% identical, or iv) 100% identical to the PSMA$_{1\text{-}20,\ 44\text{-}138,\ 169\text{-}750}$ as set forth in SEQ ID NO:19. In some aspects, the nucleic acid molecule is operably linked to a promoter. In some embodiments, the methods can comprise expressing in a host cell a nucleic acid molecule comprising a polynucleotide that is at least i) 90% identical, ii) 95% identical, iii) 99% identical, or iv) 100% identical to the NKX3.1 polynucleotide as set forth in SEQ ID NO:28 and a polynucleotide that is at least 90% identical to the PAP$_{33\text{-}386}$ polynucleotide as set forth in SEQ ID NO:13. In some aspects, the nucleic acid molecule is operably linked to a promoter.

In some embodiments, the methods can comprise expressing in a host cell a nucleic acid molecule comprising a polynucleotide that is at least i) 90% identical, ii) 95% identical, iii) 99% identical, or iv) 100% identical to ActAN100* as set forth in SEQ ID NO:1 and a polynucleotide at least i) 90% identical, ii) 95% identical, iii) 99% identical, or iv) 100% identical to the SSX2 as set forth in SEQ ID NO:9. In some aspects, the nucleic acid molecule is operably linked to a promoter.

In some embodiments, the methods can comprise expressing in a host cell a nucleic acid molecule comprising a polynucleotide that is at least i) 90% identical, ii) 95% identical, iii) 99% identical, or iv) 100% identical to ActAN100-PAP$_{30\text{-}386}$-SL8 as set forth in SEQ ID NO:32. In some aspects, the nucleic acid molecule is operably linked to a promoter.

In some embodiments, the methods can comprise expressing in a host cell any combination of the above nucleic acid molecules.

The host cells can comprise one or more of the following nucleic acid molecules:

a) a nucleotide sequence that is at least i) 90% identical, ii) 95% identical, iii) 99% identical, or iv) 100% identical to EGFRvIIIx5-SSX2 as set forth in SEQ ID NO:3;

b) a nucleotide sequence that is at least i) 90% identical, ii) 95% identical, iii) 99% identical, or iv) 100% identical to EGFRvIIIx5-PAP$_{33-386}$ as set forth in SEQ ID NO:11;

c) a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22;

d) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15;

e) a nucleotide sequence that is at least i) 90% identical, ii) 95% identical, iii) 99% identical, or iv) 100% identical to NKX3.1-PAP$_{33-386}$ as set forth in SEQ ID NO:26;

f) a nucleotide sequence that is at least i) 90% identical, ii) 95% identical, iii) 99% identical, or iv) 100% identical to ActAN100*-SSX2 as set forth in SEQ ID NO:30;

g) a nucleic acid sequence that is at least i) 90% identical, ii) 95% identical, iii) 99% identical, or iv) 100% identical to ActAN100-PAP$_{30-386}$-SL8 as set forth in SEQ ID NO:32;

h) a nucleotide sequence that is at least i) 90% identical, ii) 95% identical, iii) 99% identical, or iv) 100% identical to EGFRvIIIx1-PAP$_{33-386}$ as set forth in SEQ ID NO:34;

i) a nucleotide sequence that is at least i) 90% identical, ii) 95% identical, iii) 99% identical, or iv) 100% identical to EGFRvIIIx2-PAP$_{33-386}$ as set forth in SEQ ID NO:36;

j) a nucleotide sequence that is at least i) 90% identical, ii) 95% identical, iii) 99% identical, or iv) 100% identical to EGFRvIIIx3-PAP$_{33-386}$ as set forth in SEQ ID NO:38;

k) a nucleotide sequence that is at least i) 90% identical, ii) 95% identical, iii) 99% identical, or iv) 100% identical to EGFRvIIIx4-PAP$_{33-386}$ as set forth in SEQ ID NO:40; or l) or a combination thereof.

In some aspects, the one or more nucleic acid molecules listed in a)-l) are operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx5-SSX2 as set forth in SEQ ID NO:3. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx5-PAP$_{33-386}$ as set forth in SEQ ID NO:11. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx5-NKX3.1(R41G)$_{11-234}$-PSMA$_{11-20, 44-138, 169-750}$ as set forth in SEQ ID NO:15. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to NKX3.1-PAP$_{33-386}$ as set forth in SEQ ID NO:26. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx1-PAP$_{33-386}$ as set forth in SEQ ID NO:34. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx2-PAP$_{33-386}$ as set forth in SEQ ID NO:36. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx3-PAP$_{33-386}$ as set forth in SEQ ID NO:38. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx4-PAP$_{33-386}$ as set forth in SEQ ID NO:40. In some aspects, the nucleic acid molecule is operably linked to a promoter.

In some embodiments, the methods can comprise expressing in a host cell a nucleic acid molecule comprising a nucleotide sequence that is at least i) 90% identical, ii) 95% identical, iii) 99% identical, or iv) 100% identical to EGFRvIIIx5-PAP$_{33-386}$ as set forth in SEQ ID NO:11. In some aspects, the nucleic acid molecule is operably linked to a promoter.

As described previously herein, the nucleic acid molecules can be integrated into the actA locus, inlB locus, or tRNA$^{Arg}$ locus or can be inserted into an expression cassette on an episomal plasmid within the host cell.

In some embodiments, the methods can comprise expressing in a host cell one or more of the above nucleic acid molecules.

The methods can comprise expressing in a host cell a nucleic acid molecule comprising: (a) a nucleotide sequence that is at least i) 90% identical, ii) 95% identical, iii) 99% identical, or iv) 100% identical to EGFRvIIIx5-SSX2 as set forth in SEQ ID NO:3; (b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and (c) a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22. In some aspects, the nucleic acid molecule is operably linked to a promoter. In some aspects, the nucleotide sequence that is at least i) 90% identical, ii) 95% identical, iii) 99% identical, or iv) 100% identical to EGFRvIIIx5-SSX2 as set forth in SEQ ID NO:3 can be integrated into the actA locus; the nucleotide sequence that is at least i) 90% identical, ii) 95% identical, iii) 99% identical, or iv) 100% identical to EGFRvIIIx5-PAP$_{33-386}$ as set forth in SEQ ID NO:11 can be integrated into the inlB locus; and the nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22 can be integrated into the tRNA$^{Arg}$ locus. In some aspects, the nucleic acid molecule is operably linked to a promoter.

The methods can comprise expressing in a host cell a nucleic acid molecule comprising: (a) a nucleotide sequence that is at least i) 90% identical, ii) 95% identical, iii) 99% identical, or iv) 100% identical to EGFRvIIIx5-SSX2 as set forth in SEQ ID NO:3; (b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and (c) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15. In some aspects, the nucleic acid molecule is operably linked to a promoter. In some aspects, the nucleotide sequence that is at least i) 90% identical, ii) 95% identical, iii) 99% identical, or iv) 100% identical to EGFRvIIIx5-SSX2 as set forth in SEQ ID NO:3 can be integrated into the actA locus; the nucleotide sequence that is at least i) 90% identical, ii) 95% identical, iii) 99% identical, or iv) 100% identical to EGFRvIIIx5-PAP$_{33-386}$ as set forth in SEQ ID NO:11 can be integrated into the inlB locus; and the nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15 can be integrated into the tRNA$^{Arg}$ locus. In some aspects, the nucleic acid molecule is operably linked to a promoter.

The methods can comprise expressing in a host cell a nucleic acid molecule comprising: (a) a nucleotide sequence that is at least i) 90% identical, ii) 95% identical, iii) 99% identical, or iv) 100% identical to NKX3.1-PAP$_{33-386}$ as set forth in SEQ ID NO:26; and (b) a nucleotide sequence that is at least i) 90% identical, ii) 95% identical, iii) 99% identical, or iv) 100% identical to EGFRvIIIx5-SSX2 as set forth in SEQ ID NO:3. In some aspects, the nucleic acid molecule is operably linked to a promoter. In some aspects, the nucleotide sequence that is at least i) 90% identical, ii) 95% identical, iii) 99% identical, or iv) 100% identical to NKX3.1-PAP$_{33-386}$ as set forth in SEQ ID NO:26 can be integrated into the inlB locus and the nucleotide sequence that is at least i) 90% identical, ii) 95% identical, iii) 99% identical, or iv) 100% identical to EGFRvIIIx5-SSX2 as set forth in SEQ ID NO:3 thereof can be integrated into the tRNA$^{Arg}$ locus. In some aspects, the nucleic acid molecule is operably linked to a promoter.

The methods can comprise expressing in a host cell a nucleic acid molecule comprising: (a) a nucleotide sequence that is at least i) 90% identical, ii) 95% identical, iii) 99% identical, or iv) 100% identical to NKX3.1-PAP$_{33-386}$ as set forth in SEQ ID NO:26; and (b) a nucleotide sequence that is at least i) 90% identical, ii) 95% identical, iii) 99% identical, or iv) 100% identical to ActAN100*-SSX2 as set forth in SEQ ID NO:30. In some aspects, the nucleic acid molecule is operably linked to a promoter. In some aspects, the nucleotide sequence that is at least i) 90% identical, ii) 95% identical, iii) 99% identical, or iv) 100% identical to NKX3.1-PAP$_{33-386}$ as set forth in SEQ ID NO:26 can be integrated into the inlB locus and the nucleotide sequence that is at least i) 90% identical, ii) 95% identical, iii) 99% identical, or iv) 100% identical to ActAN100*-SSX2 as set forth in SEQ ID NO:30 can be integrated into the tRNA$^{Arg}$ locus. In some aspects, the nucleic acid molecule is operably linked to a promoter.

The disclosed methods can be performed in any host cell that supports, or can be configured to support, transcription of the disclosed nucleic acid molecules and expression of the antigenic polypeptide including, but not limited to, bacterial cells, viral cells, yeast cells, insect cells, and mammalian cells. The expressing step can be performed by introducing the nucleic acid molecule into a host cell and allowing the host cell machinery to produce the antigenic polypeptide. For example, the host cell can be a live-attenuated strain of *Listeria monocytogenes* which is genetically modified to comprise an attenuating mutation in actA and/or inlB, and preferably a deletion of all or a portion of actA and inlB (referred to herein as "Lm ΔactA/ΔinlB"), and contains a nucleic acid molecule encoding for an immunogenic fusion protein. In some embodiments, the *Listeria monocytogenes* can be an actA deletion mutant, an actA insertion mutant, an inlB deletion mutant, an inlB insertion mutant, or a combination thereof. For example, the *Listeria monocytogenes* can be a ΔactA/ΔinlB mutant.

Alternatively, the expressing step can be performed by administering the host cell to a cell of interest, wherein the antigenic polypeptide is produced within said cell of interest. In some embodiments, the expressing step can be performed by infecting a cell of interest with the host cell, wherein the antigenic polypeptide is produced within the cell of interest. In some embodiments, the expressing step can be performed by administering the host cell to a subject, wherein the antigenic polypeptide is produced within the subject.

The methods can comprise expressing in a host cell a nucleic acid molecule encoding for fusion proteins comprising:

a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4 or an immunogenic fragment thereof;

b) an amino acid sequence at least i) 90% identical, ii) 95% identical, iii) 99% identical, or iv) 100% identical to EGFRvIIIx5-PAP$_{33-386}$ as set forth in amino acid residues 89 to 606 of SEQ ID NO:12 or an immunogenic fragment thereof;

c) an amino acid sequence at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in amino acid residues 89 to 1177 of SEQ ID NO:23 or an immunogenic fragment thereof;

d) an amino acid sequence at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in amino acid residues 89 to 1177 of SEQ ID NO:16 or an immunogenic fragment thereof;

e) an amino acid sequence at least i) 90% identical, ii) 95% identical, iii) 99% identical, or iv) 100% identical to NKX3.1-PAP$_{33-386}$ as set forth in amino acid residues 89 to 678 of SEQ ID NO:27 or an immunogenic fragment thereof;

f) an amino acid sequence at least i) 90% identical, ii) 95% identical, iii) 99% identical, or iv) 100% identical to EGFRvIIIx1-PAP$_{33-386}$ as set forth in amino acid residues 89 to 476 of SEQ ID NO:35 or an immunogenic fragment thereof;

g) an amino acid sequence at least i) 90% identical, ii) 95% identical, iii) 99% identical, or iv) 100% identical to EGFRvIIIx2-PAP$_{33-386}$ as set forth in amino acid residues 89 to 509 of SEQ ID NO:37 or an immunogenic fragment thereof;

h) an amino acid sequence at least i) 90% identical, ii) 95% identical, iii) 99% identical, or iv) 100% identical to EGFRvIIIx3-PAP$_{33-386}$ as set forth in amino acid residues 89 to 541 of SEQ ID NO:39 or an immunogenic fragment thereof;

i) an amino acid sequence at least i) 90% identical, ii) 95% identical, iii) 99% identical, or iv) 100% identical to EGFRvIIIx4-PAP$_{33-386}$ as set forth in amino acid residues 89 to 573 of SEQ ID NO:41 or an immunogenic fragment thereof; or j) any combination thereof.

In some aspects, the one or more nucleic acid molecules listed in a)-j) are operably linked to a promoter.

Methods of Treating Cancer

Disclosed herein are methods of treating cancer in a subject in need thereof, said methods comprising administering to the subject a therapeutically effective amount of a composition comprising a host cell, wherein the host cell comprises one or more of the nucleic acids disclosed herein. In some embodiments, the host cells express one or more fusion proteins encoded by the one or more nucleic acid molecules. For example, the host cell can comprise one or more nucleic acid molecules comprising a nucleic acid sequence encoding:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;

c) an EGFRvIII-NKX3.1$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20;

d) an EGFRvIII-NKX3.1(R41G)$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20,\ 44-138,\ 169-750}$ as set forth in SEQ ID NO:20;

e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14;

f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; or g) an ActAN100-PAP$_{30-386}$ fusion protein, wherein the fusion protein comprises an ActAN100 polypeptide comprising an amino acid sequence at least i) 90% identical, ii) 95% identical, iii) 99% identical, or iv) 100% identical to ActAN100 as set forth in amino acid residues 1 to 100 of SEQ ID NO:33 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or h) any combination thereof.

In some aspects, the one or more nucleic acid molecules listed in a)-h) are operably linked to a promoter.

Also disclosed are methods of treating cancer in a subject in need thereof, said method comprising administering to the subject a therapeutically effective amount of a composition comprising a host cell, wherein the host cell expresses one or more fusion proteins comprising:

a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10;

b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14;

c) an EGFRvIII-NKX3.1$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11\text{-}234}$ as set forth in SEQ ID NO:25, and a PSMA polypeptide comprising an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20;

d) an EGFRvIII-NKX3.1(R41G)$_{11\text{-}234}$-PSMA$_{1\text{-}20,\ 44\text{-}138,\ 169\text{-}750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11\text{-}234}$ as set forth in SEQ ID NO:18, and a PSMA polypeptide comprising an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20;

e) a NKX3.1-PAP$_{33\text{-}386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33\text{-}386}$ as set forth in SEQ ID NO:14;

f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; or g) an ActAN100-PAP$_{30\text{-}386}$ fusion protein, wherein the fusion protein comprises an ActAN100 polypeptide comprising an amino acid sequence at least i) 90% identical, ii) 95% identical, iii) 99% identical, or iv) 100% identical to ActAN100 as set forth in to amino acid residues 1 to 100 of SEQ ID NO:33 and a PAP polypeptide comprising an amino acid sequence at least i) 90% identical, ii) 95% identical, iii) 99% identical, or iv) 100% identical to PAP$_{30\text{-}386}$ as set forth in amino acid residues 103-459 of SEQ ID NO:33; or h) any combination thereof.

In some embodiments, the host cell expresses (a), (b), and (d).

In some embodiments, the one or more nucleic acid molecules can comprise a nucleotide sequence that is at least i) 90% identical, ii) 95% identical, iii) 99% identical, or iv) 100% identical to EGFRvIIIx5-SSX2 as set forth in SEQ ID NO:3. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to EGFRvIIIx1-PAP$_{33\text{-}386}$ as set forth in SEQ ID NO:34. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to EGFRvIIIx2-PAP$_{33\text{-}386}$ as set forth in SEQ ID NO:36. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to EGFRvIIIx3-PAP$_{33\text{-}386}$ as set forth in SEQ ID NO:38. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to EGFRvIIIx4-PAP$_{33\text{-}386}$ as set forth in SEQ ID NO:40. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to EGFRvIIIx5-PAP$_{33\text{-}386}$ as set forth in SEQ ID NO:11. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to EGFRvIIIx5-NKX3.1$_{11\text{-}234}$-PSMA$_{1\text{-}20,\ 44\text{-}138,\ 169\text{-}750}$ as set forth in SEQ ID NO:22. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to EGFRvIIIx5-NKX3.1 (R41G)$_{11\text{-}234}$-PSMA$_{1\text{-}20,\ 44\text{-}138,\ 169\text{-}750}$ as set forth in SEQ ID NO:15. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to NKX3.1-PAP$_{33\text{-}386}$ as set forth in SEQ ID NO:26. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to ActAN100*-SSX2 as set forth in SEQ ID NO:30. In some aspects, the nucleic acid molecule is operably linked to a promoter. In some embodiments, the one or more nucleic acid molecules can comprise a nucleotide sequence that is at least i) 90% identical, ii) 95% identical, iii) 99% identical, or iv) 100% identical to ActAN100-PAP$_{30\text{-}386}$-SL8 as set forth in SEQ ID NO:32. In some aspects, the nucleic acid molecule is operably linked to a promoter. In some embodiments, the one or more nucleic acid molecules can comprise any combination thereof. The host cell can expresses the fusion protein encoded by any of the above nucleic acid molecules.

In some aspects, the methods comprising administering to the subject a therapeutically effective amount of a composition comprising a host cell, wherein the host cell expresses one or more fusion proteins, the fusion proteins being expressed from a nucleic acid molecule comprising:

a) a nucleotide sequence that is at least i) 90% identical, ii) 95% identical, iii) 99% identical, or iv) 100% identical to EGFRvIIIx5-SSX2 as set forth in SEQ ID NO:3;

b) a nucleotide sequence that is at least i) 90% identical, ii) 95% identical, iii) 99% identical, or iv) 100% identical to EGFRvIIIx5-PAP$_{33\text{-}386}$ as set forth in SEQ ID NO:11; and c) a nucleotide sequence that is at least i) 90% identical, ii) 95% identical, iii) 99% identical, or iv) 100% identical to EGFRvIIIx5-NKX3.1(R41G)$_{11\text{-}234}$-PSMA$_{1\text{-}20,\ 44\text{-}138,\ 169\text{-}750}$ as set forth in SEQ ID NO:15.

In some aspects, the one or more nucleic acid molecules listed in a)-c) are operably linked to a promoter.

In some embodiments, the nucleotide sequences can be operably lined to an ActA promoter. The ActA promoter can have the sequence set forth as SEQ ID NO:21.

In some aspects, the fusion proteins are expressed from a nucleic acid molecule consisting of:
a) a nucleotide sequence that is at least i) 90% identical, ii) 95% identical, iii) 99% identical, or iv) 100% identical to EGFRvIIIx5-SSX2 as set forth in SEQ ID NO:3;
b) a nucleotide sequence that is at least i) 90% identical, ii) 95% identical, iii) 99% identical, or iv) 100% identical to EGFRvIIIx5-PAP$_{33\text{-}386}$ as set forth in SEQ ID NO:11; and
c) a nucleotide sequence that is at least i) 90% identical, ii) 95% identical, iii) 99% identical, or iv) 100% identical to EGFRvIIIx5-NKX3.1(R41G)$_{11\text{-}234}$-PSMA$_{1\text{-}20,\ 44\text{-}138,\ 169\text{-}750}$ as set forth in SEQ ID NO:15.

In some aspects, the one or more nucleic acid molecules listed in a)-c) are operably linked to a promoter.

In some embodiments, the nucleotide sequences can be operably lined to an ActA promoter. The ActA promoter can have the sequence set forth as SEQ ID NO:21.

In some aspects, the fusion proteins are expressed from a nucleic acid molecule consisting of EGFRvIIIx5-SSX2 as set forth in SEQ ID NO:3, EGFRvIIIx5-PAP$_{33\text{-}386}$ as set forth in SEQ ID NO:11, and EGFRvIIIx5-NKX3.1(R41G)$_{11\text{-}234}$-PSMA$_{1\text{-}20,\ 44\text{-}138,\ 169\text{-}750}$ as set forth in SEQ ID NO:15. In some aspects, the nucleic acid molecule is operably linked to a promoter.

The host cells can comprise the nucleic acid molecules integrated into the host cell genome. Such host cells contain nucleic acids that are under the control of host cell expression sequences and thereby do not require eukaryotic transcriptional or translational elements. The nucleic acid molecule can be integrated into the actA locus, inlB locus or tRNA$^{Arg}$ locus. In some embodiments, the nucleic acid molecule can be integrated into the actA locus. In some embodiments, the nucleic acid molecule can be integrated into the inlB locus. In some embodiments, the nucleic acid molecule can be integrated into the tRNA$^{Arg}$ locus. The host cells can comprise the nucleic acid molecule encoding the fusion protein wherein the nucleic acid molecule is within the host cell extrachromosomally. For example, one or more of the disclosed nucleic acid molecules encoding an immunogenic fusion protein can be inserted into an expression cassette on an episomal plasmid within the host cell.

The methods can comprise administering to the subject a therapeutically effective amount of a composition comprising a host cell, wherein the host cell comprises one or more nucleic acid molecules comprising: (a) a nucleotide sequence that is at least i) 90% identical, ii) 95% identical, iii) 99% identical, or iv) 100% identical to EGFRvIIIx5-SSX2 as set forth in SEQ ID NO:3; (b) a nucleotide sequence that is at least i) 90% identical, ii) 95% identical, iii) 99% identical, or iv) 100% identical to EGFRvIIIx5-PAP$_{33\text{-}386}$ as set forth in SEQ ID NO:11; and (c) a nucleotide sequence that is at least i) 90% identical, ii) 95% identical, iii) 99% identical, or iv) 100% identical to EGFRvIIIx5-NKX3.1$_{11\text{-}234}$-PSMA$_{1\text{-}20,\ 44\text{-}138,\ 169\text{-}750}$ as set forth in SEQ ID NO:22. In some aspects, the nucleic acid molecule is operably linked to a promoter. In some aspects, the nucleotide sequence that is at least i) 90% identical, ii) 95% identical, iii) 99% identical, or iv) 100% identical to EGFRvIIIx5-SSX2 as set forth in SEQ ID NO:3 can be integrated into the actA locus; the nucleotide sequence that is at least i) 90% identical, ii) 95% identical, iii) 99% identical, or iv) 100% identical to EGFRvIIIx5-PAP$_{33\text{-}386}$ as set forth in SEQ ID NO:11 can be integrated into the inlB locus; and the nucleotide sequence that is at least i) 90% identical, ii) 95% identical, iii) 99% identical, or iv) 100% identical to EGFRvIIIx5-NKX3.1$_{11\text{-}234}$-PSMA$_{1\text{-}20,\ 44\text{-}138,\ 169\text{-}750}$ as set forth in SEQ ID NO:22 can be integrated into the tRNA$^{Arg}$ locus. In some aspects, the nucleic acid molecule is operably linked to a promoter.

The methods can comprise administering to the subject a therapeutically effective amount of a composition comprising a host cell, wherein the host cell comprises one or more nucleic acid molecules comprising: (a) a nucleotide sequence that is at least i) 90% identical, ii) 95% identical, iii) 99% identical, or iv) 100% identical to EGFRvIIIx5-SSX2 as set forth in SEQ ID NO:3; (b) a nucleotide sequence that is at least i) 90% identical, ii) 95% identical, iii) 99% identical, or iv) 100% identical to EGFRvIIIx5-PAP$_{33\text{-}386}$ as set forth in SEQ ID NO:11; and (c) a nucleotide sequence that is at least i) 90% identical, ii) 95% identical, iii) 99% identical, or iv) 100% identical to EGFRvIIIx5-NKX3.1(R41G)$_{11\text{-}234}$-PSMA$_{1\text{-}20,\ 44\text{-}138,\ 169\text{-}750}$ as set forth in SEQ ID NO:15. In some aspects, the nucleic acid molecule is operably linked to a promoter. In some aspects, the nucleotide sequence that is at least i) 90% identical, ii) 95% identical, iii) 99% identical, or iv) 100% identical to EGFRvIIIx5-SSX2 as set forth in SEQ ID NO:3 can be integrated into the actA locus; the nucleotide sequence that is at least i) 90% identical, ii) 95% identical, iii) 99% identical, or iv) 100% identical to EGFRvIIIx5-PAP$_{33\text{-}386}$ as set forth in SEQ ID NO:11 can be integrated into the inlB locus; and the nucleotide sequence that is at least i) 90% identical, ii) 95% identical, iii) 99% identical, or iv) 100% identical to EGFRvIIIx5-NKX3.1 (R41G)$_{11\text{-}234}$-PSMA$_{1\text{-}20,\ 44\text{-}138,\ 169\text{-}750}$ as set forth in SEQ ID NO:15 can be integrated into the tRNA$^{Arg}$ locus. In some aspects, the nucleic acid molecule is operably linked to a promoter.

The methods can comprise administering to the subject a therapeutically effective amount of a composition comprising a host cell, wherein the host cell comprises one or more nucleic acid molecules comprising: (a) a nucleotide sequence that is at least i) 90% identical, ii) 95% identical, iii) 99% identical, or iv) 100% identical to NKX3.1-PAP$_{33\text{-}386}$ as set forth in SEQ ID NO:26; and (b) a nucleotide sequence that is at least i) 90% identical, ii) 95% identical, iii) 99% identical, or iv) 100% identical to EGFRvIIIx5-SSX2 as set forth in SEQ ID NO:3. In some aspects, the nucleic acid molecule is operably linked to a promoter. In some aspects, the nucleotide sequence that is at least i) 90% identical, ii) 95% identical, iii) 99% identical, or iv) 100% identical to NKX3.1-PAP$_{33\text{-}386}$ as set forth in SEQ ID NO:26 can be integrated into the inlB locus and the nucleotide sequence that is at least i) 90% identical, ii) 95% identical, iii) 99% identical, or iv) 100% identical to EGFRvIIIx5-SSX2 as set forth in SEQ ID NO:3 can be integrated into the tRNA$^{Arg}$ locus. In some aspects, the nucleic acid molecule is operably linked to a promoter.

The methods can comprise administering to the subject a therapeutically effective amount of a composition comprising a host cell, wherein the host cell comprises one or more nucleic acid molecules comprising: (a) a nucleotide sequence that is at least i) 90% identical, ii) 95% identical, iii) 99% identical, or iv) 100% identical to NKX3.1-PAP$_{33\text{-}386}$ as set forth in SEQ ID NO:26; and (b) a nucleotide sequence that is at least i) 90% identical, ii) 95% identical, iii) 99% identical, or iv) 100% identical to SSX2 as set forth in SEQ ID NO:30. In some aspects, the nucleic acid molecule is operably linked to a promoter. In some aspects, the nucleotide sequence that is at least i) 90% identical, ii) 95% identical, iii) 99% identical, or iv) 100% identical to NKX3.1-PAP$_{33-386}$ as set forth in SEQ ID NO:26 can be integrated into the inlB locus and the nucleotide sequence that is at least i) 90% identical, ii) 95% identical, iii) 99% identical, or iv) 100% identical to SSX2 as set forth in SEQ ID NO:30 can be integrated into the tRNA$^{Arg}$ locus. In some aspects, the nucleic acid molecule is operably linked to a promoter.

PAP is one of the major proteins secreted by prostate columnar epithelium cells, both benign and malignant. The efficacy of PAP as an agent in immunotherapy was validated in the 2010 FDA approval of sipuleucel-T (Provenge®), an autologous cellular immunotherapy that targets PAP as a treatment for advanced prostate cancer.

PSMA is a 100 kDA type II transmembrane glycoprotein with folate hydrolase and neurocarboxypeptidase activity. A nonsecretory, integral cell-surface membrane protein, PSMA is expressed in virtually all prostate cancers, with expression increasing progressively in higher-grade malignancies, metastatic disease and castration-resistant prostate cancer. The role of PSMA in prostate cancer is unknown, however the expression of PSMA correlates with disease progression, which suggests that PSMA has a functional role in the progression of prostate cancer. PSMA is also expressed in the neovasculature of solid tumors but not in normal vasculature. Although the role in neovasculature is unknown, it is possible that the folate hydrolase activity of PSMA is important in facilitating vasculogenesis in epithelial tissues.

SSX proteins are cancer-testis antigens (CTAs) representing a superfamily of highly homologous CTAs with nuclear localization, restricted expression in HLA Class I-deficient testis or ovary germline cells, and frequent overexpression in tumors of various histologic origins, especially in advanced-stage cancer. The expression of SSX proteins has been associated with stem cell migration, which suggests that it plays an important biological role for the metastatic phenotype. Because germ cells do not express Class I MEW molecules, they are protected from bystander autoimmunity. The overexpression of SSX2 in cancer cells and its limited expression in normal HLA Class I-expressing cells, make SSX2 a particularly attractive immunotherapy target for T-cell-based strategies. CTAs are normally expressed only in germ cells of the testis and have been shown to be spontaneously immunogenic in cancer patients. The ectopic expression of CTA in cancer tissue make these proteins ideal immunotherapy targets. Importantly, SSX2 was selected as an immune target for prostate cancer since IgG responses and CD8$^+$ T cells specific for SSX-2 can be detected in prostate cancer patients, and expression has been demonstrated in advanced prostate cancer.

NKX3.1 is a homeobox protein and maps to the minimal region of human chromosome hp21. NKX3.1 is required for normal prostate development and is associated with all aspects of embryonic prostate development, neonatal differentiation, and adult function. It is the earliest known marker of prostate formation and continues to be expressed at all stages of prostate differentiation and in adulthood. A tissue-specific regulatory gene, NKX3.1 is essential to normal morphogenesis and function of the prostate whereas its inactivation leads to prostatic epithelial hyperplasia and dysplasia that model a preneoplastic condition. NKX3.1 marks a population of luminal cells with stem-like properties that persists in the prostate after androgen ablation. Importantly, these castration-resistant NKX3.1-expressing cells (CARNs) were shown to act as cells of origin for prostate cancer, since deletion of NKX3.1-expressing cells rendered prostate tumors unable to progress after androgen ablation and testosterone depletion. NKX3.1's unique overexpression on CARNs opens up the possibility to target the direct precursors of prostate CSC by vaccinating against this antigen. In addition, human NKX3.1 was recently identified as 1 of 7 prostate cancer susceptibility loci through a genome-wide association screen, making it an extremely attractive new antigenic target for immunotherapy of prostate cancer. Recent analyses indicate that low levels of NKX3.1 can be demonstrated in nearly all prostate cancers and metastases examined. Thus there appears to be a selection for reduction, but not loss, of NKX3.1 expression throughout cancer progression.

EGFR is a receptor tyrosine kinase critical for cell growth and survival. The EGFR gene is frequently overexpressed or mutated in human cancers, including head and neck, colon, pancreas, breast, ovary, kidney, and malignant gliomas. EGFRvIII results from a 267 amino acid deletion and the fusion of exon 1 with exon 8, yielding a tumor-specific peptide with a novel glycine at the junction. Patients with EGFRvIII-expressing breast cancers have detectable humoral and cellular immune responses against this peptide, suggesting that it serves as an immunogenic neoantigen. The EGFRvIII repeat sequence was included in the disclosed immunogenic fusion proteins due to its correlation with higher expression of the fusion proteins (PAP, PSMA, SSX2, and NKX3.1) and higher antigen-specific immune responses to the prostate cancer-relevant antigens. As native EGFR is required for signal transduction in normal-functioning cell populations, it is important to note that the disclosed immunogenic fusion proteins contain only the 21 amino acid segment of the EGVRvIII neoantigenic region expressed by deletion of exons 2 to 7 in tumor cells.

Accordingly, suitable cancers that can be treated with the disclosed methods include EGFRvIII-expressing cancer, a SSX2-expressing cancer, a PAP-expressing cancer, a NKX3.1-expressing cancer, a PSMA-expressing cancer, or any combination thereof. Preferably, the cancer is prostate cancer.

Any of the host cells disclosed herein are suitable for use in the disclosed methods. For example, the host cell can be *Listeria monocytogenes*. In a preferred aspect, the host cell can be a live-attenuated strain of *Listeria monocytogenes* which is genetically modified to comprise an attenuating mutation in actA and/or inlB, and preferably a deletion of all or a portion of actA and inlB (referred to herein as "Lm ΔactA/ΔinlB"), and contains a nucleic acid molecule encoding for one or more of the disclosed immunogenic fusion proteins. In some embodiments, the *Listeria monocytogenes* can be an actA deletion (ΔactA) mutant, an actA insertion mutant, an inlB deletion (ΔinlB) mutant, an inlB insertion mutant, or a combination thereof. For example, the *Listeria monocytogenes* can be a ΔactA/ΔinlB mutant.

The host cell can be utilized as an expression platform for expressing the immunogenic fusion proteins encoded by the nucleic acid molecules within the subject, thus eliciting an anti-tumor response to EGFRvIII-expressing tumor cells, SSX2-expressing tumor cells, PAP-expressing tumor cells, NKX3.1-expressing tumor cells, and/or PSMA-expressing tumor cells. The fusion protein can be expressed and secreted from the host cell in the cytosol of an infected cell within the subject. Infected cells include any cell within the subject that can take up the host cell. In some embodiments, the infected cell can be an antigen presenting cell.

The host cell can comprise one or more nucleic acid molecules comprising a nucleic acid sequence encoding an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to EGFRvIIIx5-PAP$_{33\text{-}386}$ as set forth in amino acid residues 89 to 606 of SEQ ID NO:12. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to EGFRvIIIx5-NKX3.1$_{11\text{-}234}$-PSMA$_{1\text{-}20,\ 44\text{-}138,\ 169\text{-}750}$ as set forth in amino acid residues 89 to 1177 of SEQ ID NO:23. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to EGFRvIIIx5-NKX3.1(R41G)$_{11\text{-}234}$-PSMA$_{1\text{-}20,\ 44\text{-}138,\ 169\text{-}750}$ as set forth in amino acid residues 89 to 1177 of SEQ ID NO:16. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to NKX3.1-PAP$_{33\text{-}386}$ as set forth in amino acid residues 89 to 678 of SEQ ID NO:27. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to ActAN100*-SSX2 as set forth in SEQ ID NO:31. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to ActAN100-PAP$_{30\text{-}386}$ as set forth in amino acid residues 1-459 of SEQ ID NO:33. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to ActAN100*-EGFRvIIIx1-PAP$_{33\text{-}386}$ as set forth in amino acid residues 89 to 476 of SEQ ID NO:35. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to ActAN100*-EGFRvIIIx2-PAP$_{33\text{-}386}$ as set forth in amino acid residues 89 to 509 of SEQ ID NO:37. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to ActAN100*-EGFRvIIIx3-PAP$_{33\text{-}386}$ as set forth in amino acid residues 89 to 541 of SEQ ID NO:39. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding an amino acid sequence at least i) 90% identical, ii) 95% identical, iii) 99% identical, or iv) 100% identical to ActAN100*-EGFRvIIIx4-PAP$_{33\text{-}386}$ as set forth in amino acid residues 89 to 573 of SEQ ID NO:41. In some aspects, the nucleic acid molecule is operably linked to a promoter. In some embodiments, the host cell expresses the fusion protein encoded by the nucleic acid molecules.

The host cell can comprise one or more nucleic acid molecules comprising a nucleic acid sequence encoding any combination of the above amino acid sequences. In some embodiments, the host cell expresses a combination of fusion proteins encoded by the one or more nucleic acid molecules. For example, the host cell can express one or more fusion proteins comprising:

a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4;

b) an amino acid sequence at least i) 90% identical, ii) 95% identical, iii) 99% identical, or iv) 100% identical to EGFRvIIIx5-PAP$_{33\text{-}386}$ as set forth in amino acid residues 89 to 606 of SEQ ID NO:12; and c) an amino acid sequence at least i) 90% identical, ii) 95% identical, iii) 99% identical, or iv) 100% identical to EGFRvIIIx5-NKX3.1(R41G)$_{11\text{-}234}$-PSMA$_{1\text{-}20,\ 44\text{-}138,\ 169\text{-}750}$ as set forth in amino acid residues 89 to 1177 of SEQ ID NO:16.

In some aspects, the one or more nucleic acid molecules listed in a)-c) are operably linked to a promoter.

The host cell can express one or more fusion proteins consisting of:

a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4;

b) an amino acid sequence at least i) 90% identical, ii) 95% identical, iii) 99% identical, or iv) 100% identical to EGFRvIIIx5-PAP$_{33\text{-}386}$ as set forth in amino acid residues 89 to 606 of SEQ ID NO:12; and c) an amino acid sequence at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in amino acid residues 89 to 1177 of SEQ ID NO:16

The host cell can express one or more fusion proteins consisting of EGFRvIIIx5-SSX2 as set forth in amino acid residues 89 to 475 of SEQ ID NO:4, EGFRvIIIx5-PAP$_{33-386}$ as set forth in amino acid residues 89 to 606 of SEQ ID NO:12, and EGFRvIIIx5-NKX3.1(R41G)$_{11-234}$-PSMA$_{1-20, 44-138, 169-750}$ as set forth in amino acid residues 89 to 1177 of SEQ ID NO:16.

The disclosed methods can further comprise measuring expression of EGFRvIII, SSX2, PAP, NKX3.1, PSMA, or any combination thereof in a biological sample from the subject prior to administering the composition. Methods for measuring expression levels of EGFRvIII, SSX2, PAP, NKX3.1, PSMA, or a combination thereof in a biological sample from the subject include, but are not limited to, immunohistochemistry (IHC), Western Blotting, microscopy, immunoprecipitation, BCA assays, spectrophotometry, in vivo imaging, or any combination thereof. EGFRvIII, SSX2, PAP, NKX3.1, and/or PSMA can be detected in biological samples including, but are not limited to, blood, lymph fluid, bone marrow, a solid tumor sample, or any combination thereof.

The compositions can further comprise a pharmaceutically acceptable excipient. For example, the host cells can be combined with any suitable buffer, including but not limited to, phosphate-buffered saline (PBS), and glycerol. In an exemplary embodiment, the composition can be formulated in Dulbecco's phosphate-buffered saline (PBS) and glycerol, stored frozen (at or below −60° C.) until administration, and administered by intravenous (IV) infusion in sodium chloride over a suitable period of time. One skilled in the art would know that the period of time for administering the composition depends, in part, on the type of cancer, the severity of the cancer, and the subject's age, weight, etc. Preferably, the composition can be administered over a period of hours. For example, the composition can be administered over a 1-2 hour period. In other embodiments, the composition can be administered in less than 1-2 hours. In yet other embodiments, the composition can be administered in greater than 1-2 hours.

Treatment can include a single dose of the composition or multiple doses of the composition. Thus, the disclosed methods can comprise administering to the subject one or more doses of a composition comprising a host cell, wherein the host cell comprises a nucleic acid molecule encoding an immunogenic fusion protein. Factors that can determine the number of doses include, for example, the progression of the cancer, the severity of the cancer symptoms, the frequency of the cancer symptoms, tumor size, or any combination thereof. Without intent to be limiting, the number of doses can increased based upon progression or failure to reduce the progression of the cancer, increased severity or no change in severity of the cancer symptoms, increased frequency or no change in the frequency of the cancer symptoms, increased size or no change in size of the tumor, or any combination thereof. For example, the subject can be administered 1 to 100 doses or more of the composition.

Factors that can determine the dose of the host cell include, for example, the progression of the cancer, the severity of the cancer symptoms, the frequency of the cancer symptoms, tumor size, or any combination thereof. In some embodiments, the composition can comprise about $1 \times 10^8$ to about $1 \times 10^9$ colony forming units (CFU) of a host cell. In some aspects, the composition can comprise about $1 \times 10^8$ CFU of a host cell. In some aspects, the composition can comprise about $1 \times 10^9$ CFU of a host cell.

The composition can be administered about once every 7 days, about once about every 14 days, about once every 21 days, about once every 28 days, about once every 35 days, about once every 42 days, about once every 49 days, about once every 56 days, about once every 63 days, about once every 70 days, about once every 77 days, about once every 84 days, or about once every 91 days.

Based on the forgoing, those skilled in the art would understand that a subject could be treated for the progression of cancer, the severity of cancer symptoms, the frequency of cancer symptoms, tumor size, or any combination thereof by administering a described dose of any one of the compositions descried herein, where the dosing is repeated at a regular interval as described. Accordingly, in one embodiment a composition may be administered to a subject at a dose of about $1 \times 10^8$ to about $1 \times 10^9$ CFU to treat the progression of cancer, the severity of cancer symptoms, the frequency of cancer symptoms, tumor size, or any combination thereof, where the dosing is repeated about once every 7 days. Furthermore, the compositions described herein could be prepared in a pharmaceutical preparation suitable for such a dose to be administered in this manner. In one embodiment a composition may be administered to a subject at a dose of about $1 \times 10^8$ to about $1 \times 10^9$ CFU to treat the progression of cancer, the severity of cancer symptoms, the frequency of cancer symptoms, tumor size, or any combination thereof, where the dosing is repeated about once every 14 days. Furthermore, the compositions described herein could be prepared in a pharmaceutical preparation suitable for such a dose to be administered in this manner. In one embodiment a composition may be administered to a subject at a dose of about $1 \times 10^8$ to about $1 \times 10^9$ CFU to treat the progression of cancer, the severity of cancer symptoms, the frequency of cancer symptoms, tumor size, or any combination thereof, where the dosing is repeated about once every 21 days. Furthermore, the compositions described herein could be prepared in a pharmaceutical preparation suitable for such a dose to be administered in this manner. In one embodiment a composition may be administered to a subject at a dose of about $1 \times 10^8$ to about $1 \times 10^9$ CFU to treat the progression of cancer, the severity of cancer symptoms, the frequency of cancer symptoms, tumor size, or any combination thereof, where the dosing is repeated about once every 35 days. Furthermore, the compositions described herein could be prepared in a pharmaceutical preparation suitable for such a dose to be administered in this manner. In one embodiment a composition may be administered to a subject at a dose of about $1 \times 10^8$ to about $1 \times 10^9$ CFU to treat the progression of cancer, the severity of cancer symptoms, the frequency of cancer symptoms, tumor size, or any combination thereof, where the dosing is repeated about once every 45 days. Furthermore, the compositions described herein could be prepared in a pharmaceutical preparation suitable for such a dose to be administered in this manner. In one embodiment a composition may be administered to a subject at a dose of about $1 \times 10^8$ to about $1 \times 10^9$ CFU to treat the progression of cancer, the severity of cancer symptoms, the frequency of cancer symptoms, tumor size, or any combination thereof, where the dosing is repeated about once every 60 days. Furthermore, the compositions described herein could be prepared in a pharmaceutical preparation suitable for such a dose to be administered in this manner. In one embodiment a composition may be administered to a subject at a dose of about $1 \times 10^8$ to about $1 \times 10^9$ CFU to treat the progression of cancer, the severity of cancer symptoms, the frequency of cancer symptoms, tumor size, or any combination thereof, where the dosing is repeated about once every 90 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 7 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 14 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 21 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 35 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 45 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 60 days. Furthermore, the compositions described herein could be prepared in a pharmaceutical preparation suitable for such a dose to be administered in this manner. In one embodiment a composition may be administered to a subject at a dose of about $1\times10^8$ CFU to treat the progression of cancer, the severity of cancer symptoms, the frequency of cancer symptoms, tumor size, or any combination thereof, where the dosing is repeated about once every 90 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 7 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 14 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 21 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 35 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 45 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 60 days. Furthermore, the compositions described herein could be prepared in a pharmaceutical preparation suitable for such a dose to be administered in this manner. In one embodiment a composition may be administered to a subject at a dose of about $1\times10^9$ CFU to treat the progression of cancer, the severity of cancer symptoms, the frequency of cancer symptoms, tumor size, or any combination thereof, where the dosing is repeated about once every 90 days. Furthermore, the compositions described herein could be prepared in a pharmaceutical preparation suitable for such a dose to be administered in this manner.

Preferably, treatment can include a period of time between doses wherein the composition is not administered to the subject. For example, the methods can comprise administering to the subject a first dose of a composition comprising a host cell, wherein the host cell comprises a nucleic acid molecule encoding an immunogenic fusion protein, monitoring the efficacy of the first dose, and, if the first dose is not efficacious, administering to the subject one or more doses of the composition. Factors that can determine the efficacy of the composition include, for example, the progression of the cancer, the severity of the cancer symptoms, the frequency of the cancer symptoms, tumor size, or any combination thereof. Without intent to be limiting, progression or failure to reduce the progression of the cancer, increased severity or no change in severity of the cancer symptoms, increased frequency or no change in the frequency of the cancer symptoms, increased size or no change in size of the tumor, or any combination thereof, can be indications that the first dose of the composition is not efficacious. Suitable periods of time between doses include days, weeks, or months. In some embodiments, the period of time between doses can be about 1 day to about 90 days, about 5 days to about 80 days, about 10 days to about 70 days, about 15 days to about 60 days, about 20 days to about 50 days, or about 25 days to about 40 days. For example, the period between doses can be about 1 day, about 2 days, about 3 days, about 4 days, about 5 days, about 6 days, about 7 days, about 14 days, about 21 days, about 28 days, about 35 days, about 42 days, about 49 days, about 56 days, about 60 days, about 65 days, about 70 days, about 80 days, about 85 days, or about 90 days.

Suitable modes of administering the composition to the subject include, but are not limited to, intravenously, orally, subcutaneously, intradermally, intramuscularly, intraperitoneally, transmucosally, nasal administration, or any combination thereof. In some embodiments, the administering step can be performed intravenously.

Treatment can further comprise administering an antibiotic to the subject after administering the composition. For example, once the final dose of the composition is administered to the patient, and after a suitable interval time, the patient can be given an antibiotic. Thus, in a preferred aspect, the antibiotic is administered after a last dose of the composition. Suitable antibiotics include, but are not limited to, amoxicillin or trimethoprim/sulfamethoxazole in subjects who are allergic to penicillin. One skilled in the art would be able to determine a sufficient dosing and dosing schedule for administering the antibiotic to the subject.

The following examples are provided to further describe some of the embodiments disclosed herein. The examples are intended to illustrate, not to limit, the disclosed embodiments.

EXAMPLES

Methods

Molecular Construction of Vaccine Strains

All vaccine strains were constructed in the Listeria monocytogenes ΔactA ΔinlB strain background as described in Brockstedt, D. G., et al., Listeria-based cancer vaccines that segregate immunogenicity from toxicity. PNAS (2004) 101 (38): 13832-13837, which is incorporated herein in its entirety. The EGFRvIII, SSX2, PAP, NKX3.1, and PSMA open reading frames were codon optimized using Listeria monocytogenes codon bias, and then the fragments described in Table 1 were PCR amplified and cloned under control of the actA promoter and operably linked with the modified ActAN100* sequence as disclosed in Int'l Publ. No. WO2014/106123; U.S. Publ. No. 2014/186387, which is hereby incorporated by reference. Antigen expression cassettes were inserted at the actA or inlB locus by allelic exchange as described in Camilli, A. et al., Dual roles of plcA in Listeria monocytogenes pathogenesis. Molecular Microbiology (1993) 8(1): 143-157, which is incorporated herein in its entirety. Allelic exchange vectors were assembled by cloning approximately 1 kilobase of DNA sequence from either side of the deleted actA or inlB into a derivative of pKSV7. The antigen expression cassette was cloned into the pKSV7 vector between the actA or inlB flanking homology.

A single expression cassette was cloned into the actA allelic exchange vector that comprised of the actA promoter, the ActAN100* coding sequence, the 5 copies of the 21 amino acid EGFRvIII junction region, and the codon optimized full-length SSX2 sequence, and was used to construct strains BH5258 and BH5290. Similarly, two expression cassettes were cloned into the inlB allelic exchange vector: the first included the actA promoter, the ActAN100* coding sequence, the 5 copies of the 21 amino acid EGFRvIII junction region, and the codon optimized PAP encoding amino acids 33-386 (used to construct BH5258 and BH5290); the second included the actA promoter, the ActAN100* coding sequence, the full-length codon-optimized NKX3.1 sequence, and the codon optimized PAP encoding amino acids 33-386 (used to construct strains BH4598 and BH4602). Allelic exchange was performed as described previously in Camilli, A. et al., Dual roles of plcA in Listeria monocytogenes pathogenesis. Molecular Microbiology (1993) 8(1): 143-157.

For antigen expression cassettes inserted at the tRNA$^{Arg}$ locus, site specific recombination was used to stably integrate the constructs on the Lm chromosome. Antigen expression cassettes were cloned into a derivative of the pPL2 integration vector as described in Lauer et al., Infect. Immun. (2008) 76: 3742-53, which is incorporated herein in its entirety, that had been modified to allow removal of extraneous vector sequences including all antibiotic resistance markers as described in Int'l Publ. No. WO2007/103225; U.S. App. No. PCT/US2007/005457, which is hereby incorporated by reference. The expression cassette including the actA promoter, the ActAN100* coding sequence, the 5 copies of EGFRvIII junctional region, the codon optimized sequences for NKX3.1 spanning amino acids 11-243, and PSMA spanning amino acids 1-20, 44-138, and 169-750 were cloned and integrated at the tRNA$^{Arg}$ locus. Two variant strains differed in a single encoded amino acid in the NKX3.1 coding sequence at amino acid 41: BH5258 encodes arginine at amino acid 41; and BH5290 encodes glycine at amino acid 41. Transient FLP recombinase expression from a temperature sensitive plasmid was used for removal of the plasmid backbone and antibiotic resistance markers. All final antigen expression cassettes were confirmed by DNA sequencing.

Intracellular Western Blots

The mouse dendritic cell line DC2.4 was inoculated with Listeria monocytogenes strains at a multiplicity of infection (MOI) of 10 for 1 hour, the cells were washed 3x with PBS and DMEM media supplemented with 50 µg/mL gentamycin. Cells were harvested at 7 hours post infection. Cells were lysed with SDS sample buffer, collected and run on 4-12% polyacrylamide gels and transferred to nitrocellulose membranes for western blot analysis. Antigen detection was visualized and quantitated with the Licor Odyssey IR detection system using a polyclonal antibody raised against the mature N-terminus of the ActA protein and were normalized to p60 expression (an unrelated Lm protein) with an anti-p60 monoclonal antibody. P60 levels correlate directly with the number of bacteria in the experiment.

Antigen-Specific Immune Responses in Vaccinated Mice 6 week old Balb/c mice (n=5) were vaccinated intravenously (IV) with $5 \times 10^6$ cfu. After seven days, spleens were harvested and immune responses measured by IFNγ ELIspot assay using an overlapping peptide libraries for SSX2, PAP, NKX3.1, or PSMA (15mer peptides overlapping by 11 amino acids) or unstimulated media control. For EGFRvIII-specific immunogenicity, 6 week old C3H/HeN mice (n=5) were vaccinated with $5 \times 10^6$ cfu IV. After seven days, spleens were harvested and immune responses measured by IFNγ ELIspot assay using the EGFRvIII$_{26-33}$—the K$^k$ binding peptide EEKKGNYV. Data for each strain/antigen are plotted with the unstimulated responses or as background (unstimulated) subtracted data. Statistical significance was determined using the unpaired T-test.

Protective Immunity to a Wild-Type *Listeria* Challenge

Balb/c mice were vaccinated once with $2 \times 10^6$ cfu of each Lm strain IV. Forty days later, mice were challenged IV with $5 \times 10^4$ cfu ($2 \times LD_{50}$ dose) of the WT Lm strain DP-L4056 as described in Lauer, 2002. Three days later, spleens were harvested and homogenized. Dilutions were plated on BHI plates containing 200 µg/mL streptomycin to determine cfu/organ. The limit of detection (LOD) in this assay was 50 CFU.

Treatment of Cancer

A first in human (FIH), Phase 1, open-label, multicenter, 2-part study is conducted to characterize the safety, determine a Phase 2 does (RP2D), evaluate the preliminary clinical efficacy, and determine the immune responses of single-agent ADU-741 (also referred to as strain BH5290), when administered to subjects with metastatic castration resistant prostate cancer. Subjects must have disease that has not responded to hormonal therapy and that is progressing at screening, and have received at least 2 prior approved therapies. Approximately 42 subjects will be enrolled in the study.

Part 1 (Dose Escalation): is designed to determine the RP2D based on safety and pharmacodynamic assessments. Two doses of ADU-741 (Dose Cohort 1A: $1 \times 10^8$ CFU and Dose Cohort 1B: $1 \times 10^9$ CFU) are administered sequentially. The total number of subjects enrolled will depend on when and/or whether dose-limiting toxicity is observed.

Part 2 (Dose Expansion): is designed to evaluate 2 expansion cohorts (Cohort 2A and 2B) after the RP2D for ADU-741 is determined. The goal of the expansion cohorts is to further evaluate the safety of ADU-741 (Cohort 2A) and to evaluate pre- and posttreatment biopsies for immune response at the tumor site (Cohort 2B).

Once a subject is determined to be eligible for the study, ADU-741 is administered intravenously every 21 days during the open-label treatment period. ADU-741 is administered via peripheral vein catheter. The study drug is administered over a 1-hour period with the option to increase the duration of the infusion, if necessary. Subjects are closely monitored for adverse events, laboratory abnormalities, and clinical and immunologic response. Treatment is administered until confirmed radiographic disease progression, unacceptable toxicity, withdrawal of consent, the investigator decides to stop treatment, the start of subsequent anti-cancer therapy, or the sponsor ends the study. Safety and efficacy is evaluated.

Study population—Subjects who are over 18 years of age with histologically confirmed adenocarcinoma of the prostate with castration-resistant metastatic disease who have received at least 2 prior approved therapies and have at least 1 of the following criteria for disease progression are eligible for the study: (1) rise in prostate specific antigen (PSA) with a minimum of 3 rising levels, with an interval of >1 week between each determination (the last determination must have a value ≥2 ng/ml, obtained within 2 weeks prior to enrollment); (2) measurable disease defined as new or progressive soft tissue disease on computed tomography (CT) or magnetic resonance imaging (MRI) scans; (3) radionuclide bone scan or 18F sodium fluoride positron emission tomography/computed tomography (NaF PET/CT) result with at least 2 new bone lesions, as determined by the Prostate Cancer Clinical Trials Working Group (PCWG2) criteria; and must have received at least 2 prior approved therapies. Subjects must have an Eastern Cooperative Oncology Group (ECOG) Performance status score of 0 or 1.

Efficacy Evaluations—Efficacy assessments are evaluated by the investigator according to the PCWG2 criteria, Response Evaluation Criteria in Solid Tumors (V1.1) (RECIST) criteria, and Immune-Related Response Criteria (irRC). Disease response is assessed using CT scans with IV contrast of the chest, abdomen, and pelvis. Subjects who are intolerant of IV CT contrast agents have CT scans performed with oral contrast. Magnetic resonance imaging (MRI) may be used to evaluate sites of disease that cannot be adequately imaged using CT. Soft tissue disease (ie, radiologically detectable tumors) is assessed by CT and/or MRI. Radionuclide bone scans or 18F-NaF PET/CT is performed to evaluate site of bone disease. These assessments are performed throughout the study at each timepoint using the same method of assessment used to assess disease at baseline. Data also is collected on subsequent anti-cancer therapies and overall survival in the posttreatment follow-up period.

Results

NKX3.1(R41G) Results in Higher Expression of all Encoded Antigens

Two multivalent vaccine strains BH5258 (containing "wild type" NKX3.1) and BH5290 (with the NKX3.1 R41G variation) differ by a single amino acid at position 41 of NKX3.1. Strains were constructed that express the five encoded antigens from three loci in the Lm genome as described (FIG. 1). These strains were used to infect the mouse dendritic cell line DC2.4, and expression was measured using semi-quantitative western blots. Each of the fusion proteins were detected at approximately the predicted sizes. Surprisingly, for each encoded fusion protein antigen (PSMA, PAP, NKX3.1, SSX2, and EGFRvIII), expression ranged from 2.1×-3.2× higher in the strains that contained the NKX3.1(R41G) variation, indicating a single amino acid change in NKX3.1 enhances expression of all encoded antigens. Specifically, NKX3.1 and PSMA were 2.7× higher in BH5290, PAP was 3.2× higher expression in BH5290, SSX2 was 2.1× higher in BH5290, and EGFRvIII was 2.1×-3.2× higher in BH5290.

NKX3.1(R41G) Results in Higher Antigen-Specific Immunogenicity

The two multivalent vaccine strains BH5258 and BH5290 were compared for T cell immunogenicity in mice (FIG. 3). Immune responses to SSX2, PAP, NKX3.1, and PSMA were measured in Balb/c mice. EGFRvIII were measured in C3H/HeN mice. Responses to 4 of 5 encoded antigens were higher in BH5290, with the single amino acid difference in the NKX3.1 coding sequence (NKX3.1(R41G)). Responses to PAP were statistically higher in BH5290 compared to BH5258. PSMA responses were essentially equivalent with both strains. The single amino acid difference between BH5290 and BH5258 resulted in higher immune responses to most of the encoded antigens, indicating that it is the more potent prostate cancer vaccine.

Figure 4:
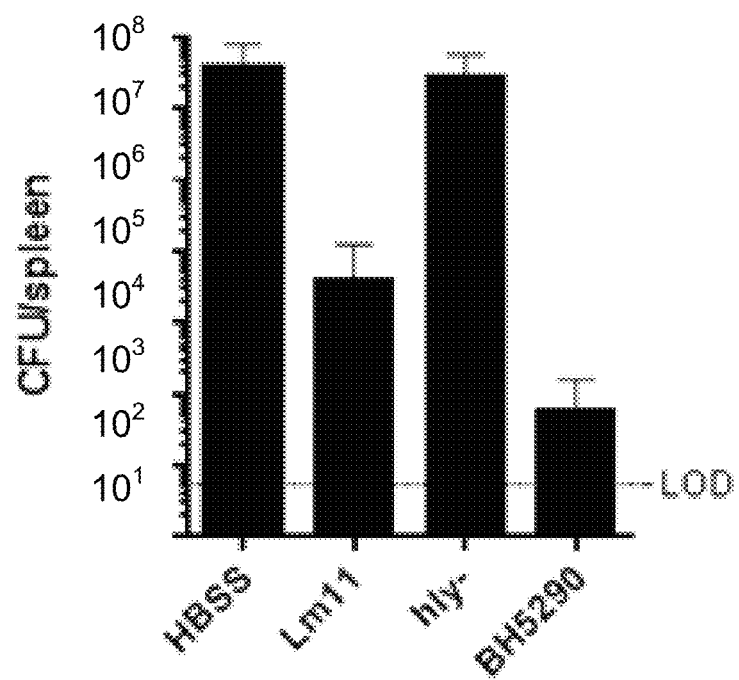
FIG. 4 illustrates the protective immunity of vaccination with BH5290 against a wild type Listeria challenge.

BH5290 Induces Fully Functional and Protective Immunity when Challenged with a WT Lm As shown in FIG. 4, a single vaccination with BH5290 induces fully protective, long-term immunity to a WT *Listeria* challenge. Vaccination with BH5290 resulted in a 5-log reduction in CFU in the spleen after WT-Lm challenge. Functional immunity is a combination of magnitude of the antigen-specific immune response and the ability of the immune response to protect from a future challenge. In this case, the functionality was tested with a fully virulent wild-type *Listeria* challenge. Vaccination with HBSS or the Lm strain DP-L4027 (hly-) were included in the experiment as negative controls.

Figure 5A:
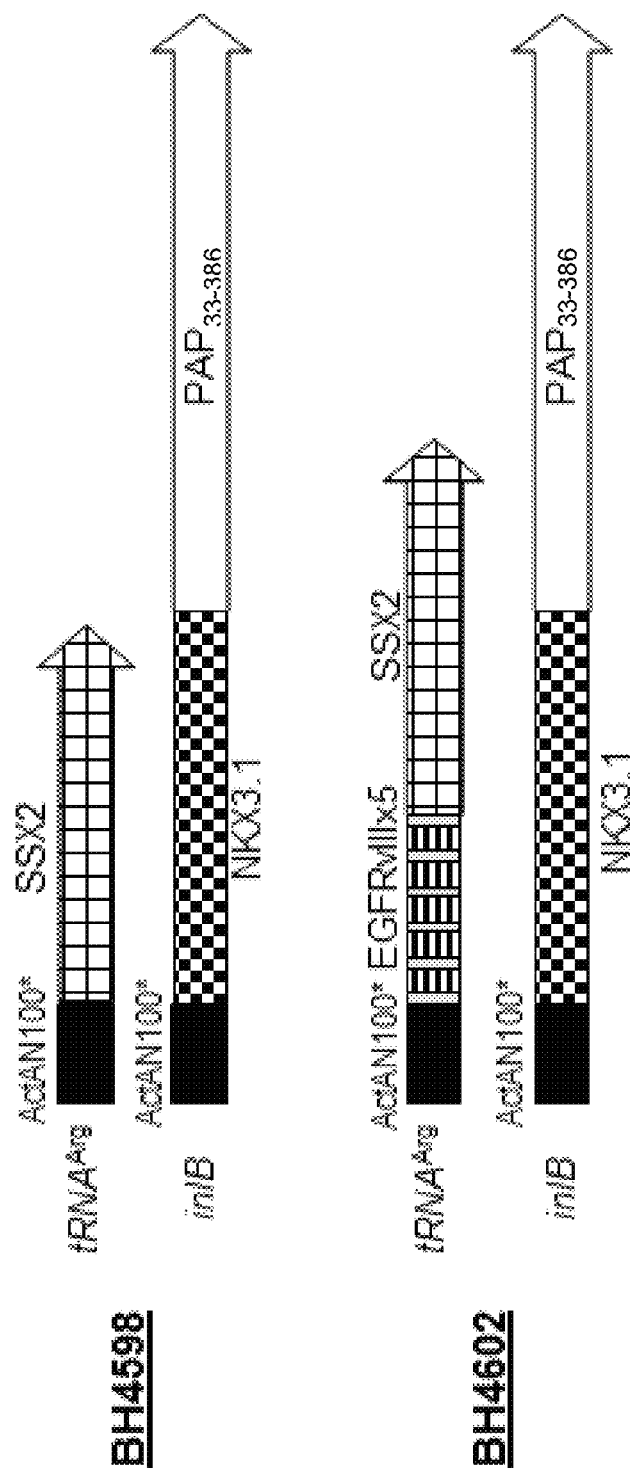
FIG. 5A-FIG. 5B illustrate the expression of SSX2 when fused to EGFRvIII. (A) Exemplary bacterial strains used to examine SSX2 expression in the presence of EGFRvIII. To assess the impact of inclusion of EGFRvIIIx5 on antigen expression, matched SSX2 expression cassettes differing only in the presence of EGFRvIIIx5 were introduced at the tRNA$^{Arg}$ locus of the same Lm background that expressed an ActAN100*-NKX3.1-PAP$_{33-386}$ fusion protein from the inlB locus. BH4598 contained the first cassette—ActAN100*-SSX2, and BH4602 contained the second cassette—ActAN100*-EGFRvIIIx5-SSX2 (FIG. 5A). All expression cassettes utilized the actA promoter.
Figure 5B:
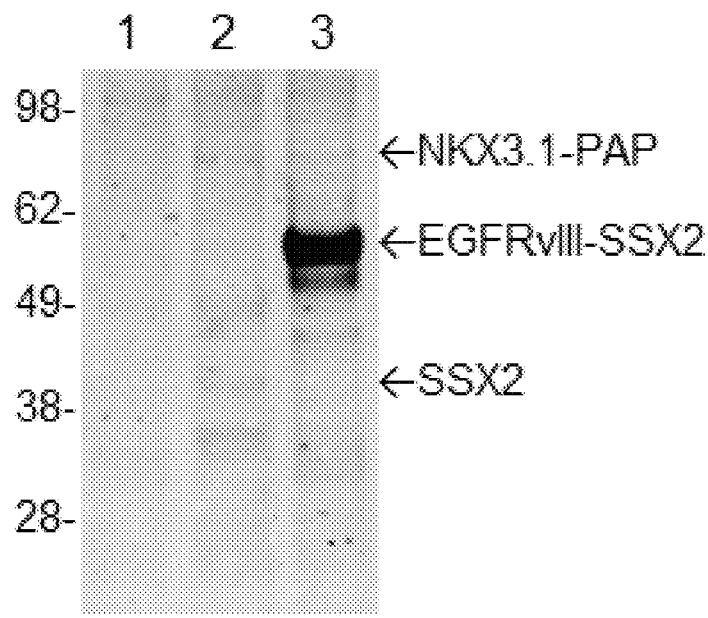
Figure 6:
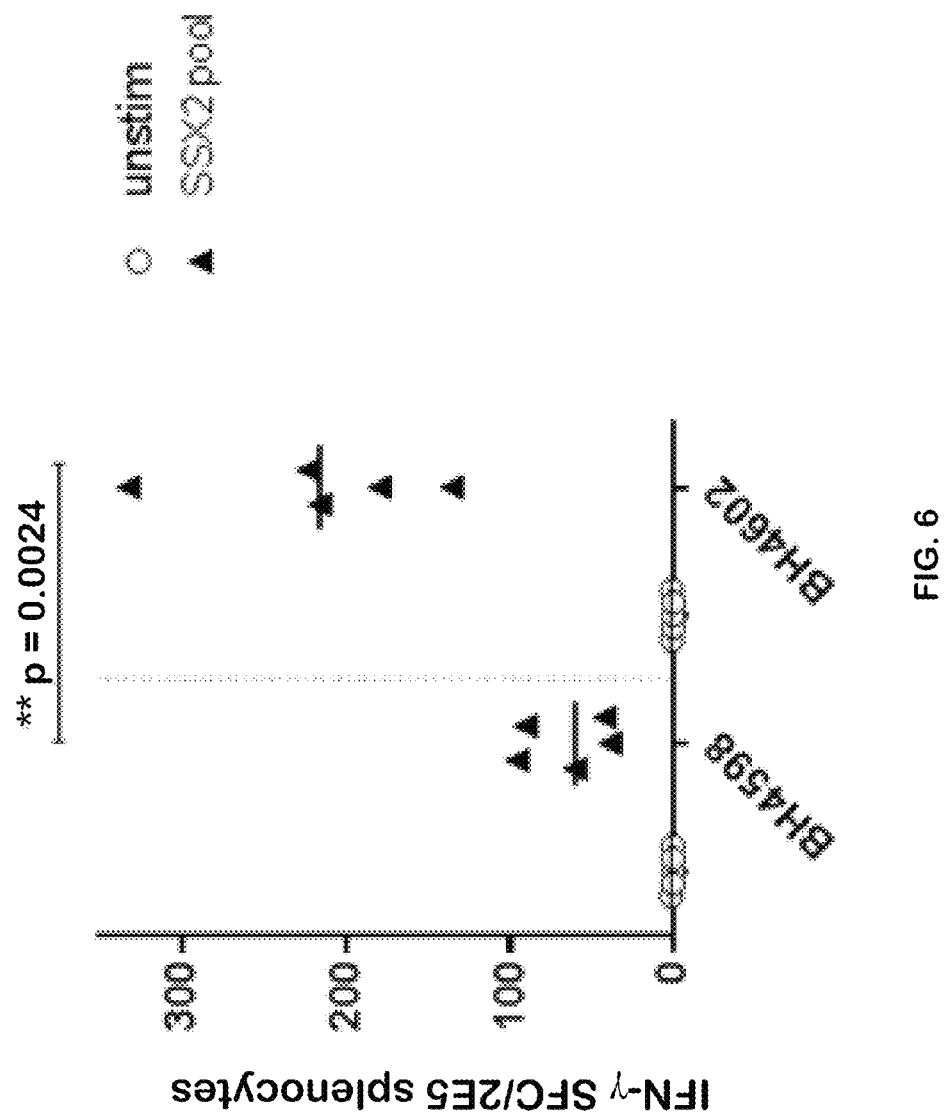
FIG. 6 illustrates SSX2 immune responses when EGFRvIIIx5 is part of the immunogenic fusion protein.

SSX2 Expression is Increased when EGFRvIIIx5 is Included as a Part of the Fusion Protein To assess the impact of inclusion of EGFRvIIIx5 on antigen expression, matched SSX2 expression cassettes differing only in the presence of EGFRvIIIx5, were introduced at the tRNA$^{Arg}$ locus of the same Lm background that expressed an ActAN100*-NKX3.1-PAP$_{33-386}$ fusion protein from the inlB locus. BH4598 contained the first cassette—ActAN100*-SSX2, and BH4602 contained the second cassette—ActAN100*-EGFRvIIIx5-SSX2 (FIG. 5A). All expression cassettes utilized the actA promoter. Expression of these cassettes was then assessed by intracellular western blot (FIG. 5B). Lane 1: Lm11 (negative control), lane 2: BH4598 (ActAN100*-SSX2), lane 3: BH4602 (ActAN100*-EGFRvIIIx5-SSX2). Full-length sized bands for each of the fusion proteins are indicated on the right. Expression levels were quantified and data was normalized to the constitutive *Listeria* P60 protein. The relative expression level of the constant expression cassette (the NKX3.1-PAP fusion) was similar between the two strains (0.43 in BH4598 and 0.33 in BH4602). However, the expression of the SSX2 fusion protein was over 200-fold higher in the strain that contained EGFRvIIIx5 as part of the fusion (1 in BH4598 and 224 in BH4602). This data clearly demonstrate that EGFRvIIIx5 augments expression of SSX2.

SSX2 Immune Responses are Significantly Higher when EGFRvIIIx5 is Part of the Immunogenic Fusion Protein Primary immune responses induced by BH4598 and BH4602 were compared. BH4602 induced significantly higher SSX2-specific immune responses than BH4598 (p=0.0024). This demonstrates that the higher expression from the EGFRvIII-SSX2 fusion protein translated to higher immune responses in mouse models of immunogenicity.

PAP Expression is Higher when Fused to Multiple Copies of EGFRvIII

Figure 7A:
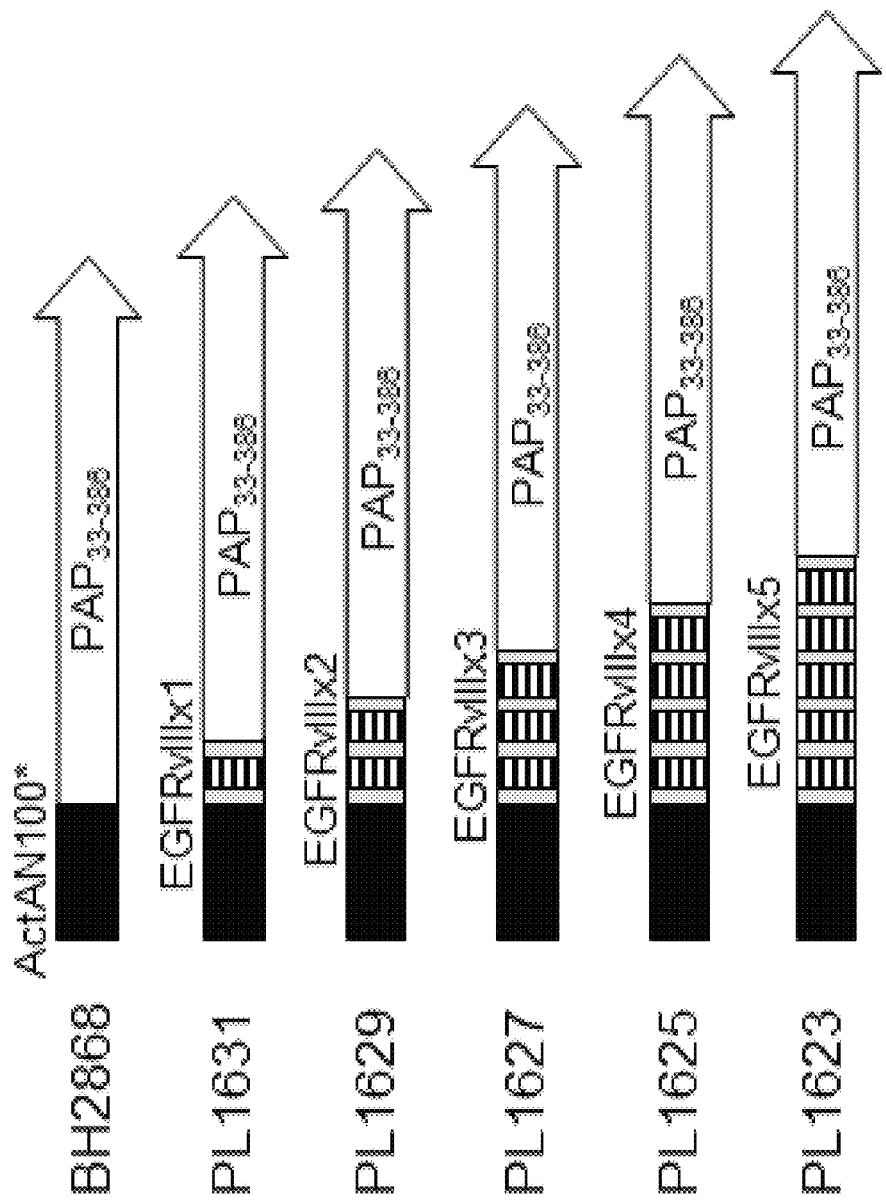
FIG. 7A-FIG. 7B illustrate PAP expression when fused to multiple copies of EGFRvIII. (A) Six PAP expression cassettes were constructed that vary in the copy number of the EGFRvIII repeat sequence included in the construct. All constructs were integrated at the tRNA$^{Arg}$ locus of Lm11 resulting in six Lm vaccine strains: BH2868, PL1631, PL1629, PL1627, PL1625, and PL1623. (B) Expression was evaluated by intracellular western. Lane 1: Lm11 (no expression cassette); Lane 2: BH2868 expresses ActAN100-PAP$_{33-386}$; Lane 3: PL1631 expresses ActAN100*-EGFRvIIIx1-PAP$_{33-386}$; Lane 4: PL1629 expresses ActAN100*-EGFRvIIIx2-PAP$_{33}$-386; Lane 5: PL1627 expresses ActAN100*-EGFRvIIIx3-PAP$_{33-386}$; Lane 6: PL1625 expresses ActAN100*-EGFRvIIIx4-PAP$_{33-386}$; Lane 7: PL1623 expresses ActAN100*-EGFRvIIIx5-PAP$_{33}$-386.
Figure 7B:
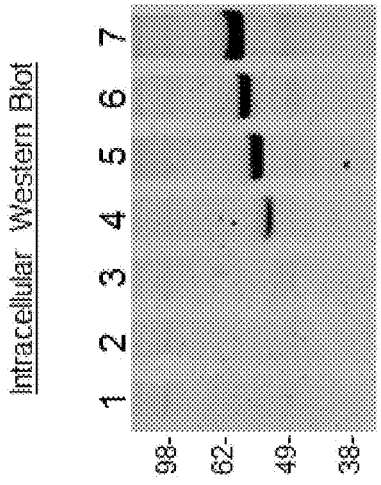
Figure 8:
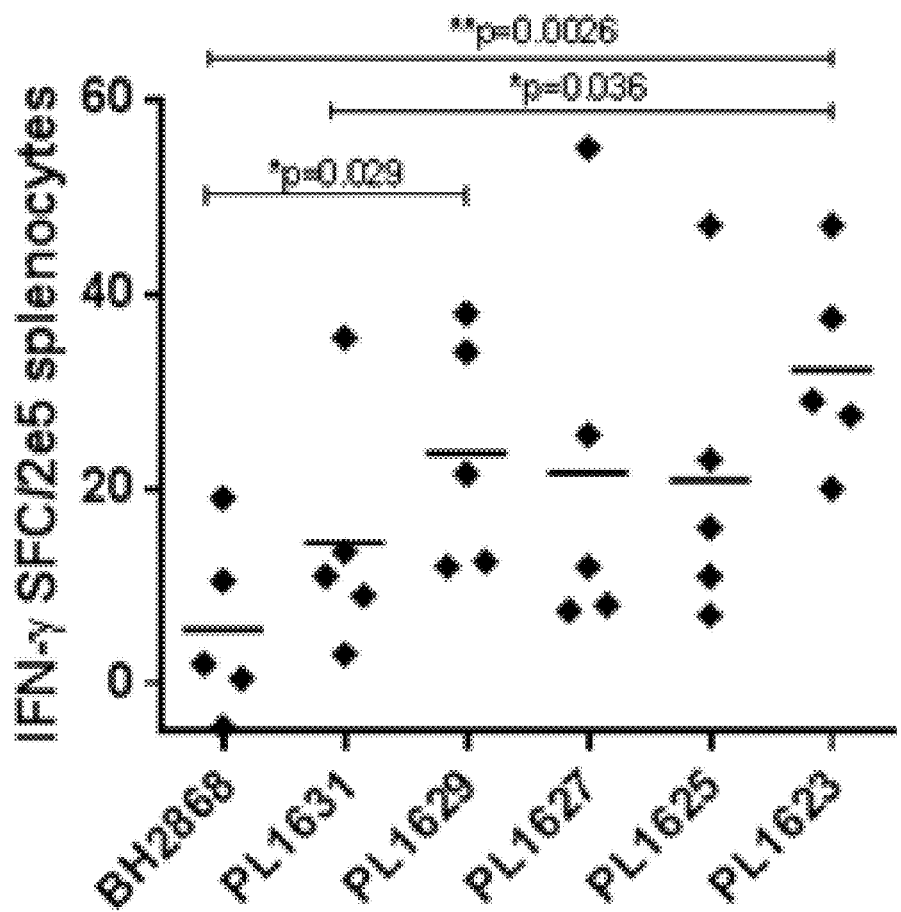
FIG. 8 illustrates PAP-specific immunogenicity when fused to multiple copies of EGFRvIII. Six PAP expressing Lm strains with the variation in EGFRvIII copy number (BH2868, PL1631, PL1629, PL1627, PL1625, and PL1623) were tested for induction of T cell responses.

As shown in FIG. 7, each additional EGFRvIII repeat unit resulted in higher expression of PAP. Relative expression measured in lanes 2-7: 1×, 2.4×, 19.6×, 127×, 156×, and 213×, respectively. Additionally, the increase in expression for fusion of EGFRvIIIx5 to both SSX2 and PAP resulted in an increase in expression over 200× for both antigens.

PAP Responses are Higher when Fused to Multiple Copies of EGFRvIII and are Significantly Higher when Fused to 5 Copies of EGFRvIII Six PAP expressing Lm strains with the variation in EGFRvIII copy number (BH2868, PL1631, PL1629, PL1627, PL1625, and PL1623) were tested for induction of T cell responses. BH2868 (zero copies of EGFRvIII) induced low but detectable PAP-specific immune responses. All strains that included at least one copy of EGFRvIII as part of the PAP fusion induced higher PAP-specific immune responses, and there was a trend in the immune responses that mirrored the increase in expression level—more copies of EGFRvIII resulted in higher immune responses. The highest immune responses were observed from PL1623 (five copies of EGFRvIII), and the response was statistically higher than strains with no EGFRvIII or one copy of the EGFRvIII repeat. Likewise, PL1629 with two copies of the repeat induced significantly higher PAP responses than the strain with zero copies of EGFRvIII.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

TABLE 5

ActAN100* nucleotide sequence (SEQ ID NO: 1)

gtgggattaaatagatttatgcgtgcgatgatggtagttttcattactgccaactgcattacgattaaccccgac
ataatatttgcagcgacagatagcgaagattccagtctaaacacagatgaatgggaagaagaatacgaaac
tgcacgtgaagtaagttcacgtgatattgaggaactagaaaaatcgaataaagtgaaaaatacgaacaaag
cagaccaagataataaacgtaaagcaaaagcagagaaaggt ActAN100* amino acid sequence (SEQ ID NO: 2)
(BamHI linker gs = underlined)

MGLNRFMRAMMVVFITANCITINPDIIFAATDSEDSSLNTDEWEEE
YETAREVSSRDIEELEKSNKVKNTNKADQDNKRKAKAEKG<u>GS</u>

*actAp-ActAN100*-EGFRvIIIx5-SSX2* nucleotide sequence (SEQ ID NO: 3)

gggaagcagttggggttaactgattaacaaatgttagagaaaaattaattctccaagtgatattcttaaaataa
ttcatgaatatttttcttatattagctaattaagaagataattaactgctaatccaattttaacggaataaattagt
gaaaatgaaggccgaattttccttgttctaaaaaggttgtattagcgtatcacgaggagggagtataagtgg
gattaaatagatttatgcgtgcgatgatggtagttttcattactgccaactgcattacgattaaccccgacataa
tatttgcagcgacagatagcgaagattccagtctaaacacagatgaatgggaagaagaatacgaaactgc
acgtgaagtaagttcacgtgatattgaggaactagaaaaatcgaataaagtgaaaaatacgaacaaagcag
accaagataataaacgtaaagcaaaagcagagaaaggtggatccgcaagcaaagtattgccagctagtc
gtgcattagaggagaaaaaggggaattacgtggtgacggatcatggatcgtgtgccgatggctcagtaaa
gactagtgcgagcaaagtggccctgcatcacgagcacttgaagagaaaaaggaaactatgttgtgacc
gatcatggtagctgcggagatggttcaattaaattatcaaaagtcttaccagcatctagagcttagaggaaa
agaagggtaactatgtcgtaacagatcatggaagttgtgctgacggaagtgttaaagcgtcgaaagtagct
ccagcttctcgcgcattagaagaaaagaaaggcaattatgttgtaacagaccatggtagttgtggtgatggc
tcgatcaaattgtcaaaagttctaccggcttctcgtgcgctagaagagaagaaaggaaattacgtagttaca
gaccacggctcttgcgcggatggttccgttaaacaattgatgaatggtgatgacgctttcgcacgccgtcct
accgtaggagcacaaattccagaaaagattcaaaaagcattgatgacatcgctaaatacttttctaaagaag
aatgggagaaaatgaaagcgagcgagaaaatcttttatgtctatatgaaacggaaatatgaagcaatgaca
aaattgggtttcaaagcaacattaccaccatttatgtgcaataaacgtgcggaagatttcaagggaatgattt
agacaatgatcctaatcgaggcaaccaagtggaaagaccgcaaatgactttcggacgtttacaagggattt
ctccaaagataatgccgaaaaagccagccgaagaaggtaatgatagtgaagaagtacctgaagcgagtg
gtccacaaaatgatggtaaagaactttgtcctccaggcaaaccgacaacgtctgagaagattcatgaacgg
tccggtaaccgtgaagctcaagagaaagaagaacgacgtggaactgctcacagatggagttcacagaat
acacataacattggccgctttagcctatcaacaagcatgggggctgttcatggaactccaaaaacgatcac
gcataacagagatccaaaaggcggaaacatgccgggtccaacagattgtgttagagaaaattcgtggtaa ActAN100*-EGFRvIIIx5-SSX2 amino acid sequence (SEQ ID NO: 4)
(ActAN100* = normal text; BamHI linker gs = underlined; EGFRvIIIx5 = double underlined; MfeI linker gl = bold underlined; SSX2 = bold)

MGLNRFMRAMMVVFITANCITINPDIIFAATDSEDSSLNTDEWEEE
YETAREVSSRDIEELEKSNKVKNTNKADQDNKRKAKAEKG<u>GS</u><u><u>ASK
VLPASRALEEKKGNYVVTDHGSCADGSVKTSASKVAPASRALEEK
KGNYVVTDHGSCGDGSIKLSKVLPASRALEEKKGNYVVTDHGSCA
DGSVKASKVAPASRALEEKKGNYVVTDHGSCGDGSIKLSRVLPAS
RALEEKKGNYVVTDHGSCADGSVK</u></u>ql**MNGDDAFARRPTVGAQIP
EKIQKAFDDIAKYFSKEEWEKMKASEKIFYVYMKRKYEAMTK
LGFKATLPPFMCNKRAEDFQGNDLDNDPNRGNQVERPQMTFG
RLQGISPKIMPKKPAEEGNDSEEVPEASGPQNDGKELCPPGKPT
TSEKIHERSGNREAQEKEERRGTAHRWSSQNTHNIGRFSLSTS
MGAVHGTPKTITHNRDPKGGNMPGPTDCVRENSW**

*EGFRvIII* nucleotide sequence (SEQ ID NO: 5)

CCdGCwwswmGhGCdyTwGArGArAArAArGGnAAyTAyGTnGTdACv
GAyCAyGGhwsbTGy

EGFRvIII amino acid sequence (SEQ ID NO: 6)

PASRALEEKKGNYVVTDHGSC

*EGFRvIIIx5* nucleotide sequence (SEQ ID NO: 7)

gcaagcaaagtattgccagctagtcgtgcattagaggagaaaaaggggaattacgtggtgacggatcatg
gatcgtgtgccgatggctcagtaaagactagtgcgagcaaagtggccctgcatcacgagcacttgaaga
gaaaaaggaaactatgttgtgaccgatcatggtagctgcggagatggttcaattaaattatcaaaagtctta
ccagcatctagagctttagaggaaaagaagggtaactatgtcgtaacagatcatggaagttgtgctgacgg
aagtgttaaagcgtcgaaagtagctccagcttctcgcgcattagaagaaaagaaaggcaattatgttgtaac TABLE 5-continued agaccatggtagttgtggtgatggctcgatcaaattgtcaaaagttctaccggcttctcgtgcgctagaagag
aagaaaggaaattacgtagttacagaccacggctcttgcgcggatggttccgttaaa

EGFRvIIIx5 amino acid sequence (SEQ ID NO: 8) (individual EGFRvIII underlined)

ASKVL<u>PASRALEEKKGNYVVTDHGSC</u>ADGSVKTSASKV<u>PASRALE
EKKGNYVVTDHGSC</u>GDGSIKLSKVL<u>PASRALEEKKGNYVVTDHGS
C</u>ADGSVKASKVA<u>PASRALEEKKGNYVVTDHGSC</u>GDGSIKLSKVL
<u>PASRALEEKKGNYVVTDHGSC</u>ADGSVK

SSX2 nucleotide sequence (SEQ ID NO: 9)

atgaatggtgatgacgcttcgcacgccgtcctaccgtaggagcacaaattccagaaaagattcaaaaagc
atttgatgacatcgctaaatacttttctaaagaagaatggggagaaaatgaaagcgagcgagaaaatctttat
gtctatatgaaacggaaatatgaagcaatgacaaaattgggtttcaaagcaacattaccaccattatgtgca
ataaacgtgcggaagattttcaagggagatgattagacaatgatcctaatcgaggcaaccaagtggaaaga
ccgcaaatgacttcggacgtttacaagggatttctccaaagataatgccgaaaaagccagccgaagaag
gtaatgatagtgaagaagtacctgaagcgagtggtccacaaatgatggtaaagaacttttgtcctccaggc
aaaccgacaacgtctgagagattcatgaacggtccggtaaccgtgaagctcaagagaaagaagaacga
cgtggaactgctcacagatggagttcacagaatacacataacattggccgcttagcctatcaacaagcatg
ggggctgttcatggaactccaaaaacgatcacgcataacagagatccaaaagcggaaacatgccgggt
ccaacagattgtgttagagaaaattcgtgg

SSX2 amino acid sequence (SEQ ID NO: 10)

**MNGDDAFARRPTVGAQIPEKIQKAFDDIAKYFSKEEWEKMKAS
EKIFYVYMKRKYEAMTKLGFKATLPPFMCNKRAEDFQGNDLD
NDPNRGNQVERPQMTFGRLQGISPKIMPKKPAEEGNDSEEVPE
ASGPQNDGKELCPPGKPTTSEKIHERSGNREAQEKEERRGTAH
RWSSQNTHNIGRFSLSTSMGAVHGTPKTITHNRDPKGGNMPGP
TDCVRENSW** actAp-ActAN100*-EGFRvIIIx5-PAP₃₃₋₃₈₆ nucleotide sequence (SEQ ID NO: 11)

gggaagcagttggggttaactgattaacaaatgttagagaaaaattaattatccaagtgatattcttaaaataa
ttcatgaatattttttcttatattagctaattaagaagataattaactgctaatccaattttttaacggaataaattagt
gaaaatgaaggccgaattttccttgttctaaaaaggttgtattagcgtatcacgaggagggagtataagtgg
gattaaatagatttatgcgtgcgatgatggtagttttcattactgccaactgcattac-
gattaaccccgacataatatttgcagcgacagatagcgaagattccagtctaaacaca-
gatgaatgggaagaagaatacgaaactgc
acgtgaagtaagttcacgtgatattgaggaactagaaaaatcgaataaagtgaaaaatacgaacaaagcag
accaagataataaacgtaaagcaaaagcagagaaaggtggatctgcaagcaaagtattgccagctagtcg
tgcattagaggagaaaaagggaatttacgtggtgacggatcatggatcgtgtgccgatggctcagtaaag
actagtgcgagcaaagtgcccctgcatcacgagcacttgaagagaaaaaggaaactatgttgtgacc
atcatggtagctgcggagatggttcaattaaattatcaaagtcttaccagcatctagagctttagaggaa
aagggtaactatgtctaacagatcatgaagttgtgctgacggaagtgttaaagcgtcgaaagtagctcc
agctctcgcgcattagaagaaagaaaggcaattatgttgtaacagaccatggtagttgtggtgatggctc
gatcaaattgtcaaagttctaccggcttctcgtgcgctagaagaagaaggaaattacgtagttacagacc
accggctcttgcgcggatggttccgttaaaggatccaaagaactaaagtttgtaacgttagtcttagacat
ggtgatcgtagtcctattgataccttcctacagatccaatcaaagagtagttggccacaaggcttcggac
aacttacacaattaggaatggaacaactattgaattaggtgaatacattcgcaaacgttatcgcaaattcctt
aatgaatgctacaaaccacgaacaagtgtatatccgttccactgacgttgatagaacactaatgtcagctatga
caaatctagctgcattagtgccaccagaaggcgttagcatttggaatcctatcttacttttggcagccaatacct
gtacatacggttccgttatctgaagatcaattacttatcttccatttcgcaactgcccacgattccaagaattag
aatccgaaacattgaaaagcgaagaatttcagaaaagattacatccataccaagactttatcgcaaccttag
gcaaattgtcagggttacacggacaggatcttatttggaatttggtcgaaagttttatgatcctttgtactgtgaat
ctgtacataacttttacattacctagtcgcgccacggaagatactatgacgaaactacgtgaactttccgaactt
tctttactatcgttgtatggtattcataaacaaaaagaaaagagcagattgcaaggtggtgttttagtaaatgaa
atcttaaaccatatgaaaagagctacacaaattccgtcttacaagaaattgattatgtatagtgctcatgatacg
acagtatctgggcttcaaatggcgttagtgtctataacggcttacttccaccgtatgcgtcatgtcaccttac
ggaactttactttgagaaaggtgagtactttgttgagatgtactatcgcaatgaaacccaacatgaaccatatc
cgttgatgttaccaggttgtagtccatcttgcccgttagaacgattgccggaattagtgggtccagtgatacca
caagactggtctactgagtgtatgactactaatagccaccaagggactgaagattcaacagattaa

ActAN100*-EGFRvIIIx5-PAP₃₃₋₃₈₆ (SEQ ID NO: 12)
(ActAN100* = normal text; BamHI linker gs = underlined; EGFRvIIIx5 = double underlined; PAP₃₃₋₃₈₆ = bold)

MGLNRFMRAMMVVFITANCITINPDIIFAATDSEDSSLNTDWEEE
YETAREVSSRDIEEELEKSNKVKNTNKADQDNKRKAKAEKG<u>GSASK
VLPASRALEEKKGNYVVTDHGSCADGSVKTSASKVAPASRALEEK
KGNYVVTDHGSCGDGSIKLSKVLPASRALEEKKGNYVVTDHGSCA
DGSVKASKVAPASRALEEKKGNYVVTDHGSCGDGSIKLASKVLPA
SRALEEKKGNYVVTDHGSCADGSVKgs</u>**KELKFVTLVFRHGDRSPI
DTFPTDPIKESSWPQGFGQLTQLGMEQHYELGEYIRKRYRKFL
NESYKHEQVYIRSTDVDRTLMSAMTNLAALVPPEGVSIWNPILL
WQPIPVHTVPLSEDQLLYLPFRNCPRFQELESETLKSEEFQKRL
HPYKDFIATLGKLSGLHGQDLFGIWSKVYDPLYCESVHNFTLPS
RATEDTMTKLRELSELSLLSLYGIHKQKEKSRLQGGVLVNEIL
NHMKRATQIPSYKKLIMYSAHDTTVSGLQMALDVYNGLLPPY
ASCHLTELYFEKGEYFVEMYYRNETQHEPYPLMLPGCSPSCPL
ERFAELVGPVIPQDWSTECMTTNSHQGTEDSTD**

PAP₃₃₋₃₈₆ nucleotide sequence (SEQ ID NO: 13)

aaagaactaaagtttgtaacgttagtcttagacatggtgatcgtagtcctattgataccttcctacagatcca
atcaaagagagtagttggccacaaggcttcggacaacttacacaattaggaatggaacaacattatgaatta
ggtgaatacattcgcaaacgttatcgcaaattccttaatgaatcgtacaaacacgaacaagtgtatatccgttc
cactgacgttgatagaacactaatgtcagctatgacaaatctagctgcattagtgccaccagaaggcgttag
catttggaatcctatcttactttggcagccaatacctgtacatacggttccgttatctgaagatcaattacttttatc
ttccatttcgcaactgcccacgattccaagaattagaatcctaggcaaattgtcagggttacacggacaggatctatttgg
aatttggtcgaaagtttatgatcctttgtactgtgaatctgtacataacttttacattacctagtcgcgccacggaa
gatactatgacgaaactacgtgaactttccgaactttctttactatcgttgtatggtattcataaacaaaaagaa
aagagcagattgcaaggtggtgttttagtaaatgaaatcttaaaccatatgaaaagagctacacaaattccgt
cttacaagaaattgattatgtatagtgctcatgatacgacagtatctgggcttcaaatggcgttagatgtctata
acggttacttccaccgtatgcgtcatgtcaccttacggaactttactttgagaaaggtgagtactttgttgaga
tgtactatcgcaatgaaacccaacatgaaccatatccgttgatgttaccaggttgtagtccatcttgcccgtta
gaacgatttgcggaattagtgggtccagtgataccacaagactggtctactgagtgtatgactactaatagc
caccaagggactgaagattcaacagat

PAP₃₃₋₃₈₆ amino acid sequence (SEQ ID NO: 14)

**KELKFVTLVFRHGDRSPIDTFPTDPIKESSWPQGFGQLTQLGME
QHYELGEYIRKRYRKFLNESYKHEQVYIRSTDVDRTLMSAMTN
LAALVPPEGVSIWNPILLWQPIPVHTVPLSEDQLLYLPFRNCPRF
QELESETLKSEEFQKRLHPYKDFIATLGKLSGLHGQDLFGIWS
KVYDPLYCESVHNFTLPSRATEDTMTKLRELSELSLLSLYGIHK
QKEKSRLQGGVLVNEILNHMKRATQIPSYKKLIMYSAHDTTVS
GLQMALDVYNGLLPPYASCHLTELYFEKGEYFVEMYYRNETQ
HEPYPLMLPGCSPSCPLERFAELVGPVIPQDWSTECMTTNSHQ
GTEDSTD** actAp-ActAN100*-EGFRvIIIx5-NKX3.1(R41G)₁₁₋₂₃₄-PSMA₁₋₂₀, ₄₄₋₁₃₈, ₁₆₉₋₇₅₀ nucleotide sequence (SEQ ID NO: 15)

gggaagcagttggggttaactgattaacaaatgttagagaaaaattaattctccaagtgatattcttaaaataa
ttcatgaatattttttcttatattagctaattaagaagataattaactgctaatccaattttttaacggaataaattagt
gaaaatgaaggccgaattttccttgttctaaaaaggttgtattagcgtatcacgaggagggagtataagtgg
gattaaatagatttatgcgtgcgatgatggtagttttcattactgccaactgcattacgattaaccccgacataa
tatttgcagcgacagatagcgaagattccagtctaaacacagatgaatgggaagaagaatacgaaactgc
acgtgaagtaagttcacgtgatattgaggaactagaaaaatcgaataaagtgaaaaatacgaacaaagcag
accaagataataaacgtaaagcaaaagcagagaaaggtggatctgcaagcaaagtattgccagctagtcg
tgcattagaggagaaaaagggaatttacgtggtgacggatcatggatcgtgtgccgatggctcagtaaag
actagcgcgagcaaagtgcccctgcatcacgagcacttgaagagaaaaaggaaactatgttgtgacc
gatcatggtagctgcggagatggttcaattaaattatcaaagtcttaccagcatctagagctttagaggaaa
agaagggtaactatgtctgtaacagatcatgaagttgtgctgacggaagtgttaaagcgtcgaaagtagct
ccagctctcgcgcattagaagaaagaaaggcaattatgttgtaacagaccatggtagttgtggtgatggc
tcgatcaaattgtcaaaagttctaccggctttctcgtgcgctagaagaagaaggaaattacgtagttaca
gaccacggctcttgcgcggatggttccgttaaaggatccgaagcaaaagctgaaggcgcagcgccaccg
actcctagtaaaccactaacaagttttcttaatccaagatattcttcgtgacggtgccacaaggacaaggcgga
cgaacttctccacaacgtcaacgagatcctgagccgaaccggagcctgaaccgggaagggggacgctcc
cgagctggaacacaaaacgatcagttatctactggtccaagagctgccctgaagaagcagagacactag
ccgaaacgggaaccagaaagacatttgggttcatacttacttgactcagaaaacacaagcggggctttaccg
agattaccacaaacaccaaaacagcctattggaaaggttttatcatcttttgcacacgcaagtcatagga
gttgaacgcaaattcagccatcaaaagtatttgtccgcaccagaacgtgctcatcttgcgaagaatttgaaa
cttacagaaacccaagtaaagattgtgtttcaaaatcgccgctataagacgaaacgtaaacaacttctctg
aactaggtgatttagaaaaacattcaagcctccggcgttaaaggaagaagcatttagtcgtgcgagctagt
ttctgtttacaatagttatccatactatccatattctactgtgtaggctcgtggtcgccagcttttggactagtat
gtggaacttattacacgaacagactcagcagtagccaacgcagcagcccctcgtttggaaatcaagcaac
gaagctaccaatatcaccccgaaacacaatatgaaagcattcctagacgactaaaagcagaaaacataa
aaaaatttcttttacaatttcacacagattccacatttagctcggtacggagcaaaactttcaattagcaaaacaaa
ttcaatctcaatggaagaattggtttagacagtgtagaattggctcattacgatgtccttttatcttatccgaat
aaaacgcatccaaattacatttcaatttattaatgaggatggaaatgaaatacaattgatgcctgagggcgattt
agtgtatgttaactatgcgcgcacagaggatttctttaaacttgaacgggatatgaaaatcaactgttctggta
aaatcgtcattgctcgttatggcaaagtattcgtggcaacaaagtaaagaatgcacaattagcgggtgcga
aaggcgtatattatccgatccagcagatttactttgcacctggagtaaaatcctatccagatggctggaa
tttgccaggtggggtgtacagcgtgcaatattcttaatctttaatggggctggtgaccctttaacctccctggtt
atccgatgataatacgcttatcgtcgtggaatcgcaaagaccgttggactacctcaattcctgtacatcc
aatcggatactatgatgctcaaaaattattagaaaagatgggggggtcgctccaccagattcgagctggc
gtggaagtctcaaagttccatacaatgtaggcccgggttttactggcaacttttcaacacaaaaagtgaaaat
gcacattcattccacgaatggacgtactcgaatatacaatgtcattggaactctccgtgggtgccgttgacca
gacagatattgtaatccttggcgacaccagatgagttgggttatttggaggtattgatccacaaagtggaacga
gcggttgttcatgaaatttgtagaagttctggtacacttaagaaagaaggggtttggcgaccacgccgtacgattt
tgtttgcttcgtgggatgccgaagagttcggactttttgggatctacagaatgggcagaagagaacagccgtt
tattgcaagaacgcgggggtagctctatattaatgctgatagtagtattgaaggtaactatacattaagagtggac
tgtacgccgttaatgtattccgctagtccataacccttacaaaagaacttaaagcccaagatgaaggttcgaag TABLE 5-continued ggaaatcgctttatgaatcatggacaaagaaatctccatcaccagagttctctggaatgcctcgtatcagtaa
atttgggtagcggaaacgactttgaagtttttcttcaacgtctaggcattgcgtcggggagagcgcggtacac
caaaaactgggaaaccaataagtttagcggctatccactctatcattctgtgtatgaaacatacagagcttgta
gaaaaattttatgatccgatgtttaaatatcatcttacagttgctcaggtccggggtggaatggtttttgagttgg
ctaattccattgtacttccatttgactgccgcgattacgctgtggtgctaagaaaatacgctgataaaatctatt
ccatttcaatgaaacacccacaagaaatgaaaacttatagcgtgagttttgatagttttattcagtgccgtaaag
aactttactgaaatcgccagcaagttttctgaaagattacaagatttcgataaatctaatcctatagtattaaga
atgatgaatgatcaactaatgtttttagaacgagcgttcattgatccgttaggttttaccggatcgaccttttctatc
gtcacgttatctacgctcccagtagccataacaaatatgcaggcgaatcttttccaggaatctatgacgccct
attcgatatagaaagtaaagttgatccgagtaaagcatggggtgaagttaaacgacaaatctatgtcgcggc
attcactgttcaagcagcggctgaaactttatcagaagttgcttaa ActAN100*-EGFRvIIIx5-NKX3.1(R41G)₁₁₋₂₃₄-PSMA₁₋₂₀, 44-138, 169-750
amino acid sequence (SEQ ID NO: 16)
(ActAN100* = normal text; BamHI linker (gs) = underlined;
EGFRvIIIx5 = double underlined; NKX3.1 (R41G)₁₁₋₂₃₄ = bold;
SpeI linker
(ts) = bold underlined)PSMA₁₋₂₀, 44-138, 169-750 = italic; MfeI linker (gl) =
dotted underlined)

MGLNRFMRAMMVVFITANCITINPDIIFAATDSEDSSLNTDEWEEE
YETAREVSSRDIEELEKSNKVKNTNKADQDNKRKAKAEKGGSASK
VLPASRALEEKKGNYVVTDHGSCADGSVKTSASKVAPASRALEEK
KGNYVVTDHGSCGDGSIKLSKVLPASRALEEKKGNYVVTDHGSCA
DGSVKASKVAPASRALEEKKGNYVVTDHGSCGDGSIKLASKVLPA
SRALEEKKGNYVVTDHGSCADGSVKgsEAKAEGAAPPTPSKPLTS
FLIQDILRDGAQGQGGRTSSQRQRDPEPEPEPEPEGGRSRAGAQ
NDQLSTGPRAAPEEAETLAETEPERHLGSYLLDSENTSGALPRL
PQTPKQPQKRSRAAFSHTQVIELERKFSHQKYLSAPERAHLAKN-
LKLTETQVKIWFQNRRYKTKRKQLSSELGDLEKHSSLPALKE
EAFSRASLVSVYNSYPYYPYLYCVGSWSPAFWtsMWNLLHETDSA
VATARRPRWKSSNEATNITPKHNMKAFLDELKAENIKKFLYNFTQIPHL
AGTEQNFQLAKQIQSQWKEFGLDSVELAHYDVLLSYPNKTHPNYISIIN
EDGNEIqlMPEGDLVYVNYARTEDFFKLERDMKINCSGKIVIARY
GKVFRGNKVKNAQLAGAKGVILYSDPADYFAPGVKSYPDGWNLPGGG
VQRGNILNLNGAGDPLTPGYPANEYAYRRGIAEAVGLPSIPVHPIGYYDA
QKLLEKMGGSAPPDSSWRGSLKVPYNVGPGFTGNFSTQKVKMHIHST
NEVTRIYNVIGTLRGAVEPDRYVILGGHRDSWVFGGIDPQSGAAVVHEI
VRSFGTLKKEGWRPRRTILFASWDAEEFGLLGSTEWAEENSRLLQERG
VAYINADSSIEGNYTLRVDCTPLMYSLVHNLTKELKSPDEGFEGKSLYES
WTKKSPSPEFSGMPRISKLGSGNDFEVFFQRLGIASGRARYTKNWETNK
FSGYPLYHSVYETYELVEKEYDPMFKYHLTVAQVRGGMVFELANSIVLP
FDCRDYAVVLRKYADKIYSISMKHPQEMKTYSVSFDSLFSAVKNFTEIAS
KFSERLQDFDKSNPIVLRMMNDQLMFLERAFIDPLGLPDRPFYRHVIY
APSSHNKYAGESFPGIYDALFDIESKVDPSKAWGEVKRQTYVAAFTVQA
AAETLSEVA

NKX3.1(R41G)₁₁₋₂₃₄ nucleotide sequence (SEQ ID NO: 17)

gaagcaaaagctgaaggcgcagcgcaccgactcctagtaaaccactaacaagtttcttaatccaagatat
tcttcgtgacggtgcacaaggacaaggcggacgaacttcttcacaacgtcaacgagatcctgagccagaa
ccggagcctgaaccggaaggggggacgctcccgagctggagcacaaaacgatcagttatctactggtcca
agagctgcccctgaagaagcagagacactagccgaaacggaaccagaaagacattttgggttcatacttac
ttgactcagaaaacacaagcggggctttaccgagattaccacaaacaccaaaacagcctcaaaaacgtag
tcgtgctgcatttctgcacacgcaagtcatagagttagaacgcaaattcagccatcaaaagtatttgtccgca
ccagaacgtgctcatcttgcgaagaatttgaaacttacagaaacccaagtaaagatttggtttcaaaatcgcc
gctataagacgaaacgtaaacaactttctctgaactaggtgatttagaaaaacattcaagccttccggcgtta
aaggaagaagcatttagtcgtgcgagcttagtttctgtttacaatagttatccatactatccatatctatactgtg
taggctcgtggtcgccagcttttttgg NKX3.1(R41G)₁₁₋₂₃₄ amino acid sequence (SEQ ID NO: 18)

**EAKAEGAAPPTPSKPLTSFLIQDILRDGAQGQGGRTSSQRQRDP
EPEPEPEPEGGRSRAGAQNDQLSTGPRAAPEEAETLAETEPERH
LGSYLLDSENTSGALPRLPQTPK**QPQKRSRAAFSHTQVIELERKFSH
QKYLSAPERAHLAKNLKLTETQVKIWFQNRRYKTKRKQLSSELGDLEK
HSSLPALKEEAFSRASLVSVYNSYPYYPYLYCVGSWSPAFW

PSMA₁₋₂₀, 44-138, 169-750 nucleotide sequence (SEQ ID NO: 19)
(MfeI linker dotted underlined)

atgtggaacttattacacgaaacagactcagcagtagcaacagccagacgccctcgttggaaatcaagca
acgaagctaccaatatcaccccgaaacacaatatgaaagcattcctagacgaactaaaagcagaaaacat
aaaaaaattcttttacaatttcacacagattccacattttagctggtacggacgaaaacttttcaattagcaaaca
aattcaatctcaatggaaagaatttggtttagacagttgtagaattggctcattacgatgtctttttatcttatccga
ataaaacgcatccaaattacatttcaattattaatgaagatggaaatgaaatacaattgatgcctgagggcga tttagtgtatgttaactatgcgcgcacagaggatttctttaaacttgaacgggatatgaaaatcaacttgttctgg
taaaatcgtcattgctcgttatggcaaagtatttcgtggcaacaaagtaaagaatgcacaattagcgggtgcg aaaggcgtcatattatactccgatccagcagattactttgcacctggagtaaaatcctatccagatggctgga
atttgccaggtgggggtgtacagcgtggcaatattcttaatcttaatggggcgctggtgaccctttaactcctggt
tatccagctaatgaatacgcttatcgtcgtggaatcgcagaagccgtgggactaccctcaattcctgtacatc
caatcggatactatgatgctcaaaaattattagaaaaagatggggggtccgctccaccagattcgagctgg
cgtggaagtctcaaagttccatacaatgtaggcccgggttttactggcaacttttcaacacaaaaagtgaaa
tgcacattcattccacgaatgaagtgactcgaatatacaatgtcattggaactctccgtggtgcggttgagcc
agacagatatgtaatccttggccggacaccgagatagttgggtatttggaggtattgatccacaaagtggagc
agcggttgttcatgaaattgttagaagtttcggtacacttaagaaagaagggtggcgaccacgccgtacgat
tttgtttgcttcgtgggatgccgaaggttcggactttttggatctacagaatgggcagaagaacagccg
tttattgcaagaacgcggggtagcttatattaatgctgatagtagtattgaaggtaactatacattaagagtgg
actgtacgccgttaatgtattcgctagtccataacccttacaaaagaacttaaaagcccagatgaagggttcga
agggaaatcgcttatgaatcatggacaaagaaatctccatcaccagagttctctggaatgcctcgtatcagt
aaatgggtagcggaaacgactttgaagtttttcttcaacgtctaggcattgcgtcggggagagcgcggtac
accaaaaactgggaaaccaataagtttagcggctatccactctatcattctgtgtatgaaacatacagagcttgt
agaaaaattttatgatccgatgtttaaatatcatcttacagttgctcaggtccggggtggaatggtttttgagttgg
gctaattccattgtacttccatttgactgccgcgattacgctgtggtgctaagaaaatacgctgataaaatctat
tccatttcaatgaaacacccacaagaaatgaaaacttatagcgtgagttttgatagttttattcagtgccgtaaa
gaactttactgaaatcgccagcaagttttctgaaagattacaagatttcgataaatctaatcctatagtattaag
aatgatgaatgatcaactaatgtttttagaacgagcgttcattgatccgttaggtttaccggatcgaccttttctat
cgtcacgttatctacgctcccagtagccataacaaatatgcaggcgaatcttttccaggaatctatgacgccc
tattcgatatagaaagtaaagttgatccgagtaaagcatggggtgaagttaaacgacaaatctatgtcgcgg
cattcactgttcaagcagcggctgaaactttatcagaagttgct PSMA₁₋₂₀, 44-138, 169-750 amino acid sequence (SEQ ID NO: 20)
(MfeI linker gl = dotted underlined)

MWNLLHETDSAVATARRPRWKSSNEATNITPKHNMKAFLDELKA
ENIKKFLYNFTQIPHLAGTEQNFQLAKQIQSQWKEFGLDSVELAHY
DVLLSYPNKTHPNYISIINEDGNEIqlMPEGDLVYVNYARTEDFFKLE
RDMKINCSGKIVIARYGKVFRGNKVKNAQLAGAKGVILYSDPADY
FAPGVKSYPDGWNLPGGGVQRGNILNLNGAGDPLTPGYPANEYA
YRRGIAEAVGLPSIPVHPIGYYDAQKLLEKMGGSAPPDSSWRGSLK
VPYNVGPGFTGNFSTQKVKMHIHSTNEVTRIYNVIGTLRGAVEPDR
YVILGGHRDSWVFGGIDPQSGAAVVHEIVRSFGTLKKEGWRPRRTI
LFASWDAEEFGLLGSTEWAEENSRLLQERGVAYINADSSIEGNYTL
RVDCTPLMYSLVHNLTKELKSPDEGFEGKSLYESWTKKSPSPEFSG
MPRISKLGSGNDFEVFFQRLGIASGRARYTKNWETNKFSGYPLYHS
VYETYELVEKFYDPMFKYHLTVAQVRGGMVFELANSIVLPFDCRD
YAVVLRKYADKIYSISMKHPQEMKTYSVSFDSLFSAVKNFTEIASK
FSERLQDFDKSNPIVLRMMNDQLMFLERAFIDPLGLPDRPFYRHVI
YAPSSHNKYAGESFPGIYDALFDIESKVDPSKAWGEVKRQIYVAAF
TVQAAAETLSEVA actA promoter nucleotide sequence (SEQ ID NO: 21)

gggaagcagttggggttaactgattaacaaatgttagagaaaaattaattctccaagtgatattcttaaaataa
tagctaattaagaagataattaactgctaatccaattttaacggaataaattagtgaaaatgaaggccgaattt
ttcatgaatattttttcttatattccttgttctaaaaaggttgtattagcgtatcacgaggagggagtataa actAp-ACTAN100*-EGFRVIIIx5-NKX3.1₁₁₋₂₃₄-PSMA₁₋₂₀, 44-138, 169-750
nucleotide sequence (SEQ ID NO: 22)

gggaagcagttggggttaactgattaacaaatgttagagaaaaattaattctccaagtgatattcttaaaataa
ttcatgaatattttttcttatatagctaattaagaagataattaactgctaatccaattttttaacggaataaattagtg
aaaatgaaggccgaattttccttgttctaaaaaggttgtattagcgtatcacgaggagggagtataagtggga
ttaaatagatttatgcgtgcgatgatggtagttttcattactgccaactgcattacgattaacccgacataatat
ttgcagcgacagatagcgaagattccagtctaaacacagatgaatgggaagaagaatacgaaactgcacg
tgaagtaagttcacgtgatattgaggaactagaaaaatcgaataaagtgaaaaatacgaacaaagcagacc
aagataataaacgtaaacgaaaagcagagaaaggtggatctgcaagcaaagtattgccagctagtcgtgc
attagaggagaaaaagggaattacgtggtgacggatcatggatcgtgtgccgatggctcagtaaagact
agcgcgagcaaagtggcccctgcatcacgagcacttgaagagaaaaaggaaactatgttgtgaccgat
catggtagctgcggagatggttcaattaaattatcaaaagtcttaccagcatctagagctttagaggaaaga
agggtaactatgtgctaacagatcatggaagtttgtgctgacggaagtgttaaagcgtcgaaaagttgctcca
gcttctcgcgcattagaagaaaaagaaggcaattatgtgttaacagaccatggtagttgtggtgatggctcg
atcaaattgtcaaaagttctaccggcttctcgtgcgctagaagagaagaaaggaaattacgtagttacgac
cacggcttctgcgcggatggttccgttaaaggatccgaagcaaaagctgaaggcgcagcgccaccgact
cctagtaaaccactaacagtttcttaatccaagatattcttcgtgacggtgcacaaagacaaggcggacga
acttcttcacaacgtcaacgagatcctgagccagaaccggagcctgaaccggaaggggggacgctcccga
gctggagcacaaaacgatcagttatctactggtccaagagctgcccctgaagaagcagagacactagccg
aaacggaaccagaaagacattttgggttcatacttacttgactcagaaaacacaagcggggctttaccgaga
ttaccacaaacaccaaaacagcctcaaaaacgtagtcgtgctgcatttctgcacacgcaagtcatagagtta
gaacgcaaattcagccatcaaaagtatttgtccgcaccagaacgtgctcatcttgcgaagaatttgaaactta
cagaaacccaagtaaagatttggtttcaaaatcgccgctataagacgaaacgtaaacaactttctctgaacta
ggtgatttagaaaaacattcaagccttccggcgttaaaggaagaagcatttagtcgtgcgagcttagtttct
gtttacaatagttatccatactatccatatctatactgtgtaggctcgtggtcgccagcttttttggactagtatgtg
gaacttattacacgaaacagactcagcagtagcaacagccagacgccctcgttggaaatcaagcaacgaa
gctaccaatatcaccccgaaacacaatatgaaagcattcctagacgaactaaaagcagaaaacataaaaa
aattctttacaatttcacacagattccacattttagctggtacggacgaagcaaaacttttcaattagcaaaacaaattc TABLE 5-continued aatctcaatggaaagaatttggtttagacagtgtagaattggctcattacgatgtccttttatcttatccgaataa
aacgcatccaaattacatttcaattattaatgaagatggaaatgaaatacaattgatgcctgagggcgatttag
tgtatgttaactatgcgcgcacagaggatttctttaaacttgaacgggatatgaaaatcaactgttctggtaaa
atcgtcattgctcgttatggcaaagtattcgtggcaacaaagtaaagaatgcacaattagcgggtgcgaaa
ggcgtcatattatactccgatccagcagattactttgcacctggagtaaaatctatccagatggctggaattt
gccaggtggggtgtacagcgtggcaatattcttaatcttaatggggctggtgacccttaactcctggttatc
cagctaatgaatacgcttatcgtcgtggaatcgcagaagccgtgggactaccctcaattcctgtacatccaat
cggatactatgatgctcaaaaattattagaaaagatgggggggtccgctccaccagattcgagctggcgtg
gaagtctcaaagttccatacaatgtaggcccgggttttactggcaacttttcaacacaaaagtgaaaatgca
cattcattccacgaatgaagtgactcgaatatacaatgtcattggaactctccgtggtgcggttgagccagac
agatatgtaatccttggcggacaccgagatagttgggtatttggaggtattgatccacaaagtggagcagcg
gttgttcatgaaattgttagaagtttcggtacacttaagaaagaagggtggcgaccacgccgtacgatttgtt
tgcttcgtggggatgccgaagagttcggactttttgggatctacagaatgggcagaagagaacagccgtttatt
gcaagaacgcggggtagcttatattaatgctgatagtagtattgaaggtaactatacattaagagtggactgt
acgccgttaatgtattcgctagtccataacctacaaaagaacttaaaagcccagatgaagggttcgaaggg
aaatcgctttatgaatcatggacaaagaaatctccatccaccagagttctctggaatgcctcgtatcagtaaatt
gggtagcggaaacgactttgaagtttttctttcaacgtctaggcattgcgtcggggagagcgcgtgcacca
aaaactgggaaaccaataagtttagccgctatccactctatcattctgtgtatgaaacatacgagcttgtaga
aaaatttatgatccgatgtttaaatatcatcttacagttgctcaggtccggggtggaatggttttttgagttggct
aattccattgtacttccatttgactgccgcgattacgctgtggtgctaagaaaatacgctgataaaatctattcc
atttcaatgaaacacccacaagaaatgaaattatagccgtgagtttttagatagtttattcagtgccgtaaagaa
ctttactgaaatcgccagcaagttttctgaaagattacaagatttcgataaatctaatcctatagtattaagaatg
atgaatgatcaactaatgtttttagaacgagcgttcattgatccgttaggtttaccggatcgaccttttctatcgt
acgttatctacgctcccagtagccataacaaatatgcaggcgaatctttttccaggaatctatgacgccctatc
gatatagaaagtaaagttgatccgagtaaagcatggggtgaagttaaacgacaaatctatgtcgcggcattc
actgttcaagcagcggctgaaactttatcagaagttgcttaa ActAN100*-EGFRvIIIx5-NKX3.1$_{11-234}$-PSMA$_{1-20, 44-138, 169-750}$ amino acid sequence (SEQ ID NO: 23)
(ActAN100* = normal text; BamHI linker (gs) = underlined; EGFRvIIIx5 = double underlined; NKX3.1$_{11-234}$ = bold; SpeI linker (ts) = bold underlined; PSMA$_{1-20, 44-138, 169-750}$ = italic; MfeI linker (gl) = dotted underlined)

MGLNRFMRAMMVVFITANCITINPDIIFAATDSEDSSLNTDEWEEE
YETAREVSSRDIEELEKSNKVKNTNKADQDNKRKAKAEKGGSASK
VLPASRALEEKKGNYVVTDHGSCADGSVKTSASKVAPASRALEEK
KGNYVVTDHGSCGDGSIKLSKVLPASRALEEKKGNYVVTDHGSCA
DGSVKASKVAPASRALEEKKGNYVVTDHGSCGDGSIKLSKVLPAS
RALEEKKGNYVVTDHGSCADGSVK
gsEAKAEGAAPPTPSKPLTSFLIQ
DILRDGAQRQGGRTSSQRQRDPEPEPEPEPEGGRSRAGAQNDQ
LSTGPRAAPEEAETLAETEPERHLGSYLLDSENTSGALPRLPQT
PKQPQKRSRAAFSHTQVIELERKFSHQKYLSAPERAHLAKNLK
LTETQVKIWFQNRRYKTKRKQLSSELGDLEKHSSLPALKEEAF
SRASLVSVYNSYPYYPYLYCVGSWSPAFWts*MWNLLHETDSAVAT
ARRPRWKSSNEATNITPKHNMKAFLDELKAENIKKFLYNFTQIPHLAGT
EQNFQLAKQIQSQWKEFGLDSVELAHYDVLLSYPNKTHPNYISIINEDG
NEIq*l*MPEGDLVYVNYARTEDFFKLERDMKINCSGKIVIARYGKVF*

*RGNKVKNAQLAGAKGVILYSDPADYFAPGVKSYPDGWNLPGGGVQRG
NILNLNGAGDPLTPGYPANEYAYRRGIAEAVGLPSIPVHPIGYYDAQKLL
EKMGGSAPPDSSWRGSLKVPYNVGPGFTGNFSTQKVKMHIHSTNEVTR
IYNVIGTLRGAVEPDRYVILGGHRDSWVFGGIDPQSGAAVVHEIVRSFG
TLKKEGWRPRRTILFASWDAEEFGLLGSTEWAEENSRLLQERGVAYINA
DSSIEGNYTLRVDCTPLMYSLVHNLTKELKSPDEGFEGKSLYESWTKKS
PSPEFSGMPRISKLGSGNDFEVFFQRLGIASGRARYTKNWETNKFSGYP
LYHSVYETYELVEKFYDPMFKYHLTVAQVRGGMVFELANSIVLPFDCR
DYAVVLRKYADKIYSISMKHPQEMKTYSVSFDSLFSAVKNFTEIASKFSE
RLQDFDKSNPIVLRMMNDQLMFLERAFIDPLGLPDRPFYRHVIYAPSSH
NKYAGESFPGIYDALFDIESKVDPSKAWGEVKRQIYVAAFTVQAAAETLS
EVA*

NKX3.1$_{11-234}$ nucleotide sequence (SEQ ID NO: 24)

gaagcaaaagctgaaggcgcagcgccaccgactcctagtaaaccactaacaagtttcttaatccaagatat
tcttcgtgacggtgcacaaagacaaggcggacgaacttcttcacaacgtcaacgagatcctgagccagaa
ccggagcctgaaccggaaggggacgctcccgagctggagcacaaaacgatcagttatctactggtcca
agagctgccctgaagaagcagagacactagccgaaacggaaccagaaagacatttgggttcatacttac
ttgactcagaaaacacaagcggggctttaccgagattaccacaaacaccaaaacagcctcaaaaacgtag
tcgtgctgcattttcgcacacgcaagtcatagagttagaacgcaaattcagccatcaaaagtatttgtccga
ccagaacgtgctcatcttgcgaagaatttgaaacttacagaaaccaagtaaagatttggtttcaaaatcgcc
gctataagacgaaacgtaaacaactttcttctgaactaggtgatttagaaaaacattcaagccttccggcgtta
aaggaagaagcatttagtcgtgcgagcttagtttctgtttacaatagttatccatactatccatatctatactgtg
taggctcgtggtcgccagcttttttgg NKX3.1$_{11-234}$ amino acid sequence (SEQ ID NO: 25)

EAKAEGAAPPTPSKPLTSFLIQDILRDGAQRQGGRTSSQRQRDP
EPEPEPEPEGGRSRAGAQNDQLSTGPRAAPEEAETLAETEPERH
LGSYLLDSENTSGALPRLPQTPKQPQKRSRAAFSHTQVIELERK
FSHQKYLSAPERAHLAKNLKLTETQVKIWFQNRRYKTKRKQL
SSELGDLEKHSSLPALKEEAFSRASLVSVYNSYPYYPYLYCVGS
WSPAFW actA-ActAN100*-NKX.3.1-PAP$_{33-386}$ nucleotide sequence (SEQ ID NO: 26)

gggaagcagttggggttaactgattaacaaatgttagagaaaaattaattctccaagtgatattcttaaaataa
ttcatgaatattttttcttatattagctaattaagaagataattaactgctaatccaattttttaacggaataaattagt
gaaaatgaaggccgaattttccttgttctaaaaaggttgtattagcgtatcacgagagggagtataagtgg
gattaaatagatttatgcgtgcgatgatggtagttttcattactgccaactgcattacgattaaccccgacataa
tattttgcagcgacagatgcgaagattccagtctaaacacagatgaatgggaagaagaatacgaaactgc
acgtgaagtaagttcacgtgatattgaggaactagaaaaatcgaataaagtgaaaaatacgaacaaagcag
accaagataataaacgtaaagcaaaagcagagaaaggtggatccatgttaagagtgcctgaaccaagac
caggagaagcaaaagctgaaggcgcagcgccaccgactcctagtaaaccactaacaagtttcttaatcca
agatattcttcgtgacggtgcacaaagacaaggcggacgaacttcttcacaacgtcaacgagatcctgagc
cagaaccggagcctgaaccggaaggggggacgctcccgagctggagcacaaaacgatcagttatctact
ggtccaagagctgccctgaagaagcagagacactagccgaaacggaaccagaaagacatttgggttca
tacttacttgactcagaaaacacaagcggggctttaccgagattaccacaaacaccaaaacagcctcaaaa
acgtagtcgtgctgcattttcgcacacgcaagtcatagagttagaacgcaaattcagccatcaaaagtatttg
tccgcaccagaacgtgctcatcttgcgaagaatttgaaacttacagaaaccaagtaaagatttggtttcaaa
atcgccgctataagacgaaacgtaaacaactttcttctgaactaggtgatttagaaaaacattcaagccttcc
ggcgttaaaggaagaagcatttagtcgtgcgagcttagtttctgtttacaatagttatccatactatccatatcta
tactgtgtaggctcgtggtcgccagatttttggactaggaaagaactaaagtttgtaacgttagtattagacat
ggtgatcgtagtcctattgatacattcctacagatccatcaagagagtagttggccacaaggcttcggac
aacttacacaattaggaatggaacaacattatgaattaggtgaatacattcgcaaacgttatcgcaaattcctt
aatgaatcgtacaaacacgaacaagtgtatatccgttccactgacgttgatagaacactaatgtcagctatga
caaatctagctgcattagtgccaccagaaggcgttagcatttggaatcctatcttactttggcagccaatacct
gtacatacggttccgttatctgaagatcaattactttatcttccatttcgcaactgcccacgattccaagaattag
aatccgaaacattgaaaagcgaagaatttcagaaaagattacatccatacaaagactttatcgcaacctag
gcaaattgtcagggttacacggacagaggatctatttggaatttggtcgaaagtttatgatcctttgtactgtgaat
ctgtacataacttttacattacctagtcgcgccacggaagatactatgacgaaactacgtgaacttccgaactt
tctttactatcgttgtatggtattcataaacaaaagaaaagagatgcaaggtggtgttttagtaaatgaa
atcttaaaccatatgaaaagagctacacaaatttccgtcttacaagaaattgattatgtatagtgctcatgatacg
acagtatctgggcttcaaatggccgttagatgtctataacggcttacttccaccgtatgcgtcatgtcaccttac
ggaacttttactttgagaaaggtgagtactttgttgagatgtactatcgcaatgaaacccaacatgaaccatatc
cgttgatgttaccaggttgtagtccatcttgcccgttagaacgattttgcggaattagtgggtccagtgatacca
caagactggtctactgagtgtatgactactaatagccaccaagggactgaagattcaacagattaa ActAN100*-NKX3.1-PAP$_{33-386}$ amino acid sequence (SEQ ID NO: 27)
(ActAN100* = normal text; BamHI linker (gs) = underlined; NKX3.1 = bold; linker (tr) = bold underlined; PAP$_{33-386}$ = italic)

MGLNRFMRAMMVVFITANCITINPDIIFAATDSEDSSLNTDEWEEE
YETAREVSSRDIEELEKSNKVKNTNKADQDNKRKAKAEKGGSML
RVPEPRPGEAKAEGAAPPTPSKPLTSFLIQDILRDGAQRQGGRT
SSQRQRDPEPEPEPEPEGGRSRAGAQNDQLSTGPRAAPEEAETL
AETEPERHLGSYLLDSENTSGALPRLPQTPKQPQKRSRAAFSHT
QVIELERKFSHQKYLSAPERAHLAKNLKLTETQVKIWFQNRRY
KTKRKQLSSELGDLEKHSSLPALKEEAFSRASLVSVYNSYPYP
YLYCVGSWSPAFWtr*KELKFVTILVFRHGDRSPIDTFPTDPIKESSWPQ
GFGQLTQLGMEQHYELGEYIRKRYRKFLNESYKHEQVYIRSTDVDRTIL
MSAMTNLAALVPPEGVSIWNPILLWQPIPVHTVPLSEDQLLYLPFRNCP
RFQELESETLKSEEFQKRLHPYDFIATLGKLSGLHGQDLFGIWSKVYD
PLYCESVHNFTLPSRATEDTMTKLRELSELSLLSLYGIHKQKEKSRLQGG
VLVNEILNHMKRATQIPSYKKLIMYSAHDTTVSGLQMALDVYNGLLPPY
ASCHLTELYFEKGEYFVEMYYRNETQHEPYPLMLPGCSPSCPLERFAEL
VGPVIPQDWSTECMTTNSHQGTEDSTD*

NKX3.1 nucleotide sequence (SEQ ID NO: 28)

atgttaagagtgcctgaaccaagaccaggagaagcaaaagctgaaggcgcagcgccaccgactcctagt
aaaccactaacaagtttcttaatccaagatattcttcgtgacggtgcacaaagacaaggcggacgaacttctt
cacaacgtcaacgagatcctgagccagaaccggagcctgaaccggaaggggggacgctcccgagctgg
agcacaaaacgatcagttatctactggtccaagagctgccctgaagaagcagagacactagccgaaac
ggaaccagaaagacatttgggttcatacttacttgactcagaaaacacaagcggggctttaccgagattacc
acaaacaccaaaacagcctcaaaaacgtagtcgtgctgcattttcgcacacgcaagtcatagagttagaac
gcaaattcagccatcaaaagtatttgtccgcaccagaacgtgctcatcttgcgaagaatttgaaacttacaga
aaccaagtaaagatttggtttcaaaatcgccgctataagacgaaacgtaaacaactttcttctgaactaggt
gatttagaaaaacattcaagccttccggcgttaaaggaagaagcatttagtcgtgcgagcttagtttctgttta
caatagttatccatactatccatatctatactgtgtaggctcgtggtcgccagcttttttgg NKX3.1 amino acid sequence (SEQ ID NO: 29)

MLRVPEPRPGEAKAEGAAPPTPSKPLTSFLIQDILRDGAQRQGG
RTSSQRQRDPEPEPEPEPEGGRSRAGAQNDQLSTGPRAAPEEAE
TLAETEPERHLGSYLLDSENTSGALPRLPQTPKQPQKRSRAAFS
HTQVIELERKFSHQKYLSAPERAHLAKNLKLTETQVKIWFQNR
RYKTKRKQLSSELGDLEKHSSLPALKEEAFSRASLVSVYNSYPY
YPYLYCVGSWSPAFW

TABLE 5-continued actA promoter-ActAN100*-SSX2 nucleotide sequence (SEQ ID NO: 30)

gggaagcagttggggttaactgattaacaaatgttagagaaaaattaattctccaagtgatattcttaaaataa
ttcatgaatattttttcttatattagctaattaagaagataattaactgctaatccaattttttaacggaataaattagt
gaaaatgaaggccgaattttccttgttctaaaaaggttgtattagcgtatcacgaggagggagtataagtgg
gattaaatagatttatgcgtgcgatgatggtagtttttcattactgccaactgcattacgattaaccccgacataa
tatttgcagcgacagatagcgaagattccagtctaaacacagatgaatgggaagaagaatacgaaactgc
acgtgaagtaagttcacgtgatattgaggaactagaaaaatcgaataaagtgaaaaatacgaacaaagcag
accaagataataaacgtaaagcaaaagcagagaaaggtggatccaatggtgatgacgctttcgcacgccg
tcctaccgtaggagcacaaattccagaaaagattcaaaaagcatttgatgacatcgctaaatactttctaaa
gaagaatgggagaaaatgaaagcgagcgagaaaatcttttatgtctatatgaaacggaaatatgaagcaat
gacaaaattgggtttcaaagcaacattaccaccattatgtgcaataaacgtgccggaagattttcaagggaat
gatttagacaatgatcctaatcgaggcaaccaagtggaaagaccgcaaatgactttcggacgtttacaagg
gatttctccaaagataatgccgaaaaagccagccgaagaaggtaatgatagtgaagaagtacctgaagcg
agtggtccacaaaatgatggtaaagaactttgtcctccaggcaaaccgacaacgtctgagaagattcatga
acggtccggtaaccgtgaagctcaagaaaagaagaacgacgtggaactgctcacagatggagttcaca
gaatacacataacattggccgctttagcctatcaacaagcatgggggctgttcatggaactccaaaaacgat
cacgcataacagagatccaaaaggcggaaacatgccgggtccaacagattgttgttagagaaaattcgtgg
taa ActAN100*-SSX2 amino acid sequence (SEQ ID NO: 31)
(BamHI linker (gs) = underlined; SSX2 = bold)

MGLNRFMRAMMVVFITANCITINPDIIFAATDSEDSSLNTDEWEEE
YETAREVSSRDIEELEKSNKVKNTNKADQDNKRKAKAEKG**GSNG
DDAFARRPTVGAQIPEKIQKAFDDIAKYFSKEEWEKMKASEKIF
YVVYMKRKYEAMTKLGFKATLPPFMCNKRAEDFQGNDLDNDP
NRGNQVERPQMTFGRLQGISPKIMPKKPAEEGNDSEEVPEASG
PQNDGKELCPPGKPTTSEKIHERSGNREAQEKEERRGTAHRWS
SQNTHNIGRFSLSTSMGAVHGTPKTITHNRDPKGGNMPGPTDC
VRENSW** actAp-ActAN100-PAP₃₀₋₃₈₆-SL8 nucleotide sequence (SEQ ID NO: 32)
(actAp = lower case italic; ActAN100 = upper case; PAP₃₀₋₃₈₆ = bold)

gggaagcagttggggttaactgattaacaaatgttagagaaaaattaattctccaagtgatattcttaaaataa
ttcatgaatattttttcttatattagctaattaagaagataattaactgctaatccaattttttaacggaataaattagt
gaaaatgaaggccgaattttccttgttctaaaaaggttgtattagcgtatcacgaggagggagtataaGTG
GGATTAAATAGATTTATGCGTGCGATGATGGTAGTTTTCATTACT
GCCAACTGCATTACGATTAACCCCGACATAATATTTGCAGCGAC
AGATAGCGAAGATTCCAGTCTAAACACAGATGAATGGGAAGAA
GAAAAAAACAGAAGAGCAGCCAAGCGAGGTAAATACGGGACCA
AGATACGAAACTGCACGTGAAGTAAGTTCACGTGATATTGAGG
AACTAGAAAAATCGAATAAAGTGAAAAATACGAACAAAGCAGA
CCTAATAGCAATGTTGAAAAGCAAAAGCAGAGAAAGGT**ggatccGT
ATTGGCAAAAGAACTAAAGTTTGTAACGTTAGTCTTTAGACA
TGGTGATCGTAGTCCTATTGATACCTTTCCTACAGATCCAAT
CAAAGAGAGTAGTTGGCCACAAGGCTTCGGACAACTTACAC
AATTAGGAATGGAACAACATTATGAATTAGGTGAATACATTC
GCAAACGTTATCGCAAATTCCTTAATGAATCGTACAAACACG
AACAAGTGTATATCCGTTCCACTGACGTTGATAGAACACTAA
TGTCAGCTATGACAAATCTAGCTGCATTAGTGCCACCAGAA
GGCGTTAGCATTTGGAATCCTATCTTACTTTGGCAGCCAATA
CCTGTACATACGGTTCCGTTATCTGAAGATCAATTACTTTAT
CTTCCATTTCGCAACTGCCCACGATTCCAAGAATTAGAATCC
GAAACATTGAAAAGCGAAGAATTTCAGAAAAGATTACATCC
ATACAAAGACTTTATCGCAACCTTAGGCAAATTGTCAGGGTT
ACACGGACAGGATCTATTTGGAATTTGGTCGAAAGTTTATGA
TCCTTTGTACTGTGAATCTGTACATAACTTTACATTACCTAG
TCGCGCCACGGAAGATACTATGACGAAACTACGTGAACTTT
CCGAACTTTCTTTACTATCGTTGTATGGTATTCATAAACAAA
AAGAAAAGAGCAGATTGCAAGGTGGTGTTTTAGTAAATGAA
ATCTTAAACCATATGAAAAGAGCTACACAAATTCCGTCTTAC
AAGAAATTGATTATGTATAGTGCTCATGATACGACAGTATCT
GGGCTTCAAATGGCGTTAGATGTCTATAACGGCTTACTTCCA
CCGTATGCGTCATGTCACCTTACGGAACTTTACTTTGAGAAA
GGTGAGTACTTTGTTGAGATGTACTATCGCAATGAAACCCAA
CATGAACCATATCCGTTGATGTTACCAGGTTGTAGTCCATCT
TGCCCGTTAGAACGATTTGCGGAATTAGTGGGTCCAGTGAT
ACCACAAGACTGGTCTACTGAGTGTATGACTACTAATAGCCA
CCAAGGGACTGAAGATTCAACAGAT**actagtcaattgggtgacggtagtattaa
acttagcaaagtattacaattagaaagtattattaattttgaaaaattagctgatggtcagttaaataa

ActAN100-PAP₃₀₋₃₈₆-SL8 amino acid sequence (SEQ ID NO: 33)
(PAP₃₀₋₃₈₆ = bold)

MGLNRFMRAMMVVFITANCITINPDIIFAATDSEDSSLNTDEWEEE
KTEEQPSEVNTGPRYETAREVSSRDIEELEKSNKVKNTNKADLIAM
LKAKAEKG**GSVLAKELKFVTLVFRHGDRSPIDTFPTDPIKESSW
PQGFGQLTQLGMEQHYELGEYIRKRYRKFLNESYKHEQVYIRS
TDVDRTLMSAMTNLAALVPPEGVSIWNPILLWQPIPVHTVPLSE
DQLLYLPFRNCPRFQELESETLKSEEFQKRLHPYKDFIATLGKL
SGLHGQDLFGIWSKVYDPLYCESVHNFTLPSRATEDTMTKLRE
LSELSLLSLYGIHKQKEKSRLQGGVLVNEILNHMKRATQIPSYK
KLIMYSAHDTTVSGLQMALDVYNGLLPPYASCHLTELYFEKGE
YFVEMYYRNETQHEPYPLMLPGCSPSCPLERFAELVGPVIPQD
WSTECMTTNSHQGTEDSTD**TSQLGDGSIKLSKVLQLESIINFEKLA
DGSVK actAp-ActAN100*-EGFRvIIIx1-PAP₃₃₋₃₈₆ nucleotide sequence (SEQ ID NQ: 34)

gggaagcagttggggttaactgattaacaaatgttagagaaaaattaattctccaagtgatattcttaaaataa
ttcatgaatattttttcttatattagctaattaagaagataattaactgctaatccaattttttaacggaataaattagt
gaaaatgaaggccgaattttccttgttctaaaaaggttgtattagcgtatcacgaggagggagtataaGTG
GGATTAAATAGATTTATGCGTGCGATGATGGTAGTTTTCATTACT
GCCAACTGCATTACGATTAACCCCGACATAATATTTGCAGCGAC
AGATAGCGAAGATTCCAGTCTAAACACAGATGAATGGGAAGAA
GAATACGAAACTGCACGTGAAGTAAGTTCACGTGATATTGAGG
AACTAGAAAAATCGAATAAAGTGAAAAATACGAACAAAGCAGA
CCAAGATAATAAACGTAAAGCAAAAGCAGAGAAAGGT*ggatctGC
AAGCAAAGTATTGCCAGCTAGTCGTGCATTAGAGGAGAAAAAGGGG
AATTACGTGGTGACGGATCATGGATCGTGTGCCGATGGCTCAGTAAA
G*ggatccAAAGAACTAAAGTTTGTAACGTTAGTCTTTAGACATG
GTGATCGTAGTCCTATTGATACCTTTCCTACAGATCCAATA
AAGAGAGTAGTTGGCCACAAGGCTTCGGACAACTTACACAA
TTAGGAATGGAACAACATTATGAATTAGGTGAATACATTCGC
AAACGTTATCGCAAATTCCTTAATGAATCGTACAAACACGAA
CAAGTGTATATCCGTTCCACTGACGTTGATAGAACACTAATG
TCAGCTATGACAAATCTAGCTGCATTAGTGCCACCAGAAGG
CGTTAGCATTTGGAATCCTATCTTACTTTGGCAGCCAATACC
TGTACATACGGTTCCGTTATCTGAAGATCAATTACTTTATCT
TCCATTTCGCAACTGCCCCACGATTCCAAGAATTAGAATCCG
AACATTGAAAAGCGAAGAATTTCAGAAAAGATTACATCCATA
CAAAGACTTTATCGCAACCTTAGGCAAATTGTCAGGGTTACA
CGGACAGGATCTATTTGGAATTTGGTCGAAAGTTTATGATCC
TTTGTACTGTGAATCTGTACATAACTTTACATTACCTAGTCG
CGCCACGGAAGATACTATGACGAAACTACGTGAACTTTCCG
AACTTTCTTTACTATCGTTGTATGGTATTCATAAACAAAAAG
AAAAGAGCAGATTGCAAGGTGGTGTTTAGTAAATGAAATC
TTAAACCATATGAAAAGAGCTACACAAATTCCGTCTTACAAG
AAATTGATTATGTATAGTGCTCATGATACGACAGTATCTGGG
CTTCAAATGGCGTTAGATGTCTATAACGGCTTACTTCCACCG
TATGCGTCATGTCACCTTACGGAACTTTACTTTGAGAAAGGT
GAGTACTTTGTTGAGATGTACTATCGCAATGAAACCCAACAT
GAACCATATCCGTTGATGTTACCAGGTTGTAGTCCATCTTGC
CCGTTAGAACGATTTGCGGAATTAGTGGGTCCAGTGATACC
ACAAGACTGGTCTACTGAGTGTATGACTACTAATAGCCACCA
AGGGACTGAAGATTCAACAGATtaa

ActAN100*-EGFRvIIIx1-PAP₃₃₋₃₈₆ amino acid sequence (SEQ ID NO: 35)

MGLNRFMRAMMVVFITANCITINPDIIFAATDSEDSSLNTDEWEEE
YETAREVSSRDIEELEKSNKVKNTNKADQDNKRKAKAEKGGS*ASK
VLPASRALEEKKGNYVVTDHGSCADGSVKGS***KELKFVTLVFRHGDR
SPIDTFPTDPIKESSWPQGFGQLTQLGMEQHYELGEYIRKRYRK
FLNESYKHEQVYIRSTDVDRTLMSAMTNLAALVPPEGVSIWNPI
LLWQPIPVHTVPLSEDQLLYLPFRNCPRFQELESETLKSEEFQK
RLHPYKDFIATLGKLSGLHGQDLFGIWSKVYDPLYCESVHNFT
LPSRATEDTMTKLRELSELSLLSLYGIHKQKEKSRLQGGVLVN
EILNHMKRATQIPSYKKLIMYSAHDTTVSGLQMALDVYNGLLP
PYASCHLTELYFEKGEYFVEMYYRNETQHEPYPLMLPGCSPSC
PLERFAELVGPVIPQDWSTECMTTNSHQGTEDSTD actAp-ActAN100*-EGFRvIIIx2-PAP₃₃₋₃₈₆ nucleotide sequence (SEQ ID NO: 36)

gggaagcagttggggttaactgattaacaaatgttagagaaaaattaattctccaagtgatattcttaaaataa
ttcatgaatattttttcttatattagctaattaagaagataattaactgctaatccaattttttaacggaataaattagt
gaaaatgaaggccgaattttccttgttctaaaaaggttgtattagcgtatcacgaggagggagtataaGTG
GGATTAAATAGATTTATGCGTGCGATGATGGTAGTTTTCATTACT
GCCAACTGCATTACGATTAACCCCGACATAATATTTGCAGCGAC
AGATAGCGAAGATTCCAGTCTAAACACAGATGAATGGGAAGAA
GAATACGAAACTGCACGTGAAGTAAGTTCACGTGATATTGAGG
AACTAGAAAAATCGAATAAAGTGAAAAATACGAACAAAGCAGA
CCAAGATAATAAACGTAAAGCAAAAGCAGAGAAAGGTGGATC
TGCAAGCAAAGTATTGCCAGCTAGTCGTGCATTAGAGGAGAAAAAGG
GGAATTACGTGGTGACGGATCATGGATCGTGTGCCGATGGCTCAGT
AAAGACTAGCGCGAGCAAAGTGGCCCCTGCATCACGAGCACTTGAA TABLE 5-continued GAGAAAAAAGGAAACTATGTTGTGACCGATCATGGTAGCTGCGGAGA
TGGTTCAAAAGGATCCAAAGAACTAAAGTTTGTAACGTTAGTC
TTTAGACATGGTGATCGTAGTCCTATTGATACCTTTCCTACA
GATCCAATCAAAGAGAGTAGTTGGCCACAAGGCTTCGGACA
ACTTACACAATTAGGAATGGAACAACATTATGAATTAGGTGA
ATACATTCGCAAACGTTATCGCAAATTCCTTAATGAATCGTA
CAAACACGAACAAGTGTATATCCGTTCCACTGACGTTGATAG
AACACTAATGTCAGCTATGACAAATCTAGCTGCATTAGTGCC
ACCAGAAGGCGTTAGCATTTGGAATCCTATCTTACTTTGGCA
GCCAATACCTGTACATACGGTTCCGTTATCTGAAGATCAATT
ACTTTATCTTCCATTTCGCAACTGCCCACGATTCCAAGAATT
AGAATCCGAAACATTGAAAAGCGAAGAATTTCAGAAAAGAT
TACATCCATACAAAGACTTTATCGCAACCTTAGGCAAATTGT
CAGGGTTACACGGACAGGATCTATTTGGAATTTGGTCGAAA
GTTTATGATCCTTTGTACTGTGAATCTGTACATAACTTTACA
TTACCTAGTCGCGCCACGGAAGATACTATGACGAAACTACG
TGAACTTTCCGAACTTTCTTTACTATCGTTGTATGGTATTCA
TAAACAAAAAGAAAAGAGCAGATTGCAAGGTGGTGTTTTAG
TAAATGAAATCTTAAACCATATGAAAAGAGCTACACAAATTC
CGTCTTACAAGAAATTGATTATGTATAGTGCTCATGATACGA
CAGTATCTGGGCTTCAAATGGCGTTAGATGTCTATAACGGCT
TACTTCCACCGTATGCGTCATGTCACCTTACGGAACTTTACT
TTGAGAAAGGTGAGTACTTTGTTGAGATGTACTATCGCAATG
AAACCCAACATGAACCATATCCGTTGATGTTACCAGGTTGTA
GTCCATCTTGCCCGTTAGAACGATTTGCGGAATTAGTGGGT
CCAGTGATACCACAAGACTGGTCTACTGAGTGTATGACTACT
AATAGCCACCAAGGGACTGAAGATTCAACAGATTAA ActAN100*-EGFRvIIIx2-PAP33-386 amino acid sequence
(SEQ ID NO: 37)

MGLNRFMRAMMVVFITANCITINPDIIFAATDSEDSSLNTDEWEEE
YETAREVSSRDIEELEKSNKVKNTNKADQDNKRKAKAEKG<u>GS</u>*ASK
VLPASRALEEKKGNYVVTDHGSCADGSVKTSASKVAPASRALEEKKGNY
VVTDHGSCGDGSK<u>GS</u>*KELKFVTLVFRHGDRSPIDTFPTDPIKESS
WPQGFGQLTQLGMEQHYELGEYIRKRYRKFLNESYKHEQVYI
RSTDVDRTLMSAMTNLAALVPPEGVSIWNPILLWQPIPVHTVPL
SEDQLLYLPFRNCPRFQELESETLKSEEFQKRLHPYKDFIATLG
KLSGLHGQDLFGIWSKVYDPLYCESVHNFTLPSRATEDTMTKL
RELSELSLLSLYGIHKQKEKSRLQGGVLVNEILNHMKRATQIPS
YKKLIMYSAHDTTVSGLQMALDVYNGLLPPYASCHLTELYFEK
GEYFVEMYYRNETQHEPYPLMLPGCSPSCPLERFAELVGPVIP
QDWSTECMTTNSHQGTEDSTD actAp-ActAN100*-EGFRvIIIx3-PAP33-386 nucleotide sequence
(SEQ ID NO: 38)

gggaagcagttggggttaactgattaacaaatgttagagaaaaattaattctccaagtgatattcttaaaataa
ttcatgaatatttttttcttatattagctaattaagaagataattaactgctaatccaattttttaacggaataaattagt
gaaaatgaaggccgaattttccttgttctaaaaaggttgtattagcgtatcacgaggagggagtataaGTG
GGATTAAATAGATTTATGCGTGCGATGATGGTAGTTTTCATTACT
GCCAACTGCATTACGATTAACCCCGACATAATATTTGCAGCGAC
AGATAGCGAAGATTCCAGTCTAAACACAGATGAATGGGAAGAA
GAATACGAAACTGCACGTGAAGTAAGTTCACGTGATATTGAGG
AACTAGAAAAATCGAATAAAGTGAAAAATACGAACAAAGCAGA
CCAAGATAATAAAACGTAAAGCAAAAGCAGAGAAAGGT<u>ggatct</u>*GC
AAGCAAAGTATTGCCAGCTAGTCGTGCATTAGAGGAGAAAAAGG
GGAATTACGTGGTGACGGATCATGGATCGTGTGCCGATGGCTCAGT
AAAGACTAGCGCGAGCAAAGTGGCCCCTGCATCACGAGCACTTGAAGAG
AAAAAAGGAAACTATGTTGTGACCGATCATGGTAGCTGCGGAGATGG
TTCAATTAAATTATCAAAAGTCTTACCAGCATCTAGAGCTTTAGA
AAAGAAGGGTAACTATGTCGTAACAGATCATGGAAGTTGTGCTGACG
GAAGTGT*ggatccAAAGAACTAAAGTTTGTAACGTTAGTCTTTA
GACATGGTGATCGTAGTCCTATTGATACCTTTCCTACAGATC
CAATCAAAGAGAGTAGTTGGCCACAAGGCTTCGGACACTT
ACACAATTAGGAATGGAACAACATTATGAATTAGGTGAATAC
ATTCGCAAACGTTATCGCAAATTCCTTAATGAATCGTACAAA
CACGAACAAGTGTATATCCGTTCCACTGACGTTGATAGAACA
CTAATGTCAGCTATGACAAATCTAGCTGCATTAGTGCCACCA
GAAGGCGTTAGCATTTGGAATCCTATCTTACTTTGGCAGCCA
ATACCTGTACATACGGTTCCGTTATCTGAAGATCAATTACTT
TATCTTCCATTTCGCAACTGCCCACGATTCCAAGAATTAGAA
TCCGAAACATTGAAAAGCGAAGAATTTCAGAAAAGATTACAT
CCATACAAAGACTTTATCGCAACCTTAGGCAAATTGTCAGGG
TTACACGGACAGGATCTATTTGGAATTTGGTCGAAAGTTTAT
GATCCTTTGTACTGTGAATCTGTACATAACTTTACATTACCT
AGTCGCGCCACGGAAGATACTATGACGAAACTACGTGAACT
TTCCGAACTTTCTTTACTATCGTTGTATGGTATTCATAAACA
AAAAGAAAAGAGCAGATTGCAAGGTGGTGTTTTAGTAAATG
AAATCTTAAACCATATGAAAAGAGCTACACAAATTCCGTCTT
ACAAGAAATTGATTATGTATAGTGCTCATGATACGACAGTAT TABLE 5-continued CTGGGCTTCAAATGGCGTTAGATGTCTATAACGGCTTACTTC
CACCGTATGCGTCATGTCACCTTACGGAACTTTACTTTGAGA
AAGGTGAGTACTTTGTTGAGATGTACTATCGCAATGAAACCC
AACATGAACCATATCCGTTGATGTTACCAGGTTGTAGTCCAT
CTTGCCCGTTAGAACGATTTGCGGAATTAGTGGGTCCAGTG
ATACCACAAGACTGGTCTACTGAGTGTATGACTACTAATAGC
CACCAAGGGACTGAAGATTCAACAGATtaa ActAN100*-EGFRvIIIx3-PAP33-386 amino acid sequence
(SECS ID NO: 39)

MGLNRFMRAMMVVFITANCITINPDIIFAATDSEDSSLNTDEWEEE
YETAREVSSRDIEELEKSNKVKNTNKADQDNKRKAKAEKG<u>GS</u>*ASK
VLPASRALEEKKGNYVVTDHGSCADGSVKTSASKVAPASRALEEKKGNY
VVTDHGSCGDGSIKLSKVLPASRALEEKKGNYVVTDHGSCADGSV*G<u>GS</u>K
**ELKFVTLVFRHGDRSPIDTFPTDPIKESSWPQGFGQLTQLGMEQ
HYELGEYIRKRYRKFLNESYKHEQVYIRSTDVDRTLMSAMTNL
AALVPPEGVSIWNPILLWQPIPVHTVPLSEDQLLYLPFRNCPRF
QELESETLKSEEFQKRLHPYKDFIATLGKLSGLHGQDLFGIWS
KVYDPLYCESVHNFTLPSRATEDTMTKLRELSELSLLSLYGIHK
QKEKSRLQGGVLVNEILNHMKRATQIPSYKKLIMYSAHDTTVS
GLQMALDVYNGLLPPYASCHLTELYFEKGEYFVEMYYRNETQ
HEPYPLMLPGCSPSCPLERFAELVGPVIPQDWSTECMTTNSHQ
GTEDSTD** actAp-ActAN100*-EGFRvIIIx4-PAP33-386 nucleotide sequence
(SEQ ID NO: 40)

gggaagcagttggggttaactgattaacaaatgttagagaaaaattaattctccaagtgatattcttaaaataa
ttcatgaatatttttttcttatattagctaattaagaagataattaactgctaatccaattttttaacggaataaattagt
gaaaatgaaggccgaattttccttgttctaaaaaggttgtattagcgtatcacgaggagggagtataaGTG
GGATTAAATAGATTTATGCGTGCGATGATGGTAGTTTTCATTACT
GCCAACTGCATTACGATTAACCCCGACATAATATTTGCAGCGAC
AGATAGCGAAGATTCCAGTCTAAACACAGATGAATGGGAAGAA
GAATACGAAACTGCACGTGAAGTAAGTTCACGTGATATTGAGG
AACTAGAAAAATCGAATAAAGTGAAAAATACGAACAAAGCAGA
CCAAGATAATAAACGTAAAGCAAAAGCAGAGAAAGGT<u>GGATCT</u>
*GCAAGCAAAGTATTGCCAGCTAGTCGTGCATTAGAGGAGAAAAAGG
GGAATTACGTGGTGACGGATCATGGATCGTGTGCCGATGGCTCAGT
AAAGACTAGCGCGAGCAAAGTGGCCCCTGCATCACGAGCACTTGAA
GAGAAAAAAGGAAACTATGTTGTGACCGATCATGGTAGCTGCGGAGA
TGGTTCAATTAAATTATCAAAAGTCTTACCAGCATCTAGAGCTTTAGA
GGAAAAGAAGGGTAACTATGTCGTAACAGATCATGGAAGTTGTGCTG
ACGGAAGTGTTAAAGCGTCGAAAGTAGCTCCAGCTTCTCGCGCATTA
GAAGAAAAGAAAGGCAATTATGTTGTAACAGACCATGGTAGTTGTGG
TGATGGCTCGAAAG*GATCC**AAAGAACTAAAGTTTGTAACGTTA
GTCTTTAGACATGGTGATCGTAGTCCTATTGATACCTTTCCT
ACAGATCCAATCAAAGAGAGTAGTTGGCCACAAGGCTTCGG
ACAACTTACACAATTAGGAATGGAACAACATTATGAATTAGG
TGAATACATTCGCAAACGTTATCGCAAATTCCTTAATGAATC
GTACAAACACGAACAAGTGTATATCCGTTCCACTGACGTTGA
TAGAACACTAATGTCAGCTATGACAAATCTAGCTGCATTAGT
GCCACCAGAAGGCGTTAGCATTTGGAATCCTATCTTACTTTG
GCAGCCAATACCTGTACATACGGTTCCGTTATCTGAAGATCA
ATTACTTTATCTTCCATTTCGCAACTGCCCACGATTCCAAGA
ATTAGAATCCGAAACATTGAAAAGCGAAGAATTTCAGAAAA
GATTACATCCATACAAAGACTTTATCGCAACCTTAGGCAAAT
TGTCAGGGTTACACGGACAGGATCTATTTGGAATTTGGTCGA
AAAGTTTATGATCCTTTGTACTGTGAATCTGTACATAACTTT
ACATTACCTAGTCGCGCCACGGAAGATACTATGACGAAACT
ACGTGAACTTTCCGAACTTTCTTTACTATCGTTGTATGGTAT
TCATAAACAAAAAGAAAAGAGCAGATTGCAAGGTGGTGTTT
TAGTAAATGAAATCTTAAACCATATGAAAAGAGCTACACAAA
TTCCGTCTTACAAGAAATTGATTATGTATAGTGCTCATGATA
CGACAGTATCTGGGCTTCAAATGGCGTTAGATGTCTATAAC
GGCTTACTTCCACCGTATGCGTCATGTCACCTTACGGAACTT
TACTTTGAGAAAGGTGAGTACTTTGTTGAGATGTACTATCGC
AATGAAACCCAACATGAACCATATCCGTTGATGTTACCAGGT
TGTAGTCCATCTTGCCCGTTAGAACGATTTGCGGAATTAGTG
GGTCCAGTGATACCACAAGACTGGTCTACTGAGTGTATGAC
TACTAATAGCCACCAAGGGACTGAAGATTCAACAGATTAA ActAN100*-EGFRvIIIx4-PAP33-386 amino acid sequence
(SEQ ID NO: 41)

MGLNRFMRAMMVVFITANCITINPDIIFAATDSEDSSLNTDEWEEE
YETAREVSSRDIEELEKSNKVKNTNKADQDNKRKAKAEKG<u>GS</u>*ASK
VLPASRALEEKKGNYVVTDHGSCADGSVKTSASKVAPASRALEEKKGNY
VVTDHGSCGDGSIKLSKVLPASRALEEKKGNYVVTDHGSCGDGS*K<u>GS</u>**KELKFVTLVFRHGDR
SPIDTFPTDPIKESSWPQGFGQLTQLGMEQHYELGEYIRKRYRK**

TABLE 5-continued

FLNESYKHEQVYIRSTDVDRTLMSAMTNLAALVPPEGVSIWNPI
LLWQPIPVHTVPLSEDQLLYLPFRNCPRFQELESETLKSEEFQK
RLHPYKDFIATLGKLSGLHGQDLFGIWSKVYDPLYCESVHNFT
LPSRATEDTMTKLRELSELSLLSLYGIHKQKEKSRLQGGVLVN
EILNHMKRATQIPSYKKLIMYSAHDTTVSGLQMALDVYNGLLP
PYASCHLTELYFEKGEYFVEMYYRNETQHEPYPLMLPGCSPSC
PLERFAELVGPVIPQDWSTECMTTNSHQGTEDSTD

EGFRvIII nucleotide sequence 1 (SEQ ID NO: 42)

CCAGCTAGTCGTGCATTAGAGGAGAAAAAGGGGAATTACGTGG
TGACGGATCATGGATCGTGT

EGFRvIII nucleotide sequence 2 (SEQ ID NO: 43)

CCTGCATCACGAGCACTTGAAGAGAAAAAAGGAAACTATGTTG
TGACCGATCATGGTAGCTGC

EGFRvIII nucleotide sequence 3 (SEQ ID NO: 44)

CCAGCATCTAGAGCTTTAGAGGAAAAGAAGGGTAACTATGTCGT
AACAGATCATGGAAGTTGT

EGFRvIII nucleotide sequence 4 (SEQ ID NO: 45)

CCAGCTTCTCGCGCATTAGAAGAAAAGAAAGGCAATTATGTTGT
AACAGACCATGGTAGTTGT

EGFRvIII nucleotide sequence 5 (SEQ ID NO: 46)

CCGGCTTCTCGTGCGCTAGAAGAGAAGAAAGGAAATTACGTAG
TTACAGACCACGGCTCTTGC hly promoter nucleotide sequence (SEQ ID NO: 47)

tcctttgattagtatattcctatcttaaagttacttttatgtgaggcattaacatttgttaatgacgtcaaaaggat
agcaagactagaataaagctataaagcaagcatataatattgcgtttcatctttagaagcgaatttcgccaata
ttataattatcaaaagagaggggtggcaaacggtatttggcattattaggttaaaaaatgtagaaggagagtg
aaacccc

LLO441 nucleotide sequence (SEQ ID NO: 48)

ATGAAAAAAATAATGCTAGTTTTTATTACACTTATATTAGTTAGT
CTACCAATTGCGCAACAAACTGAAGCAAAGGATGCATCTGCATT
CAATAAAGAAAATTCAATTTCATCCATGGCACCACCAGCATCTC
CGCCTGCAAGTCCTAAGACGCCAATCGAAAAGAAACACGCGGA
TGAAATCGATAAGTATATACAAGGATTGGATTACAATAAAAAC
AATGTATTAGTATACCACGGAGATGCAGTGACAAATGTGCCGCC
AAGAAAAGGTTACAAAGATGGAAATGAATATATTGTTGTGGAG
AAAAAGAAGAAATCCATCAATCAAAATAATGCAGACATTCAAG
TTGTGAATGCAATTTCGAGCCTAACCTATCCAGGTGCTCTCGTA
AAAGCGAATTCGGAATTAGTAGAAAATCAACCAGATGTTCTCCC
TGTAAAACGTGATTCATTAACACTCAGCATTGATTTGCCAGGTA
TGACTAATCAAGACAATAAAATAGTTGTAAAAAATGCCACTAA
ATCAAACGTTAACAACGCAGTAAATACATTAGTGGAAAGATGG
AATGAAAAATATGCTCAAGCTTATCCAAATGTAAGTGCAAAAAT
TGATTATGATGACGAAATGGCTTACAGTGAATCACAATTAATTG
CGAAATTTGGTACAGCATTTAAAGCTGTAAATAATAGCTTGAAT
GTAAACTTCGGCGCAATCAGTGAAGGGAAAATGCAAGAAGAAG
TCATTAGTTTTAAACAAATTTACTATAACGTGAATGTTAATGAA
CCTACAAGACCTTCCAGATTTTTCGGCAAAGCTGTTACTAAAGA
GCAGTTGCAAGCGCTTGGAGTGAATGCAGAAAATCCTCCTGCAT
ATATCTCAAGTGTGGCGTATGGCCGTCAAGTTTATTTGAAATTAT
CAACTAATTCCCATAGTACTAAAGTAAAAGCTGCTTTTGATGCT
GCCGTAAGCGGAAAATCTGTCTCAGGTGATGTAGAACTAACAA
ATATCATCAAAAATTCTTCCTTCAAAGCCGTAATTTACGGAGGT
TCCGCAAAAGATGAAGTTCAAATCATCGACGGCAACCTCGGAG
ACTTACGCGATATTTTGAAAAAAGGCGCTACTTTTAATCGAGAA
ACACCAGGAGTTCCCATTGCTTATACAACAAACTTCCTAAAAGA
CAATGAATTAGCTGTTATTAAAAACAACTCAGAATATATTGAAA
CAACTTCAAAAGCTTATACAGATGGAAAAATTAACATCGATCAC
TCTGGAGGATACGTTGCTCAATTCAACATTTCTTGGGATGAAGT
AAATTATGAT

LLO441 amino acid sequence (SEQ ID NO: 49)

MKKIMLVFITLILVSLPIAQQTEAKDASAFNKENSISSMAPPASPPAS
PKTPIEKKHADEIDKYIQGLDYNKNNVLVYHGDAVTNVPPRKGYK
DGNEYIVVEKKKKSINQNNADIQVVNAISSLTYPGALVKANSELVE
NQPDVLPVKRDSLTLSIDLPGMTNQDNKIVVKNATKSNVNNAVNT
LVERWNEKYAQAYPNVSAKIDYDDEMAYSESQLIAKFGTAFKAVN
NSLNVNFGAISEGKMQEEVISFKQIYYNVNVNEPTRPSRFFGKAVT
KEQLQALGVNAENPPAYISSVAYGRQVYLKLSTNSHSTKVKAAFD
AAVSGKSVSGDVELTNIIKNSSFKAVIYGGSAKDEVQIIDGNLGDLR
DILKKGATFNRETPGVPIAYTTNFLKDNELAVIKNNSEYIETTSKAY
TDGKINIDHSGGYVAQFNISWDEVNYD

LLO441ΔPEST nucleotide sequence (SEQ ID NO: 50)

ATGAAAAAAATAATGCTAGTTTTTATTACACTTATATTAGTTAGT
CTACCAATTGCGCAACAAACTGAAGCAAAGGATGCATCTGCATT
CAATAAAGAAAATTCAATTTCATCCATGGCACCACCAGCATCTC
CAATGCGAAATCGATAAGTATATACAAGGATTGGATTACAATAAAAACAATGTATTAGTATA
CCACGGAGATGCAGTGACAAATGTGCCGCCAAGAAAAGGTTAC
AAAGATGGAAATGAATATATTGTTGTGGAGAAAAAGAAGAAAT
CCATCAATCAAAATAATGCAGACATTCAAGTTGTGAATGCAATT
TCGAGCCTAACCTATCCAGGTGCTCTCGTAAAAGCGAATTCGGA
ATTAGTAGAAAATCAACCAGATGTTCTCCCTGTAAAACGTGATT
CATTAACACTCAGCATTGATTTGCCAGGTATGACTAATCAAGAC
AATAAAATAGTTGTAAAAAATGCCACTAAATCAAACGTTAACA
ACGCAGTAAATACATTAGTGGAAAGATGGAATGAAAAATATGC
TCAAGCTTATCCAAATGTAAGTGCAAAAATTGATTATGATGACG
AAATGGCTTACAGTGAATCACAATTAATTGCGAAATTTGGTACA
GCATTTAAAGCTGTAAATAATAGCTTGAATGTAAACTTCGGCGC
AATCAGTGAAGGGAAAATGCAAGAAGAAGTCATTAGTTTTAAA
CAAATTTACTATAACGTGAATGTTAATGAACCTACAAGACCTTC
CAGATTTTTCGGCAAAGCTGTTACTAAAGAGCAGTTGCAAGCGC
TTGGAGTGAATGCAGAAAATCCTCCTGCATATATCTCAAGTGTG
GCGTATGGCCGTCAAGTTTATTTGAAATTATCAACTAATTCCCAT
AGTACTAAAGTAAAAGCTGCTTTTGATGCTGCCGTAAGCGGAAA
ATCTGTCTCAGGTGATGTAGAACTAACAAATATCATCAAAAATT
CTTCCTTCAAAGCCGTAATTTACGGAGGTTCCGCAAAAGATGAA
GTTCAAATCATCGACGGCAACCTCGGAGACTTACGCGATATTTT
GAAAAAAGGCGCTACTTTTAATCGAGAAACACCAGGAGTTCCC
ATTGCTTATACAACAAACTTCCTAAAAGACAATGAATTAGCTGT
TATTAAAAACAACTCAGAATATATTGAAACAACTTCAAAAGCTT
ATACAGATGGAAAAATTAACATCGATCACTCTGGAGGATACGTT
GCTCAATTCAACATTTCTTGGGATGAAGTAAATTATGAT

LLO441ΔPEST amino acid sequence (SEQ ID NO: 51)

MKKIMLVFITLILVSLPIAQQTEAKDASAFNTPIEKKHADEIDKYIQG
LDYNKNNVLVYHGDAVTNVPPRKGYKDGNEYIVVEKKKKSINQN
NADIQVVNAISSLTYPGALVKANSELVENQPDVLPVKRDSLTLSIDL
PGMTNQDNKIVVKNATKSNVNNAVNTLVERWNEKYAQAYPNVS
AKIDYDDEMAYSESQLIAKFGTAFKAVNNSLNVNFGAISEGKMQE
EVISFKQIYYNVNVNEPTRPSRFFGKAVTKEQLQALGVNAENPPAY
ISSVAYGRQVYLKLSTNSHSTKVKAAFDAAVSGKSVSGDVELTNII
KNSSFKAVIYGGSAKDEVQIIDGNLGDLRDILKKGATFNRETPGVPI
AYTTNFLKDNELAVIKNNSEYIETTSKAYTDGKINIDHSGGYVAQF
NISWDEVNYD

LLO441Δ26 nucleotide sequence (SEQ ID NO: 52)

ATGAAAAAAATAATGCTAGTTTTTATTACACTTATATTAGTTAGT
CTACCAATTGCGCAACAAACTGAAGCAAAGGATGCATCTGCATT
CAATAAAGAAGAAATCGATAAGTATATACAAGGATTGGATTAC
AATAAAAACAATGTATTAGTATACCACGGAGATGCAGTGACAA
ATGTGCCGCCAAGAAAAGGTTACAAAGATGGAAATGAATATAT
TGTTGTGGAGAAAAAGAAGAAATCCATCAATCAAAATAATGCA
GACATTCAAGTTGTGAATGCAATTTCGAGCCTAACCTATCCAGG
TGCTCTCGTAAAAGCGAATTCGGAATTAGTAGAAAATCAACCAG
ATGTTCTCCCTGTAAAACGTGATTCATTAACACTCAGCATTGATT
TGCCAGGTATGACTAATCAAGACAATAAAATAGTTGTAAAAAAT
GCCACTAAATCAAACGTTAACAACGCAGTAAATACATTAGTGGA
AAGATGGAATGAAAAATATGCTCAAGCTTATCCAAATGTAAGTG
CAAAAATTGATTATGATGACGAAATGGCTTACAGTGAATCACAA
TTAATTGCGAAATTTGGTACAGCATTTAAAGCTGTAAATAATAG
CTTGAATGTAAACTTCGGCGCAATCAGTGAAGGGAAAATGCAA
GAAGAAGTCATTAGTTTTAAACAAATTTACTATAACGTGAATGT
TAATGAACCTACAAGACCTTCCAGATTTTTCGGCAAAGCTGTTA
CTAAAGAGCAGTTGCAAGCGCTTGGAGTGAATGCAGAAAATCC
TCCTGCATATATCTCAAGTGTGGCGTATGGCCGTCAAGTTTATTT
GAAATTATCAACTAATTCCCATAGTACTAAAGTAAAAGCTGCTT
TTGATGCTGCCGTAAGCGGAAAATCTGTCTCAGGTGATGTAGAA
CTAACAAATATCATCAAAAATTCTTCCTTCAAAGCCGTAATTTA
CGGAGGTTCCGCAAAAGATGAAGTTCAAATCATCGACGGCAAC
CTCGGAGACTTACGCGATATTTTGAAAAAAGGCGCTACTTTTAA
TCGAGAAACACCAGGAGTTCCCATTGCTTATACAACAAACTTCC
TAAAAGACAATGAATTAGCTGTTATTAAAAACAACTCAGAATAT

TABLE 5-continued

ATTGAAACAACTTCAAAAGCTTATACAGATGGAAAAATTAACAT
CGATCACTCTGGAGGATACGTTGCTCAATTCAACATTTCTTGGG
ATGAAGTAAATTATGAT

LLO441Δ26 amino acid sequence (SEQ ID NO: 53)

MKKIMLVFITLILVSLPIAQQTEAKDASAFNKEEIDKYIQGLDYNKN
NVLVYHGDAVTNVPPRKGYKDGNEYIVVEKKKKSINQNNADIQV
VNAISSLTYPGALVKANSELVENQPDVLPVKRDSLTLSIDLPGMTN
QDNKIVVKNATKSNVNNAVNTLVERWNEKYAQAYPNVSAKIDYD
DEMAYSESQLIAKFGTAFKAVNNSLNVNFGAISEGKMQEEVISFKQ
IYYNVNVNEPTRPSRFFGKAVTKEQLQALGVNAENPPAYISSVAYG
RQVYLKLSTNSHSTKVKAAFDAAVSGKSVSGDVELTNIIKNSSFKA
VIYGGSAKDEVQIIDGNLGDLRDILKKGATFNRETPGVPIAYTTNFL
KDNELAVIKNNSEYIETTSKAYTDGKINIDHSGGYVAQFNISWDEV
NYD

ActAN100 nucleotide sequence (SEQ ID NO: 59)

GTGGGATTAAATAGATTTATGCGTGCGATGATGGTAGTTTTCAT
TACTGCCAACTGCATTACGATTAACCCCGACATAATATTTGCAG
CGACAGATAGCGAAGATTCCAGTCTAAACACAGATGAATGGGA
AGAAGAAAAAACAGAAGAGCAGCCAAGCGAGGTAAATACGGG
ACCAAGATACGAAACTGCACGTGAAGTAAGTTCACGTGATATTG
AGGAACTAGAAAAATCGAATAAAGTGAAAAATACGAACAAAGC
AGACCTAATAGCAATGTTGAAAGCAAAAGCAGAGAAAGGT

ActAN100 amino acid sequence (SEQ ID NO: 60)

MGLNRFMRAMMVVFITANCITINPDIIFAATDSEDSSLNTDEWEEE
KTEEQPSEVNTGPRYETAREVSSRDIEELEKSNKVKNTNKADLIAM
LKAKAEKG

In some embodiments, the present invention relates to a fusion protein comprising an epidermal growth factor receptor variant III (EGFRvIII) polypeptide and a synovial sarcoma, X breakpoint 2 (SSX2) polypeptide. In some embodiments, said EGFRvIII polypeptide comprises an amino acid sequence at least i) 90% identical, ii) 95% identical, iii) 99% identical, or iv) 100% identical to SEQ ID NO:6. In some embodiments, said fusion protein comprises a plurality of EGFRvIII polypeptides. In some embodiments, said fusion protein comprises five copies of the EGFRvIII polypeptide. In certain embodiments, said EGFRvIII polypeptide is flanked by one or more cleaver sequences. In certain embodiments, the EGFRvIII polypeptide is fused to the N-terminus of the SSX2 polypeptide. In certain embodiments, the SSX2 polypeptide comprises an amino acid sequence at least i) 90% identical, ii) 95% identical, iii) 99% identical, or iv) 100% identical to SSX2 as set forth in SEQ ID NO:10.

In some embodiments, the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10. In certain embodiments, the fusion protein comprises an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4.

In some embodiments, the fusion protein comprises a signal sequence, wherein the signal sequence is in translational reading frame with the EGFRvIII polypeptide and the SSX2 polypeptide. In certain embodiments, the signal sequence is at least i) 90% identical, ii) 95% identical, iii) 99% identical, or iv) 100% identical to ActAN100* as set forth as SEQ ID NO:2.

In certain embodiments, said fusion protein is expressed in a bacterium. In one embodiment, the bacterium is *Listeria monocytogenes*.

In various embodiments, the present invention also provides nucleic acid molecule encoding the fusion protein of any of the preceding embodiments.

In certain embodiments, said nucleic acid molecule comprises one or more EGFRvIII polynucleotides that are at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the SSX2 polynucleotide as set forth in SEQ ID NO:9.

In some embodiments, the nucleic acid molecule further comprises a promoter, a signal sequence, or both, wherein the promoter, signal sequence, or both are operably linked with the nucleotide sequence encoding the EGFRvIII polypeptide and the nucleotide sequence encoding the SSX2 polypeptide. In certain embodiments, the promoter is at least i) 90% identical, ii) 95% identical, iii) 99% identical, or iv) 100% identical to an actA promoter as set forth in SEQ ID NO:21. In various embodiments, the signal sequence is at least i) 90% identical, ii) 95% identical, iii) 99% identical, or iv) 100% identical to ActAN100* as set forth in SEQ ID NO:1. In some embodiments, the nucleic acid molecule is part of an expression cassette.

In some embodiments, the present invention provides a vector comprising the nucleic acid molecule of any of the preceding embodiments.

In some embodiments, the present invention also provides a host cell comprising the nucleic acid molecule of any of the preceding embodiments. In certain embodiments, said host cell is a bacterium. In one embodiment, the bacterium is *Listeria monocytogenes*. In some embodiments, the *Listeria monocytogenes* is an actA deletion mutant, an actA insertion mutant, an inlB deletion mutant, an inlB insertion mutant, or a combination thereof. In one embodiment, the *Listeria monocytogenes* is a ΔactA/ΔinlB mutant. In certain embodiments, the nucleic acid molecule is integrated into the host cell genome. In certain embodiments, the nucleic acid molecule is integrated into the actA locus, inlB locus or tRNA$^{Arg}$ locus.

In various embodiments, the host cell of any of the preceding embodiments is in combination with a pharmaceutically acceptable excipient.

In some embodiments, the present invention provides a vaccine comprising the host cell of any of the preceding embodiments and a pharmaceutically acceptable excipient.

In certain embodiments, the present invention provides a fusion protein comprising an EGFRvIII polypeptide and a prostatic acid phosphatase (PAP) polypeptide. In some embodiments, said EGFRvIII polypeptide comprises an amino acid sequence at least i) 90% identical, ii) 95% identical, iii) 99% identical, or iv) 100% identical to SEQ ID NO:6. In certain embodiments, said fusion protein comprises a plurality of EGFRvIII polypeptides. In one embodiment, said fusion protein comprises five copies of the EGFRvIII polypeptide.

In certain embodiments, said EGFRvIII polypeptide is flanked by one or more cleaver sequences. In some embodiments, the EGFRvIII polypeptide is fused to the N-terminus of the PAP polypeptide.

In some embodiments, the PAP polypeptide comprises an amino acid sequence at least i) 90% identical, ii) 95% identical, iii) 99% identical, or iv) 100% identical to PAP$_{33-386}$ as set forth in SEQ ID NO:14. In certain embodiments, the fusion protein comprises an amino acid sequence at least i) 90% identical, ii) 95% identical, iii) 99% identical, or iv) 100% identical to EGFRvIIIx5-PAP$_{33-386}$ as set forth in amino acid residues 89 to 606 SEQ ID NO:12.

In certain embodiments, the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14.

In some embodiments, the fusion protein further comprises a signal sequence, wherein the signal sequence is in translational reading frame with the EGFRvIII polypeptide and the PAP polypeptide. In certain embodiments, the signal sequence is at least i) 90% identical, ii) 95% identical, iii) 99% identical, or iv) 100% identical to ActAN100* as set forth in SEQ ID NO:2.

In various embodiments, the fusion protein is expressed in a bacterium. In some embodiments, the bacterium is *Listeria monocytogenes*.

In certain embodiments, the present invention provides a nucleic acid molecule encoding the fusion protein of any of the preceding embodiments. In some embodiments, said nucleic acid molecule comprises one or more EGFRvIII polynucleotides that are at least i) 90% identical, ii) 95% identical, iii) 99% identical, or iv) 100% identical to the EGFRvIII polynucleotide as set forth in SEQ ID NO:5 and a polynucleotide that is at least i) 90% identical, ii) 95% identical, iii) 99% identical, or iv) 100% identical to the PAP$_{33-386}$ polynucleotide as set forth in SEQ ID NO:13.

In some embodiments, the nucleic acid further comprises a promoter, a signal sequence, or both, wherein the promoter, signal sequence, or both are in translational frame with the nucleotide sequence encoding the EGFRvIII polypeptide and the nucleotide sequence encoding the PAP polypeptide. In certain embodiments, the promoter is at least i) 90% identical, ii) 95% identical, iii) 99% identical, or iv) 100% identical to an actA promoter as set forth in SEQ ID NO:21. In some embodiments, the signal sequence is at least i) 90% identical, ii) 95% identical, iii) 99% identical, or iv) 100% identical to ActAN100* as set forth in SEQ ID NO:1.

In one embodiment, said nucleic acid molecule is part of an expression cassette.

In certain embodiments, the present invention provides a vector comprising the nucleic acid molecule of any of the preceding embodiments.

In some embodiments, the present invention provides a host cell comprising the nucleic acid molecule of any of the preceding embodiments. In certain embodiments, said host cell is a bacterium. In one embodiment, the bacterium is *Listeria monocytogenes*. In various embodiments, the *Listeria monocytogenes* is an actA deletion mutant, an actA insertion mutant, an inlB deletion mutant, an inlB insertion mutant, or a combination thereof. In one embodiment, the *Listeria monocytogenes* is a ΔactA/ΔinlB mutant.

In some embodiments, the nucleic acid molecule is integrated into the host cell genome. In certain embodiments, the nucleic acid molecule is integrated into the actA locus, inlB locus or tRNA$^{Arg}$ locus.

In certain embodiments, the host cell is in combination with a pharmaceutically acceptable excipient.

In some embodiments, the present invention provides a vaccine comprising the host cell of any of the preceding embodiments and a pharmaceutically acceptable excipient.

In certain embodiments, the present invention provides a fusion protein comprising an EGFRvIII polypeptide, an NK3 homeobox 1 (NKX3.1) polypeptide, and a prostate-specific membrane antigen (PSMA) polypeptide. In some embodiments, said EGFRvIII polypeptide comprises an amino acid sequence at least i) 90% identical, ii) 95% identical, iii) 99% identical, or iv) 100% identical to SEQ ID NO:6. In some embodiments, the fusion protein comprises a plurality of EGFRvIII polypeptides. In one embodiment, the fusion protein comprises five copies of the EGFRvIII polypeptide.

In some embodiments, said EGFRvIII polypeptide is flanked by one or more cleaver sequences.

In certain embodiments, the EGFRvIII polypeptide is fused to the N-terminus of the NKX3.1 polypeptide, and wherein the NKX3.1 polypeptide is fused to the N-terminus of the PSMA polypeptide.

In some embodiments, the PSMA polypeptide comprises an amino acid sequence at least i) 90% identical, ii) 95% identical, iii) 99% identical, or iv) 100% identical to PSMA$_{1-20, 44-138, 169-750}$ as set forth in SEQ ID NO:20.

In certain embodiments, the NKX3.1 polypeptide comprises an amino acid sequence at least i) 90% identical, ii) 95% identical, iii) 99% identical, or iv) 100% identical to NKX3.1$_{11-234}$ as set forth in SEQ ID NO:25.

In certain embodiments, the NKX3.1 polypeptide comprises an amino acid sequence at least i) 90% identical, ii) 95% identical, iii) 99% identical, or iv) 100% identical to NKX3.1$_{11-234}$ (R41G) as set forth in SEQ ID NO:18.

In some embodiments, the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20.

In one embodiment, the fusion protein comprises an amino acid sequence at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in amino acid residues 89 to 1177 of SEQ ID NO:23.

In certain embodiments, the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20.

In some embodiments, the fusion protein comprises an amino acid sequence at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in amino acid residues 89 to 1177 of SEQ ID NO:16.

In some embodiments, the fusion protein further comprises a signal sequence, wherein the signal sequence is in translational reading frame with the EGFRvIII polypeptide, NKX3.1 polypeptide, and the PSMA polypeptide. In some embodiments, the signal sequence is at least i) 90% identical, ii) 95% identical, iii) 99% identical, or iv) 100% identical to ActAN100* as set forth in SEQ ID NO:2.

In various embodiments, the fusion protein is expressed in a bacterium. In one embodiment, the bacterium is *Listeria monocytogenes*.

In some embodiments, the present invention provides a nucleic acid molecule encoding the fusion protein of any of the preceding embodiments. In certain embodiments, said nucleic acid molecule comprises one or more EGFRvIII polynucleotides that are at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1$_{11\text{-}234}$ polynucleotide as set forth in SEQ ID NO:24, and a polynucleotide that is at least i) 90% identical, ii) 95% identical, iii) 99% identical, or iv) 100% identical to the PSMA$_{1\text{-}20,\ 44\text{-}138,\ 169\text{-}750}$ as set forth in SEQ ID NO:19.

In some embodiments, nucleic acid molecule comprises one or more EGFRvIII polynucleotides that are at least i) 90% identical, ii) 95% identical, iii) 99% identical, or iv) 100% identical to the EGFRvIII polynucleotide as set forth in SEQ ID NO:5, a polynucleotide that is at least i) 90% identical, ii) 95% identical, iii) 99% identical, or iv) 100% identical to the NKX3.1(R41G)$_{11\text{-}234}$ polynucleotide as set forth in SEQ ID NO:17, and a polynucleotide that is at least i) 90% identical, ii) 95% identical, iii) 99% identical, or iv) 100% identical to the PSMA$_{1\text{-}20,\ 44\text{-}138,\ 169\text{-}750}$ as set forth in SEQ ID NO: 19.

In some embodiments, the nucleic acid further comprises a promoter, a signal sequence, or both, wherein the promoter, signal sequence, or both are in translational frame with the nucleotide sequence encoding the EGFRvIII polypeptide, NKX3.1 polypeptide, and the PSMA polypeptide. In some embodiment, the promoter is at least i) 90% identical, ii) 95% identical, iii) 99% identical, or iv) 100% identical to an actA promoter as set forth in SEQ ID NO:21. In some embodiments, the signal sequence is at least i) 90% identical, ii) 95% identical, iii) 99% identical, or iv) 100% identical to ActAN100* as set forth in SEQ ID NO:1.

In some embodiments, the nucleic acid molecule of any of the preceding embodiments is part of an expression cassette.

In some embodiments, the present invention provides a vector comprising the nucleic acid molecule of any of the preceding embodiments.

In some embodiments, the present invention provides a host cell comprising the nucleic acid molecule of any of the preceding embodiments. In some embodiments, host cell is a bacterium. In one embodiment, the bacterium is *Listeria monocytogenes*. In some embodiments, the *Listeria monocytogenes* is an actA deletion mutant, an actA insertion mutant, an inlB deletion mutant, an inlB insertion mutant, or a combination thereof. In some embodiments, the *Listeria monocytogenes* is a ΔactA/ΔinlB mutant.

In some embodiments, the nucleic acid molecule is integrated into the host cell genome. In some embodiments, the nucleic acid molecule is integrated into the actA locus, inlB locus or tRNA$^{Arg}$ locus.

In some embodiments, the host cell of any of the preceding embodiments is in combination with a pharmaceutically acceptable excipient.

In various embodiments, the present invention provides a vaccine comprising the host cell of any of the preceding embodiments and a pharmaceutically acceptable excipient.

In some embodiments, the present invention provides a fusion protein comprising an NK3 homeobox 1 (NKX3.1) polypeptide and a PAP polypeptide. In some embodiments, the NKX3.1 polypeptide comprises an amino acid sequence at least i) 90% identical, ii) 95% identical, iii) 99% identical, or iv) 100% identical to NKX3.1 as set forth in SEQ ID NO:29.

In some embodiments, the NKX3.1 polypeptide is fused to the N-terminus of the PAP polypeptide.

In some embodiments, the PAP polypeptide comprises an amino acid sequence at least i) 90% identical, ii) 95% identical, iii) 99% identical, or iv) 100% identical to PAP$_{33\text{-}386}$ as set forth in SEQ ID NO:14.

In some embodiments, the fusion protein comprises an amino acid sequence at least i) 90% identical, ii) 95% identical, iii) 99% identical, or iv) 100% identical to NKX3.1-PAP$_{33\text{-}386}$ as set forth in amino acid residues 89 to 678 of SEQ ID NO:27.

In some embodiments, the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33\text{-}386}$ as set forth in SEQ ID NO:14.

In some embodiments, the fusion protein further comprises a signal sequence, wherein the signal sequence is in translational reading frame with the NKX3.1 polypeptide and the PAP polypeptide. In some embodiments, the signal sequence is at least i) 90% identical, ii) 95% identical, iii) 99% identical, or iv) 100% identical to ActAN100* as set forth in SEQ ID NO:2.

In some embodiments, said fusion protein is expressed in a bacterium. In one embodiment, the bacterium is *Listeria monocytogenes*.

In some embodiments, the present invention provides a nucleic acid molecule encoding the fusion protein of any of the preceding embodiments. In some embodiments, said nucleic acid molecule comprises a polynucleotide that is at least i) 90% identical, ii) 95% identical, iii) 99% identical, or iv) 100% identical to the NKX3.1 polynucleotide as set forth in SEQ ID NO:28 and a polynucleotide that is at least i) 90% identical, ii) 95% identical, iii) 99% identical, or iv) 100% identical to the PAP$_{33\text{-}386}$ polynucleotide as set forth in SEQ ID NO:13.

In some embodiments, the nucleic acid further comprises a promoter, a signal sequence, or both, wherein the promoter, signal sequence, or both are in translational frame with the nucleotide sequence encoding the NKX3.1 polypeptide and the nucleotide sequence encoding the PAP polypeptide. In some embodiments, the promoter is at least i) 90% identical, ii) 95% identical, iii) 99% identical, or iv) 100% identical to an actA promoter as set forth in SEQ ID NO:21. In some embodiments, the signal sequence is at least i) 90% identical, ii) 95% identical, iii) 99% identical, or iv) 100% identical to ActAN100* as set forth in SEQ ID NO:1.

In some embodiments, said nucleic acid molecule being part of an expression cassette.

In some embodiments, the present invention provides a vector comprising the nucleic acid molecule of any of the preceding embodiments.

In some embodiments, the present invention provides a host cell comprising the nucleic acid molecule of any of the preceding. In one embodiment, said host cell is a bacterium. In some embodiments, the bacterium is *Listeria monocytogenes*. In some embodiments, the *Listeria monocytogenes* is an actA deletion mutant, an actA insertion mutant, an inlB deletion mutant, an inlB insertion mutant, or a combination thereof. In certain embodiments, the *Listeria monocytogenes* is a ΔactA/ΔinlB mutant. In some embodiments, the nucleic acid molecule is integrated into the host cell genome. In various embodiments, the nucleic acid molecule is integrated into the actA locus, inlB locus or tRNA$^{Arg}$ locus.

In some embodiments, the host cell of any of the preceding embodiments is in combination with a pharmaceutically acceptable excipient.

In some embodiments, the present invention provides a vaccine comprising the host cell of any of the preceding embodiments and a pharmaceutically acceptable excipient.

In some embodiments, the present invention provides a host cell comprising one or more nucleic acid molecules, said nucleic acid molecules comprising a nucleic acid sequence encoding: a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10; b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14; c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20; d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20; e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14; f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; g) an ActAN100-PAP$_{30-386}$ fusion protein, wherein the fusion protein comprises an ActAN100 polypeptide comprising an amino acid sequence at least i) 90% identical, ii) 95% identical, iii) 99% identical, or iv) 100% identical to amino acid residues 1 to 100 of SEQ ID NO:33 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or h) any combination thereof.

In some embodiments, the nucleic acid molecules of the host cell comprises: a) a nucleotide sequence that is at least i) 90% identical, ii) 95% identical, iii) 99% identical, or iv) 100% identical to EGFRvIIIx5-SSX2 as set forth in SEQ ID NO:3; b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; c) a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22; d) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15; e) a nucleotide sequence that is at least i) 90% identical, ii) 95% identical, iii) 99% identical, or iv) 100% identical to NKX3.1-PAP$_{33-386}$ as set forth in SEQ ID NO:26; f) a nucleotide sequence that is at least i) 90% identical, ii) 95% identical, iii) 99% identical, or iv) 100% identical to ActAN100*-SSX2 as set forth in SEQ ID NO:30; g) a nucleic acid sequence that is at least i) 90% identical, ii) 95% identical, iii) 99% identical, or iv) 100% identical to ActAN100*-PAP$_{30-386}$-SL8 as set forth in SEQ ID NO:32; h) a nucleotide sequence that is at least i) 90% identical, ii) 95% identical, iii) 99% identical, or iv) 100% identical to EGFRvIIIx1-PAP$_{33-386}$ as set forth in SEQ ID NO:34; i) a nucleotide sequence that is at least i) 90% identical, ii) 95% identical, iii) 99% identical, or iv) 100% identical to EGFRvIIIx2-PAP$_{33-386}$ as set forth in SEQ ID NO:36; j) a nucleotide sequence that is at least i) 90% identical, ii) 95% identical, iii) 99% identical, or iv) 100% identical to EGFRvIIIx3-PAP$_{33-386}$ as set forth in SEQ ID NO:38; k) a nucleotide sequence that is at least i) 90% identical, ii) 95% identical, iii) 99% identical, or iv) 100% identical to EGFRvIIIx4-PAP$_{33-386}$ as set forth in SEQ ID NO:40; or l) any combination thereof.

In some embodiments, the host cell is a bacterium. In one embodiment, the bacterium is *Listeria monocytogenes*. In some embodiments, the *Listeria monocytogenes* is a ΔactA/ΔinlB mutant.

In some embodiments, the host cell of any of the preceding embodiments comprises: a) a nucleotide sequence that is at least i) 90% identical, ii) 95% identical, iii) 99% identical, or iv) 100% identical to EGFRvIIIx5-SSX2 as set forth in SEQ ID NO:3; b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and c) a nucleotide sequence that is at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in SEQ ID NO:22. In some embodiments, (a) is integrated into the actA locus, (b) is integrated into the inlB locus, and (c) is integrated into the tRNA$^{Arg}$ locus.

In some embodiments, the host cell of any of the preceding embodiments comprises: a) a nucleotide sequence that is at least i) 90% identical, ii) 95% identical, iii) 99% identical, or iv) 100% identical to EGFRvIIIx5-SSX2 as set forth in SEQ ID NO:3; b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and c) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in SEQ ID NO:15. In some embodiments, (a) is integrated into the actA locus, (b) is integrated into the inlB locus, and (c) is integrated into the tRNA$^{Arg}$ locus.

In some embodiments, the host cell of any of the preceding embodiments comprises: a) a nucleotide sequence that is at least i) 90% identical, ii) 95% identical, iii) 99% identical, or iv) 100% identical to NKX3.1-PAP$_{33-386}$ as set forth in SEQ ID NO:26; and b) a nucleotide sequence that is at least i) 90% identical, ii) 95% identical, iii) 99% identical, or iv) 100% identical to EGFRvIIIx5-SSX2 as set forth in SEQ ID NO:3. In some embodiments, (a) is integrated into the inlB locus, and (b) is integrated into the tRNA$^{Arg}$ locus.

In some embodiments, the host cell of any of the preceding embodiments comprises: a) a nucleotide sequence that is at least i) 90% identical, ii) 95% identical, iii) 99% identical, or iv) 100% identical to NKX3.1-PAP$_{33-386}$ as set forth in SEQ ID NO:26; and b) a nucleotide sequence that is at least i) 90% identical, ii) 95% identical, iii) 99% identical, or iv) 100% identical to ActAN100*-SSX2 as set forth in SEQ ID NO:30. In some embodiments, (a) is integrated into the inlB locus, and (b) is integrated into the tRNA$^{Arg}$ locus.

In some embodiments, the nucleic acid molecules of the host cell of any of the preceding embodiments comprise a nucleic acid sequence encoding: a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4; b) an amino acid sequence at least i) 90% identical, ii) 95% identical, iii) 99% identical, or iv) 100% identical to EGFRvIIIx5-PAP$_{33-386}$ as set forth in amino acid residues 89 to 606 of SEQ ID NO:12; c) an amino acid sequence at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in amino acid residues 89 to 1177 of SEQ ID NO:23; d) an amino acid sequence at least i) 90% identical, ii) 95% identical, iii) 99% identical, or iv) 100% identical to EGFRvIIIx5-NKX3.1(R41G)$_{11-234}$-PSMA$_{1-20, 44-138, 169-750}$ as set forth in amino acid residues 89 to 1177 of SEQ ID NO:16; e) an amino acid sequence at least i) 90% identical, ii) 95% identical, iii) 99% identical, or iv) 100% identical to NKX3.1-PAP$_{33-386}$ as set forth in amino acid residues 89 to 678 of SEQ ID NO:27; f) an amino acid sequence at least i) 90% identical, ii) 95% identical, iii) 99% identical, or iv) 100% identical to ActAN100*-SSX2 as set forth in SEQ ID NO:31; g) an amino acid sequence at least i) 90% identical, ii) 95% identical, iii) 99% identical, or iv) 100% identical to ActAN100*-PAP$_{30-386}$ as set forth in amino acid residues 1-459 of SEQ ID NO:33; h) an amino acid sequence at least i) 90% identical, ii) 95% identical, iii) 99% identical, or iv) 100% identical to EGFRvIIIx1-PAP$_{33-386}$ as set forth in amino acid residues 89 to 476 of SEQ ID NO:35; i) an amino acid sequence at least i) 90% identical, ii) 95% identical, iii) 99% identical, or iv) 100% identical to EGFRvIIIx2-PAP$_{33-386}$ as set forth in amino acid residues 89 to 509 of SEQ ID NO:37; j) an amino acid sequence at least i) 90% identical, ii) 95% identical, iii) 99% identical, or iv) 100% identical to EGFRvIIIx3-PAP$_{33-386}$ as set forth in amino acid residues 89 to 541 of SEQ ID NO:39; k) an amino acid sequence at least i) 90% identical, ii) 95% identical, iii) 99% identical, or iv) 100% identical to EGFRvIIIx4-PAP$_{33-386}$ as set forth in amino acid residues 89 to 573 of SEQ ID NO:41; or l) any combination thereof.

In some embodiments, the present invention provides a method of eliciting an immune response in a subject comprising administering to the subject a composition comprising the host cell of any of the preceding embodiments.

In some embodiments, the present invention provides a method of eliciting an immune response in a subject comprising, administering to the subject a composition comprising a host cell, wherein the host cell expresses one or more fusion proteins comprising: a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10; b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14; c) an EGFRvIII-NKX3.1$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20; d) an EGFRvIII-NKX3.1(R41G)$_{11-234}$-PSMA$_{1-20, 44-138, 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20, 44-138, 169-750}$ as set forth in SEQ ID NO:20; e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14; f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; g) an ActAN100*-PAP$_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to PAP$_{30\text{-}386}$ as set forth in amino acid residues 103-459 of SEQ ID NO:33; or h) any combination thereof.

In some embodiments, the one or more fusion proteins are expressed from a nucleic acid molecule comprising: a) a nucleotide sequence that is at least i) 90% identical, ii) 95% identical, iii) 99% identical, or iv) 100% identical to EGFRvIIIx5-SSX2 as set forth in SEQ ID NO:3; b) a nucleotide sequence that is at least i) 90% identical, ii) 95% identical, iii) 99% identical, or iv) 100% identical to EGFRvIIIx5-PAP$_{33\text{-}386}$ as set forth in SEQ ID NO:11; c) a nucleotide sequence that is at least i) 90% identical, ii) 95% identical, iii) 99% identical, or iv) 100% identical to EGFRvIIIx5-NKX3.1$_{11\text{-}234}$-PSMA$_{1\text{-}20,\ 44\text{-}138,\ 169\text{-}750}$ as set forth in SEQ ID NO:22; d) a nucleotide sequence that is at least i) 90% identical, ii) 95% identical, iii) 99% identical, or iv) 100% identical to EGFRvIIIx5-NKX3.1(R41G)$_{11\text{-}234}$-PSMA$_{1\text{-}20,\ 44\text{-}138,\ 169\text{-}750}$ as set forth in SEQ ID NO:15; e) a nucleotide sequence that is at least i) 90% identical, ii) 95% identical, iii) 99% identical, or iv) 100% identical to NKX3.1-PAP$_{33\text{-}386}$ as set forth in SEQ ID NO:26; f) a nucleotide sequence that is at least i) 90% identical, ii) 95% identical, iii) 99% identical, or iv) 100% identical to ActAN100*-SSX2 as set forth in SEQ ID NO:30; g) a nucleic acid sequence that is at least i) 90% identical, ii) 95% identical, iii) 99% identical, or iv) 100% identical to ActAN100*-PAP$_{30\text{-}386}$-SL8 as set forth in SEQ ID NO:32; h) a nucleotide sequence that is at least i) 90% identical, ii) 95% identical, iii) 99% identical, or iv) 100% identical to EGFRvIIIx1-PAP$_{33\text{-}386}$ as set forth in SEQ ID NO:34; i) a nucleotide sequence that is at least i) 90% identical, ii) 95% identical, iii) 99% identical, or iv) 100% identical to EGFRvIIIx2-PAP$_{33\text{-}386}$ as set forth in SEQ ID NO:36; j) a nucleotide sequence that is at least i) 90% identical, ii) 95% identical, iii) 99% identical, or iv) 100% identical to EGFRvIIIx3-PAP$_{33\text{-}386}$ as set forth in SEQ ID NO:38; k) a nucleotide sequence that is at least i) 90% identical, ii) 95% identical, iii) 99% identical, or iv) 100% identical to EGFRvIIIx4-PAP$_{33\text{-}386}$ as set forth in SEQ ID NO:40; or l) any combination thereof. In some embodiments, (a) is integrated into the actA locus, (b) is integrated into the inlB locus, and (c) is integrated into the tRNA$^{Arg}$ locus. In certain embodiments, (a) is integrated into the actA locus, (b) is integrated into the inlB locus, and (d) is integrated into the tRNA$^{Arg}$ locus. In some embodiments, (e) is integrated into the inlB locus, and (f) is integrated into the tRNA$^{Arg}$ locus. In various embodiments, (e) is integrated into the inlB locus and (a) is integrated into the tRNA$^{Arg}$ locus.

In some embodiments, the one or more fusion proteins comprise: a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4; b) an amino acid sequence at least i) 90% identical, ii) 95% identical, iii) 99% identical, or iv) 100% identical to EGFRvIIIx5-PAP$_{33\text{-}386}$ as set forth in amino acid residues 89 to 606 of SEQ ID NO:12; c) an amino acid sequence at least i) 90% identical, ii) 95% identical, iii) 99% identical, or iv) 100% identical to EGFRvIIIx5-NKX3.1$_{11\text{-}234}$-PSMA$_{1\text{-}20,\ 44\text{-}138,\ 169\text{-}750}$ as set forth in amino acid residues 89 to 1177 of SEQ ID NO:23; d) an amino acid sequence at least i) 90% identical, ii) 95% identical, iii) 99% identical, or iv) 100% identical to EGFRvIIIx5-NKX3.1(R41G)$_{11\text{-}234}$-PSMA$_{1\text{-}20,\ 44\text{-}138,\ 169\text{-}750}$ as set forth in amino acid residues 89 to 1177 of SEQ ID NO:16; e) an amino acid sequence at least i) 90% identical, ii) 95% identical, iii) 99% identical, or iv) 100% identical to NKX3.1-PAP$_{33\text{-}386}$ as set forth in amino acid residues 89 to 678 of SEQ ID NO:27; f) an amino acid sequence at least i) 90% identical, ii) 95% identical, iii) 99% identical, or iv) 100% identical to EGFRvIIIx1-PAP$_{33\text{-}386}$ as set forth in amino acid residues 89 to 476 of SEQ ID NO:35; g) an amino acid sequence at least i) 90% identical, ii) 95% identical, iii) 99% identical, or iv) 100% identical to EGFRvIIIx2-PAP$_{33\text{-}386}$ as set forth in amino acid residues 89 to 509 of SEQ ID NO:37; h) an amino acid sequence at least i) 90% identical, ii) 95% identical, iii) 99% identical, or iv) 100% identical to EGFRvIIIx3-PAP$_{33\text{-}386}$ as set forth in amino acid residues 89 to 541 of SEQ ID NO:39; i) an amino acid sequence at least i) 90% identical, ii) 95% identical, iii) 99% identical, or iv) 100% identical to EGFRvIIIx4-PAP$_{33\text{-}386}$ as set forth in amino acid residues 89 to 573 of SEQ ID NO:41; or j) any combination thereof.

In some embodiments of any of the preceding methods, said host cell is a bacterium. In one embodiment, the bacterium is *Listeria monocytogenes*. In certain embodiments, the *Listeria monocytogenes* is a ΔactA/ΔinlB mutant. In various embodiments, the administering step is performed intravenously. In some embodiments, the one or more fusion proteins are expressed and secreted from the host cell in the cytosol of an infected cell within the subject. In some embodiments, the infected cell is an antigen presenting cell.

In some embodiments, the present invention provides a method of increasing expression of an antigenic polypeptide, said method comprising expressing in a host cell a nucleic acid molecule, said nucleic acid molecule comprising a nucleic acid sequence encoding: a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10; b) an EGFRvIII-PAP$_{33\text{-}386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33\text{-}386}$ as set forth in SEQ ID NO:14; c) an EGFRvIII-NKX3.1$_{11\text{-}234}$-PSMA$_{1\text{-}20,\ 44\text{-}138,\ 169\text{-}750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11\text{-}234}$ as set forth in SEQ ID NO:25, and a PSMA polypeptide comprising an amino acid sequence at least i) 90% identical, ii) 95% identical, iii) 99% identical, or iv) 100% identical to PSMA$_{1\text{-}20,\ 44\text{-}138,\ 169\text{-}750}$ as set forth in SEQ ID NO:20; d) an EGFRvIII-NKX3.1(R41G)$_{11\text{-}234}$-PSMA$_{1\text{-}20,\ 44\text{-}138,\ 169\text{-}750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11\text{-}234}$ as set forth in SEQ ID NO:18, and a PSMA polypeptide comprising an amino acid sequence at least i) 90% identical, ii) 95% identical, iii) 99% identical, or iv) 100% identical to $PSMA_{1-20,\ 44-138,\ 169-750}$ as set forth in SEQ ID NO:20; e) a NKX3.1-$PAP_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to $PAP_{33-386}$ as set forth in SEQ ID NO:14; f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; g) an ActAN100*-$PAP_{30-386}$ fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a PAP polypeptide comprising an amino acid sequence at least i) 90% identical, ii) 95% identical, iii) 99% identical, or iv) 100% identical to $PAP_{30-386}$ as set forth in amino acid residues 103-459 of SEQ ID NO:33; or h) any combination thereof.

In certain embodiments, the one or more nucleic acid molecules comprise: a) a nucleotide sequence that is at least i) 90% identical, ii) 95% identical, iii) 99% identical, or iv) 100% identical to EGFRvIIIx5-SSX2 as set forth in SEQ ID NO:3; b) a nucleotide sequence that is at least i) 90% identical, ii) 95% identical, iii) 99% identical, or iv) 100% identical to EGFRvIIIx5-$PAP_{33-386}$ as set forth in SEQ ID NO:11; c) a nucleotide sequence that is at least i) 90% identical, ii) 95% identical, iii) 99% identical, or iv) 100% identical to EGFRvIIIx5-NKX3.$1_{11-234}$-$PSMA_{1-20,\ 44-138,\ 169-750}$ as set forth in SEQ ID NO:22; d) a nucleotide sequence that is at least i) 90% identical, ii) 95% identical, iii) 99% identical, or iv) 100% identical to EGFRvIIIx5-NKX3.1(R41G)$_{11-234}$-$PSMA_{1-20,\ 44-138,\ 169-750}$ as set forth in SEQ ID NO:15; e) a nucleotide sequence that is at least i) 90% identical, ii) 95% identical, iii) 99% identical, or iv) 100% identical to NKX3.1-$PAP_{33-386}$ as set forth in SEQ ID NO:26; f) a nucleotide sequence that is at least i) 90% identical, ii) 95% identical, iii) 99% identical, or iv) 100% identical to ActAN100*-SSX2 as set forth in SEQ ID NO:30; g) a nucleic acid sequence that is at least i) 90% identical, ii) 95% identical, iii) 99% identical, or iv) 100% identical to ActAN100*-$PAP_{30}$-386-SL8 as set forth in SEQ ID NO:32; h) a nucleotide sequence that is at least i) 90% identical, ii) 95% identical, iii) 99% identical, or iv) 100% identical to EGFRvIIIx1-$PAP_{33-386}$ as set forth in SEQ ID NO:34; i) a nucleotide sequence that is at least i) 90% identical, ii) 95% identical, iii) 99% identical, or iv) 100% identical to EGFRvIIIx2-$PAP_{33-386}$ as set forth in SEQ ID NO:36; j) a nucleotide sequence that is at least i) 90% identical, ii) 95% identical, iii) 99% identical, or iv) 100% identical to EGFRvIIIx3-$PAP_{33-386}$ as set forth in SEQ ID NO:38; k) a nucleotide sequence that is at least i) 90% identical, ii) 95% identical, iii) 99% identical, or iv) 100% identical to EGFRvIIIx4-$PAP_{33-386}$ as set forth in SEQ ID NO:40; or 1) any combination thereof. In some embodiments, (a) is integrated into the actA locus, (b) is integrated into the inlB locus, and (c) is integrated into the tRNA$^{Arg}$ locus. In some embodiments, (a) is integrated into the actA locus, (b) is integrated into the inlB locus, and (d) is integrated into the tRNA$^{Arg}$ locus. In some embodiments, (e) is integrated into the inlB locus, and (f) is integrated into the tRNA$^{Arg}$ locus. In some embodiments, (e) is integrated into the inlB locus and (a) is integrated into the tRNA$^{Arg}$ locus.

In some embodiments of any of the preceding methods, the nucleic acid molecules encode for fusion proteins comprising: a) an amino acid sequence at least i) 90% identical, ii) 95% identical, iii) 99% identical, or iv) 100% identical to EGFRvIII-SSX2 as set forth in amino acid residues 89 to 475 of SEQ ID NO:4; b) an amino acid sequence at least i) 90% identical, ii) 95% identical, iii) 99% identical, or iv) 100% identical to EGFRvIII-$PAP_{33-386}$ as set forth in amino acid residues 89 to 606 of SEQ ID NO:12; c) an amino acid sequence at least i) 90% identical, ii) 95% identical, iii) 99% identical, or iv) 100% identical to EGFRvIII-NKX3.$1_{11-234}$-$PSMA_{1-20,\ 44-138,\ 169-750}$ as set forth in amino acid residues 89 to 1177 of SEQ ID NO:23; d) an amino acid sequence at least i) 90% identical, ii) 95% identical, iii) 99% identical, or iv) 100% identical to EGFRvIII-NKX3.1(R41G)$_{11-234}$-$PSMA_{1-20,\ 44-138,\ 169-750}$ as set forth in amino acid residues 89 to 1177 of SEQ ID NO:16; e) an amino acid sequence at least i) 90% identical, ii) 95% identical, iii) 99% identical, or iv) 100% identical to NKX3.1-$PAP_{33-386}$ as set forth in amino acid residues 89 to 678 of SEQ ID NO:27; f) an amino acid sequence at least i) 90% identical, ii) 95% identical, iii) 99% identical, or iv) 100% identical to EGFRvIIIx1-$PAP_{33-386}$ as set forth in amino acid residues 89 to 476 of SEQ ID NO:35; g) an amino acid sequence at least i) 90% identical, ii) 95% identical, iii) 99% identical, or iv) 100% identical to EGFRvIIIx2-$PAP_{33-386}$ as set forth in amino acid residues 89 to 509 of SEQ ID NO:37; h) an amino acid sequence at least i) 90% identical, ii) 95% identical, iii) 99% identical, or iv) 100% identical to EGFRvIIIx3-$PAP_{33-386}$ as set forth in amino acid residues 89 to 541 of SEQ ID NO:39; i) an amino acid sequence at least i) 90% identical, ii) 95% identical, iii) 99% identical, or iv) 100% identical to EGFRvIIIx4-$PAP_{33-386}$ as set forth in amino acid residues 89 to 573 of SEQ ID NO:41; or j) any combination thereof.

In some embodiments of any of the preceding methods, said host cell is a bacterium. In certain embodiments, the bacterium is *Listeria monocytogenes*.

In some embodiments of any of the preceding methods the expressing step comprises infecting a cell of interest with the host cell. In some embodiments, said expressing step comprises administering the host cell to a subject.

In some embodiments, the nucleic acid molecule of any of the preceding host cell is inserted into an expression cassette on an episomal plasmid within the host cell.

In some embodiments, the nucleic acid molecules of any of the preceding host cell comprises EGFRvIIIx5-SSX2 as set forth in SEQ ID NO:3, EGFRvIIIx5-$PAP_{33-386}$ as set forth in SEQ ID NO:11, and EGFRvIIIx5-NKX3.1 (R41G)$_{11-234}$-$PSMA_{1-20,\ 44-138,\ 169-750}$ as set forth in SEQ ID NO:15.

In some embodiments, the nucleic acid molecules of any of the preceding host cell consist of EGFRvIIIx5-SSX2 as set forth in SEQ ID NO:3, EGFRvIIIx5-$PAP_{33-386}$ as set forth in SEQ ID NO:11, and EGFRvIIIx5-NKX3.1 (R41G)$_{11-234}$-$PSMA_{1-20,\ 44-138,\ 169-750}$ as set forth in SEQ ID NO:15.

In some embodiments of any of the preceding methods, the one or more nucleic acid molecules comprise: a) a nucleotide sequence that is at least i) 90% identical, ii) 95% identical, iii) 99% identical, or iv) 100% identical to EGFRvIIIx5-SSX2 as set forth in SEQ ID NO:3; b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; and c) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20,\ 44-138,\ 169-750}$ as set forth in SEQ ID NO:15.

In some embodiments of any of the preceding methods, the one or more nucleic acid molecules consist of EGFRvIIIx5-SSX2 as set forth in SEQ ID NO:3, EGFRvIIIx5-PAP$_{33-386}$ as set forth in SEQ ID NO:11, and EGFRvIIIx5-NKX3.1(R41G)$_{11-234}$-PSMA$_{1-20,\ 44-138,\ 169-750}$ as set forth in SEQ ID NO:15.

In some embodiments, the present invention provides a method of treating cancer in a subject in need thereof, said method comprising administering to the subject a therapeutically effective amount of a composition comprising a host cell, wherein the host cell expresses one or more fusion proteins comprising: a) an EGFRvIII-SSX2 fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a SSX2 polypeptide comprising an amino acid sequence at least i) 90% identical, ii) 95% identical, iii) 99% identical, or iv) 100% identical to SSX2 as set forth in SEQ ID NO:10; b) an EGFRvIII-PAP$_{33-386}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6 and a PAP polypeptide comprising an amino acid sequence at least i) 90% identical, ii) 95% identical, iii) 99% identical, or iv) 100% identical to PAP$_{33-386}$ as set forth in SEQ ID NO:14; c) an EGFRvIII-NKX3.1$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1$_{11-234}$ as set forth in SEQ ID NO:25, and a PSMA polypeptide comprising an amino acid sequence at least i) 90% identical, ii) 95% identical, iii) 99% identical, or iv) 100% identical to PSMA$_{1-20,\ 44-138,\ 169-750}$ as set forth in SEQ ID NO:20; d) an EGFRvIII-NKX3.1 (R41G)$_{11-234}$-PSMA$_{1-20,\ 44-138,\ 169-750}$ fusion protein, wherein the fusion protein comprises one or more EGFRvIII polypeptides comprising an amino acid sequence at least i) 90% identical, ii) 95% identical, iii) 99% identical, or iv) 100% identical to SEQ ID NO:6, a NKX3.1 polypeptide comprising an amino acid sequence at least i) 90% identical, ii) 95% identical, iii) 99% identical, or iv) 100% identical to NKX3.1(R41G)$_{11-234}$ as set forth in SEQ ID NO:18, and a PSMA polypeptide comprising an amino acid sequence at least i) 90% identical, ii) 95% identical, iii) 99% identical, or iv) 100% identical to PSMA$_{1-20,\ 44-138,\ 169-750}$ as set forth in SEQ ID NO:20; e) a NKX3.1-PAP$_{33-386}$ fusion protein, wherein the fusion protein comprises a NKX3.1 polypeptide comprising an amino acid sequence at least i) 90% identical, ii) 95% identical, iii) 99% identical, or iv) 100% identical to NKX3.1 as set forth in SEQ ID NO:29 and a PAP polypeptide comprising an amino acid sequence at least i) 90% identical, ii) 95% identical, iii) 99% identical, or iv) 100% identical to PAP$_{33-386}$ as set forth in SEQ ID NO:14; f) an ActAN100*-SSX2 fusion protein, wherein the fusion protein comprises an ActAN100* polypeptide comprising an amino acid sequence at least i) 90% identical, ii) 95% identical, iii) 99% identical, or iv) 100% identical to ActAN100* as set forth as SEQ ID NO:2 and a SSX2 polypeptide comprising an amino acid sequence at least i) 90% identical, ii) 95% identical, iii) 99% identical, or iv) 100% identical to SSX2 as set forth in SEQ ID NO:10; g) an ActAN100-PAP$_{30-386}$ fusion protein, wherein the fusion protein comprises an ActAN100 polypeptide comprising an amino acid sequence at least i) 90% identical, ii) 95% identical, iii) 99% identical, or iv) 100% identical to ActAN100 as set forth in to amino acid residues 1 to 100 of SEQ ID NO:33 and a PAP polypeptide comprising an amino acid sequence at least i) 90% identical, ii) 95% identical, iii) 99% identical, or iv) 100% identical to PAP$_{30-386}$ as set forth in amino acid residues 103-459 of SEQ ID NO:33; or h) any combination thereof. In some embodiments, the host cell expresses (a), (b), and (d).

In some embodiments, the one or more fusion proteins are expressed from a nucleic acid molecule comprising: a) a nucleotide sequence that is at least i) 90% identical, ii) 95% identical, iii) 99% identical, or iv) 100% identical to EGFRvIIIx5-SSX2 as set forth in SEQ ID NO:3; b) a nucleotide sequence that is at least i) 90% identical, ii) 95% identical, iii) 99% identical, or iv) 100% identical to EGFRvIIIx5-PAP$_{33-386}$ as set forth in SEQ ID NO:11; c) a nucleotide sequence that is at least i) 90% identical, ii) 95% identical, iii) 99% identical, or iv) 100% identical to EGFRvIIIx5-NKX3.1$_{11-234}$-PSMA$_{1-20,\ 44-138,\ 169-750}$ as set forth in SEQ ID NO:22; d) a nucleotide sequence that is at least i) 90% identical, ii) 95% identical, iii) 99% identical, or iv) 100% identical to EGFRvIIIx5-NKX3.1(R41G)$_{11-234}$-PSMA$_{1-20,\ 44-138,\ 169-750}$ as set forth in SEQ ID NO:15; e) a nucleotide sequence that is at least i) 90% identical, ii) 95% identical, iii) 99% identical, or iv) 100% identical to NKX3.1-PAP$_{33-386}$ as set forth in SEQ ID NO:26; f) a nucleotide sequence that is at least i) 90% identical, ii) 95% identical, iii) 99% identical, or iv) 100% identical to ActAN100*-SSX2 as set forth in SEQ ID NO:30; g) a nucleic acid sequence that is at least i) 90% identical, ii) 95% identical, iii) 99% identical, or iv) 100% identical to ActAN100-PAP$_{30-386}$-SL8 as set forth in SEQ ID NO:32; h) a nucleotide sequence that is at least i) 90% identical, ii) 95% identical, iii) 99% identical, or iv) 100% identical to EGFRvIIIx1-PAP$_{33-386}$ as set forth in SEQ ID NO:34; i) a nucleotide sequence that is at least i) 90% identical, ii) 95% identical, iii) 99% identical, or iv) 100% identical to EGFRvIIIx2-PAP$_{33-386}$ as set forth in SEQ ID NO:36; j) a nucleotide sequence that is at least i) 90% identical, ii) 95% identical, iii) 99% identical, or iv) 100% identical to EGFRvIIIx3-PAP$_{33-386}$ as set forth in SEQ ID NO:38; k) a nucleotide sequence that is at least i) 90% identical, ii) 95% identical, iii) 99% identical, or iv) 100% identical to EGFRvIIIx4-PAP$_{33-386}$ as set forth in SEQ ID NO:40; or 1) any combination thereof.

In some embodiments, the one or more fusion proteins are expressed from a nucleic acid molecule comprising (a), (b), and (d). In some embodiments, the one or more fusion proteins are expressed from a nucleic acid molecule consisting of (a), (b), and (d). In some embodiments, (a), (b), and (d) are operably linked to an ActA promoter. In some embodiments, the ActA promoter is set forth as SEQ ID NO:21. In some embodiments, (a) is integrated into the actA locus, (b) is integrated into the inlB locus, and (c) is integrated into the tRNA$^{Arg}$ locus. In certain embodiments, (a) is integrated into the actA locus, (b) is integrated into the inlB locus, and (d) is integrated into the tRNA$^{Arg}$ locus. In some embodiments, (e) is integrated into the inlB locus, and (f) is integrated into the tRNA$^{Arg}$ locus. In certain embodiments, (e) is integrated into the inlB locus and (a) is integrated into the tRNA$^{Arg}$ locus.

In some embodiments, the one or more fusion proteins are expressed from a nucleic acid molecule consisting of EGFRvIIIx5-SSX2 as set forth in SEQ ID NO:3, EGFRvIIIx5-PAP$_{33-386}$ as set forth in SEQ ID NO:11, and EGFRvIIIx5-NKX3.1(R41G)$_{11-234}$-PSMA$_{1-20, 44-138, 169-750}$ as set forth in SEQ ID NO:15.

In certain embodiments, the cancer is an EGFRvIII-expressing cancer, a SSX2-expressing cancer, a PAP-expressing cancer, a NKX3.1-expressing cancer, a PSMA-expressing cancer, or any combination thereof. In one embodiment, the cancer is prostate cancer.

In certain embodiments, the host cell is *Listeria monocytogenes*. In various embodiments, the *Listeria monocytogenes* is an actA deletion (ΔactA) mutant, an actA insertion mutant, an inlB deletion (ΔinlB) mutant, an inlB insertion mutant, or a combination thereof. In one embodiment, the *Listeria monocytogenes* is a ΔactA/ΔinlB mutant.

In some embodiments of any of the preceding methods of treating cancer, the fusion protein is expressed and secreted from the host cell in the cytosol of an infected cell within the subject. In certain embodiments, the infected cell is an antigen presenting cell.

In some embodiments of any of the preceding methods of treating cancer, the one or more fusion proteins comprise: a) an amino acid sequence at least i) 90% identical, ii) 95% identical, iii) 99% identical, or iv) 100% identical to EGFRvIIIx5-SSX2 as set forth in amino acid residues 89 to 475 of SEQ ID NO:4; b) an amino acid sequence at least i) 90% identical, ii) 95% identical, iii) 99% identical, or iv) 100% identical to EGFRvIIIx5-PAP$_{33-386}$ as set forth in amino acid residues 89 to 606 of SEQ ID NO:12; c) an amino acid sequence at least i) 90% identical, ii) 95% identical, iii) 99% identical, or iv) 100% identical to EGFRvIIIx5-NKX3.1$_{11-234}$-PSMA$_{1-20, 44-138, 169-750}$ as set forth in amino acid residues 89 to 1177 of SEQ ID NO:23; d) an amino acid sequence at least i) 90% identical, ii) 95% identical, iii) 99% identical, or iv) 100% identical to EGFRvIIIx5-NKX3.1(R41G)$_{11-234}$-jPSMA$_{1-20, 44-138, 169-750}$ as set forth in amino acid residues 89 to 1177 of SEQ ID NO:16; e) an amino acid sequence at least i) 90% identical, ii) 95% identical, iii) 99% identical, or iv) 100% identical to NKX3.1-PAP$_{33-386}$ as set forth in amino acid residues 89 to 678 of SEQ ID NO:27; f) an amino acid sequence at least i) 90% identical, ii) 95% identical, iii) 99% identical, or iv) 100% identical to ActAN100*-SSX2 as set forth in SEQ ID NO:31; g) an amino acid sequence at least i) 90% identical, ii) 95% identical, iii) 99% identical, or iv) 100% identical to ActAN100-PAP$_{30-386}$ as set forth in amino acid residues 1-459 of SEQ ID NO:33; h) an amino acid sequence at least i) 90% identical, ii) 95% identical, iii) 99% identical, or iv) 100% identical to EGFRvIIIx1-PAP$_{33-386}$ as set forth in amino acid residues 89 to 476 of SEQ ID NO:35; i) an amino acid sequence at least i) 90% identical, ii) 95% identical, iii) 99% identical, or iv) 100% identical to EGFRvIIIx2-PAP$_{33-386}$ as set forth in amino acid residues 89 to 509 of SEQ ID NO:37; j) an amino acid sequence at least i) 90% identical, ii) 95% identical, iii) 99% identical, or iv) 100% identical to EGFRvIIIx3-PAP$_{33-386}$ as set forth in amino acid residues 89 to 541 of SEQ ID NO:39; k) an amino acid sequence at least i) 90% identical, ii) 95% identical, iii) 99% identical, or iv) 100% identical to EGFRvIIIx4-PAP$_{33-386}$ as set forth in amino acid residues 89 to 573 of SEQ ID NO:41; or any combination thereof.

In some embodiments of any of the preceding methods of treating cancer, the one or more fusion proteins comprise (a), (b), and (d).

In some embodiments of any of the preceding methods of treating cancer, the one or more fusion proteins consist of (a), (b), and (d).

In some embodiments of any of the preceding methods of treating cancer, the one or more fusion proteins consist of EGFRvIIIx5-SSX2 as set forth in amino acid residues 89 to 475 of SEQ ID NO:4, EGFRvIIIx5-PAP$_{33-386}$ as set forth in amino acid residues 89 to 606 of SEQ ID NO:12, and EGFRvIIIx5-NKX3.1(R41G)$_{11-234}$-PSMA$_{1-20, 44-138, 169-750}$ as set forth in amino acid residues 89 to 1177 of SEQ ID NO:16.

In some embodiments, the method further comprises measuring expression of EGFRvIII, SSX2, PAP, NKX3.1, PSMA, or any combination thereof in a biological sample from the subject prior to administering the composition.

In some embodiments of any of the preceding methods of treating cancer, the composition further comprises a pharmaceutically acceptable excipient. In certain embodiments, the administering step is performed intravenously.

In some embodiments, the method of treating cancer further comprises administering an antibiotic to the subject after administering the composition. In certain embodiments, the antibiotic is administered after a last dose of the composition. In related embodiments, the antibiotic is amoxicillin or trimethoprim/sulfamethoxazole.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A recombinant *Listeria monocytogenes* host cell comprising a nucleic acid molecule encoding three separate fusion proteins, wherein the three separate fusion proteins are EGFRvIIIx5-SSX2, EGFRvIIIx5-PAP$_{33-386}$, and EGFRvIIIx5-NKX3.1(R41G)$_{11-234}$-PSMA$_{1-20, 44-138, 169-750}$; and wherein:
   a) EGFRvIIIx5-SSX2 is encoded by a nucleic acid sequence comprising the sequence set forth in SEQ ID NO:3;
   b) EGFRvIIIx5-PAP$_{33-386}$ is encoded by a nucleic acid sequence comprising the sequence set forth in SEQ ID NO:11; and
   c) EGFRvIIIx5-NKX3.1(R41G)$_{11-234}$-PSMA$_{1-20, 44-138, 169-750}$ is encoded by a nucleic acid sequence comprising the sequence set forth in SEQ ID NO:15.

2. The recombinant *Listeria monocytogenes* host cell of claim 1, wherein the *Listeria monocytogenes* is a ΔactA/ΔinlB mutant.

3. The recombinant *Listeria monocytogenes* host cell of claim 1, wherein the nucleic acid molecule is operably linked to an ActA promoter, said ActA promoter having the sequence set forth in SEQ ID NO:21.

4. A method of eliciting an immune response in a subject, said method comprising administering to the subject a therapeutically effective amount of a composition comprising a recombinant *Listeria monocytogenes* host cell, wherein the host cell expresses the fusion proteins EGFRvIIIx5-SSX2, EGFRvIIIx5-PAP$_{33-386}$, and EGFRvIIIx5-NKX3.1(R41G)$_{11-234}$-PSMA$_{1-20, 44-138, 169-750}$, and wherein the fusion proteins are encoded by a nucleic acid molecule as follows:
   a) EGFRvIIIx5-SSX2 is encoded by a nucleic acid sequence comprising the sequence set forth in SEQ ID NO:3;
   b) EGFRvIIIx5-PAP$_{33-386}$ is encoded by a nucleic acid sequence comprising the sequence set forth in SEQ ID NO:11; and
   c) EGFRvIIIx5-NKX3.1(R41G)$_{11-234}$-PSMA$_{1-20, 44-138, 169-750}$ is encoded by a nucleic acid sequence comprising the sequence set forth in SEQ ID NO:15.

5. The method of claim 4, wherein the *Listeria monocytogenes* is a ΔactA/ΔinlB mutant.

6. The method of claim 4, wherein the nucleic acid molecule is operably linked to an ActA promoter, said ActA promoter having the sequence set forth in SEQ ID NO:21.

7. A method of treating cancer in a subject in need thereof, said method comprising administering to the subject a therapeutically effective amount of a composition comprising a *Listeria monocytogenes* host cell, wherein the host cell expresses the fusion proteins EGFRvIIIx5-SSX2, EGFRvIIIx5-PAP$_{33-386}$, and EGFRvIIIx5-NKX3.1(R41G)$_{11-234}$-PSMA$_{1-20, 44-138, 169-750}$, and wherein:
   a) EGFRvIIIx5-SSX2 is encoded by a nucleic acid sequence comprising the sequence set forth in SEQ ID NO:3;
   b) EGFRvIIIx5-PAP$_{33-386}$ is encoded by a nucleic acid sequence comprising the sequence set forth in SEQ ID NO:11; and
   c) EGFRvIIIx5-NKX3.1(R41G)$_{11-234}$-PSMA$_{1-20, 44-138, 169-750}$ is encoded by a nucleic acid sequence comprising the sequence set forth in SEQ ID NO:15.

8. The method of claim 7, wherein the *Listeria monocytogenes* is a ΔactA/ΔinlB mutant.

9. The method of claim 7, wherein the nucleic acid molecule is operably linked to an ActA promoter, said ActA promoter having the sequence set forth in SEQ ID NO:21.

* * * * *

UNITED STATES PATENT AND TRADEMARK OFFICE
CERTIFICATE OF CORRECTION

| | | |
|---|---|---|
| PATENT NO. | : 9,808,516 B2 | Page 1 of 1 |
| APPLICATION NO. | : 15/097271 | |
| DATED | : November 7, 2017 | |
| INVENTOR(S) | : Dirk Brockstedt et al. | |

It is certified that error appears in the above-identified patent and that said Letters Patent is hereby corrected as shown below:

In the Specification

In the Government Support paragraph, in Column 1, at Line 16, please delete "W81WH-12-1-0439" and insert -- W81XWH-12-1-0439 --.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 64

<210> SEQ ID NO 1
<211> LENGTH: 258
<212> TYPE: DNA
<213> ORGANISM: Artificial Sequence
<220> FEATURE:
<223> OTHER INFORMATION: ActAN100* nucleotide sequence

<400> SEQUENCE: 1
gtgggattaa atagatttat gcgtgcgatg atggtagttt tcattactgc caactgcatt          60
```

```
acgattaacc ccgacataat atttgcagcg acagatagcg aagattccag tctaaacaca    120
gatgaatggg aagaagaata cgaaactgca cgtgaagtaa gttcacgtga tattgaggaa    180
ctagaaaaat cgaataaagt gaaaaatacg aacaaagcag accaagataa taaacgtaaa    240
gcaaaagcag agaaaggt                                                  258
```

```
<210> SEQ ID NO 2
<211> LENGTH: 88
<212> TYPE: PRT
<213> ORGANISM: Artificial Sequence
<220> FEATURE:
<223> OTHER INFORMATION: ActAN100* amino acid sequence

<400> SEQUENCE: 2
```

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Tyr Glu
            35                  40                  45

Thr Ala Arg Glu Val Ser Ser Arg Asp Ile Glu Glu Leu Glu Lys Ser
        50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser
                85

```
<210> SEQ ID NO 3
<211> LENGTH: 1649
<212> TYPE: DNA
<213> ORGANISM: Artificial Sequence
<220> FEATURE:
<223> OTHER INFORMATION: actAp-ActAN100*-EGFRvIIIx5-SSX2 nucleotide
      sequence

<400> SEQUENCE: 3
gggaagcagt tggggttaac tgattaacaa atgttagaga aaaattaatt ctccaagtga    60
tattcttaaa ataattcatg aatatttttt cttatattag ctaattaaga agataattaa   120
ctgctaatcc aatttttaac ggaataaatt agtgaaaatg aaggccgaat tttccttgtt   180
ctaaaaaggt tgtattagcg tatcacgagg agggagtata agtgggatta aatagattta   240
tgcgtgcgat gatggtagtt ttcattactg ccaactgcat tacgattaac cccgacataa   300
tatttgcagc gacagatagc gaagattcca gtctaaacac agatgaatgg gaagaagaat   360
acgaaactgc acgtgaagta agttcacgtg atattgagga actagaaaaa tcgaataaag   420
tgaaaaatac gaacaaagca gaccaagata taaacgtaaa gcaaaagcag agaaaggtg   480 gatccgcaag caaagtattg ccagctagtc gtgcattaga ggagaaaaag gggaattacg   540
tggtgacgga tcatggatcg tgtgccgatg gctcagtaaa gactagtgcg agcaaagtgg   600
cccctgcatc acgagcactt gaagagaaaa aaggaaacta tgttgtgacc gatcatggta   660
gctgcggaga tggttcaatt aaattatcaa aagtcttacc agcatctaga gctttagagg   720
aaaagaaggg taactatgtc gtaacagatc atggaagttg tgctgacgga agtgttaaag   780
cgtcgaaagt agctccagct tctcgcgcat tagaagaaaa gaaaggcaat tatgttgtaa   840
cagaccatgg tagttgtggt gatggctcga tcaaattgtc aaaagttcta ccggcttctc   900
gtgcgctaga agagaagaaa ggaaattacg tagttacaga ccacggctct tgcgcggatg   960
```

```
gttccgttaa acaattgatg aatggtgatg acgctttcgc acgccgtcct accgtaggag    1020
cacaaattcc agaaaagatt caaaaagcat tgatgacat cgctaaatac ttttctaaag    1080
aagaatggga gaaatgaaa gcgagcgaga aaatctttta tgtctatatg aaacggaaat    1140
atgaagcaat gacaaaattg ggtttcaaag caacattacc accatttatg tgcaataaac    1200
gtgcggaaga ttttcaaggg aatgatttag acaatgatcc taatcgaggc aaccaagtgg    1260
aaagaccgca aatgactttc ggacgtttac aagggatttc tccaaagata atgccgaaaa    1320
agccagccga agaaggtaat gatagtgaag aagtacctga agcgagtggt ccacaaaatg    1380
atggtaaaga actttgtcct ccaggcaaac cgacaacgtc tgagaagatt catgaacggt    1440
ccggtaaccg tgaagctcaa gagaaagaag aacgacgtgg aactgctcac agatggagtt    1500
cacagaatac acataacatt ggccgcttta gcctatcaac aagcatgggg gctgttcatg    1560
gaactccaaa aacgatcacg cataacgag atccaaaagg cggaaacatg ccgggtccaa    1620
cagattgtgt tagagaaaat tcgtggtaa                                     1649
```

<210> SEQ ID NO 4
<211> LENGTH: 475
<212> TYPE: PRT
<213> ORGANISM: Artificial Sequence
<220> FEATURE:
<223> OTHER INFORMATION: ActAN100*-EGFRvIIIx5-SSX2 amino acid sequence

<400> SEQUENCE: 4

```
Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Tyr Glu
            35                  40                  45

Thr Ala Arg Glu Val Ser Ser Arg Asp Ile Glu Glu Leu Glu Lys Ser
        50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser Ala Ser Lys Val Leu Pro Ala Ser
                85                  90                  95

Arg Ala Leu Glu Glu Lys Lys Gly Asn Tyr Val Val Thr Asp His Gly
            100                 105                 110

Ser Cys Ala Asp Gly Ser Val Lys Thr Ser Ala Ser Lys Val Ala Pro
        115                 120                 125

Ala Ser Arg Ala Leu Glu Glu Lys Lys Gly Asn Tyr Val Val Thr Asp
    130                 135                 140

His Gly Ser Cys Gly Asp Gly Ser Ile Lys Leu Ser Lys Val Leu Pro
145                 150                 155                 160

Ala Ser Arg Ala Leu Glu Glu Lys Lys Gly Asn Tyr Val Val Thr Asp
                165                 170                 175

His Gly Ser Cys Ala Asp Gly Ser Val Lys Ala Ser Lys Val Ala Pro
            180                 185                 190

Ala Ser Arg Ala Leu Glu Glu Lys Lys Gly Asn Tyr Val Val Thr Asp
        195                 200                 205

His Gly Ser Cys Gly Asp Gly Ser Ile Lys Leu Ser Lys Val Leu Pro
    210                 215                 220

Ala Ser Arg Ala Leu Glu Glu Lys Lys Gly Asn Tyr Val Val Thr Asp
225                 230                 235                 240
```

```
His Gly Ser Cys Ala Asp Gly Ser Val Lys Gln Leu Met Asn Gly Asp
                245                 250                 255

Asp Ala Phe Ala Arg Arg Pro Thr Val Gly Ala Gln Ile Pro Glu Lys
            260                 265                 270

Ile Gln Lys Ala Phe Asp Asp Ile Ala Lys Tyr Phe Ser Lys Glu Glu
        275                 280                 285

Trp Glu Lys Met Lys Ala Ser Glu Lys Ile Phe Tyr Val Tyr Met Lys
    290                 295                 300

Arg Lys Tyr Glu Ala Met Thr Lys Leu Gly Phe Lys Ala Thr Leu Pro
305                 310                 315                 320

Pro Phe Met Cys Asn Lys Arg Ala Glu Asp Phe Gln Gly Asn Asp Leu
                325                 330                 335

Asp Asn Asp Pro Asn Arg Gly Asn Gln Val Glu Arg Pro Gln Met Thr
            340                 345                 350

Phe Gly Arg Leu Gln Gly Ile Ser Pro Lys Ile Met Pro Lys Lys Pro
        355                 360                 365

Ala Glu Glu Gly Asn Asp Ser Glu Glu Val Pro Glu Ala Ser Gly Pro
    370                 375                 380

Gln Asn Asp Gly Lys Glu Leu Cys Pro Pro Gly Lys Pro Thr Thr Ser
385                 390                 395                 400

Glu Lys Ile His Glu Arg Ser Gly Asn Arg Glu Ala Gln Lys Glu
                405                 410                 415

Glu Arg Arg Gly Thr Ala His Arg Trp Ser Ser Gln Asn Thr His Asn
            420                 425                 430

Ile Gly Arg Phe Ser Leu Ser Thr Ser Met Gly Ala Val His Gly Thr
        435                 440                 445

Pro Lys Thr Ile Thr His Asn Arg Asp Pro Lys Gly Gly Asn Met Pro
    450                 455                 460

Gly Pro Thr Asp Cys Val Arg Glu Asn Ser Trp
465                 470                 475

<210> SEQ ID NO 5
<211> LENGTH: 63
<212> TYPE: DNA
<213> ORGANISM: Artificial Sequence
<220> FEATURE:
<223> OTHER INFORMATION: EGFRvIII nucleotide sequence
<220> FEATURE:
<221> NAME/KEY: misc_feature
<222> LOCATION: 33, 42
<223> OTHER INFORMATION: n = A,T,C or G

<400> SEQUENCE: 5
ccdgcwwswm ghgcdytwga rgaraaraar ggnaaytayg tngtdacvga ycayggghwsb        60 tgy                                                                     63

<210> SEQ ID NO 6
<211> LENGTH: 21
<212> TYPE: PRT
<213> ORGANISM: Artificial Sequence
<220> FEATURE:
<223> OTHER INFORMATION: EGFRvIII amino acid sequence

<400> SEQUENCE: 6

Pro Ala Ser Arg Ala Leu Glu Glu Lys Lys Gly Asn Tyr Val Val Thr
1               5                   10                  15

Asp His Gly Ser Cys
            20
```

<210> SEQ ID NO 7
<211> LENGTH: 486
<212> TYPE: DNA
<213> ORGANISM: Artificial Sequence
<220> FEATURE:
<223> OTHER INFORMATION: EGFRvIIIx5 nucleotide sequence

<400> SEQUENCE: 7

```
gcaagcaaag tattgccagc tagtcgtgca ttagaggaga aaaaggggaa ttacgtggtg      60
acggatcatg gatcgtgtgc cgatggctca gtaaagacta gtgcgagcaa agtggcccct     120
gcatcacgag cacttgaaga gaaaaaagga aactatgttg tgaccgatca tggtagctgc     180
ggagatggtt caattaaatt atcaaaagtc ttaccagcat ctagagcttt agaggaaaag     240
aagggtaact atgtcgtaac agatcatgga agttgtgctg acggaagtgt taaagcgtcg     300
aaagtagctc cagcttctcg cgcattagaa gaaaagaaag gcaattatgt tgtaacagac     360
catggtagtt gtggtgatgg ctcgatcaaa ttgtcaaaag ttctaccggc ttctcgtgcg     420
ctagaagaga gaaaggaaa ttacgtagtt acagaccacg gctcttgcgc ggatggttcc     480
gttaaa                                                                486
```

<210> SEQ ID NO 8
<211> LENGTH: 162
<212> TYPE: PRT
<213> ORGANISM: Artificial Sequence
<220> FEATURE:
<223> OTHER INFORMATION: EGFRvIIIx5 amino acid sequence

<400> SEQUENCE: 8

```
Ala Ser Lys Val Leu Pro Ala Ser Arg Ala Leu Glu Glu Lys Lys Gly
 1               5                  10                  15

Asn Tyr Val Val Thr Asp His Gly Ser Cys Ala Asp Gly Ser Val Lys
            20                  25                  30

Thr Ser Ala Ser Lys Val Ala Pro Ala Ser Arg Ala Leu Glu Glu Lys
        35                  40                  45

Lys Gly Asn Tyr Val Val Thr Asp His Gly Ser Cys Gly Asp Gly Ser
    50                  55                  60

Ile Lys Leu Ser Lys Val Leu Pro Ala Ser Arg Ala Leu Glu Glu Lys
65                  70                  75                  80

Lys Gly Asn Tyr Val Val Thr Asp His Gly Ser Cys Ala Asp Gly Ser
                85                  90                  95

Val Lys Ala Ser Lys Val Ala Pro Ala Ser Arg Ala Leu Glu Glu Lys
            100                 105                 110

Lys Gly Asn Tyr Val Val Thr Asp His Gly Ser Cys Gly Asp Gly Ser
        115                 120                 125

Ile Lys Leu Ser Lys Val Leu Pro Ala Ser Arg Ala Leu Glu Glu Lys
    130                 135                 140

Lys Gly Asn Tyr Val Val Thr Asp His Gly Ser Cys Ala Asp Gly Ser
145                 150                 155                 160

Val Lys
```

<210> SEQ ID NO 9
<211> LENGTH: 669
<212> TYPE: DNA
<213> ORGANISM: Artificial Sequence
<220> FEATURE:
<223> OTHER INFORMATION: SSX2 nucleotide sequence

<400> SEQUENCE: 9

```
atgaatggtg atgacgcttt cgcacgccgt cctaccgtag gagcacaaat tccagaaaag      60
attcaaaaag catttgatga catcgctaaa tactttteta aagaagaatg ggagaaaatg     120
aaagcgagcg agaaaatctt ttatgtctat atgaaacgga aatatgaagc aatgacaaaa     180
ttgggtttca aagcaacatt accaccattt atgtgcaata acgtgcgga agattttcaa      240 gggaatgatt tagacaatga tcctaatcga ggcaaccaag tggaaagacc gcaaatgact     300
ttcggacgtt tacaagggat ttctccaaag ataatgccga aaaagccagc cgaagaaggt     360
aatgatagtg aagaagtacc tgaagcgagt ggtccacaaa atgatggtaa agaactttgt     420
cctccaggca aaccgacaac gtctgagaag attcatgaac ggtccggtaa ccgtgaagct     480
caagagaaag aagaacgacg tggaactgct cacagatgga gttcacagaa tacacataac     540
attggccgct ttagcctatc aacaagcatg ggggctgttc atggaactcc aaaaacgatc     600
acgcataaca gagatccaaa aggcggaaac atgccgggtc caacagattg tgttagagaa     660
aattcgtgg                                                            669
```

<210> SEQ ID NO 10
<211> LENGTH: 223
<212> TYPE: PRT
<213> ORGANISM: Artificial Sequence
<220> FEATURE:
<223> OTHER INFORMATION: SSX2 amino acid sequence

<400> SEQUENCE: 10

```
Met Asn Gly Asp Asp Ala Phe Ala Arg Arg Pro Thr Val Gly Ala Gln
 1               5                  10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Asn Arg Glu Ala
145                 150                 155                 160

Gln Glu Lys Glu Glu Arg Arg Gly Thr Ala His Arg Trp Ser Ser Gln
                165                 170                 175

Asn Thr His Asn Ile Gly Arg Phe Ser Leu Ser Thr Ser Met Gly Ala
            180                 185                 190

Val His Gly Thr Pro Lys Thr Ile Thr His Asn Arg Asp Pro Lys Gly
        195                 200                 205

Gly Asn Met Pro Gly Pro Thr Asp Cys Val Arg Glu Asn Ser Trp
    210                 215                 220
```

<210> SEQ ID NO 11

<211> LENGTH: 2042
<212> TYPE: DNA
<213> ORGANISM: Artificial Sequence
<220> FEATURE:
<223> OTHER INFORMATION: actAp-ActAN100*-EGFRvIIIx5-PAP33-386 nucleotide sequence

<400> SEQUENCE: 11

```
gggaagcagt tggggttaac tgattaacaa atgttagaga aaaattaatt ctccaagtga        60
tattcttaaa ataattcatg aatatttttt cttatattag ctaattaaga agataattaa       120
ctgctaatcc aattttaac ggaataaatt agtgaaaatg aaggccgaat tttccttgtt        180
ctaaaaaggt tgtattagcg tatcacgagg agggagtata agtgggatta aatagattta       240
tgcgtgcgat gatggtagtt ttcattactg ccaactgcat tacgattaac cccgacataa       300
tatttgcagc gacagatagc gaagattcca gtctaaacac agatgaatgg gaagaagaat       360
acgaaactgc acgtgaagta agttcacgtg atattgagga actagaaaaa tcgaataaag       420
tgaaaaatac gaacaaagca gaccaagata taaacgtaa agcaaaagca gagaaaggtg        480
gatctgcaag caaagtattg ccagctagtc gtgcattaga ggagaaaaag gggaattacg       540
tggtgacgga tcatggatcg tgtgccgatg gctcagtaaa gactagtgcg agcaaagtgg       600
cccctgcatc acgagcactt gaagagaaaa aggaaacta tgttgtgacc gatcatggta        660
gctgcggaga tggttcaatt aaattatcaa aagtcttacc agcatctaga gctttagagg       720
aaaagaaggg taactatgtc gtaacagatc atggaagttg tgctgacgga agtgttaaag       780
cgtcgaaagt agctccagct tctcgcgcat tagaagaaaa gaaaggcaat tatgttgtaa       840
cagaccatgg tagttgtggt gatggctcga tcaaattgtc aaaagttcta ccggcttctc       900
gtgcgctaga agagaagaaa ggaaattacg tagttacaga ccacggctct tgcgcggatg       960
gttccgttaa aggatccaaa gaactaaagt ttgtaacgtt agtctttaga catggtgatc      1020
gtagtcctat tgatacccttt cctacagatc caatcaaaga gagtagttgg ccacaaggct      1080
tcggacaact tacacaatta ggaatggaac aacattatga attaggtgaa tacattcgca      1140
aacgttatcg caaattcctt aatgaatcgt acaaacacga acaagtgtat atccgttcca      1200
ctgacgttga tagaacacta atgtcagcta tgacaaatct agctgcatta gtgccaccag      1260
aaggcgttag catttggaat cctatcttac tttggcagcc aatacctgta catacggttc      1320
cgttatctga agatcaatta cttttatctt catttcgcaa ctgcccacga ttccaagaat      1380
tagaatccga acattgaaa agcgaagaat ttcagaaaag attacatcca tacaaagact       1440
ttatcgcaac cttaggcaaa ttgtcagggt tacacggaca ggatctattt ggaatttggt      1500
cgaaagttta tgatcctttg tactgtgaat ctgtacataa ctttacatta cctagtcgcg      1560
ccacggaaga tactatgacg aaactacgtg aactttccga actttctttta ctatcgttgt     1620
atggtattca taaacaaaaa gaaaagagca gattgcaagg tggtgtttta gtaaatgaaa      1680
tcttaaacca tatgaaaaga gctacacaaa ttccgtctta caagaaattg attatgtata      1740
gtgctcatga tacgacagta tctgggcttc aaatggcgtt agatgtctat aacggcttac      1800
ttccaccgta tgcgtcatgt caccttacgg aactttactt tgagaaaggt gagtactttg      1860
ttgagatgta ctatcgcaat gaaacccaac atgaaccata tccgttgatg ttaccaggtt      1920
gtagtccatc ttgcccgtta gaacgatttg cggaattagt gggtccagtg ataccacaag      1980
actggtctac tgagtgtatg actactaata gccaccaagg gactgaagat tcaacagatt      2040
aa                                                                      2042
```

<210> SEQ ID NO 12
<211> LENGTH: 606
<212> TYPE: PRT
<213> ORGANISM: Artificial Sequence
<220> FEATURE:
<223> OTHER INFORMATION: ActAN100*-EGFRvIIIx5-PAP33-386

<400> SEQUENCE: 12

```
Met Gly Leu Asn Arg Phe Met Arg Ala Met Met Val Val Phe Ile Thr
  1               5                  10                  15

Ala Asn Cys Ile Thr Ile Asn Pro Asp Ile Ile Phe Ala Ala Thr Asp
                 20                  25                  30

Ser Glu Asp Ser Ser Leu Asn Thr Asp Glu Trp Glu Glu Glu Tyr Glu
             35                  40                  45

Thr Ala Arg Glu Val Ser Ser Arg Asp Ile Glu Glu Leu Glu Lys Ser
 50                  55                  60

Asn Lys Val Lys Asn Thr Asn Lys Ala Asp Gln Asp Asn Lys Arg Lys
 65                  70                  75                  80

Ala Lys Ala Glu Lys Gly Gly Ser Ala Ser Lys Val Leu Pro Ala Ser
                 85                  90                  95

Arg Ala Leu Glu Glu Lys Lys Gly Asn Tyr Val Val Thr Asp His Gly
            100                 105                 110

Ser Cys Ala Asp Gly Ser Val Lys Thr Ser Ala Ser Lys Val Ala Pro
            115                 120                 125

Ala Ser Arg Ala Leu Glu Glu Lys Lys Gly Asn Tyr Val Val Thr Asp
        130                 135                 140

His Gly Ser Cys Gly Asp Gly Ser Ile Lys Leu Ser Lys Val Leu Pro
145                 150                 155                 160

Ala Ser Arg Ala Leu Glu Glu Lys Lys Gly Asn Tyr Val Val Thr Asp
                165                 170                 175

His Gly Ser Cys Ala Asp Gly Ser Val Lys Ala Ser Lys Val Ala Pro
            180                 185                 190

Ala Ser Arg Ala Leu Glu Glu Lys Lys Gly Asn Tyr Val Val Thr Asp
            195                 200                 205

His Gly Ser Cys Gly Asp Gly Ser Ile Lys Leu Ser Lys Val Leu Pro
        210                 215                 220

Ala Ser Arg Ala Leu Glu Glu Lys Lys Gly Asn Tyr Val Val Thr Asp
225                 230                 235                 240

His Gly Ser Cys Ala Asp Gly Ser Val Lys Gly Ser Lys Glu Leu Lys
                245                 250                 255

Phe Val Thr Leu Val Phe Arg His Gly Asp Arg Ser Pro Ile Asp Thr
            260                 265                 270

Phe Pro Thr Asp Pro Ile Lys Glu Ser Ser Trp Pro Gln Gly Phe Gly
            275                 280                 285

Gln Leu Thr Gln Leu Gly Met Glu Gln His Tyr Glu Leu Gly Glu Tyr
        290                 295                 300

Ile Arg Lys Arg Tyr Arg Lys Phe Leu Asn Glu Ser Tyr Lys His Glu
305                 310                 315                 320

Gln Val Tyr Ile Arg Ser Thr Asp Val Asp Arg Thr Leu Met Ser Ala
                325                 330                 335

Met Thr Asn Leu Ala Ala Leu Val Pro Pro Glu Gly Val Ser Ile Trp
            340                 345                 350

Asn Pro Ile Leu Leu Trp Gln Pro Ile Pro Val His Thr Val Pro Leu
            355                 360                 365
```

Ser Glu Asp Gln Leu Leu Tyr Leu Pro Phe Arg Asn Cys Pro Arg Phe
370                 375                 380

Gln Glu Leu Glu Ser Glu Thr Leu Lys Ser Glu Glu Phe Gln Lys Arg
385                 390                 395                 400

Leu His Pro Tyr Lys Asp Phe Ile Ala Thr Leu Gly Lys Leu Ser Gly
                405                 410                 415

Leu His Gly Gln Asp Leu Phe Gly Ile Trp Ser Lys Val Tyr Asp Pro
            420                 425                 430

Leu Tyr Cys Glu Ser Val His Asn Phe Thr Leu Pro Ser Arg Ala Thr
                435                 440                 445

Glu Asp Thr Met Thr Lys Leu Arg Glu Leu Ser Glu Leu Ser Leu Leu
450                 455                 460

Ser Leu Tyr Gly Ile His Lys Gln Lys Glu Lys Ser Arg Leu Gln Gly
465                 470                 475                 480

Gly Val Leu Val Asn Glu Ile Leu Asn His Met Lys Arg Ala Thr Gln
                485                 490                 495

Ile Pro Ser Tyr Lys Lys Leu Ile Met Tyr Ser Ala His Asp Thr Thr
                500                 505                 510

Val Ser Gly Leu Gln Met Ala Leu Asp Val Tyr Asn Gly Leu Leu Pro
            515                 520                 525

Pro Tyr Ala Ser Cys His Leu Thr Glu Leu Tyr Phe Glu Lys Gly Glu
            530                 535                 540

Tyr Phe Val Glu Met Tyr Tyr Arg Asn Glu Thr Gln His Glu Pro Tyr
545                 550                 555                 560

Pro Leu Met Leu Pro Gly Cys Ser Pro Ser Cys Pro Leu Glu Arg Phe
                565                 570                 575

Ala Glu Leu Val Gly Pro Val Ile Pro Gln Asp Trp Ser Thr Glu Cys
                580                 585                 590

Met Thr Thr Asn Ser His Gln Gly Thr Glu Asp Ser Thr Asp
                595                 600                 605

<210> SEQ ID NO 13
<211> LENGTH: 1062
<212> TYPE: DNA
<213> ORGANISM: Artificial Sequence
<220> FEATURE:
<223> OTHER INFORMATION: PAP33-386 nucleotide sequence

<400> SEQUENCE: 13
aaagaactaa agtttgtaac gttagtcttt agacatggtg atcgtagtcc tattgatacc    60
tttcctacag atccaatcaa agagagtagt tggccacaag gcttcggaca acttacacaa   120
ttaggaatgg aacaacatta tgaattaggt gaatacattc gcaaacgtta tcgcaaattc   180
cttaatgaat cgtacaaaca cgaacaagtg tatatccgtt ccactgacgt tgatagaaca   240
ctaatgtcag ctatgacaaa tctagctgca ttagtgccac cagaaggcgt tagcatttgg   300
aatcctatct tactttggca gccaataccg gtacatacgg ttccgttatc tgaagatcaa   360
ttactttatc ttccatttcg caactgccca cgattccaag aattagaatc cgaaacattg   420
aaaagcgaag aatttcagaa aagattacat ccatacaaag actttatcgc aaccttaggc   480
aaattgtcag ggttacacgg acaggatcta tttggaattt ggtcgaaagt ttatgatcct   540
ttgtactgtg aatctgtaca taactttaca ttacctagtc gcgccacgga agatactatg   600
acgaaactac gtgaactttc gaactttct ttactatcgt tgtatggtat tcataaacaa   660
aaagaaaaga gcagattgca aggtggtgtt ttagtaaatg aaatcttaaa ccatatgaaa   720

```
agagctacac aaattccgtc ttacaagaaa ttgattatgt atagtgctca tgatacgaca    780
gtatctgggc ttcaaatggc gttagatgtc tataacggct tacttccacc gtatgcgtca    840
tgtcacctta cggaactttg ctttgagaaa ggtgagtact tgttgagat gtactatcgc     900 aatgaaaccc aacatgaacc atatccgttg atgttaccag gttgtagtcc atcttgcccg    960
ttagaacgat ttgcggaatt agtgggtcca gtgataccac aagactggtc tactgagtgt   1020
atgactacta atagccacca agggactgaa gattcaacag at                      1062
```

<210> SEQ ID NO 14
<211> LENGTH: 354
<212> TYPE: PRT
<213> ORGANISM: Artificial Sequence
<220> FEATURE:
<223> OTHER INFORMATION: PAP33-386 amino acid sequence

<400> SEQUENCE: 14

```
Lys Glu Leu Lys Phe Val Thr Leu Val Phe Arg His Gly Asp Arg Ser
 1               5                  10                  15

Pro Ile Asp Thr Phe Pro Thr Asp Pro Ile Lys Glu Ser Ser Trp Pro
            20                  25                  30

Gln Gly Phe Gly Gln Leu Thr Gln Leu Gly Met Glu Gln His Tyr Glu
        35                  40                  45

Leu Gly Glu Tyr Ile Arg Lys Arg Tyr Arg Lys Phe Leu Asn Glu Ser
    50                  55                  60

Tyr Lys His Glu Gln Val Tyr Ile Arg Ser Thr Asp Val Asp Arg Thr
65                  70                  75                  80

Leu Met Ser Ala Met Thr Asn Leu Ala Ala Leu Val Pro Pro Glu Gly
                85                  90                  95

Val Ser Ile Trp Asn Pro Ile Leu Leu Trp Gln Pro Ile Pro Val His
            100                 105                 110

Thr Val Pro Leu Ser Glu Asp Gln Leu Leu Tyr Leu Pro Phe Arg Asn
        115                 120                 125

Cys Pro Arg Phe Gln Glu Leu Glu Ser Glu Thr Leu Lys Ser Glu Glu
    130                 135                 140

Phe Gln Lys Arg Leu His Pro Tyr Lys Asp Phe Ile Ala Thr Leu Gly
145                 150                 155                 160

Lys Leu Ser Gly Leu His Gly Gln Asp Leu Phe Gly Ile Trp Ser Lys
                165                 170                 175

Val Tyr Asp Pro Leu Tyr Cys Glu Ser Val His Asn Phe Thr Leu Pro
            180                 185                 190

Ser Arg Ala Thr Glu Asp Thr Met Thr Lys Leu Arg Glu Leu Ser Glu
        195                 200                 205

Leu Ser Leu Leu Ser Leu Tyr Gly Ile His Lys Gln Lys Glu Lys Ser
    210                 215                 220

Arg Leu Gln Gly Gly Val Leu Val Asn Glu Ile Leu Asn His Met Lys
225                 230                 235                 240

Arg Ala Thr Gln Ile Pro Ser Tyr Lys Lys Leu Ile Met Tyr Ser Ala
                245                 250                 255

His Asp Thr Thr Val Ser Gly Leu Gln Met Ala Leu Asp Val Tyr Asn
            260                 265                 270

Gly Leu Leu Pro Pro Tyr Ala Ser Cys His Leu Thr Glu Leu Tyr Phe
        275                 280                 285

Glu Lys Gly Glu Tyr Phe Val Glu Met Tyr Tyr Arg Asn Glu Thr Gln
    290                 295                 300
```

```
His Glu Pro Tyr Pro Leu Met Leu Pro Gly Cys Ser Pro Ser Cys Pro
305                 310                 315                 320

Leu Glu Arg Phe Ala Glu Leu Val Gly Pro Val Ile Pro Gln Asp Trp
                325                 330                 335

Ser Thr Glu Cys Met Thr Thr Asn Ser His Gln Gly Thr Glu Asp Ser
            340                 345                 350

Thr Asp

<210> SEQ ID NO 15
<211> LENGTH: 3755
<212> TYPE: DNA
<213> ORGANISM: Artificial Sequence
<220> FEATURE:
<223> OTHER INFORMATION: actAp-ActAN100*-EGFRvIIIx5-NKX3.1(R41G)11-234-
      PSMA1-20, 44-138, 169-750 nucleotide sequence

<400> SEQUENCE: 15
gggaagcagt tggggttaac tgattaacaa atgttagaga aaaattaatt ctccaagtga      60
tattcttaaa ataattcatg aatatttttt cttatattag ctaattaaga agataattaa     120
ctgctaatcc aattttaac ggaataaatt agtgaaaatg aaggccgaat tttccttgtt     180 ctaaaaggt tgtattagcg tatcacgagg agggagtata agtgggatta aatagattta      240
tgcgtgcgat gatggtagtt ttcattactg ccaactgcat tacgattaac cccgacataa     300
tatttgcagc gacagatagc gaagattcca gtctaaacac agatgaatgg gaagaagaat     360
acgaaactgc acgtgaagta agttcacgtg atattgagga actagaaaaa tcgaataaag     420
tgaaaaatac gaacaaagca gaccaagata taaacgtaaa gcaaaagca gagaaaggtg     480 gatctgcaag caaagtattg ccagctagtc gtgcattaga ggagaaaaag gggaattacg     540
tggtgacgga tcatggatcg tgtgccgatg gctcagtaaa gactagcgcg agcaaagtgg     600
cccctgcatc acgagcactt gaagagaaaa aaggaaacta tgttgtgacc gatcatggta     660
gctgcggaga tggttcaatt aaattatcaa aagtcttacc agcatctaga gctttagagg     720
aaaagaaggg taactatgtc gtaacagatc atggaagttg tgctgacgga agtgttaaag     780
cgtcgaaagt agctccagct tctcgcgcat tagaagaaaa gaaaggcaat tatgttgtaa     840
cagaccatgg tagttgtggt gatggctcga tcaaattgtc aaaagttcta ccggcttctc     900
gtgcgctaga agaagaaaa ggaaattacg tagttacaga ccacggctct tgcgcgatg     960 gttccgttaa aggatccgaa gcaaagctg aaggcgcagc gccaccgact cctagtaaac    1020
cactaacaag tttcttaatc caagatattc ttcgtgacgg tgcacaagga caaggcggac    1080
gaacttcttc acaacgtcaa cgagatcctg agccagaacc ggagcctgaa ccggaagggg    1140
gacgctcccg agctggagca caaaacgatc agttatctac tggtccaaga gctgcccctg    1200
aagaagcaga gacactagcc gaaacggaac cagaaagaca tttgggttca tacttacttg    1260
actcagaaaa cacaagcggg gctttaccga gattaccaca acaccaaaa cagcctcaaa    1320 aacgtagtcg tgctgcattt tcgcacacgc aagtcataga gttagaacgc aaattcagcc    1380
atcaaaagta tttgtccgca ccagaacgtg ctcatcttgc gaagaatttg aaacttacag    1440
aaacccaagt aaagatttgg tttcaaaatc gccgctataa gacgaaacgt aaacaacttt    1500
cttctgaact aggtgattta gaaaaacatt caagccttcc ggcgttaaag gaagaagcat    1560
ttagtcgtgc gagcttagtt tctgtttaca atagttatcc atactatcca tatctatact    1620
gtgtaggctc gtggtcgcca gcttttttgga ctagtatgtg gaacttatta cacgaaacag    1680
actcagcagt agcaacagcc agacgccctc gttggaaatc aagcaacgaa gctaccaata    1740
```

| tcaccccgaa acacaatatg aaagcattcc tagacgaact aaaagcagaa aacataaaaa | 1800 |
| aatttcttta caatttcaca cagattccac atttagctgg tacggagcaa aactttcaat | 1860 |
| tagcaaaaca aattcaatct caatggaaag aatttggttt agacagtgta gaattggctc | 1920 |
| attacgatgt cctttatct tatccgaata aaacgcatcc aaattacatt tcaattatta | 1980 |
| atgaagatgg aaatgaaata caattgatgc ctgagggcga tttagtgtat gttaactatg | 2040 |
| cgcgcacaga ggatttcttt aaacttgaac gggatatgaa aatcaactgt tctggtaaaa | 2100 |
| tcgtcattgc tcgttatggc aaagtatttc gtggcaacaa agtaaagaat gcacaattag | 2160 |
| cgggtgcgaa aggcgtcata ttatactccg atccagcaga ttactttgca cctggagtaa | 2220 |
| aatcctatcc agatggctgg aatttgccag gtggggtgt acagcgtggc aatattctta | 2280 |
| atcttaatgg ggctggtgac cctttaactc ctggttatcc agctaatgaa tacgcttatc | 2340 |
| gtcgtggaat cgcagaagcc gtgggactac cctcaattcc tgtacatcca atcggatact | 2400 |
| atgatgctca aaaattatta gaaagatgg ggggtccgc tccaccagat tcgagctggc | 2460 |
| gtggaagtct caaagttcca tacaatgtag gcccgggttt tactggcaac ttttcaacac | 2520 |
| aaaaagtgaa aatgcacatt cattccacga atgaagtgac tcgaatatac aatgtcattg | 2580 |
| gaactctccg tggtgcggtt gagccagaca gatatgtaat ccttggcgga caccgagata | 2640 |
| gttgggtatt tggaggtatt gatccacaaa gtggagcagc ggttgttcat gaaattgtta | 2700 |
| gaagtttcgg tacacttaag aaagaagggt ggcgaccacg ccgtacgatt ttgtttgctt | 2760 |
| cgtgggatgc cgaagagttc ggacttttgg gatctacaga atgggcagaa gagaacagcc | 2820 |
| gtttattgca agaacgcggg gtagcttata ttaatgctga tagtagtatt gaaggtaact | 2880 |
| atacattaag agtggactgt acgccgttaa tgtattcgct agtccataac cttacaaaag | 2940 |
| aacttaaaag cccagatgaa gggttcgaag ggaaatcgct ttatgaatca tggacaaaga | 3000 |
| aatctccatc accagagttc tctggaatgc ctcgtatcag taaattgggt agcgaaacg | 3060 |
| actttgaagt tttctttcaa cgtctaggca ttgcgtcggg gagagcgcgg tacaccaaaa | 3120 |
| actgggaaac caataagttt agcggctatc cactctatca ttctgtgtat gaaacatacg | 3180 |
| agcttgtaga aaaattttat gatccgatgt ttaaatatca tcttacagtt gctcaggtcc | 3240 |
| ggggtggaat ggttttgag ttggctaatt ccattgtact tccatttgac tgccgcgatt | 3300 |
| acgctgtggt gctaagaaaa tacgctgata aaatctattc catttcaatg aaacacccac | 3360 |
| aagaaatgaa aacttatagc gtgagttttg atagtttatt cagtgccgta aagaacttta | 3420 |
| ctgaaatcgc cagcaagttt tctgaaagat tacaagattt cgataaatct aatcctatag | 3480 |
| tattaagaat gatgaatgat caactaatgt ttttagaacg agcgttcatt gatccgttag | 3540 |
| gtttaccgga tcgacctttc tatcgtcacg ttatctacgc tcccagtagc cataacaaat | 3600 |
| atgcaggcga atcttttcca ggaatctatg acgccctatt cgatatagaa agtaaagttg | 3660 |
| atccgagtaa agcatggggt gaagttaaac gacaaatcta tgtcgcggca ttcactgttc | 3720 |
| aagcagcggc tgaaacttta tcagaagttg cttaa | 3755 |

<210> SEQ ID NO 16
<211> LENGTH: 1177
<212> TYPE: PRT
<213> ORGANISM: Artificial Sequence
<220> FEATURE:
<223> OTHER INFORMATION: ActAN100*-EGFRvIIIx5-NKX3.1(R41G)11-234-
      PSMA1-20, 44-138, 169-750 amino acid sequence

<400> SEQUENCE: 16

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser Ala Ser Lys Val Leu Pro Ala Ser
                85                  90                  95

Arg Ala Leu Glu Glu Lys Lys Gly Asn Tyr Val Val Thr Asp His Gly
                100                 105                 110

Ser Cys Ala Asp Gly Ser Val Lys Thr Ser Ala Ser Lys Val Ala Pro
        115                 120                 125

Ala Ser Arg Ala Leu Glu Glu Lys Lys Gly Asn Tyr Val Val Thr Asp
    130                 135                 140

His Gly Ser Cys Gly Asp Gly Ser Ile Lys Leu Ser Lys Val Leu Pro
145                 150                 155                 160

Ala Ser Arg Ala Leu Glu Glu Lys Lys Gly Asn Tyr Val Val Thr Asp
                165                 170                 175

His Gly Ser Cys Ala Asp Gly Ser Val Lys Ala Ser Lys Val Ala Pro
            180                 185                 190

Ala Ser Arg Ala Leu Glu Glu Lys Lys Gly Asn Tyr Val Val Thr Asp
                195                 200                 205

His Gly Ser Cys Gly Asp Gly Ser Ile Lys Leu Ser Lys Val Leu Pro
        210                 215                 220

Ala Ser Arg Ala Leu Glu Glu Lys Lys Gly Asn Tyr Val Val Thr Asp
225                 230                 235                 240

His Gly Ser Cys Ala Asp Gly Ser Val Lys Gly Ser Glu Ala Lys Ala
            245                 250                 255

Glu Gly Ala Ala Pro Pro Thr Pro Ser Lys Pro Leu Thr Ser Phe Leu
            260                 265                 270

Ile Gln Asp Ile Leu Arg Asp Gly Ala Gln Gly Gln Gly Gly Arg Thr
        275                 280                 285

Ser Ser Gln Arg Gln Arg Asp Pro Glu Pro Glu Pro Glu Pro Glu Pro
    290                 295                 300

Glu Gly Gly Arg Ser Arg Ala Gly Ala Gln Asn Asp Gln Leu Ser Thr
305                 310                 315                 320

Gly Pro Arg Ala Ala Pro Glu Glu Ala Glu Thr Leu Ala Glu Thr Glu
                325                 330                 335

Pro Glu Arg His Leu Gly Ser Tyr Leu Leu Asp Ser Glu Asn Thr Ser
            340                 345                 350

Gly Ala Leu Pro Arg Leu Pro Gln Thr Pro Lys Gln Pro Gln Lys Arg
        355                 360                 365

Ser Arg Ala Ala Phe Ser His Thr Gln Val Ile Glu Leu Glu Arg Lys
    370                 375                 380

Phe Ser His Gln Lys Tyr Leu Ser Ala Pro Glu Arg Ala His Leu Ala
385                 390                 395                 400

Lys Asn Leu Lys Leu Thr Glu Thr Gln Val Lys Ile Trp Phe Gln Asn
                405                 410                 415
```

-continued

```
Arg Arg Tyr Lys Thr Lys Arg Lys Gln Leu Ser Ser Glu Leu Gly Asp
            420                 425                 430

Leu Glu Lys His Ser Ser Leu Pro Ala Leu Lys Glu Glu Ala Phe Ser
            435                 440                 445

Arg Ala Ser Leu Val Ser Val Tyr Asn Ser Tyr Pro Tyr Tyr Pro Tyr
        450                 455                 460

Leu Tyr Cys Val Gly Ser Trp Ser Pro Ala Phe Trp Thr Ser Met Trp
465                 470                 475                 480

Asn Leu Leu His Glu Thr Asp Ser Ala Val Ala Thr Ala Arg Arg Pro
                485                 490                 495

Arg Trp Lys Ser Ser Asn Glu Ala Thr Asn Ile Thr Pro Lys His Asn
            500                 505                 510

Met Lys Ala Phe Leu Asp Glu Leu Lys Ala Glu Asn Ile Lys Lys Phe
        515                 520                 525

Leu Tyr Asn Phe Thr Gln Ile Pro His Leu Ala Gly Thr Glu Gln Asn
530                 535                 540

Phe Gln Leu Ala Lys Gln Ile Gln Ser Gln Trp Lys Glu Phe Gly Leu
545                 550                 555                 560

Asp Ser Val Glu Leu Ala His Tyr Asp Val Leu Leu Ser Tyr Pro Asn
                565                 570                 575

Lys Thr His Pro Asn Tyr Ile Ser Ile Ile Asn Glu Asp Gly Asn Glu
            580                 585                 590

Ile Gln Leu Met Pro Glu Gly Asp Leu Val Tyr Val Asn Tyr Ala Arg
        595                 600                 605

Thr Glu Asp Phe Phe Lys Leu Glu Arg Asp Met Lys Ile Asn Cys Ser
610                 615                 620

Gly Lys Ile Val Ile Ala Arg Tyr Gly Lys Val Phe Arg Gly Asn Lys
625                 630                 635                 640

Val Lys Asn Ala Gln Leu Ala Gly Ala Lys Gly Val Ile Leu Tyr Ser
                645                 650                 655

Asp Pro Ala Asp Tyr Phe Ala Pro Gly Val Lys Ser Tyr Pro Asp Gly
            660                 665                 670

Trp Asn Leu Pro Gly Gly Gly Val Gln Arg Gly Asn Ile Leu Asn Leu
        675                 680                 685

Asn Gly Ala Gly Asp Pro Leu Thr Pro Gly Tyr Pro Ala Asn Glu Tyr
690                 695                 700

Ala Tyr Arg Arg Gly Ile Ala Glu Ala Val Gly Leu Pro Ser Ile Pro
705                 710                 715                 720

Val His Pro Ile Gly Tyr Tyr Asp Ala Gln Lys Leu Leu Glu Lys Met
                725                 730                 735

Gly Gly Ser Ala Pro Pro Asp Ser Ser Trp Arg Gly Ser Leu Lys Val
            740                 745                 750

Pro Tyr Asn Val Gly Pro Gly Phe Thr Gly Asn Phe Ser Thr Gln Lys
        755                 760                 765

Val Lys Met His Ile His Ser Thr Asn Glu Val Thr Arg Ile Tyr Asn
770                 775                 780

Val Ile Gly Thr Leu Arg Gly Ala Val Glu Pro Asp Arg Tyr Val Ile
785                 790                 795                 800

Leu Gly Gly His Arg Asp Ser Trp Val Phe Gly Gly Ile Asp Pro Gln
                805                 810                 815

Ser Gly Ala Ala Val Val His Glu Ile Val Arg Ser Phe Gly Thr Leu
            820                 825                 830

Lys Lys Glu Gly Trp Arg Pro Arg Arg Thr Ile Leu Phe Ala Ser Trp
```

Asp Ala Glu Glu Phe Gly Leu Leu Gly Ser Thr Glu Trp Ala Glu
835                 840                 845

Asn Ser Arg Leu Leu Gln Glu Arg Gly Val Ala Tyr Ile Asn Ala Asp
850                 855                 860

Ser Ser Ile Glu Gly Asn Tyr Thr Leu Arg Val Asp Cys Thr Pro Leu
865                 870                 875                 880

Met Tyr Ser Leu Val His Asn Leu Thr Lys Glu Leu Lys Ser Pro Asp
    885                 890                 895

Glu Gly Phe Glu Gly Lys Ser Leu Tyr Glu Ser Trp Thr Lys Lys Ser
900                 905                 910

Pro Ser Pro Glu Phe Ser Gly Met Pro Arg Ile Ser Lys Leu Gly Ser
    915                 920                 925

Gly Asn Asp Phe Glu Val Phe Phe Gln Arg Leu Gly Ile Ala Ser Gly
930                 935                 940

Arg Ala Arg Tyr Thr Lys Asn Trp Glu Thr Asn Lys Phe Ser Gly Tyr
945                 950                 955                 960

Pro Leu Tyr His Ser Val Tyr Glu Thr Tyr Glu Leu Val Glu Lys Phe
    965                 970                 975

Tyr Asp Pro Met Phe Lys Tyr His Leu Thr Val Ala Gln Val Arg Gly
980                 985                 990

Gly Met Val Phe Glu Leu Ala Asn Ser Ile Val Leu Pro Phe Asp Cys
    995                 1000                1005

Arg Asp Tyr Ala Val Val Leu Arg Lys Tyr Ala Asp Lys Ile Tyr Ser
1010                1015                1020

Ile Ser Met Lys His Pro Gln Glu Met Lys Thr Tyr Ser Val Ser Phe
1025                1030                1035                1040

Asp Ser Leu Phe Ser Ala Val Lys Asn Phe Thr Glu Ile Ala Ser Lys
    1045                1050                1055

Phe Ser Glu Arg Leu Gln Asp Phe Asp Lys Ser Asn Pro Ile Val Leu
1060                1065                1070

Arg Met Met Asn Asp Gln Leu Met Phe Leu Glu Arg Ala Phe Ile Asp
    1075                1080                1085

Pro Leu Gly Leu Pro Asp Arg Pro Phe Tyr Arg His Val Ile Tyr Ala
1090                1095                1100

Pro Ser Ser His Asn Lys Tyr Ala Gly Glu Ser Phe Pro Gly Ile Tyr
1105                1110                1115                1120

Asp Ala Leu Phe Asp Ile Glu Ser Lys Val Asp Pro Ser Lys Ala Trp
    1125                1130                1135

Gly Glu Val Lys Arg Gln Ile Tyr Val Ala Ala Phe Thr Val Gln Ala
1140                1145                1150

Ala Ala Glu Thr Leu Ser Glu Val Ala
    1155                1160

<210> SEQ ID NO 17
<211> LENGTH: 672
<212> TYPE: DNA
<213> ORGANISM: Artificial Sequence
<220> FEATURE:
<223> OTHER INFORMATION: NKX3.1(R41G)11-234 nucleotide sequence

<400> SEQUENCE: 17
gaagcaaaag ctgaaggcgc agcgccaccg actcctagta aaccactaac aagtttctta    60
atccaagata ttcttcgtga cggtgcacaa ggacaaggcg acgaacttc ttcacaacgt    120

```
caacgagatc ctgagccaga accggagcct gaaccggaag ggggacgctc ccgagctgga    180
gcacaaaacg atcagttatc tactggtcca agagctgccc ctgaagaagc agagacacta    240
gccgaaacgg aaccagaaag acatttgggt tcatacttac ttgactcaga aaacacaagc    300
ggggctttac cgagattacc acaaacacca aacagcctc aaaaacgtag tcgtgctgca    360
ttttcgcaca cgcaagtcat agagttagaa cgcaaattca gccatcaaaa gtatttgtcc    420
gcaccgaaac gtgctcatct tgcgaagaat ttgaaactta cagaaaccca agtaaagatt    480
tggtttcaaa atcgccgcta taagacgaaa cgtaaacaac tttcttctga actaggtgat    540
ttagaaaaac attcaagcct tccggcgtta aaggaagaag catttagtcg tgcgagctta    600
gtttctgttt acaatagtta tccatactat ccatatctat actgtgtagg ctcgtggtcg    660
ccagcttttt gg                                                        672
```

<210> SEQ ID NO 18
<211> LENGTH: 224
<212> TYPE: PRT
<213> ORGANISM: Artificial Sequence
<220> FEATURE:
<223> OTHER INFORMATION: NKX3.1(R41G)11-234 amino acid sequence

<400> SEQUENCE: 18

```
Glu Ala Lys Ala Glu Gly Ala Ala Pro Pro Thr Pro Ser Lys Pro Leu
 1               5                  10                  15
Thr Ser Phe Leu Ile Gln Asp Ile Leu Arg Asp Gly Ala Gln Gly Gln
             20                  25                  30
Gly Gly Arg Thr Ser Ser Gln Arg Gln Arg Asp Pro Glu Pro Glu Pro
         35                  40                  45
Glu Pro Glu Pro Glu Gly Gly Arg Ser Arg Ala Gly Ala Gln Asn Asp
     50                  55                  60
Gln Leu Ser Thr Gly Pro Arg Ala Ala Pro Glu Glu Ala Glu Thr Leu
 65                  70                  75                  80
Ala Glu Thr Glu Pro Glu Arg His Leu Gly Ser Tyr Leu Leu Asp Ser
                 85                  90                  95
Glu Asn Thr Ser Gly Ala Leu Pro Arg Leu Pro Gln Thr Pro Lys Gln
            100                 105                 110
Pro Gln Lys Arg Ser Arg Ala Ala Phe Ser His Thr Gln Val Ile Glu
        115                 120                 125
Leu Glu Arg Lys Phe Ser His Gln Lys Tyr Leu Ser Ala Pro Glu Arg
    130                 135                 140
Ala His Leu Ala Lys Asn Leu Lys Leu Thr Glu Thr Gln Val Lys Ile
145                 150                 155                 160
Trp Phe Gln Asn Arg Arg Tyr Lys Thr Lys Arg Lys Gln Leu Ser Ser
                165                 170                 175
Glu Leu Gly Asp Leu Glu Lys His Ser Ser Leu Pro Ala Leu Lys Glu
            180                 185                 190
Glu Ala Phe Ser Arg Ala Ser Leu Val Ser Val Tyr Asn Ser Tyr Pro
        195                 200                 205
Tyr Tyr Pro Tyr Leu Tyr Cys Val Gly Ser Trp Ser Pro Ala Phe Trp
    210                 215                 220
```

<210> SEQ ID NO 19
<211> LENGTH: 2097
<212> TYPE: DNA
<213> ORGANISM: Artificial Sequence
<220> FEATURE:
<223> OTHER INFORMATION: PSMA1-20, 44-138, 169-750 nucleotide sequence

<400> SEQUENCE: 19

```
atgtggaact tattacacga aacagactca gcagtagcaa cagccagacg ccctcgttgg      60
aaatcaagca acgaagctac caatatcacc ccgaaacaca atatgaaagc attcctagac    120
gaactaaaag cagaaaacat aaaaaaattt ctttacaatt tcacacagat tccacattta    180
gctggtacgg agcaaaactt tcaattagca aaacaaattc aatctcaatg gaaagaattt    240
ggtttagaca gtgtagaatt ggctcattac gatgtccttt tatcttatcc gaataaaacg    300
catccaaatt acatttcaat tattaatgaa gatggaaatg aaatacaatt gatgcctgag    360
ggcgatttag tgtatgttaa ctatgcgcgc acagaggatt tctttaaact tgaacgggat    420
atgaaaatca actgttctgg taaaatcgtc attgctcgtt atggcaaagt atttcgtggc    480
aacaaagtaa agaatgcaca attagcgggt gcgaaaggcg tcatattata ctccgatcca    540
gcagattact ttgcacctgg agtaaaatcc tatccagatg gctggaattt gccaggtggg    600
ggtgtacagc gtggcaatat tcttaatctt aatggggctg gtgacccttt aactcctggt    660
tatccagcta atgaatacgc ttatcgtcgt ggaatcgcag aagccgtggg actaccctca    720
attcctgtac atccaatcgg atactatgat gctcaaaaat tattagaaaa gatgggggg     780
tccgctccac cagattcgag ctggcgtgga agtctcaaag ttccatacaa tgtaggcccg    840
ggttttactg gcaacttttc aacacaaaaa gtgaaaatgc acattcattc cacgaatgaa    900
gtgactcgaa tatacaatgt cattggaact ctccgtggtg cggttgagcc agacagatat    960
gtaatccttg gcggacaccg agatagttgg gtatttggag gtattgatcc acaaagtgga   1020
gcagcggttg ttcatgaaat tgttagaagt ttcggtacac ttaagaaaga agggtggcga   1080
ccacgccgta cgattttgtt tgcttcgtgg gatgccgaag agttcggact tttgggatct   1140
acagaatggg cagaagagaa cagccgttta ttgcaagaac gcggggtagc ttatattaat   1200
gctgatagta gtattgaagg taactataca ttaagagtgg actgtacgcc gttaatgtat   1260
tcgctagtcc ataaccttac aaaagaactt aaaagcccag atgaagggtt cgaagggaaa   1320
tcgctttatg aatcatggac aaagaaatct ccatcaccag agttctctgg aatgcctcgt   1380
atcagtaaat tgggtagcgg aaacgacttt gaagttttct ttcaacgtct aggcattgcg   1440
tcggggagag cgcggtacac caaaaactgg gaaaccaata agtttagcgg ctatccactc   1500
tatcattctg tgtatgaaac atacgagctt gtagaaaaat tttatgatcc gatgtttaaa   1560
tatcatctta cagttgctca ggtccggggt ggaatggttt ttgagttggc taattccatt   1620
gtacttccat ttgactgccg cgattacgct gtggtgctaa gaaaatacgc tgataaaatc   1680
tattccattt caatgaaaca cccacaagaa atgaaaactt atagcgtgag ttttgatagt   1740
ttattcagtg ccgtaaagaa ctttactgaa atcgccagca gtttctga aagattacaa     1800
gatttcgata aatctaatcc tatagtatta agaatgatga atgatcaact aatgttttta   1860
gaacgagcgt tcattgatcc gttaggttta ccggatcgac ctttctatcg tcacgttatc   1920
tacgctccca gtagccataa caaatatgca ggcgaatctt ttccaggaat ctatgacgcc   1980
ctattcgata tagaaagtaa agttgatccg agtaaagcat ggggtgaagt taaacgacaa   2040
atctatgtcg cggcattcac tgttcaagca gcggctgaaa ctttatcaga agttgct     2097
```

<210> SEQ ID NO 20
<211> LENGTH: 699
<212> TYPE: PRT
<213> ORGANISM: Artificial Sequence
<220> FEATURE:

-continued

<223> OTHER INFORMATION: PSMA1-20, 44-138, 169-750 amino acid sequence

<400> SEQUENCE: 20

```
Met Trp Asn Leu Leu His Glu Thr Asp Ser Ala Val Ala Thr Ala Arg
1               5                   10                  15

Arg Pro Arg Trp Lys Ser Ser Asn Glu Ala Thr Asn Ile Thr Pro Lys
            20                  25                  30

His Asn Met Lys Ala Phe Leu Asp Glu Leu Lys Ala Glu Asn Ile Lys
        35                  40                  45

Lys Phe Leu Tyr Asn Phe Thr Gln Ile Pro His Leu Ala Gly Thr Glu
    50                  55                  60

Gln Asn Phe Gln Leu Ala Lys Gln Ile Gln Ser Gln Trp Lys Glu Phe
65                  70                  75                  80

Gly Leu Asp Ser Val Glu Leu Ala His Tyr Asp Val Leu Leu Ser Tyr
                85                  90                  95

Pro Asn Lys Thr His Pro Asn Tyr Ile Ser Ile Ile Asn Glu Asp Gly
            100                 105                 110

Asn Glu Ile Gln Leu Met Pro Glu Gly Asp Leu Val Tyr Val Asn Tyr
        115                 120                 125

Ala Arg Thr Glu Asp Phe Phe Lys Leu Glu Arg Asp Met Lys Ile Asn
130                 135                 140

Cys Ser Gly Lys Ile Val Ile Ala Arg Tyr Gly Lys Val Phe Arg Gly
145                 150                 155                 160

Asn Lys Val Lys Asn Ala Gln Leu Ala Gly Ala Lys Gly Val Ile Leu
                165                 170                 175

Tyr Ser Asp Pro Ala Asp Tyr Phe Ala Pro Gly Val Lys Ser Tyr Pro
            180                 185                 190

Asp Gly Trp Asn Leu Pro Gly Gly Val Gln Arg Gly Asn Ile Leu
        195                 200                 205

Asn Leu Asn Gly Ala Gly Asp Pro Leu Thr Pro Gly Tyr Pro Ala Asn
210                 215                 220

Glu Tyr Ala Tyr Arg Arg Gly Ile Ala Glu Ala Val Gly Leu Pro Ser
225                 230                 235                 240

Ile Pro Val His Pro Ile Gly Tyr Tyr Asp Ala Gln Lys Leu Leu Glu
                245                 250                 255

Lys Met Gly Gly Ser Ala Pro Pro Asp Ser Ser Trp Arg Gly Ser Leu
            260                 265                 270

Lys Val Pro Tyr Asn Val Gly Pro Gly Phe Thr Gly Asn Phe Ser Thr
        275                 280                 285

Gln Lys Val Lys Met His Ile His Ser Thr Asn Glu Val Thr Arg Ile
290                 295                 300

Tyr Asn Val Ile Gly Thr Leu Arg Gly Ala Val Glu Pro Asp Arg Tyr
305                 310                 315                 320

Val Ile Leu Gly Gly His Arg Asp Ser Trp Val Phe Gly Gly Ile Asp
                325                 330                 335

Pro Gln Ser Gly Ala Ala Val Val His Glu Ile Val Arg Ser Phe Gly
            340                 345                 350

Thr Leu Lys Lys Glu Gly Trp Arg Pro Arg Arg Thr Ile Leu Phe Ala
        355                 360                 365

Ser Trp Asp Ala Glu Glu Phe Gly Leu Leu Gly Ser Thr Glu Trp Ala
370                 375                 380

Glu Glu Asn Ser Arg Leu Leu Gln Glu Arg Gly Val Ala Tyr Ile Asn
385                 390                 395                 400
```

-continued

```
Ala Asp Ser Ser Ile Glu Gly Asn Tyr Thr Leu Arg Val Asp Cys Thr
            405                 410                 415

Pro Leu Met Tyr Ser Leu Val His Asn Leu Thr Lys Glu Leu Lys Ser
        420                 425                 430

Pro Asp Glu Gly Phe Glu Gly Lys Ser Leu Tyr Glu Ser Trp Thr Lys
    435                 440                 445

Lys Ser Pro Ser Pro Glu Phe Ser Gly Met Pro Arg Ile Ser Lys Leu
450                 455                 460

Gly Ser Gly Asn Asp Phe Glu Val Phe Phe Gln Arg Leu Gly Ile Ala
465                 470                 475                 480

Ser Gly Arg Ala Arg Tyr Thr Lys Asn Trp Glu Thr Asn Lys Phe Ser
            485                 490                 495

Gly Tyr Pro Leu Tyr His Ser Val Tyr Glu Thr Tyr Glu Leu Val Glu
        500                 505                 510

Lys Phe Tyr Asp Pro Met Phe Lys Tyr His Leu Thr Val Ala Gln Val
    515                 520                 525

Arg Gly Gly Met Val Phe Glu Leu Ala Asn Ser Ile Val Leu Pro Phe
530                 535                 540

Asp Cys Arg Asp Tyr Ala Val Val Leu Arg Lys Tyr Ala Asp Lys Ile
545                 550                 555                 560

Tyr Ser Ile Ser Met Lys His Pro Gln Glu Met Lys Thr Tyr Ser Val
            565                 570                 575

Ser Phe Asp Ser Leu Phe Ser Ala Val Lys Asn Phe Thr Glu Ile Ala
        580                 585                 590

Ser Lys Phe Ser Glu Arg Leu Gln Asp Phe Asp Lys Ser Asn Pro Ile
    595                 600                 605

Val Leu Arg Met Met Asn Asp Gln Leu Met Phe Leu Glu Arg Ala Phe
610                 615                 620

Ile Asp Pro Leu Gly Leu Pro Asp Arg Pro Phe Tyr Arg His Val Ile
625                 630                 635                 640

Tyr Ala Pro Ser Ser His Asn Lys Tyr Ala Gly Glu Ser Phe Pro Gly
            645                 650                 655

Ile Tyr Asp Ala Leu Phe Asp Ile Glu Ser Lys Val Asp Pro Ser Lys
        660                 665                 670

Ala Trp Gly Glu Val Lys Arg Gln Ile Tyr Val Ala Ala Phe Thr Val
    675                 680                 685

Gln Ala Ala Ala Glu Thr Leu Ser Glu Val Ala
690                 695

<210> SEQ ID NO 21
<211> LENGTH: 221
<212> TYPE: DNA
<213> ORGANISM: Artificial Sequence
<220> FEATURE:
<223> OTHER INFORMATION: actA promoter nucleotide sequence

<400> SEQUENCE: 21
gggaagcagt tgggggttaac tgattaacaa atgttagaga aaaattaatt ctccaagtga      60
tattcttaaa ataattcatg aatattttt cttatattag ctaattaaga agataattaa     120
ctgctaatcc aattttaac ggaataaatt agtgaaaatg aaggccgaat tttccttgtt      180
ctaaaaaggt tgtattagcg tatcacgagg agggagtata a                          221

<210> SEQ ID NO 22
<211> LENGTH: 3755
<212> TYPE: DNA
```

<213> ORGANISM: Artificial Sequence
<220> FEATURE:
<223> OTHER INFORMATION: actAp-ActAN100*-EGFRvIIIx5-NKX3.111-234-
PSMA1-20, 44-138, 169-750 nucleotide sequence

<400> SEQUENCE: 22

| | | |
|---|---|---|
| gggaagcagt tggggttaac tgattaacaa atgttagaga aaaattaatt ctccaagtga | 60 |
| tattcttaaa ataattcatg aatattttt cttatattag ctaattaaga agataattaa | 120 |
| ctgctaatcc aattttaac ggaataaatt agtgaaaatg aaggccgaat tttccttgtt | 180 |
| ctaaaaaggt tgtattagcg tatcacgagg agggagtata agtgggatta aatagattta | 240 |
| tgcgtgcgat gatggtagtt ttcattactg ccaactgcat tacgattaac cccgacataa | 300 |
| tatttgcagc gacagatagc gaagattcca gtctaaacac agatgaatgg gaagaagaat | 360 |
| acgaaactgc acgtgaagta agttcacgtg atattgagga actagaaaaa tcgaataaag | 420 |
| tgaaaaatac gaacaaagca gaccaagata taaacgtaa agcaaaagca gagaaaggtg | 480 |
| gatctgcaag caaagtattg ccagctagtc gtgcattaga ggagaaaaag gggaattacg | 540 |
| tggtgacgga tcatggatcg tgtgccgatg gctcagtaaa gactagcgcg agcaaagtgg | 600 |
| cccctgcatc acgagcactt gaagagaaaa aaggaaacta tgttgtgacc gatcatggta | 660 |
| gctgcggaga tggttcaatt aaattatcaa agtcttacc agcatctaga gctttagagg | 720 |
| aaaagaaggg taactatgtc gtaacagatc atggaagttg tgctgacgga agtgttaaag | 780 |
| cgtcgaaagt agctccagct tctcgcgcat tagaagaaaa gaaaggcaat tatgttgtaa | 840 |
| cagaccatgg tagttgtggt gatggctcga tcaaattgtc aaaagttcta ccggcttctc | 900 |
| gtgcgctaga agagaagaaa ggaaattacg tagttacaga ccacggctct tgcgcggatg | 960 |
| gttccgttaa aggatccgaa gcaaaagctg aaggcgcagc gccaccgact cctagtaaac | 1020 |
| cactaacaag tttcttaatc caagatattc ttcgtgacgg tgcacaaaga caaggcggac | 1080 |
| gaacttcttc acaacgtcaa cgagatcctg agccagaacc ggagcctgaa ccggaagggg | 1140 |
| gacgctcccg agctggagca caaaacgatc agttatctac tggtccaaga gctgcccctg | 1200 |
| aagaagcaga gacactagcc gaaacggaac cagaaagaca tttgggttca tacttacttg | 1260 |
| actcagaaaa cacaagcggg gctttaccga gattaccaca aacaccaaaa cagcctcaaa | 1320 |
| aacgtagtcg tgctgcattt tcgcacacgc aagtcataga gttagaacgc aaattcagcc | 1380 |
| atcaaaagta tttgtccgca ccagaacgtg ctcatcttgc gaagaatttg aaacttacag | 1440 |
| aaacccaagt aaagatttgg tttcaaaatc gccgctataa gacgaaacgt aaacaacttt | 1500 |
| cttctgaact aggtgattta gaaaaacatt caagccttcc ggcgttaaag gaagaagcat | 1560 |
| ttagtcgtgc gagcttagtt tctgtttaca atagttatcc atactatcca tatctatact | 1620 |
| gtgtaggctc gtggtcgcca gcttttggga ctagtatgtg gaacttatta cacgaaacag | 1680 |
| actcagcagt agcaacagcc agacgccctc gttggaaatc aagcaacgaa gctaccaata | 1740 |
| tcacccccgaa acacaatatg aaagcattcc tagacgaact aaaagcagaa aacataaaaa | 1800 |
| aatttcttta caatttcaca cagattccac atttagctgg tacggagcaa aacttttcaat | 1860 |
| tagcaaaaca aattcaatct caatggaaag aatttggttt agacagtgta gaattggctc | 1920 |
| attacgatgt cctttatctt tatccgaata aaacgcatcc aaattacatt tcaattatta | 1980 |
| atgaagatgg aaatgaaata caattgatgc ctgagggcga tttagtgtat gttaactatg | 2040 |
| cgcgcacaga ggatttcttt aaacttgaac gggatatgaa aatcaactgt tctggtaaaa | 2100 |
| tcgtcattgc tcgttatggc aaagtatttc gtggcaacaa agtaaagaat gcacaattag | 2160 |

-continued

```
cgggtgcgaa aggcgtcata ttatactccg atccagcaga ttactttgca cctggagtaa    2220
aatcctatcc agatggctgg aatttgccag gtggggtgt acagcgtggc aatattctta    2280
atcttaatgg ggctggtgac cctttaactc ctggttatcc agctaatgaa tacgcttatc    2340
gtcgtggaat cgcagaagcc gtgggactac cctcaattcc tgtacatcca atcggatact    2400
atgatgctca aaaattatta gaaaagatgg ggggtccgc tccaccagat tcgagctggc    2460
gtggaagtct caaagttcca tacaatgtag gcccgggttt tactggcaac ttttcaacac    2520
aaaaagtgaa aatgcacatt cattccacga atgaagtgac tcgaatatac aatgtcattg    2580
gaactctccg tggtgcggtt gagccagaca gatatgtaat ccttggcgga caccgagata    2640
gttgggtatt tggaggtatt gatccacaaa gtggagcagc ggttgttcat gaaattgtta    2700
gaagtttcgg tacacttaag aaagaagggg ggcgaccacg ccgtacgatt ttgtttgctt    2760
cgtgggatgc cgaagagttc ggactttggg gatctacaga atgggcagaa gagaacagcc    2820
gtttattgca agaacgcggg gtagcttata ttaatgctga tagtagtatt gaaggtaact    2880
atacattaag agtggactgt acgccgttaa tgtattcgct agtccataac cttacaaaag    2940
aacttaaaag cccagatgaa gggttcgaag ggaaatcgct ttatgaatca tggacaaaga    3000
aatctccatc accagagttc tctggaatgc ctcgtatcag taaattgggt agcggaaacg    3060
actttgaagt tttctttcaa cgtctaggca ttgcgtcggg gagagcgcgg tacaccaaaa    3120
actgggaaac caataagttt agcggctatc cactctatca ttctgtgtat gaaacatacg    3180
agcttgtaga aaaattttat gatccgatgt ttaaatatca tcttacagtt gctcaggtcc    3240
ggggtggaat ggttttttgag ttggctaatt ccattgtact tccatttgac tgccgcgatt    3300
acgctgtggt gctaagaaaa tacgctgata aaatctattc catttcaatg aaacacccac    3360
aagaaatgaa aacttatagc gtgagttttg atagtttatt cagtgccgta aagaacttta    3420
ctgaaatcgc cagcaagttt tctgaaagat tacaagattt cgataaatct aatcctatag    3480
tattaagaat gatgaatgat caactaatgt ttttagaacg agcgttcatt gatccgttag    3540
gtttaccgga tcgaccttc tatcgtcacg ttatctacgc tcccagtagc cataacaaat    3600
atgcaggcga atcttttcca ggaatctatg acgccctatt cgatatagaa agtaaagttg    3660
atccgagtaa agcatggggt gaagttaaac gacaaatcta tgtcgcggca ttcactgttc    3720
aagcagcggc tgaaacttta tcagaagttg cttaa                              3755
```

<210> SEQ ID NO 23
<211> LENGTH: 1177
<212> TYPE: PRT
<213> ORGANISM: Artificial Sequence
<220> FEATURE:
<223> OTHER INFORMATION: ActAN100*-EGFRvIIIx5-NKX3.111-234-PSMA1-20,
      44-138, 169-750 amino acid sequence

<400> SEQUENCE: 23

```
Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Tyr Glu
            35                  40                  45

Thr Ala Arg Glu Val Ser Ser Arg Asp Ile Glu Glu Leu Glu Lys Ser
        50                  55                  60

Asn Lys Val Lys Asn Thr Asn Lys Ala Asp Gln Asp Asn Lys Arg Lys
65                  70                  75                  80
```

```
Ala Lys Ala Glu Lys Gly Gly Ser Ala Ser Lys Val Leu Pro Ala Ser
             85                  90                  95

Arg Ala Leu Glu Glu Lys Lys Gly Asn Tyr Val Val Thr Asp His Gly
            100                 105                 110

Ser Cys Ala Asp Gly Ser Val Lys Thr Ser Ala Ser Lys Val Ala Pro
        115                 120                 125

Ala Ser Arg Ala Leu Glu Glu Lys Lys Gly Asn Tyr Val Val Thr Asp
    130                 135                 140

His Gly Ser Cys Gly Asp Gly Ser Ile Lys Leu Ser Lys Val Leu Pro
145                 150                 155                 160

Ala Ser Arg Ala Leu Glu Glu Lys Lys Gly Asn Tyr Val Val Thr Asp
                165                 170                 175

His Gly Ser Cys Ala Asp Gly Ser Val Lys Ala Ser Lys Val Ala Pro
            180                 185                 190

Ala Ser Arg Ala Leu Glu Glu Lys Lys Gly Asn Tyr Val Val Thr Asp
        195                 200                 205

His Gly Ser Cys Gly Asp Gly Ser Ile Lys Leu Ser Lys Val Leu Pro
    210                 215                 220

Ala Ser Arg Ala Leu Glu Glu Lys Lys Gly Asn Tyr Val Val Thr Asp
225                 230                 235                 240

His Gly Ser Cys Ala Asp Gly Ser Val Lys Gly Ser Glu Ala Lys Ala
                245                 250                 255

Glu Gly Ala Ala Pro Pro Thr Pro Ser Lys Pro Leu Thr Ser Phe Leu
            260                 265                 270

Ile Gln Asp Ile Leu Arg Asp Gly Ala Gln Arg Gln Gly Gly Arg Thr
        275                 280                 285

Ser Ser Gln Arg Gln Arg Asp Pro Glu Pro Glu Pro Glu Pro Glu Pro
    290                 295                 300

Glu Gly Gly Arg Ser Arg Ala Gly Ala Gln Asn Asp Gln Leu Ser Thr
305                 310                 315                 320

Gly Pro Arg Ala Ala Pro Glu Glu Ala Glu Thr Leu Ala Glu Thr Glu
                325                 330                 335

Pro Glu Arg His Leu Gly Ser Tyr Leu Leu Asp Ser Glu Asn Thr Ser
            340                 345                 350

Gly Ala Leu Pro Arg Leu Pro Gln Thr Pro Lys Gln Pro Gln Lys Arg
        355                 360                 365

Ser Arg Ala Ala Phe Ser His Thr Gln Val Ile Glu Leu Glu Arg Lys
    370                 375                 380

Phe Ser His Gln Lys Tyr Leu Ser Ala Pro Glu Arg Ala His Leu Ala
385                 390                 395                 400

Lys Asn Leu Lys Leu Thr Glu Thr Gln Val Lys Ile Trp Phe Gln Asn
                405                 410                 415

Arg Arg Tyr Lys Thr Lys Arg Lys Gln Leu Ser Ser Glu Leu Gly Asp
            420                 425                 430

Leu Glu Lys His Ser Ser Leu Pro Ala Leu Lys Glu Glu Ala Phe Ser
        435                 440                 445

Arg Ala Ser Leu Val Ser Val Tyr Asn Ser Tyr Pro Tyr Tyr Pro Tyr
    450                 455                 460

Leu Tyr Cys Val Gly Ser Trp Ser Pro Ala Phe Trp Thr Ser Met Trp
465                 470                 475                 480

Asn Leu Leu His Glu Thr Asp Ser Ala Val Ala Thr Ala Arg Arg Pro
                485                 490                 495
```

```
Arg Trp Lys Ser Ser Asn Glu Ala Thr Asn Ile Thr Pro Lys His Asn
            500                 505                 510
Met Lys Ala Phe Leu Asp Glu Leu Lys Ala Glu Asn Ile Lys Lys Phe
        515                 520                 525
Leu Tyr Asn Phe Thr Gln Ile Pro His Leu Ala Gly Thr Glu Gln Asn
    530                 535                 540
Phe Gln Leu Ala Lys Gln Ile Gln Ser Gln Trp Lys Glu Phe Gly Leu
545                 550                 555                 560
Asp Ser Val Glu Leu Ala His Tyr Asp Val Leu Leu Ser Tyr Pro Asn
                565                 570                 575
Lys Thr His Pro Asn Tyr Ile Ser Ile Ile Asn Glu Asp Gly Asn Glu
            580                 585                 590
Ile Gln Leu Met Pro Glu Gly Asp Leu Val Tyr Val Asn Tyr Ala Arg
        595                 600                 605
Thr Glu Asp Phe Phe Lys Leu Glu Arg Asp Met Lys Ile Asn Cys Ser
    610                 615                 620
Gly Lys Ile Val Ile Ala Arg Tyr Gly Lys Val Phe Arg Gly Asn Lys
625                 630                 635                 640
Val Lys Asn Ala Gln Leu Ala Gly Ala Lys Gly Val Ile Leu Tyr Ser
                645                 650                 655
Asp Pro Ala Asp Tyr Phe Ala Pro Gly Val Lys Ser Tyr Pro Asp Gly
            660                 665                 670
Trp Asn Leu Pro Gly Gly Val Gln Arg Gly Asn Ile Leu Asn Leu
        675                 680                 685
Asn Gly Ala Gly Asp Pro Leu Thr Pro Gly Tyr Pro Ala Asn Glu Tyr
    690                 695                 700
Ala Tyr Arg Arg Gly Ile Ala Glu Ala Val Gly Leu Pro Ser Ile Pro
705                 710                 715                 720
Val His Pro Ile Gly Tyr Tyr Asp Ala Gln Lys Leu Leu Glu Lys Met
                725                 730                 735
Gly Gly Ser Ala Pro Pro Asp Ser Ser Trp Arg Gly Ser Leu Lys Val
            740                 745                 750
Pro Tyr Asn Val Gly Pro Gly Phe Thr Gly Asn Phe Ser Thr Gln Lys
        755                 760                 765
Val Lys Met His Ile His Ser Thr Asn Glu Val Thr Arg Ile Tyr Asn
    770                 775                 780
Val Ile Gly Thr Leu Arg Gly Ala Val Glu Pro Asp Arg Tyr Val Ile
785                 790                 795                 800
Leu Gly Gly His Arg Asp Ser Trp Val Phe Gly Gly Ile Asp Pro Gln
                805                 810                 815
Ser Gly Ala Ala Val Val His Glu Ile Val Arg Ser Phe Gly Thr Leu
            820                 825                 830
Lys Lys Glu Gly Trp Arg Pro Arg Arg Thr Ile Leu Phe Ala Ser Trp
        835                 840                 845
Asp Ala Glu Glu Phe Gly Leu Leu Gly Ser Thr Glu Trp Ala Glu Glu
    850                 855                 860
Asn Ser Arg Leu Leu Gln Glu Arg Gly Val Ala Tyr Ile Asn Ala Asp
865                 870                 875                 880
Ser Ser Ile Glu Gly Asn Tyr Thr Leu Arg Val Asp Cys Thr Pro Leu
                885                 890                 895
Met Tyr Ser Leu Val His Asn Leu Thr Lys Glu Leu Lys Ser Pro Asp
            900                 905                 910
Glu Gly Phe Glu Gly Lys Ser Leu Tyr Glu Ser Trp Thr Lys Lys Ser
```

```
            915                 920                 925
Pro Ser Pro Glu Phe Ser Gly Met Pro Arg Ile Ser Lys Leu Gly Ser
    930                 935                 940

Gly Asn Asp Phe Glu Val Phe Phe Gln Arg Leu Gly Ile Ala Ser Gly
945                 950                 955                 960

Arg Ala Arg Tyr Thr Lys Asn Trp Glu Thr Asn Lys Phe Ser Gly Tyr
                965                 970                 975

Pro Leu Tyr His Ser Val Tyr Glu Thr Tyr Glu Leu Val Glu Lys Phe
            980                 985                 990

Tyr Asp Pro Met Phe Lys Tyr His Leu Thr Val Ala Gln Val Arg Gly
        995                 1000                1005

Gly Met Val Phe Glu Leu Ala Asn Ser Ile Val Leu Pro Phe Asp Cys
    1010                1015                1020

Arg Asp Tyr Ala Val Val Leu Arg Lys Tyr Ala Asp Lys Ile Tyr Ser
1025                1030                1035                1040

Ile Ser Met Lys His Pro Gln Glu Met Lys Thr Tyr Ser Val Ser Phe
                1045                1050                1055

Asp Ser Leu Phe Ser Ala Val Lys Asn Phe Thr Glu Ile Ala Ser Lys
            1060                1065                1070

Phe Ser Glu Arg Leu Gln Asp Phe Asp Lys Ser Asn Pro Ile Val Leu
        1075                1080                1085

Arg Met Met Asn Asp Gln Leu Met Phe Leu Gly Arg Ala Phe Ile Asp
    1090                1095                1100

Pro Leu Gly Leu Pro Asp Arg Pro Phe Tyr Arg His Val Ile Tyr Ala
1105                1110                1115                1120

Pro Ser Ser His Asn Lys Tyr Ala Gly Glu Ser Phe Pro Gly Ile Tyr
                1125                1130                1135

Asp Ala Leu Phe Asp Ile Glu Ser Lys Val Asp Pro Ser Lys Ala Trp
            1140                1145                1150

Gly Glu Val Lys Arg Gln Ile Tyr Val Ala Ala Phe Thr Val Gln Ala
        1155                1160                1165

Ala Ala Glu Thr Leu Ser Glu Val Ala
    1170                1175

<210> SEQ ID NO 24
<211> LENGTH: 672
<212> TYPE: DNA
<213> ORGANISM: Artificial Sequence
<220> FEATURE:
<223> OTHER INFORMATION: NKX3.111-234 nucleotide sequence

<400> SEQUENCE: 24
gaagcaaaag ctgaaggcgc agcgccaccg actcctagta aaccactaac aagtttctta      60
atccaagata ttcttcgtga cggtgcacaa agacaaggcg acgaacttc ttcacaacgt     120 caacgagatc ctgagccaga accggagcct gaaccggaag ggggacgctc ccgagctgga     180
gcacaaaacg atcagttatc tactggtcca agagctgccc ctgaagaagc agagacacta     240
gccgaaacgg aaccagaaag acatttgggt tcatacttac ttgactcaga aaacacaagc     300
ggggctttac cgagattacc acaaacacca aacagcctc aaaaacgtag tcgtgctgca      360
ttttcgcaca cgcaagtcat agagttagaa cgcaaattca gccatcaaaa gtatttgtcc     420
gcaccagaac gtgctcatct tgcgaagaat ttgaaactta cagaaaccca agtaaagatt     480
tggtttcaaa atcgccgcta taagacgaaa cgtaaacaac tttcttctga actaggtgat     540
ttagaaaaac attcaagcct tccggcgtta aggaagaag catttagtcg tgcgagctta      600
```

```
gtttctgttt acaatagtta tccatactat ccatatctat actgtgtagg ctcgtggtcg    660 ccagctttt gg                                                         672
```

<210> SEQ ID NO 25
<211> LENGTH: 224
<212> TYPE: PRT
<213> ORGANISM: Artificial Sequence
<220> FEATURE:
<223> OTHER INFORMATION: NKX3.111-234 amino acid sequence

<400> SEQUENCE: 25

```
Glu Ala Lys Ala Glu Gly Ala Ala Pro Pro Thr Pro Ser Lys Pro Leu
 1               5                  10                  15

Thr Ser Phe Leu Ile Gln Asp Ile Leu Arg Asp Gly Ala Gln Arg Gln
             20                  25                  30

Gly Gly Arg Thr Ser Ser Gln Arg Gln Arg Asp Pro Glu Pro Glu Pro
         35                  40                  45

Glu Pro Glu Pro Glu Gly Gly Arg Ser Arg Ala Gly Ala Gln Asn Asp
     50                  55                  60

Gln Leu Ser Thr Gly Pro Arg Ala Ala Pro Glu Glu Ala Glu Thr Leu
 65                  70                  75                  80

Ala Glu Thr Glu Pro Glu Arg His Leu Gly Ser Tyr Leu Leu Asp Ser
                 85                  90                  95

Glu Asn Thr Ser Gly Ala Leu Pro Arg Leu Pro Gln Thr Pro Lys Gln
            100                 105                 110

Pro Gln Lys Arg Ser Arg Ala Ala Phe Ser His Thr Gln Val Ile Glu
        115                 120                 125

Leu Glu Arg Lys Phe Ser His Gln Lys Tyr Leu Ser Ala Pro Glu Arg
    130                 135                 140

Ala His Leu Ala Lys Asn Leu Lys Leu Thr Glu Thr Gln Val Lys Ile
145                 150                 155                 160

Trp Phe Gln Asn Arg Arg Tyr Lys Thr Lys Arg Lys Gln Leu Ser Ser
                165                 170                 175

Glu Leu Gly Asp Leu Glu Lys His Ser Ser Leu Pro Ala Leu Lys Glu
            180                 185                 190

Glu Ala Phe Ser Arg Ala Ser Leu Val Ser Val Tyr Asn Ser Tyr Pro
        195                 200                 205

Tyr Tyr Pro Tyr Leu Tyr Cys Val Gly Ser Trp Ser Pro Ala Phe Trp
    210                 215                 220
```

<210> SEQ ID NO 26
<211> LENGTH: 2258
<212> TYPE: DNA
<213> ORGANISM: Artificial Sequence
<220> FEATURE:
<223> OTHER INFORMATION: actA-ActAN100*-NKX3.1-PAP33-386 nucleotide
      sequence

<400> SEQUENCE: 26

```
gggaagcagt tggggttaac tgattaacaa atgttagaga aaaattaatt ctccaagtga     60
tattcttaaa ataattcatg aatatttttt cttatattag ctaattaaga agataattaa    120
ctgctaatcc aattttttaac ggaataaatt agtgaaaatg aaggccgaat tttccttgtt   180
ctaaaaaggt tgtattagcg tatcacgagg agggagtata agtgggatta aatagattta    240
tgcgtgcgat gatggtagtt ttcattactg ccaactgcat tacgattaac ccgacataa    300 tatttgcagc gacagatagc gaagattcca gtctaaacac agatgaatgg gaagaagaat   360
```

```
acgaaactgc acgtgaagta agttcacgtg atattgagga actagaaaaa tcgaataaag      420
tgaaaaatac gaacaaagca gaccaagata ataaacgtaa agcaaaagca gagaaaggtg      480
gatccatgtt aagagtgcct gaaccaagac caggagaagc aaaagctgaa ggcgcagcgc      540
caccgactcc tagtaaacca ctaacaagtt tcttaatcca agatattctt cgtgacggtg      600
cacaaagaca aggcggacga acttcttcac aacgtcaacg agatcctgag ccagaaccgg      660
agcctgaacc ggaaggggga cgctcccgag ctggagcaca aaacgatcag ttatctactg      720
gtccaagagc tgcccctgaa gaagcagaga cactagccga acggaaccag aaagacatt       780
tgggttcata cttacttgac tcagaaaaca caagcgggc tttaccgaga ttaccacaaa       840
caccaaaaca gcctcaaaaa cgtagtcgtg ctgcattttc gcacacgcaa gtcatagagt      900
tagaacgcaa attcagccat caaaagtatt tgtccgcacc agaacgtgct catcttgcga      960
agaatttgaa acttacagaa acccaagtaa agatttggtt tcaaaatcgc cgctataaga     1020
cgaaacgtaa acaactttct tctgaactag gtgatttaga aaaacattca agccttccgg     1080
cgttaaagga agaagcattt agtcgtgcga gcttagtttc tgtttacaat agttatccat     1140
actatccata tctatactgt gtaggctcgt ggtcgccagc tttttggact aggaaagaac     1200
taaagtttgt aacgttagtc tttagacatg gtgatcgtag tcctattgat accttttccta    1260
cagatccaat caaagagagt agttggccac aaggcttcgg acaacttaca caattaggaa     1320
tggaacaaca ttatgaatta ggtgaataca ttcgcaaacg ttatcgcaaa ttccttaatg     1380
aatcgtacaa acacgaacaa gtgtatatcc gttccactga cgttgataga acactaatgt     1440
cagctatgac aaatctagct gcattagtgc caccagaagg cgttagcatt tggaatccta     1500
tcttactttg gcagccaata cctgtacata cggttccgtt atctgaagat caattacttt     1560
atcttccatt tcgcaactgc ccacgattcc aagaattaga atccgaaaca ttgaaaagcg     1620
aagaatttca gaaagatta catccataca aagactttat cgcaacctta ggcaaattgt      1680
cagggttaca cggacaggat ctatttggaa tttggtcgaa agtttatgat cctttgtact     1740
gtgaatctgt acataacttt acattaccta gtcgcgccac ggaagatact atgacgaaac     1800
tacgtgaact ttccgaactt tctttactat cgttgtatgg tattcataaa caaaagaaa      1860
agagcagatt gcaaggtggt gttttagtaa atgaaatctt aaaccatatg aaaagagcta     1920
cacaaattcc gtcttacaag aaattgatta tgtatagtgc tcatgatacg acagtatctg     1980
ggcttcaaat ggcgttagat gtctataacg gcttacttcc accgtatgcg tcatgtcacc     2040
ttacggaact ttactttgag aaaggtgagt actttgttga gatgtactat cgcaatgaaa     2100
cccaacatga accatatccg ttgatgttac caggttgtag tccatcttgc ccgttagaac     2160
gatttgcgga attagtgggt ccagtgatac cacaagactg gtctactgag tgtatgacta     2220
ctaatagcca ccaagggact gaagattcaa cagattaa                             2258
```

<210> SEQ ID NO 27
<211> LENGTH: 678
<212> TYPE: PRT
<213> ORGANISM: Artificial Sequence
<220> FEATURE:
<223> OTHER INFORMATION: ActAN100*-NKX3.1-PAP33-386 amino acid sequence

<400> SEQUENCE: 27

Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp

-continued

```
                20                  25                  30
Ser Glu Asp Ser Ser Leu Asn Thr Asp Glu Trp Glu Glu Tyr Glu
                35                  40                  45

Thr Ala Arg Glu Val Ser Ser Arg Asp Ile Glu Glu Leu Glu Lys Ser
        50                  55                  60

Asn Lys Val Lys Asn Thr Asn Lys Ala Asp Gln Asp Asn Lys Arg Lys
 65                  70                  75                  80

Ala Lys Ala Glu Lys Gly Gly Ser Met Leu Arg Val Pro Glu Pro Arg
                85                  90                  95

Pro Gly Glu Ala Lys Ala Glu Gly Ala Ala Pro Thr Pro Ser Lys
            100                 105                 110

Pro Leu Thr Ser Phe Leu Ile Gln Asp Ile Leu Arg Asp Gly Ala Gln
            115                 120                 125

Arg Gln Gly Gly Arg Thr Ser Ser Gln Arg Gln Arg Asp Pro Glu Pro
            130                 135                 140

Glu Pro Glu Pro Glu Pro Glu Gly Gly Arg Ser Arg Ala Gly Ala Gln
145                 150                 155                 160

Asn Asp Gln Leu Ser Thr Gly Pro Arg Ala Ala Pro Glu Glu Ala Glu
                165                 170                 175

Thr Leu Ala Glu Thr Glu Pro Glu Arg His Leu Gly Ser Tyr Leu Leu
            180                 185                 190

Asp Ser Glu Asn Thr Ser Gly Ala Leu Pro Arg Leu Pro Gln Thr Pro
            195                 200                 205

Lys Gln Pro Gln Lys Arg Ser Arg Ala Ala Phe Ser His Thr Gln Val
            210                 215                 220

Ile Glu Leu Glu Arg Lys Phe Ser His Gln Lys Tyr Leu Ser Ala Pro
225                 230                 235                 240

Glu Arg Ala His Leu Ala Lys Asn Leu Lys Leu Thr Glu Thr Gln Val
                245                 250                 255

Lys Ile Trp Phe Gln Asn Arg Arg Tyr Lys Thr Lys Arg Lys Gln Leu
            260                 265                 270

Ser Ser Glu Leu Gly Asp Leu Glu Lys His Ser Ser Leu Pro Ala Leu
            275                 280                 285

Lys Glu Glu Ala Phe Ser Arg Ala Ser Leu Val Ser Val Tyr Asn Ser
            290                 295                 300

Tyr Pro Tyr Tyr Pro Tyr Leu Tyr Cys Val Gly Ser Trp Ser Pro Ala
305                 310                 315                 320

Phe Trp Thr Arg Lys Glu Leu Lys Phe Val Thr Leu Val Phe Arg His
                325                 330                 335

Gly Asp Arg Ser Pro Ile Asp Thr Phe Pro Thr Asp Pro Ile Lys Glu
            340                 345                 350

Ser Ser Trp Pro Gln Gly Phe Gly Gln Leu Thr Gln Leu Gly Met Glu
            355                 360                 365

Gln His Tyr Glu Leu Gly Glu Tyr Ile Arg Lys Arg Tyr Arg Lys Phe
            370                 375                 380

Leu Asn Glu Ser Tyr Lys His Glu Gln Val Tyr Ile Arg Ser Thr Asp
385                 390                 395                 400

Val Asp Arg Thr Leu Met Ser Ala Met Thr Asn Leu Ala Ala Leu Val
                405                 410                 415

Pro Pro Glu Gly Val Ser Ile Trp Asn Pro Ile Leu Leu Trp Gln Pro
            420                 425                 430

Ile Pro Val His Thr Val Pro Leu Ser Glu Asp Gln Leu Leu Tyr Leu
            435                 440                 445
```

```
Pro Phe Arg Asn Cys Pro Arg Phe Gln Glu Leu Glu Ser Glu Thr Leu
    450                 455                 460

Lys Ser Glu Glu Phe Gln Lys Arg Leu His Pro Tyr Lys Asp Phe Ile
465                 470                 475                 480

Ala Thr Leu Gly Lys Leu Ser Gly Leu His Gly Gln Asp Leu Phe Gly
                485                 490                 495

Ile Trp Ser Lys Val Tyr Asp Pro Leu Tyr Cys Glu Ser Val His Asn
                500                 505                 510

Phe Thr Leu Pro Ser Arg Ala Thr Glu Asp Thr Met Thr Lys Leu Arg
            515                 520                 525

Glu Leu Ser Glu Leu Ser Leu Leu Ser Leu Tyr Gly Ile His Lys Gln
            530                 535                 540

Lys Glu Lys Ser Arg Leu Gln Gly Gly Val Leu Val Asn Glu Ile Leu
545                 550                 555                 560

Asn His Met Lys Arg Ala Thr Gln Ile Pro Ser Tyr Lys Lys Leu Ile
                565                 570                 575

Met Tyr Ser Ala His Asp Thr Thr Val Ser Gly Leu Gln Met Ala Leu
                580                 585                 590

Asp Val Tyr Asn Gly Leu Leu Pro Pro Tyr Ala Ser Cys His Leu Thr
                595                 600                 605

Glu Leu Tyr Phe Glu Lys Gly Glu Tyr Phe Val Glu Met Tyr Tyr Arg
            610                 615                 620

Asn Glu Thr Gln His Glu Pro Tyr Pro Leu Met Leu Pro Gly Cys Ser
625                 630                 635                 640

Pro Ser Cys Pro Leu Glu Arg Phe Ala Glu Leu Val Gly Pro Val Ile
                645                 650                 655

Pro Gln Asp Trp Ser Thr Glu Cys Met Thr Thr Asn Ser His Gln Gly
                660                 665                 670

Thr Glu Asp Ser Thr Asp
        675

<210> SEQ ID NO 28
<211> LENGTH: 702
<212> TYPE: DNA
<213> ORGANISM: Artificial Sequence
<220> FEATURE:
<223> OTHER INFORMATION: NKX3.1 nucleotide sequence

<400> SEQUENCE: 28
atgttaagag tgcctgaacc aagaccagga gaagcaaaag ctgaaggcgc agcgccaccg      60
actcctagta aaccactaac aagtttctta atccaagata ttcttcgtga cggtgcacaa     120
agacaaggcg gacgaacttc ttcacaacgt caacgagatc ctgagccaga accggagcct     180
gaaccggaag ggggacgctc ccgagctgga gcacaaaacg atcagttatc tactggtcca     240
agagctgccc ctgaagaagc agagacacta gccgaaacgg aaccagaaag acatttgggt     300
tcatacttac ttgactcaga aaacacaagc ggggctttac cgagattacc acaaacacca     360
aaacagcctc aaaaacgtag tcgtgctgca ttttcgcaca cgcaagtcat agagttagaa     420
cgcaaattca gccatcaaaa gtatttgtcc gcaccgaaac gtgctcatct tgcgaagaat     480
ttgaaactta cagaaaccca agtaaagatt tggtttcaaa atcgccgcta taagacgaaa     540
cgtaaacaac tttcttctga actaggtgat ttagaaaaac attcaagcct tccggcgtta     600
aaggaagaag catttagtcg tgcgagctta gtttctgttt acaatagtta tccatactat     660
ccatatctat actgtgtagg ctcgtggtcg ccagcttttt gg                        702
```

<210> SEQ ID NO 29
<211> LENGTH: 234
<212> TYPE: PRT
<213> ORGANISM: Homo sapiens

<400> SEQUENCE: 29

Met Leu Arg Val Pro Glu Pro Arg Pro Gly Glu Ala Lys Ala Glu Gly
1               5                   10                  15

Ala Ala Pro Thr Pro Ser Lys Pro Leu Thr Ser Phe Leu Ile Gln
            20                  25                  30

Asp Ile Leu Arg Asp Gly Ala Gln Arg Gln Gly Gly Arg Thr Ser Ser
            35                  40                  45

Gln Arg Gln Arg Asp Pro Glu Pro Glu Pro Glu Pro Glu Pro Glu Gly
        50                  55                  60

Gly Arg Ser Arg Ala Gly Ala Gln Asn Asp Gln Leu Ser Thr Gly Pro
65                  70                  75                  80

Arg Ala Ala Pro Glu Glu Ala Glu Thr Leu Ala Glu Thr Glu Pro Glu
                85                  90                  95

Arg His Leu Gly Ser Tyr Leu Leu Asp Ser Glu Asn Thr Ser Gly Ala
            100                 105                 110

Leu Pro Arg Leu Pro Gln Thr Pro Lys Gln Pro Gln Lys Arg Ser Arg
            115                 120                 125

Ala Ala Phe Ser His Thr Gln Val Ile Glu Leu Glu Arg Lys Phe Ser
        130                 135                 140

His Gln Lys Tyr Leu Ser Ala Pro Glu Arg Ala His Leu Ala Lys Asn
145                 150                 155                 160

Leu Lys Leu Thr Glu Thr Gln Val Lys Ile Trp Phe Gln Asn Arg Arg
                165                 170                 175

Tyr Lys Thr Lys Arg Lys Gln Leu Ser Ser Glu Leu Gly Asp Leu Glu
            180                 185                 190

Lys His Ser Ser Leu Pro Ala Leu Lys Glu Glu Ala Phe Ser Arg Ala
        195                 200                 205

Ser Leu Val Ser Val Tyr Asn Ser Tyr Pro Tyr Tyr Pro Tyr Leu Tyr
    210                 215                 220

Cys Val Gly Ser Trp Ser Pro Ala Phe Trp
225                 230

<210> SEQ ID NO 30
<211> LENGTH: 1154
<212> TYPE: DNA
<213> ORGANISM: Artificial Sequence
<220> FEATURE:
<223> OTHER INFORMATION: actA promoter-ActAN100*-SSX2 nucleotide
      sequence

<400> SEQUENCE: 30
gggaagcagt tggggttaac tgattaacaa atgttagaga aaaattaatt ctccaagtga        60
tattcttaaa ataattcatg aatatttttt cttatattag ctaattaaga agataattaa       120
ctgctaatcc aattttttaac ggaataaatt agtgaaaatg aaggccgaat tttccttgtt      180
ctaaaaaggt tgtattagcg tatcacgagg agggagtata agtgggatta aatagattta      240
tgcgtgcgat gatggtagtt ttcattactg ccaactgcat tacgattaac cccgacataa      300
tatttgcagc gacagatagc gaagattcca gtctaaacac agatgaatgg gaagaagaat      360
acgaaactgc acgtgaagta agttcacgtg atattgagga actagaaaaa tcgaataaag      420

```
tgaaaaatac gaacaaagca gaccaagata ataaacgtaa agcaaaagca gagaaaggtg      480
gatccaatgg tgatgacgct ttcgcacgcc gtcctaccgt aggagcacaa attccagaaa      540
agattcaaaa agcatttgat gacatcgcta aatactttc taaagaagaa tgggagaaaa       600
tgaaagcgag cgagaaaatc ttttatgtct atatgaaacg gaaatatgaa gcaatgacaa      660
aattgggttt caaagcaaca ttaccaccat ttatgtgcaa taaacgtgcg gaagattttc      720
aagggaatga tttagacaat gatcctaatc gaggcaacca agtggaaaga ccgcaaatga      780
ctttcggacg tttacaaggg atttctccaa agataatgcc gaaaaagcca gccgaagaag      840
gtaatgatag tgaagaagta cctgaagcga gtggtccaca aaatgatggt aaagaacttt      900
gtcctccagg caaaccgaca acgtctgaga agattcatga acggtccggt aaccgtgaag      960
ctcaagagaa agaagaacga cgtggaactg ctcacagatg gagttcacag aatacacata     1020
acattggccg ctttagccta tcaacaagca tgggggctgt tcatggaact ccaaaaacga     1080
tcacgcataa cagagatcca aaaggcggaa acatgccggg tccaacagat tgtgttagag     1140
aaaattcgtg gtaa                                                        1154
```

<210> SEQ ID NO 31
<211> LENGTH: 310
<212> TYPE: PRT
<213> ORGANISM: Artificial Sequence
<220> FEATURE:
<223> OTHER INFORMATION: ActAN100*-SSX2 amino acid sequence

<400> SEQUENCE: 31

```
Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Tyr Glu
            35                  40                  45

Thr Ala Arg Glu Val Ser Ser Arg Asp Ile Glu Glu Leu Glu Lys Ser
        50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser Asn Gly Asp Asp Ala Phe Ala Arg
                85                  90                  95

Arg Pro Thr Val Gly Ala Gln Ile Pro Glu Lys Ile Gln Lys Ala Phe
            100                 105                 110

Asp Asp Ile Ala Lys Tyr Phe Ser Lys Glu Glu Trp Glu Lys Met Lys
        115                 120                 125

Ala Ser Glu Lys Ile Phe Tyr Val Tyr Met Lys Arg Lys Tyr Glu Ala
    130                 135                 140

Met Thr Lys Leu Gly Phe Lys Ala Thr Leu Pro Pro Phe Met Cys Asn
145                 150                 155                 160

Lys Arg Ala Glu Asp Phe Gln Gly Asn Asp Leu Asp Asn Asp Pro Asn
                165                 170                 175

Arg Gly Asn Gln Val Glu Arg Pro Gln Met Thr Phe Gly Arg Leu Gln
            180                 185                 190

Gly Ile Ser Pro Lys Ile Met Pro Lys Lys Pro Ala Glu Glu Gly Asn
        195                 200                 205

Asp Ser Glu Glu Val Pro Glu Ala Ser Gly Pro Gln Asn Asp Gly Lys
    210                 215                 220

Glu Leu Cys Pro Pro Gly Lys Pro Thr Thr Ser Glu Lys Ile His Glu
```

```
                225                 230                 235                 240
Arg Ser Gly Asn Arg Glu Ala Gln Glu Lys Glu Glu Arg Arg Gly Thr
                245                 250                 255

Ala His Arg Trp Ser Ser Gln Asn Thr His Asn Ile Gly Arg Phe Ser
                260                 265                 270

Leu Ser Thr Ser Met Gly Ala Val His Gly Thr Pro Lys Thr Ile Thr
                275                 280                 285

His Asn Arg Asp Pro Lys Gly Gly Asn Met Pro Gly Pro Thr Asp Cys
                290                 295                 300

Val Arg Glu Asn Ser Trp
305                 310

<210> SEQ ID NO 32
<211> LENGTH: 1697
<212> TYPE: DNA
<213> ORGANISM: Artificial Sequence
<220> FEATURE:
<223> OTHER INFORMATION: actAp-ActAN100-PAP30-386-SL8 nucleotide
      sequence

<400> SEQUENCE: 32
gggaagcagt tggggttaac tgattaacaa atgttagaga aaaattaatt ctccaagtga      60
tattcttaaa ataattcatg aatattttt cttatattag ctaattaaga agataattaa     120
ctgctaatcc aattttaac ggaataaatt agtgaaaatg aaggccgaat tttccttgtt     180
ctaaaaaggt tgtattagcg tatcacgagg agggagtata agtgggatta aatagattta     240
tgcgtgcgat gatggtagtt ttcattactg ccaactgcat tacgattaac cccgacataa     300
tatttgcagc gacagatagc gaagattcca gtctaaacac agatgaatgg gaagaagaaa     360
aaacagaaga gcagccaagc gaggtaaata cgggaccaag atacgaaact gcacgtgaag     420
taagttcacg tgatattgag gaactagaaa aatcgaataa agtgaaaaat acgaacaaag     480
cagacctaat agcaatgttg aaagcaaaag cagagaaagg tggatccgta ttggcaaaag     540
aactaaagtt tgtaacgtta gtctttagac atggtgatcg tagtcctatt gataccttc     600 ctacagatcc aatcaaagag agtagttggc acaaggcttt cggacaactt acacaattag     660
gaatggaaca acattatgaa ttaggtgaat acattcgcaa acgttatcgc aaattcctta     720
atgaatcgta caaacacgaa caagtgtata tccgttccac tgacgttgat agaacactaa     780
tgtcagctat gacaaatcta gctgcattag tgccaccaga aggcgttagc atttggaatc     840
ctatcttact ttggcagcca atacctgtac atacggttcc gttatctgaa gatcaattac     900
tttatcttcc atttcgcaac tgcccacgat tccaagaatt agaatccgaa acattgaaaa     960
gcgaagaatt tcagaaaaga ttacatccat acaaagactt tatcgcaacc ttaggcaaat    1020
tgtcagggtt acacggacag gatctatttg gaatttggtc gaaagtttat gatcctttgt    1080
actgtgaatc tgtacataac tttacattac ctagtcgcgc cacggaagat actatgacga    1140
aactacgtga acttttccgaa ctttctttac tatcgttgta tggtattcat aaacaaaaag    1200
aaaagagcag attgcaaggt ggtgttttag taaatgaaat cttaaaccat atgaaaagag    1260
ctacacaaat tccgtcttac aagaaattga ttatgtatag tgctcatgat acgacagtat    1320
ctgggcttca aatggcgtta gatgtctata acggcttact tccaccgtat gcgtcatgtc    1380
accttacgga actttacttt gagaaaggtg agtactttgt tgagatgtac tatcgcaatg    1440
aaacccaaca tgaaccatat ccgttgatgt taccaggttg tagtccatct tgcccgttag    1500
aacgatttgc ggaattagtg ggtccagtga taccacaaga ctggtctact gagtgtatga    1560
```

```
ctactaatag ccaccaaggg actgaagatt caacagatac tagtcaattg ggtgacggta    1620
gtattaaact tagcaaagta ttacaattag aaagtattat taattttgaa aaattagctg    1680
atggttcagt taaataa                                                  1697
```

<210> SEQ ID NO 33
<211> LENGTH: 491
<212> TYPE: PRT
<213> ORGANISM: Artificial Sequence
<220> FEATURE:
<223> OTHER INFORMATION: ActAN100-PAP30-386-SL8 amino acid sequence

<400> SEQUENCE: 33

```
Met Gly Leu Asn Arg Phe Met Arg Ala Met Met Val Val Phe Ile Thr
  1               5                  10                  15

Ala Asn Cys Ile Thr Ile Asn Pro Asp Ile Ile Phe Ala Ala Thr Asp
                 20                  25                  30

Ser Glu Asp Ser Ser Leu Asn Thr Asp Glu Trp Glu Glu Glu Lys Thr
             35                  40                  45

Glu Glu Gln Pro Ser Glu Val Asn Thr Gly Pro Arg Tyr Glu Thr Ala
         50                  55                  60

Arg Glu Val Ser Ser Arg Asp Ile Glu Glu Leu Glu Lys Ser Asn Lys
 65                  70                  75                  80

Val Lys Asn Thr Asn Lys Ala Asp Leu Ile Ala Met Leu Lys Ala Lys
                 85                  90                  95

Ala Glu Lys Gly Gly Ser Val Leu Ala Lys Glu Leu Lys Phe Val Thr
            100                 105                 110

Leu Val Phe Arg His Gly Asp Arg Ser Pro Ile Asp Thr Phe Pro Thr
        115                 120                 125

Asp Pro Ile Lys Glu Ser Ser Trp Pro Gln Gly Phe Gly Gln Leu Thr
    130                 135                 140

Gln Leu Gly Met Glu Gln His Tyr Glu Leu Gly Glu Tyr Ile Arg Lys
145                 150                 155                 160

Arg Tyr Arg Lys Phe Leu Asn Glu Ser Tyr Lys His Glu Gln Val Tyr
                165                 170                 175

Ile Arg Ser Thr Asp Val Asp Arg Thr Leu Met Ser Ala Met Thr Asn
            180                 185                 190

Leu Ala Ala Leu Val Pro Pro Glu Gly Val Ser Ile Trp Asn Pro Ile
        195                 200                 205

Leu Leu Trp Gln Pro Ile Pro Val His Thr Val Pro Leu Ser Glu Asp
    210                 215                 220

Gln Leu Leu Tyr Leu Pro Phe Arg Asn Cys Pro Arg Phe Gln Glu Leu
225                 230                 235                 240

Glu Ser Glu Thr Leu Lys Ser Glu Glu Phe Gln Lys Arg Leu His Pro
                245                 250                 255

Tyr Lys Asp Phe Ile Ala Thr Leu Gly Lys Leu Ser Gly Leu His Gly
            260                 265                 270

Gln Asp Leu Phe Gly Ile Trp Ser Lys Val Tyr Asp Pro Leu Tyr Cys
        275                 280                 285

Glu Ser Val His Asn Phe Thr Leu Pro Ser Arg Ala Thr Glu Asp Thr
    290                 295                 300

Met Thr Lys Leu Arg Glu Leu Ser Glu Leu Ser Leu Leu Ser Leu Tyr
305                 310                 315                 320

Gly Ile His Lys Gln Lys Glu Lys Ser Arg Leu Gln Gly Gly Val Leu
                325                 330                 335
```

```
Val Asn Glu Ile Leu Asn His Met Lys Arg Ala Thr Gln Ile Pro Ser
                340                 345                 350

Tyr Lys Lys Leu Ile Met Tyr Ser Ala His Asp Thr Thr Val Ser Gly
            355                 360                 365

Leu Gln Met Ala Leu Asp Val Tyr Asn Gly Leu Leu Pro Pro Tyr Ala
        370                 375                 380

Ser Cys His Leu Thr Glu Leu Tyr Phe Glu Lys Gly Glu Tyr Phe Val
385                 390                 395                 400

Glu Met Tyr Tyr Arg Asn Glu Thr Gln His Glu Pro Tyr Pro Leu Met
                405                 410                 415

Leu Pro Gly Cys Ser Pro Ser Cys Pro Leu Glu Arg Phe Ala Glu Leu
            420                 425                 430

Val Gly Pro Val Ile Pro Gln Asp Trp Ser Thr Glu Cys Met Thr Thr
        435                 440                 445

Asn Ser His Gln Gly Thr Glu Asp Ser Thr Asp Thr Ser Gln Leu Gly
    450                 455                 460

Asp Gly Ser Ile Lys Leu Ser Lys Val Leu Gln Leu Glu Ser Ile Ile
465                 470                 475                 480

Asn Phe Glu Lys Leu Ala Asp Gly Ser Val Lys
                485                 490

<210> SEQ ID NO 34
<211> LENGTH: 1652
<212> TYPE: DNA
<213> ORGANISM: Artificial Sequence
<220> FEATURE:
<223> OTHER INFORMATION: actAp-ActAN100*-EGFRvIIIx1-PAP33-386 nucleotide
      sequence

<400> SEQUENCE: 34
gggaagcagt tggggttaac tgattaacaa atgttagaga aaaattaatt ctccaagtga      60
tattcttaaa ataattcatg aatattttt cttatattag ctaattaaga agataattaa     120
ctgctaatcc aattttaac ggaataaatt agtgaaaatg aaggccgaat tttccttgtt     180
ctaaaaaggt tgtattagcg tatcacgagg agggagtata agtgggatta aatagattta     240
tgcgtgcgat gatggtagtt ttcattactg ccaactgcat tacgattaac cccgacataa     300
tatttgcagc gacagatagc gaagattcca gtctaaacac agatgaatgg gaagaagaat     360
acgaaactgc acgtgaagta agttcacgtg atattgagga actagaaaaa tcgaataaag     420
tgaaaaatac gaacaaagca gaccaagata taaacgtaaa agcaaaagca gagaaaggtg     480
gatctgcaag caaagtattg ccagctagtc gtgcattaga ggagaaaaag gggaattacg     540
tggtgacgga tcatggatcg tgtgccgatg gctcagtaaa gggatccaaa gaactaaagt     600
ttgtaacgtt agtctttaga catggtgatc gtagtcctat tgatacccttt cctacagatc     660 caatcaaaga gagtagttgg ccacaaggct tcggacaact tacacaatta ggaatggaac     720
aacattatga attaggtgaa tacattcgca acgttatcg caaattcctt aatgaatcgt     780
acaaacacga acaagtgtat atccgttcca ctgacgttga tagaacacta atgtcagcta     840
tgacaaatct agctgcatta gtgccaccag aaggcgttag catttggaat cctatcttac     900
tttggcagcc aatacctgta catacggttc cgttatctga agatcaatta ctttatcttc     960
catttcgcaa ctgcccacga ttccaagaat tagaatccga aacattgaaa agcgaagaat    1020
ttcagaaaag attacatcca tacaaagact ttatcgcaac cttaggcaaa ttgtcagggt    1080
tacacggaca ggatctattt ggaatttggt cgaaagttta tgatcctttg tactgtgaat    1140
```

-continued

```
ctgtacataa ctttacatta cctagtcgcg ccacggaaga tactatgacg aaactacgtg    1200
aactttccga actttcttta ctatcgttgt atggtattca taaacaaaaa gaaaagagca    1260
gattgcaagg tggtgtttta gtaaatgaaa tcttaaacca tatgaaaaga gctacacaaa    1320
ttccgtctta caagaaattg attatgtata gtgctcatga tacgcacagta tctgggcttc    1380 aaatggcgtt agatgtctat aacggcttac ttccaccgta tgcgtcatgt caccttacgg    1440
aactttactt tgagaaaggt gagtactttg ttgagatgga ctatcgcaat gaaacccaac    1500
atgaaccata tccgttgatg ttaccaggtt gtagtccatc ttgcccgtta gaacgatttg    1560
cggaattagt gggtccagtg ataccacaag actggtctac tgagtgtatg actactaata    1620
gccaccaagg gactgaagat tcaacagatt aa                                  1652
```

<210> SEQ ID NO 35
<211> LENGTH: 476
<212> TYPE: PRT
<213> ORGANISM: Artificial Sequence
<220> FEATURE:
<223> OTHER INFORMATION: ActAN100*-EGFRvIIIx1-PAP33-386 amino acid
      sequence

<400> SEQUENCE: 35

```
Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Tyr Glu
             35                  40                  45

Thr Ala Arg Glu Val Ser Ser Arg Asp Ile Glu Glu Leu Glu Lys Ser
     50                  55                  60

Asn Lys Val Lys Asn Thr Asn Lys Ala Asp Gln Asp Asn Lys Arg Lys
 65                  70                  75                  80

Ala Lys Ala Glu Lys Gly Gly Ser Ala Ser Lys Val Leu Pro Ala Ser
                 85                  90                  95

Arg Ala Leu Glu Glu Lys Lys Gly Asn Tyr Val Val Thr Asp His Gly
            100                 105                 110

Ser Cys Ala Asp Gly Ser Val Lys Gly Ser Lys Glu Leu Lys Phe Val
        115                 120                 125

Thr Leu Val Phe Arg His Gly Asp Arg Ser Pro Ile Asp Thr Phe Pro
    130                 135                 140

Thr Asp Pro Ile Lys Glu Ser Ser Trp Pro Gln Gly Phe Gly Gln Leu
145                 150                 155                 160

Thr Gln Leu Gly Met Glu Gln His Tyr Glu Leu Gly Glu Tyr Ile Arg
                165                 170                 175

Lys Arg Tyr Arg Lys Phe Leu Asn Glu Ser Tyr Lys His Glu Gln Val
            180                 185                 190

Tyr Ile Arg Ser Thr Asp Val Asp Arg Thr Leu Met Ser Ala Met Thr
        195                 200                 205

Asn Leu Ala Ala Leu Val Pro Pro Glu Gly Val Ser Ile Trp Asn Pro
    210                 215                 220

Ile Leu Leu Trp Gln Pro Ile Pro Val His Thr Val Pro Leu Ser Glu
225                 230                 235                 240

Asp Gln Leu Leu Tyr Leu Pro Phe Arg Asn Cys Pro Arg Phe Gln Glu
                245                 250                 255

Leu Glu Ser Glu Thr Leu Lys Ser Glu Glu Phe Gln Lys Arg Leu His
```

```
            260                 265                 270
Pro Tyr Lys Asp Phe Ile Ala Thr Leu Gly Lys Leu Ser Gly Leu His
            275                 280                 285

Gly Gln Asp Leu Phe Gly Ile Trp Ser Lys Val Tyr Asp Pro Leu Tyr
            290                 295                 300

Cys Glu Ser Val His Asn Phe Thr Leu Pro Ser Arg Ala Thr Glu Asp
305                 310                 315                 320

Thr Met Thr Lys Leu Arg Glu Leu Ser Glu Leu Ser Leu Leu Ser Leu
                325                 330                 335

Tyr Gly Ile His Lys Gln Lys Glu Lys Ser Arg Leu Gln Gly Gly Val
            340                 345                 350

Leu Val Asn Glu Ile Leu Asn His Met Lys Arg Ala Thr Gln Ile Pro
            355                 360                 365

Ser Tyr Lys Lys Leu Ile Met Tyr Ser Ala His Asp Thr Thr Val Ser
            370                 375                 380

Gly Leu Gln Met Ala Leu Asp Val Tyr Asn Gly Leu Leu Pro Pro Tyr
385                 390                 395                 400

Ala Ser Cys His Leu Thr Glu Leu Tyr Phe Glu Lys Gly Glu Tyr Phe
                405                 410                 415

Val Glu Met Tyr Tyr Arg Asn Glu Thr Gln His Glu Pro Tyr Pro Leu
            420                 425                 430

Met Leu Pro Gly Cys Ser Pro Ser Cys Pro Leu Glu Arg Phe Ala Glu
            435                 440                 445

Leu Val Gly Pro Val Ile Pro Gln Asp Trp Ser Thr Glu Cys Met Thr
            450                 455                 460

Thr Asn Ser His Gln Gly Thr Glu Asp Ser Thr Asp
465                 470                 475

<210> SEQ ID NO 36
<211> LENGTH: 1751
<212> TYPE: DNA
<213> ORGANISM: Artificial Sequence
<220> FEATURE:
<223> OTHER INFORMATION: actAp-ActAN100*-EGFRvIIIx2-PAP33-386 nucleotide
      sequence

<400> SEQUENCE: 36
gggaagcagt tggggttaac tgattaacaa atgttagaga aaaattaatt ctccaagtga    60
tattcttaaa ataattcatg aatatttttt cttatattag ctaattaaga agataattaa   120
ctgctaatcc aattttttaac ggaataaatt agtgaaaatg aaggccgaat tttccttgtt   180
ctaaaaaggt tgtattagcg tatcacgagg agggagtata agtgggatta aatagattta   240
tgcgtgcgat gatggtagtt ttcattactg ccaactgcat tacgattaac cccgacataa   300
tatttgcagc gacagatagc gaagattcca gtctaaacac agatgaatgg gaagaagaat   360
acgaaactgc acgtgaagta agttcacgtg atattgagga actagaaaaa tcgaataaag   420
tgaaaaatac gaacaaagca gaccaagata ataaacgtaa agcaaaagca gagaaaggtg   480
gatctgcaag caaagtattg ccagctagtc gtgcattaga ggagaaaaag gggaattacg   540
tggtgacgga tcatggatcg tgtgccgatg gctcagtaaa gactagcgcg agcaaagtgg   600 ccctgcatc acgagcactt gaagagaaaa aaggaaacta tgttgtgacc gatcatggta   660
gctgcggaga tggttcaaaa ggatccaaag aactaaagtt tgtaacgtta gtctttagac   720
atggtgatcg tagtcctatt gatacctttc ctacagatcc aatcaaagag agtagttggc   780
cacaaggctt cggacaactt acacaattag gaatggaaca acattatgaa ttaggtgaat   840
```

```
acattcgcaa acgttatcgc aaattcctta atgaatcgta caaacacgaa caagtgtata    900
tccgttccac tgacgttgat agaacactaa tgtcagctat gacaaatcta gctgcattag    960
tgccaccaga aggcgttagc atttggaatc ctatcttact ttggcagcca atacctgtac   1020
atacggttcc gttatctgaa gatcaattac tttatcttcc atttcgcaac tgcccacgat   1080
tccaagaatt agaatccgaa acattgaaaa gcgaagaatt tcagaaaaga ttacatccat   1140
acaaagactt tatcgcaacc ttaggcaaat tgtcagggtt acacggacag gatctatttg   1200
gaatttggtc gaaagtttat gatcctttgt actgtgaatc tgtacataac tttacattac   1260
ctagtcgcgc cacggaagat actatgacga aactacgtga actttccgaa ctttctttac   1320
tatcgttgta tggtattcat aaacaaaaag aaaagagcag attgcaaggt ggtgttttag   1380
taaatgaaat cttaaaccat atgaaaagag ctacacaaat tccgtcttac aagaaattga   1440
ttatgtatag tgctcatgat acgacagtat ctgggcttca aatggcgtta gatgtctata   1500
acggcttact tccaccgtat gcgtcatgtc accttacgga actttacttt gagaaaggtg   1560
agtactttgt tgagatgtac tatcgcaatg aaacccaaca tgaaccatat ccgttgatgt   1620
taccaggttg tagtccatct tgcccgttag aacgatttgc ggaattagtg ggtccagtga   1680
taccacaaga ctggtctact gagtgtatga ctactaatag ccaccaaggg actgaagatt   1740
caacagatta a                                                       1751

<210> SEQ ID NO 37
<211> LENGTH: 509
<212> TYPE: PRT
<213> ORGANISM: Artificial Sequence
<220> FEATURE:
<223> OTHER INFORMATION: ActAN100*-EGFRvIIIx2-PAP33-386 amino acid
      sequence

<400> SEQUENCE: 37

Met Gly Leu Asn Arg Phe Met Arg Ala Met Met Val Val Phe Ile Thr
  1               5                  10                  15

Ala Asn Cys Ile Thr Ile Asn Pro Asp Ile Ile Phe Ala Ala Thr Asp
                 20                  25                  30

Ser Glu Asp Ser Ser Leu Asn Thr Asp Glu Trp Glu Glu Glu Tyr Glu
             35                  40                  45

Thr Ala Arg Glu Val Ser Ser Arg Asp Ile Glu Glu Leu Glu Lys Ser
         50                  55                  60

Asn Lys Val Lys Asn Thr Asn Lys Ala Asp Gln Asp Asn Lys Arg Lys
 65                  70                  75                  80

Ala Lys Ala Glu Lys Gly Gly Ser Ala Ser Lys Val Leu Pro Ala Ser
                 85                  90                  95

Arg Ala Leu Glu Glu Lys Lys Gly Asn Tyr Val Val Thr Asp His Gly
            100                 105                 110

Ser Cys Ala Asp Gly Ser Val Lys Thr Ser Ala Ser Lys Val Ala Pro
            115                 120                 125

Ala Ser Arg Ala Leu Glu Glu Lys Lys Gly Asn Tyr Val Val Thr Asp
        130                 135                 140

His Gly Ser Cys Gly Asp Gly Ser Lys Gly Ser Lys Glu Leu Lys Phe
145                 150                 155                 160

Val Thr Leu Val Phe Arg His Gly Asp Arg Ser Pro Ile Asp Thr Phe
                165                 170                 175

Pro Thr Asp Pro Ile Lys Glu Ser Ser Trp Pro Gln Gly Phe Gly Gln
            180                 185                 190
```

Leu Thr Gln Leu Gly Met Glu Gln His Tyr Glu Leu Gly Glu Tyr Ile
            195                 200                 205

Arg Lys Arg Tyr Arg Lys Phe Leu Asn Glu Ser Tyr Lys His Glu Gln
    210                 215                 220

Val Tyr Ile Arg Ser Thr Asp Val Asp Arg Thr Leu Met Ser Ala Met
225                 230                 235                 240

Thr Asn Leu Ala Ala Leu Val Pro Pro Glu Gly Val Ser Ile Trp Asn
                245                 250                 255

Pro Ile Leu Leu Trp Gln Pro Ile Pro Val His Thr Val Pro Leu Ser
            260                 265                 270

Glu Asp Gln Leu Leu Tyr Leu Pro Phe Arg Asn Cys Pro Arg Phe Gln
        275                 280                 285

Glu Leu Glu Ser Glu Thr Leu Lys Ser Glu Glu Phe Gln Lys Arg Leu
    290                 295                 300

His Pro Tyr Lys Asp Phe Ile Ala Thr Leu Gly Lys Leu Ser Gly Leu
305                 310                 315                 320

His Gly Gln Asp Leu Phe Gly Ile Trp Ser Lys Val Tyr Asp Pro Leu
                325                 330                 335

Tyr Cys Glu Ser Val His Asn Phe Thr Leu Pro Ser Arg Ala Thr Glu
            340                 345                 350

Asp Thr Met Thr Lys Leu Arg Glu Leu Ser Glu Leu Ser Leu Leu Ser
        355                 360                 365

Leu Tyr Gly Ile His Lys Gln Lys Glu Lys Ser Arg Leu Gln Gly Gly
    370                 375                 380

Val Leu Val Asn Glu Ile Leu Asn His Met Lys Arg Ala Thr Gln Ile
385                 390                 395                 400

Pro Ser Tyr Lys Lys Leu Ile Met Tyr Ser Ala His Asp Thr Thr Val
                405                 410                 415

Ser Gly Leu Gln Met Ala Leu Asp Val Tyr Asn Gly Leu Leu Pro Pro
            420                 425                 430

Tyr Ala Ser Cys His Leu Thr Glu Leu Tyr Phe Glu Lys Gly Glu Tyr
        435                 440                 445

Phe Val Glu Met Tyr Tyr Arg Asn Glu Thr Gln His Glu Pro Tyr Pro
    450                 455                 460

Leu Met Leu Pro Gly Cys Ser Pro Ser Cys Pro Leu Glu Arg Phe Ala
465                 470                 475                 480

Glu Leu Val Gly Pro Val Ile Pro Gln Asp Trp Ser Thr Glu Cys Met
                485                 490                 495

Thr Thr Asn Ser His Gln Gly Thr Glu Asp Ser Thr Asp
            500                 505

<210> SEQ ID NO 38
<211> LENGTH: 1847
<212> TYPE: DNA
<213> ORGANISM: Artificial Sequence
<220> FEATURE:
<223> OTHER INFORMATION: actAp-ActAN100*-EGFRvIIIx3-PAP33-386 nucleotide
      sequence

<400> SEQUENCE: 38
gggaagcagt tggggttaac tgattaacaa atgttagaga aaaattaatt ctccaagtga      60
tattcttaaa ataattcatg aatattttt cttatattag ctaattaaga agataattaa     120
ctgctaatcc aatttttaac ggaataaatt agtgaaaatg aaggccgaat ttccttgtt     180 ctaaaaaggt tgtattagcg tatcacgagg agggagtata agtgggatta aatagattta    240

```
tgcgtgcgat gatggtagtt ttcattactg ccaactgcat tacgattaac cccgacataa    300
tatttgcagc gacagatagc gaagattcca gtctaaacac agatgaatgg gaagaagaat    360
acgaaactgc acgtgaagta agttcacgtg atattgagga actagaaaaa tcgaataaag    420
tgaaaaatac gaacaaagca gaccaagata taaacgtaa agcaaaagca gagaaaggtg     480
gatctgcaag caaagtattg ccagctagtc gtgcattaga ggagaaaaag gggaattacg    540
tggtgacgga tcatggatcg tgtgccgatg gctcagtaaa gactagcgcg agcaaagtgg    600
cccctgcatc acgagcactt gaagagaaaa aaggaaacta tgttgtgacc gatcatggta    660
gctgcggaga tggttcaatt aaattatcaa aagtcttacc agcatctaga gctttagagg    720
aaaagaaggg taactatgtc gtaacagatc atggaagttg tgctgacgga agtgttggat    780
ccaaagaact aaagtttgta acgttagtct ttagacatgg tgatcgtagt cctattgata    840
cctttcctac agatccaatc aaagagagta gttggccaca aggcttcgga caacttacac    900
aattaggaat ggaacaacat tatgaattag gtgaatacat tcgcaaacgt tatcgcaaat    960
tccttaatga atcgtacaaa cacgaacaag tgtatatccg ttccactgac gttgatagaa    1020
cactaatgtc agctatgaca aatctagctg cattagtgcc accagaaggc gttagcattt    1080
ggaatcctat cttactttgg cagccaatac ctgtacatac ggttccgtta tctgaagatc    1140 aattactttta tcttccattt cgcaactgcc cacgattcca agaattagaa tccgaaacat    1200
tgaaaagcga agaatttcag aaaagattac atccatacaa agactttatc gcaaccttag    1260
gcaaattgtc agggttacac ggacaggatc tatttggaat ttggtcgaaa gtttatgatc    1320 cttgtactg tgaatctgta cataacttta cattacctag tcgcgccacg gaagatacta    1380
tgacgaaact acgtgaactt tccgaacttt ctttactatc gttgtatggt attcataaac    1440
aaaaagaaaa gagcagattg caaggtggtg ttttagtaaa tgaaatctta aaccatatga    1500
aaagagctac acaaattccg tcttacaaga aattgattat gtatagtgct catgatacga    1560
cagtatctgg gcttcaaatg gcgttagatg tctataacgg cttacttcca ccgtatgcgt    1620
catgtcacct tacggaactt tactttgaga aaggtgagta ctttgttgag atgtactatc    1680
gcaatgaaac ccaacatgaa ccatatccgt tgatgttacc aggttgtagt ccatcttgcc    1740
cgttagaacg atttgcggaa ttagtgggtc cagtgatacc acaagactgg tctactgagt    1800
gtatgactac taatagccac caagggactg aagattcaac agattaa               1847
```

<210> SEQ ID NO 39
<211> LENGTH: 541
<212> TYPE: PRT
<213> ORGANISM: Artificial Sequence
<220> FEATURE:
<223> OTHER INFORMATION: ActAN100*-EGFRvIIIx3-PAP33-386 amino acid
      sequence

<400> SEQUENCE: 39

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys

-continued

```
                65                  70                  75                  80
Ala Lys Ala Glu Lys Gly Gly Ser Ala Ser Lys Val Leu Pro Ala Ser
                        85                  90                  95

Arg Ala Leu Glu Glu Lys Lys Gly Asn Tyr Val Val Thr Asp His Gly
                100                 105                 110

Ser Cys Ala Asp Gly Ser Val Lys Thr Ser Ala Ser Lys Val Ala Pro
                115                 120                 125

Ala Ser Arg Ala Leu Glu Glu Lys Lys Gly Asn Tyr Val Val Thr Asp
        130                 135                 140

His Gly Ser Cys Gly Asp Gly Ser Ile Lys Leu Ser Lys Val Leu Pro
145                 150                 155                 160

Ala Ser Arg Ala Leu Glu Glu Lys Lys Gly Asn Tyr Val Val Thr Asp
                165                 170                 175

His Gly Ser Cys Ala Asp Gly Ser Val Gly Ser Lys Glu Leu Lys Phe
                180                 185                 190

Val Thr Leu Val Phe Arg His Gly Asp Arg Ser Pro Ile Asp Thr Phe
                195                 200                 205

Pro Thr Asp Pro Ile Lys Glu Ser Ser Trp Pro Gln Gly Phe Gly Gln
        210                 215                 220

Leu Thr Gln Leu Gly Met Glu Gln His Tyr Glu Leu Gly Glu Tyr Ile
225                 230                 235                 240

Arg Lys Arg Tyr Arg Lys Phe Leu Asn Glu Ser Tyr Lys His Glu Gln
                245                 250                 255

Val Tyr Ile Arg Ser Thr Asp Val Asp Arg Thr Leu Met Ser Ala Met
                260                 265                 270

Thr Asn Leu Ala Ala Leu Val Pro Pro Glu Gly Val Ser Ile Trp Asn
                275                 280                 285

Pro Ile Leu Leu Trp Gln Pro Ile Pro Val His Thr Val Pro Leu Ser
        290                 295                 300

Glu Asp Gln Leu Leu Tyr Leu Pro Phe Arg Asn Cys Pro Arg Phe Gln
305                 310                 315                 320

Glu Leu Glu Ser Glu Thr Leu Lys Ser Glu Glu Phe Gln Lys Arg Leu
                325                 330                 335

His Pro Tyr Lys Asp Phe Ile Ala Thr Leu Gly Lys Leu Ser Gly Leu
                340                 345                 350

His Gly Gln Asp Leu Phe Gly Ile Trp Ser Lys Val Tyr Asp Pro Leu
                355                 360                 365

Tyr Cys Glu Ser Val His Asn Phe Thr Leu Pro Ser Arg Ala Thr Glu
        370                 375                 380

Asp Thr Met Thr Lys Leu Arg Glu Leu Ser Glu Leu Ser Leu Leu Ser
385                 390                 395                 400

Leu Tyr Gly Ile His Lys Gln Lys Glu Lys Ser Arg Leu Gln Gly Gly
                405                 410                 415

Val Leu Val Asn Glu Ile Leu Asn His Met Lys Arg Ala Thr Gln Ile
                420                 425                 430

Pro Ser Tyr Lys Lys Leu Ile Met Tyr Ser Ala His Asp Thr Thr Val
        435                 440                 445

Ser Gly Leu Gln Met Ala Leu Asp Val Tyr Asn Gly Leu Leu Pro Pro
450                 455                 460

Tyr Ala Ser Cys His Leu Thr Glu Leu Tyr Phe Glu Lys Gly Glu Tyr
465                 470                 475                 480

Phe Val Glu Met Tyr Tyr Arg Asn Glu Thr Gln His Glu Pro Tyr Pro
                485                 490                 495
```

Leu Met Leu Pro Gly Cys Ser Pro Ser Cys Pro Leu Glu Arg Phe Ala
            500                 505                 510

Glu Leu Val Gly Pro Val Ile Pro Gln Asp Trp Ser Thr Glu Cys Met
        515                 520                 525

Thr Thr Asn Ser His Gln Gly Thr Glu Asp Ser Thr Asp
        530                 535                 540

<210> SEQ ID NO 40
<211> LENGTH: 1943
<212> TYPE: DNA
<213> ORGANISM: Artificial Sequence
<220> FEATURE:
<223> OTHER INFORMATION: actAp-ActAN100*-EGFRvIIIx4-PAP33-386 nucleotide
      sequence

<400> SEQUENCE: 40

```
gggaagcagt tggggttaac tgattaacaa atgttagaga aaaattaatt ctccaagtga      60
tattcttaaa ataattcatg aatatttttt cttatattag ctaattaaga agataattaa     120
ctgctaatcc aattttaac  ggaataaatt agtgaaaatg aaggccgaat tttccttgtt     180
ctaaaaaggt tgtattagcg tatcacgagg agggagtata agtgggatta aatagattta     240
tgcgtgcgat gatggtagtt ttcattactg ccaactgcat tacgattaac cccgacataa     300
tatttgcagc gacagatagc gaagattcca gtctaaacac agatgaatgg gaagaagaat     360
acgaaactgc acgtgaagta agttcacgtg atattgagga actagaaaaa tcgaataaag     420
tgaaaaatac gaacaaagca gaccaagata taaacgtaa  agcaaaagca gagaaaggtg     480
gatctgcaag caaagtattg ccagctagtc gtgcattaga ggagaaaaag gggaattacg     540
tggtgacgga tcatggatcg tgtgccgatg gctcagtaaa gactagcgcg agcaaagtgg     600
cccctgcatc acgagcactt gaagagaaaa aaggaaacta tgttgtgacc gatcatggta     660
gctgcggaga tggttcaatt aaattatcaa agtcttacc  agcatctaga gctttagagg     720
aaaagaaggg taactatgtc gtaacagatc atggaagttg tgctgacgga agtgttaaag     780
cgtcgaaagt agctccagct tctcgcgcat tagaagaaaa gaaaggcaat tatgttgtaa     840
cagaccatgg tagttgtggt gatggctcga aaggatccaa agaactaaag tttgtaacgt     900
tagtctttag acatggtgat cgtagtccta ttgatacctt tcctacagat ccaatcaaag     960
agagtagttg gccacaaggc ttcggacaac ttacacaatt aggaatggaa caacattatg    1020
aattaggtga atacattcgc aaacgttatc gcaaattcct taatgaatcg tacaaacacg    1080
aacaagtgta tatccgttcc actgacgttg atagaacact aatgtcagct atgacaaatc    1140
tagctgcatt agtgccacca gaaggcgtta gcatttggaa tcctatctta ctttggcagc    1200
caatacctgt acatacggtt ccgttatctg aagatcaatt actttatctt ccatttcgca    1260
actgcccacg attccaagaa ttagaatccg aaacattgaa aagcgaagaa tttcagaaaa    1320
gattacatcc atacaaagac tttatcgcaa cctaggcaa  attgtcaggg ttacacggac    1380
aggatctatt tggaatttgg tcgaaagttt atgatccttt gtactgtgaa tctgtacata    1440
actttacatt acctagtcgc gccacggaag atactatgac gaaactacgt gaactttccg    1500
aactttcttt actatcgttg tatggtattc ataaacaaaa agaaaagagc agattgcaag    1560
gtggtgtttt agtaaatgaa atcttaaacc atatgaaaag agctacacaa attccgtctt    1620
acaagaaatt gattatgtat agtgctcatg atacgacagt atctgggctt caaatggcgt    1680
tagatgtcta taacggctta cttccaccgt atgcgtcatg tcaccttacg gaactttact    1740
```

```
ttgagaaagg tgagtacttt gttgagatgt actatcgcaa tgaaacccaa catgaaccat    1800
atccgttgat gttaccaggt tgtagtccat cttgcccgtt agaacgattt gcggaattag    1860
tgggtccagt gataccacaa gactggtcta ctgagtgtat gactactaat agccaccaag    1920
ggactgaaga ttcaacagat taa                                            1943
```

<210> SEQ ID NO 41
<211> LENGTH: 573
<212> TYPE: PRT
<213> ORGANISM: Artificial Sequence
<220> FEATURE:
<223> OTHER INFORMATION: ActAN100*-EGFRvIIIx4-PAP33-386 amino acid sequence

<400> SEQUENCE: 41

```
Met Gly Leu Asn Arg Phe Met Arg Ala Met Met Val Val Phe Ile Thr
 1               5                  10                  15
Ala Asn Cys Ile Thr Ile Asn Pro Asp Ile Ile Phe Ala Ala Thr Asp
                20                  25                  30
Ser Glu Asp Ser Ser Leu Asn Thr Asp Glu Trp Glu Glu Glu Tyr Glu
            35                  40                  45
Thr Ala Arg Glu Val Ser Ser Arg Asp Ile Glu Glu Leu Glu Lys Ser
        50                  55                  60
Asn Lys Val Lys Asn Thr Asn Lys Ala Asp Gln Asp Asn Lys Arg Lys
65                  70                  75                  80
Ala Lys Ala Glu Lys Gly Gly Ser Ala Ser Lys Val Leu Pro Ala Ser
                85                  90                  95
Arg Ala Leu Glu Glu Lys Lys Gly Asn Tyr Val Val Thr Asp His Gly
            100                 105                 110
Ser Cys Ala Asp Gly Ser Val Lys Thr Ser Ala Ser Lys Val Ala Pro
        115                 120                 125
Ala Ser Arg Ala Leu Glu Glu Lys Lys Gly Asn Tyr Val Val Thr Asp
    130                 135                 140
His Gly Ser Cys Gly Asp Gly Ser Ile Lys Leu Ser Lys Val Leu Pro
145                 150                 155                 160
Ala Ser Arg Ala Leu Glu Glu Lys Lys Gly Asn Tyr Val Val Thr Asp
                165                 170                 175
His Gly Ser Cys Ala Asp Gly Ser Val Lys Ala Ser Lys Val Ala Pro
            180                 185                 190
Ala Ser Arg Ala Leu Glu Glu Lys Lys Gly Asn Tyr Val Val Thr Asp
        195                 200                 205
His Gly Ser Cys Gly Asp Gly Ser Lys Gly Ser Lys Glu Leu Lys Phe
    210                 215                 220
Val Thr Leu Val Phe Arg His Gly Asp Arg Ser Pro Ile Asp Thr Phe
225                 230                 235                 240
Pro Thr Asp Pro Ile Lys Glu Ser Ser Trp Pro Gln Gly Phe Gly Gln
                245                 250                 255
Leu Thr Gln Leu Gly Met Glu Gln His Tyr Glu Leu Gly Glu Tyr Ile
            260                 265                 270
Arg Lys Arg Tyr Arg Lys Phe Leu Asn Glu Ser Tyr Lys His Glu Gln
        275                 280                 285
Val Tyr Ile Arg Ser Thr Asp Val Asp Arg Thr Leu Met Ser Ala Met
    290                 295                 300
Thr Asn Leu Ala Ala Leu Val Pro Pro Glu Gly Val Ser Ile Trp Asn
305                 310                 315                 320
```

```
Pro Ile Leu Leu Trp Gln Pro Ile Pro Val His Thr Val Pro Leu Ser
            325                 330                 335

Glu Asp Gln Leu Leu Tyr Leu Pro Phe Arg Asn Cys Pro Arg Phe Gln
        340                 345                 350

Glu Leu Glu Ser Glu Thr Leu Lys Ser Glu Glu Phe Gln Lys Arg Leu
    355                 360                 365

His Pro Tyr Lys Asp Phe Ile Ala Thr Leu Gly Lys Leu Ser Gly Leu
370                 375                 380

His Gly Gln Asp Leu Phe Gly Ile Trp Ser Lys Val Tyr Asp Pro Leu
385                 390                 395                 400

Tyr Cys Glu Ser Val His Asn Phe Thr Leu Pro Ser Arg Ala Thr Glu
                405                 410                 415

Asp Thr Met Thr Lys Leu Arg Glu Leu Ser Glu Leu Ser Leu Leu Ser
            420                 425                 430

Leu Tyr Gly Ile His Lys Gln Lys Glu Lys Ser Arg Leu Gln Gly Gly
        435                 440                 445

Val Leu Val Asn Glu Ile Leu Asn His Met Lys Arg Ala Thr Gln Ile
    450                 455                 460

Pro Ser Tyr Lys Lys Leu Ile Met Tyr Ser Ala His Asp Thr Thr Val
465                 470                 475                 480

Ser Gly Leu Gln Met Ala Leu Asp Val Tyr Asn Gly Leu Leu Pro Pro
                485                 490                 495

Tyr Ala Ser Cys His Leu Thr Glu Leu Tyr Phe Glu Lys Gly Glu Tyr
            500                 505                 510

Phe Val Glu Met Tyr Tyr Arg Asn Glu Thr Gln His Glu Pro Tyr Pro
        515                 520                 525

Leu Met Leu Pro Gly Cys Ser Pro Ser Cys Pro Leu Glu Arg Phe Ala
530                 535                 540

Glu Leu Val Gly Pro Val Ile Pro Gln Asp Trp Ser Thr Glu Cys Met
545                 550                 555                 560

Thr Thr Asn Ser His Gln Gly Thr Glu Asp Ser Thr Asp
                565                 570

<210> SEQ ID NO 42
<211> LENGTH: 63
<212> TYPE: DNA
<213> ORGANISM: Artificial Sequence
<220> FEATURE:
<223> OTHER INFORMATION: EGFRvIII nucleotide sequence 1

<400> SEQUENCE: 42
ccagctagtc gtgcattaga ggagaaaaag gggaattacg tggtgacgga tcatggatcg      60
tgt                                                                   63

<210> SEQ ID NO 43
<211> LENGTH: 63
<212> TYPE: DNA
<213> ORGANISM: Artificial Sequence
<220> FEATURE:
<223> OTHER INFORMATION: EGFRvIII nucleotide sequence 2

<400> SEQUENCE: 43
cctgcatcac gagcacttga agagaaaaaa ggaaactatg ttgtgaccga tcatggtagc      60
tgc                                                                   63

<210> SEQ ID NO 44
<211> LENGTH: 63
```

```
<212> TYPE: DNA
<213> ORGANISM: Artificial Sequence
<220> FEATURE:
<223> OTHER INFORMATION: EGFRvIII nucleotide sequence 3

<400> SEQUENCE: 44
ccagcatcta gagctttaga ggaaaagaag ggtaactatg tcgtaacaga tcatggaagt    60
tgt                                                                 63

<210> SEQ ID NO 45
<211> LENGTH: 63
<212> TYPE: DNA
<213> ORGANISM: Artificial Sequence
<220> FEATURE:
<223> OTHER INFORMATION: EGFRvIII nucleotide sequence 4

<400> SEQUENCE: 45
ccagcttctc gcgcattaga agaaaagaaa ggcaattatg ttgtaacaga ccatggtagt    60
tgt                                                                 63

<210> SEQ ID NO 46
<211> LENGTH: 63
<212> TYPE: DNA
<213> ORGANISM: Artificial Sequence
<220> FEATURE:
<223> OTHER INFORMATION: EGFRvIII nucleotide sequence 5

<400> SEQUENCE: 46
ccggcttctc gtgcgctaga agagaagaaa ggaaattacg tagttacaga ccacggctct    60
tgc                                                                 63

<210> SEQ ID NO 47
<211> LENGTH: 231
<212> TYPE: DNA
<213> ORGANISM: Artificial Sequence
<220> FEATURE:
<223> OTHER INFORMATION: hly promoter nucleotide sequence

<400> SEQUENCE: 47
tcctttgatt agtatattcc tatcttaaag ttacttttat gtggaggcat aacatttgt    60 taatgacgtc aaaaggatag caagactaga ataaagctat aaagcaagca tataatattg   120
cgtttcatct ttagaagcga atttcgccaa tattataatt atcaaaagag aggggtggca   180
aacggtattt ggcattatta ggttaaaaaa tgtagaagga gagtgaaacc c            231

<210> SEQ ID NO 48
<211> LENGTH: 1323
<212> TYPE: DNA
<213> ORGANISM: Artificial Sequence
<220> FEATURE:
<223> OTHER INFORMATION: LLO441 nucleotide sequence

<400> SEQUENCE: 48
atgaaaaaaa taatgctagt ttttattaca cttatattag ttagtctacc aattgcgcaa    60
caaactgaag caaggatgc atctgcattc aataaagaaa attcaatttc atccatggca   120
ccaccagcat ctccgcctgc aagtcctaag acgccaatcg aaaagaaaca cgcggatgaa   180
atcgataagt atatacaagg attggattac aataaaaaca atgtattagt ataccacgga   240
gatgcagtga caaatgtgcc gccaagaaaa ggttacaaag atggaaatga atatattgtt   300
gtggagaaaa agaagaaatc catcaatcaa aataatgcag acattcaagt tgtgaatgca   360
```

```
atttcgagcc taacctatcc aggtgctctc gtaaaagcga attcggaatt agtagaaaat    420
caaccagatg ttctccctgt aaaacgtgat tcattaacac tcagcattga tttgccaggt    480
atgactaatc aagacaataa aatagttgta aaaaatgcca ctaaatcaaa cgttaacaac    540 gcagtaaaata cattagtgga aagatggaat gaaaaatatg ctcaagctta tccaaatgta    600
agtgcaaaaa ttgattatga tgacgaaatg gcttacagtg aatcacaatt aattgcgaaa    660
tttggtacag catttaaagc tgtaaataat agcttgaatg taaacttcgg cgcaatcagt    720
gaagggaaaa tgcaagaaga agtcattagt tttaaacaaa tttactataa cgtgaatgtt    780
aatgaaccta caagaccttc cagattttc ggcaaagctg ttactaaaga gcagttgcaa    840
gcgcttggag tgaatgcaga aaatcctcct gcatatatct caagtgtggc gtatggccgt    900
caagtttatt tgaaattatc aactaattcc catagtacta aagtaaaagc tgcttttgat    960
gctgccgtaa gcggaaaatc tgtctcaggt gatgtagaac taacaaatat catcaaaaat   1020
tcttccttca aagccgtaat ttacggaggt tccgcaaaag atgaagttca aatcatcgac   1080
ggcaacctcg gagacttacg cgatattttg aaaaaaggcg ctacttttaa tcgagaaaca   1140
ccaggagttc ccattgctta tacaacaaac ttcctaaaag acaatgaatt agctgttatt   1200
aaaaacaact cagaatatat tgaaacaact tcaaaagctt atacagatgg aaaaattaac   1260
atcgatcact ctggaggata cgttgctcaa ttcaacattt cttgggatga agtaaattat   1320
gat                                                                  1323

<210> SEQ ID NO 49
<211> LENGTH: 441
<212> TYPE: PRT
<213> ORGANISM: Artificial Sequence
<220> FEATURE:
<223> OTHER INFORMATION: LLO441 amino acid sequence

<400> SEQUENCE: 49

Met Lys Lys Ile Met Leu Val Phe Ile Thr Leu Ile Leu Val Ser Leu
 1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190
```

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
        435                 440

<210> SEQ ID NO 50
<211> LENGTH: 1266
<212> TYPE: DNA
<213> ORGANISM: Artificial Sequence
<220> FEATURE:
<223> OTHER INFORMATION: LLO441 (delta) PEST nucleotide sequence

<400> SEQUENCE: 50
atgaaaaaaa taatgctagt ttttattaca cttatattag ttagtctacc aattgcgcaa      60
caaactgaag caaggatgc atctgcattc aatacgccaa tcgaaaagaa acacgcggat     120
gaaatcgata gtatataca aggattggat tacaataaaa acaatgtatt agtataccac     180
ggagatgcag tgacaaatgt gccgccaaga aaaggttaca agatggaaa tgaatatatt     240 gttgtggaga aaagaagaa atccatcaat caaaataatg cagacattca agttgtgaat     300
gcaatttcga gcctaaccta tccaggtgct ctcgtaaaag cgaattcgga attagtagaa     360
aatcaaccag atgttctccc tgtaaaacgt gattcattaa cactcagcat tgatttgcca     420
ggtatgacta atcaagacaa taaatagtt gtaaaaaatg ccactaaatc aaacgttaac     480
aacgcagtaa atacattagt ggaaagatgg aatgaaaaat atgctcaagc ttatccaaat     540
gtaagtgcaa aaattgatta tgatgacgaa atggcttaca gtgaatcaca attaattgcg     600

-continued

```
aaatttggta cagcatttaa agctgtaaat aatagcttga atgtaaactt cggcgcaatc    660
agtgaaggga aaatgcaaga agaagtcatt agtttttaaac aaatttacta taacgtgaat   720
gttaatgaac ctacaagacc ttccagattt ttcggcaaag ctgttactaa agagcagttg    780
caagcgcttg gagtgaatgc agaaaatcct cctgcatata tctcaagtgt ggcgtatggc    840
cgtcaagttt atttgaaatt atcaactaat tcccatagta ctaaagtaaa agctgctttt    900
gatgctgccg taagcggaaa atctgtctca ggtgatgtag aactaacaaa tatcatcaaa    960
aattcttcct tcaaagccgt aatttacgga ggttccgcaa agatgaagt tcaaatcatc    1020
gacggcaacc tcggagactt acgcgatatt ttgaaaaaag gcgctacttt taatcgagaa   1080
acaccaggag ttcccattgc ttatacaaca aacttcctaa aagacaatga attagctgtt    1140
attaaaaaca actcagaata tattgaaaca acttcaaaag cttatacaga tggaaaaatt    1200
aacatcgatc actctggagg atacgttgct caattcaaca tttcttggga tgaagtaaat    1260
tatgat                                                              1266
```

<210> SEQ ID NO 51
<211> LENGTH: 422
<212> TYPE: PRT
<213> ORGANISM: Artificial Sequence
<220> FEATURE:
<223> OTHER INFORMATION: LLO441?PEST amino acid sequence

<400> SEQUENCE: 51

```
Met Lys Lys Ile Met Leu Val Phe Ile Thr Leu Ile Leu Val Ser Leu
 1               5                  10                  15
Pro Ile Ala Gln Gln Thr Glu Ala Lys Asp Ala Ser Ala Phe Asn Thr
             20                  25                  30
Pro Ile Glu Lys Lys His Ala Asp Glu Ile Asp Lys Tyr Ile Gln Gly
         35                  40                  45
Leu Asp Tyr Asn Lys Asn Asn Val Leu Val Tyr His Gly Asp Ala Val
     50                  55                  60
Thr Asn Val Pro Pro Arg Lys Gly Tyr Lys Asp Gly Asn Glu Tyr Ile
 65                  70                  75                  80
Val Val Glu Lys Lys Lys Lys Ser Ile Asn Gln Asn Asn Ala Asp Ile
                 85                  90                  95
Gln Val Val Asn Ala Ile Ser Ser Leu Thr Tyr Pro Gly Ala Leu Val
            100                 105                 110
Lys Ala Asn Ser Glu Leu Val Glu Asn Gln Pro Asp Val Leu Pro Val
        115                 120                 125
Lys Arg Asp Ser Leu Thr Leu Ser Ile Asp Leu Pro Gly Met Thr Asn
    130                 135                 140
Gln Asp Asn Lys Ile Val Val Lys Asn Ala Thr Lys Ser Asn Val Asn
145                 150                 155                 160
Asn Ala Val Asn Thr Leu Val Glu Arg Trp Asn Glu Lys Tyr Ala Gln
                165                 170                 175
Ala Tyr Pro Asn Val Ser Ala Lys Ile Asp Tyr Asp Glu Met Ala
            180                 185                 190
Tyr Ser Glu Ser Gln Leu Ile Ala Lys Phe Gly Thr Ala Phe Lys Ala
        195                 200                 205
Val Asn Asn Ser Leu Asn Val Asn Phe Gly Ala Ile Ser Glu Gly Lys
    210                 215                 220
Met Gln Glu Glu Val Ile Ser Phe Lys Gln Ile Tyr Tyr Asn Val Asn
225                 230                 235                 240
```

```
Val Asn Glu Pro Thr Arg Pro Ser Arg Phe Phe Gly Lys Ala Val Thr
                245                 250                 255

Lys Glu Gln Leu Gln Ala Leu Gly Val Asn Ala Glu Asn Pro Pro Ala
            260                 265                 270

Tyr Ile Ser Ser Val Ala Tyr Gly Arg Gln Val Tyr Leu Lys Leu Ser
        275                 280                 285

Thr Asn Ser His Ser Thr Lys Val Lys Ala Ala Phe Asp Ala Ala Val
    290                 295                 300

Ser Gly Lys Ser Val Ser Gly Asp Val Glu Leu Thr Asn Ile Ile Lys
305                 310                 315                 320

Asn Ser Ser Phe Lys Ala Val Ile Tyr Gly Gly Ser Ala Lys Asp Glu
                325                 330                 335

Val Gln Ile Ile Asp Gly Asn Leu Gly Asp Leu Arg Asp Ile Leu Lys
            340                 345                 350

Lys Gly Ala Thr Phe Asn Arg Glu Thr Pro Gly Val Pro Ile Ala Tyr
        355                 360                 365

Thr Thr Asn Phe Leu Lys Asp Asn Glu Leu Ala Val Ile Lys Asn Asn
    370                 375                 380

Ser Glu Tyr Ile Glu Thr Thr Ser Lys Ala Tyr Thr Asp Gly Lys Ile
385                 390                 395                 400

Asn Ile Asp His Ser Gly Gly Tyr Val Ala Gln Phe Asn Ile Ser Trp
                405                 410                 415

Asp Glu Val Asn Tyr Asp
            420

<210> SEQ ID NO 52
<211> LENGTH: 1245
<212> TYPE: DNA
<213> ORGANISM: Artificial Sequence
<220> FEATURE:
<223> OTHER INFORMATION: LLO441 (delta) 26 nucleotide sequence

<400> SEQUENCE: 52
atgaaaaaaa taatgctagt ttttattaca cttatattag ttagtctacc aattgcgcaa     60
caaactgaag caaggatgc atctgcattc aataaagaag aaatcgataa gtatatacaa    120
ggattggatt acaataaaaa caatgtatta gtataccacg gagatgcagt gacaaatgtg    180
ccgccaagaa aaggttacaa agatggaaat gaatatattg ttgtggagaa aaagaagaaa    240
tccatcaatc aaaataatgc agacattcaa gttgtgaatg caatttcgag cctaacctat    300
ccaggtgctc tcgtaaaagc gaattcggaa ttagtagaaa atcaaccaga tgttctccct    360
gtaaaacgtg attcattaac actcagcatt gatttgccag gtatgactaa tcaagacaat    420
aaaatagttg taaaaaatgc cactaaatca aacgttaaca acgcagtaaa tacattagtg    480
gaaagatgga tgaaaaata tgctcaagct tatccaaatg taagtgcaaa aattgattat    540
gatgacgaaa tggcttacag tgaatcacaa ttaattgcga aatttggtac agcatttaaa    600
gctgtaaata atagcttgaa tgtaaacttc ggcgcaatca gtgaagggaa aatgcaagaa    660
gaagtcatta gttttaaaca aatttactat aacgtgaatg ttaatgaacc tacaagacct    720
tccagatttt tcggcaaagc tgttactaaa gagcagttgc aagcgcttgg agtgaatgca    780
gaaaatcctc ctgcatatat ctcaagtgtg gcgtatggcc gtcaagttta tttgaaatta    840
tcaactaatt cccatagtac taaagtaaaa gctgcttttg atgctgccgt aagcggaaaa    900
tctgtctcag gtgatgtaga actaacaaat atcatcaaaa attcttcctt caaagccgta    960
atttacggag gttccgcaaa agatgaagtt caaatcatcg acggcaacct cggagactta   1020
```

```
cgcgatattt tgaaaaaagg cgctactttt aatcgagaaa caccaggagt tcccattgct   1080
tatacaacaa acttcctaaa agacaatgaa ttagctgtta ttaaaaacaa ctcagaatat   1140
attgaaacaa cttcaaaagc ttatacagat ggaaaaatta acatcgatca ctctggagga   1200
tacgttgctc aattcaacat ttcttgggat gaagtaaatt atgat                   1245
```

<210> SEQ ID NO 53
<211> LENGTH: 415
<212> TYPE: PRT
<213> ORGANISM: Artificial Sequence
<220> FEATURE:
<223> OTHER INFORMATION: LLO441 (delta) 26 amino acid sequence

<400> SEQUENCE: 53

```
Met Lys Lys Ile Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Lys
                20                  25                  30

Glu Glu Ile Asp Lys Tyr Ile Gln Gly Leu Asp Tyr Asn Lys Asn Asn
            35                  40                  45

Val Leu Val Tyr His Gly Asp Ala Val Thr Asn Val Pro Pro Arg Lys
 50                  55                  60

Gly Tyr Lys Asp Gly Asn Glu Tyr Ile Val Val Glu Lys Lys Lys
65                  70                  75                  80

Ser Ile Asn Gln Asn Asn Ala Asp Ile Gln Val Val Asn Ala Ile Ser
                85                  90                  95

Ser Leu Thr Tyr Pro Gly Ala Leu Val Lys Ala Asn Ser Glu Leu Val
            100                 105                 110

Glu Asn Gln Pro Asp Val Leu Pro Val Lys Arg Asp Ser Leu Thr Leu
        115                 120                 125

Ser Ile Asp Leu Pro Gly Met Thr Asn Gln Asp Asn Lys Ile Val Val
130                 135                 140

Lys Asn Ala Thr Lys Ser Asn Val Asn Asn Ala Val Asn Thr Leu Val
145                 150                 155                 160

Glu Arg Trp Asn Glu Lys Tyr Ala Gln Ala Tyr Pro Asn Val Ser Ala
                165                 170                 175

Lys Ile Asp Tyr Asp Asp Glu Met Ala Tyr Ser Glu Ser Gln Leu Ile
            180                 185                 190

Ala Lys Phe Gly Thr Ala Phe Lys Ala Val Asn Asn Ser Leu Asn Val
        195                 200                 205

Asn Phe Gly Ala Ile Ser Glu Gly Lys Met Gln Glu Glu Val Ile Ser
    210                 215                 220

Phe Lys Gln Ile Tyr Tyr Asn Val Asn Val Asn Glu Pro Thr Arg Pro
225                 230                 235                 240

Ser Arg Phe Phe Gly Lys Ala Val Thr Lys Glu Gln Leu Gln Ala Leu
                245                 250                 255

Gly Val Asn Ala Glu Asn Pro Pro Ala Tyr Ile Ser Ser Val Ala Tyr
            260                 265                 270

Gly Arg Gln Val Tyr Leu Lys Leu Ser Thr Asn Ser His Ser Thr Lys
        275                 280                 285

Val Lys Ala Ala Phe Asp Ala Ala Val Ser Gly Lys Ser Val Ser Gly
    290                 295                 300

Asp Val Glu Leu Thr Asn Ile Ile Lys Asn Ser Ser Phe Lys Ala Val
305                 310                 315                 320
```

```
Ile Tyr Gly Gly Ser Ala Lys Asp Glu Val Gln Ile Ile Asp Gly Asn
                325                 330                 335

Leu Gly Asp Leu Arg Asp Ile Leu Lys Lys Gly Ala Thr Phe Asn Arg
            340                 345                 350

Glu Thr Pro Gly Val Pro Ile Ala Tyr Thr Thr Asn Phe Leu Lys Asp
        355                 360                 365

Asn Glu Leu Ala Val Ile Lys Asn Asn Ser Gly Tyr Ile Glu Thr Thr
    370                 375                 380

Ser Lys Ala Tyr Thr Asp Gly Lys Ile Asn Ile Asp His Ser Gly Gly
385                 390                 395                 400

Tyr Val Ala Gln Phe Asn Ile Ser Trp Asp Glu Val Asn Tyr Asp
                405                 410                 415

<210> SEQ ID NO 54
<211> LENGTH: 13
<212> TYPE: PRT
<213> ORGANISM: Artificial Sequence
<220> FEATURE:
<223> OTHER INFORMATION: cleaver sequence

<400> SEQUENCE: 54

Ala Ser Lys Val Leu Ala Asp Gly Ser Val Lys Thr Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: cleaver sequence

<400> SEQUENCE: 55

Ala Ser Lys Val Ala Gly Asp Gly Ser Ile Lys
1               5                   10

<210> SEQ ID NO 56
<211> LENGTH: 11
<212> TYPE: PRT
<213> ORGANISM: Artificial Sequence
<220> FEATURE:
<223> OTHER INFORMATION: cleaver sequence

<400> SEQUENCE: 56

Leu Ser Lys Val Leu Ala Asp Gly Ser Val Lys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: cleaver sequence

<400> SEQUENCE: 57

Ala Ser Lys Val Ala Gly Asp Gly Ser Ile Lys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: cleaver sequence

<400> SEQUENCE: 58
```

```
Leu Ser Lys Val Leu Ala Asp Gly Ser Val Lys
1               5                   10
```

<210> SEQ ID NO 59
<211> LENGTH: 300
<212> TYPE: DNA
<213> ORGANISM: Artificial Sequence
<220> FEATURE:
<223> OTHER INFORMATION: ActAN100 nucleotide sequence

<400> SEQUENCE: 59

```
gtgggattaa atagatttat gcgtgcgatg atggtagttt tcattactgc caactgcatt      60
acgattaacc ccgacataat atttgcagcg acagatagcg aagattccag tctaaacaca    120
gatgaatggg aagaagaaaa aacagaagag cagccaagcg aggtaaatac gggaccaaga    180
tacgaaactg cacgtgaagt aagttcacgt gatattgagg aactagaaaa atcgaataaa    240
gtgaaaaata cgaacaaagc agacctaata gcaatgttga aagcaaaagc agagaaaggt    300
```

<210> SEQ ID NO 60
<211> LENGTH: 100
<212> TYPE: PRT
<213> ORGANISM: Artificial Sequence
<220> FEATURE:
<223> OTHER INFORMATION: ActAN100 amino acid sequence

<400> SEQUENCE: 60

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100
```

<210> SEQ ID NO 61
<211> LENGTH: 10
<212> TYPE: PRT
<213> ORGANISM: Artificial Sequence
<220> FEATURE:
<223> OTHER INFORMATION: N-terminal residues for EGFRVIII mutation

<400> SEQUENCE: 61

```
Leu Glu Glu Lys Lys Gly Asn Tyr Val Val
1               5                   10
```

<210> SEQ ID NO 62
<211> LENGTH: 188
<212> TYPE: PRT
<213> ORGANISM: Homo sapiens

<400> SEQUENCE: 62

```
Met Asn Gly Asp Asp Ala Phe Ala Arg Arg Pro Thr Val Gly Ala Gln
1               5                   10                  15
```

```
Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185

<210> SEQ ID NO 63
<211> LENGTH: 750
<212> TYPE: PRT
<213> ORGANISM: Homo sapiens

<400> SEQUENCE: 63

Met Trp Asn Leu Leu His Glu Thr Asp Ser Ala Val Ala Thr Ala Arg
  1               5                  10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205
```

```
Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620
```

-continued

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
            725                 730                 735

Phe Thr Val Gln Ala Ala Ala Glu Thr Leu Ser Glu Val Ala
            740                 745                 750

<210> SEQ ID NO 64
<211> LENGTH: 386
<212> TYPE: PRT
<213> ORGANISM: Homo sapiens

<400> SEQUENCE: 64

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

-continued

```
Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Gly Thr Glu Asp Ser
    370                 375                 380

Thr Asp
385
```